United States Patent [19]

Cuomo et al.

[11] Patent Number: 4,980,367
[45] Date of Patent: Dec. 25, 1990

[54] ANTIFUNGAL CARBINOLS

[75] Inventors: John Cuomo, Newark; Richard S. Greenberg, Fairlawn, both of N.J.; Richard E. Olson, Wilmington, Del.

[73] Assignee: E. I. Du Pont de Nemours and Company, Wilmington, Del.

[21] Appl. No.: 423,243

[22] Filed: Oct. 18, 1989

Related U.S. Application Data

[60] Division of Ser. No. 134,261, Dec. 17, 1987, which is a continuation-in-part of Ser. No. 42,541, Apr. 29, 1987, abandoned, which is a continuation-in-part of Ser. No. 877,525, Jun. 23, 1986, abandoned.

[51] Int. Cl.$^5$ ............... A01N 43/653; C07D 249/08
[52] U.S. Cl. .................................. 514/383; 544/124; 544/131; 544/132; 544/364; 544/366; 546/193; 546/194; 546/210; 546/256; 546/276; 548/263.2; 548/263.8; 548/264.2; 548/264.4; 548/266.2; 548/266.6; 548/266.8; 548/267.8; 548/268.6; 548/336; 548/337; 548/341; 548/342; 549/59; 514/235.5; 514/236.2; 514/255; 514/318; 514/326; 514/333; 514/340; 514/383; 514/384; 514/397; 514/398; 514/399; 514/400; 514/444

[58] Field of Search .............. 546/193, 194, 210, 256; 544/364, 366, 124, 131, 132; 548/336, 337, 341, 342, 263.2, 263.8, 264.2, 264.4, 266.2, 266.6, 266.8, 267.8, 268.6; 549/59, 60; 514/318, 326, 255, 236.2, 235.5, 333, 340, 397, 398, 399, 400, 383, 384, 444

[56] References Cited

U.S. PATENT DOCUMENTS

| | | | |
|---|---|---|---|
| 4,427,673 | 1/1984 | Krämer et al. | 514/383 |
| 4,507,140 | 3/1985 | Sugavaran | 71/76 |
| 4,530,922 | 7/1985 | Moberg | 514/63 |
| 4,623,654 | 11/1986 | Parry et al. | 514/383 |
| 4,654,332 | 3/1987 | Parry et al. | 514/184 |

FOREIGN PATENT DOCUMENTS

| | | |
|---|---|---|
| 542110 | 5/1981 | Australia . |
| 114487 | 12/1983 | European Pat. Off. . |
| 0097425 | 1/1984 | European Pat. Off. . |
| 117578 | 2/1984 | European Pat. Off. . |
| 0143384 | 6/1985 | European Pat. Off. . |
| 3018865 | 11/1981 | Fed. Rep. of Germany . |
| 3314548 | 10/1984 | Fed. Rep. of Germany . |
| 2146987 | 5/1985 | United Kingdom . |

OTHER PUBLICATIONS

Chem. Abstracts, vol. 102, No. 13, Apr. 1, 1985, Columbus, Ohio, U.S.A.
Chem. Abstracts, vol. 104, No. 13, Mar. 31, 1986, Columbus, Ohio, U.S.A.
Chem. Abstracts, vol. 84, No. 13, Mar. 29, 1976, Columbus, Ohio, U.S.A.
Chem. Abstracts, vol. 99, No. 15, Oct. 10, 1983, Columbus, Ohio U.S.A.

Primary Examiner—Glennon H. Hollrah
Assistant Examiner—Patricia L. Morris

[57] ABSTRACT

Antifungal carbionols, particularly α-styryl carbinols, and the corresponding epoxy carbinols are provided. These carbinol compounds have the formula:

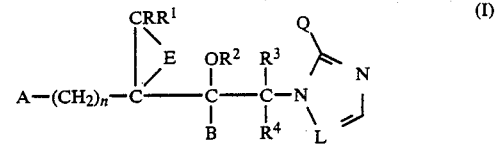

or a pharmaceutically or agriculturally suitable salt thereof wherein
E is a bond or an oxygen atom with the proviso that when E is oxygen; R, R$^1$ are not halogen; and
L, A, B, Q, R$^2$, R$^3$, R$^4$ and n are as defined in the specification.

3 Claims, No Drawings

ANTIFUNGAL CARBINOLS

This is a division of application Ser. No. 07/134,261, filed Dec. 17, 1987, which is a continuation-in-part of application Ser. No. 042,541, filed Apr. 29, 1987 (now abandoned), which in turn is a continuation-in-part of application Ser. No. 877,525, filed June 23, 1986 (now abandoned).

FIELD OF THE INVENTION

This invention relates to antifungal carbinols, particularly α-styryl carbinols, and the corresponding epoxy carbinols, pharmaceutical and agricultural compositions containing them, processes for preparing them and methods of using them as antifungal agents in mammals and plants.

BACKGROUND INCLUDING PRIOR ART

Systemic fungal infections are of increasing importance because of continued and expanded use of immunosuppressive therapies, antimicrobial therapies and indwelling catheters. Currently there are limited therapies available to treat such fungal infections. Amphotericin B remains the drug of choice because it has the widest spectrum of antifungal activity of any systemic antifungal drug, however its utility is limited by its toxicity. Because of the potential seriousness of its toxic effects, intravenous use of amphotericin B is primarily for patients with progressive, potentially fatal infections in which the patient is hospitalized during the course of therapy. Thus, there is a continuing need to develop safer and more effective drugs which are useful for the treatment of fungal infections.

Plant pathogenic fungi and other disease incitants also cause extensive losses in crops annually. While there are commercially available materials used to control many plant diseases, further improvement in this art is needed if full food and fiber production is to be realized.

There are a large number of patent and literature references in the area of azole antifungal drugs and plant disease control agents. Most pertinent to the α-styryl carbinol compounds of this invention are the following references:

B. Sugavanam in U.S. Pat. No. 4,507,140 issued Mar. 26, 1985 discloses fungicidal or plant growth regulating β-styryl triazoles or imidazoles, amongst others of the formula:

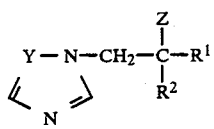

where $R^1$ is CH=CH—X; —C≡C—X or —CH$_2$—CH$_2$—X;

X is substituted aryl, aralkyl, or heterocycle;

$R^2$ is alkyl, cycloalkyl, or optionally substituted aryl;

Z is OR$^3$;

$R^3$ is H, acetyl;

Y is —N— or —CH—.

German Patent No. 3,018,865, published May 16, 1980 discloses antimycotic agents of the formula:

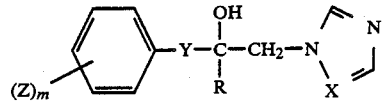

where amongst others

R is alkyl, optionally substituted cycloalkyl or optionally substituted phenyl radical;

X is N, or a CH group;

Y is —OCH$_2$—, —CH$_2$CH$_2$— or CH=CH;

Z is halogen, alkyl, cycloalkyl, alkoxy, alkythio, etc.

German Patent No. 3,314,548-A, published Apr. 21, 1983 discloses substituted 1-hydroxy-ethyl-thiazole derivatives of the formula:

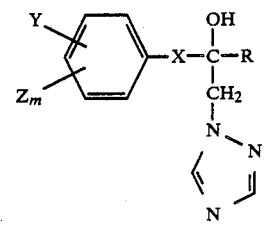

where amongst others

R is alkyl, cycloalkyl or phenyl optionally substituted;

X is —OCH$_2$—, —SCH$_2$—, —(CH$_2$)$_p$ or —CH=CH—;

Z is halogen, alkyl, alkoxy, alkylthio, haloalkyl, haloalkoxy, or haloalkylthio;

m and p are 0, 1 and 2.

The compounds are antimycotics for treating dermatophytomycoses and systemic mycoses caused, e.g., by Candida sp., Aspergillus sp., Trichophyton sp.

The above three references, which pertain to β-styryl azoles, are believed to be the most relevant. The β-styryl azole analog of one of the preferred compounds of the instant invention was prepared and found to be significantly less active.

European Patent Application No. 114,487 which published Aug. 1, 1984 discloses azolylethanol derivatives of the formula:

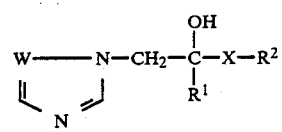

Where amongst others $R^1$ and $R^2$ which may be the same or different are hydrogen, alkyl, cycloalkyl, alkenyl, heterocyclyl aryl, or aralkyl optionally substituted; W is N or CH; and X is C=O. The compounds have fungicidal activity and plant growth regulating activity.

European Patent No. 117,578-A, published Feb. 23, 1984 discloses heterocyclic-hydroxy-alkyl alkyl ketone(s) and analogues of the formula:

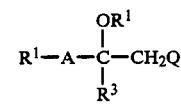

where

A is CO amongst others;
Q is imidazoyl or 1H- or 4H-1,2,4-triazol-1-yl;
R¹ is H, 1–5C alkyl, or 1–8C acyl;
R² and R³ are 1–5C alkyl, 3–6C cycloalkyl, 2–6C alkenyl, benzyl (optionally substituted by 1–3 halogen), pyridyl, furyl, thienyl, or phenyl optionally substitutes by 1–3 halogen, 1–3 alkyl, or 1–3C alkoxy.

Belgian Patent No. 900,594-A published Sept. 22, 1983 discloses 1-phenyl-1-azolyl-hydroxyethyl cycloalkane derivatives of the formula:

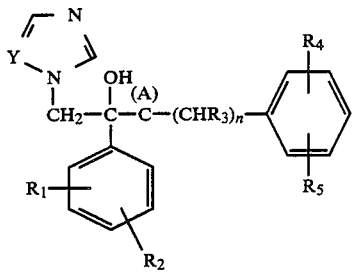

where
R₁ and R₂=H, halo, NO₂, lower alkyl, alkenyl, alkynyl, alkoxy or alkylthio (all optionally substituted by 1 or more halo), or optionally substituted phenyl or phenoxy;
R₃=H or lower alkyl;
R₄ and R₅=H or halo;
Y=CH or N;
A=2–7C alkylene;
n=0 or 1.

The compounds are useful as agricultural fungicides and antimycotics.

None of the cited references nor any known references suggest the novel antifungal compounds of this invention.

SUMMARY OF THE INVENTION

According to the present invention compounds are provided having the formula:

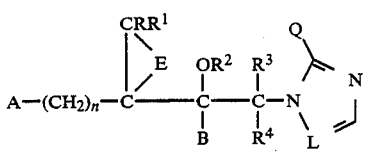

or a pharmaceutically or agriculturally suitable salt thereof wherein
E is a bond or an oxygen atom with the proviso that when E is oxygen; R, R¹ are not halogen;
A is perfluoroalkyl of 1–8 carbon atoms, N(CH₃)₂, OH, naphthyl optionally substituted with a total of 1–3 substituents each of which is independently selected from halogen and CF₃,

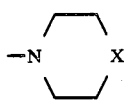

optionally substituted with 1 or 2 methyl groups, phenyl optionally substituted with a total of 1–3 substituents each of which is independently selected from:
halogen, alkyl of 1–4 carbon atoms, haloalkyl of 1–4 carbon atoms, alkoxy of 1–4 carbon atoms, and with no more than one group selected from:
haloalkoxy of 1–4 carbon atoms, CN, CO₂R₁₄, CH=NOR₁₄, S(O)ₘR⁵, R₆, 2-,3-, or 4-pyridyl or an N-oxide thereof, imidazol-1-yl, 1,2,4-triazol-1-yl, and

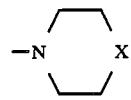

optionally substituted with 1 and 2 methyl groups,
or a heterocycle selected from imidazol-1-yl, 1,2,4-triazol-1-yl, 2- or 3-thienyl, and 2-,3-, or 4-pyridyl or an N-oxide thereof, optionally substituted with one or two substituents each of which is independently selected from:
halogen, alkyl of 1–4 carbon atoms, CF₃, alkoxy of 1—4 carbon atoms, haloalkoxy of 1–4 carbon atoms, and S(O)ₘR⁵;
B is alkyl of 1–8 carbon atoms, naphthyl, biphenyl,

perfluoroalkyl of 1–8 carbon atoms, phenyl optionally substituted with 1–3 substituents each of which is independently selected from: halogen, alkyl of 1–4 carbon atoms, haloalkyl of 1–4 carbon atoms, alkoxy of 1–4 carbon atoms, and with no more than one group selected from haloalkoxy of 1–4 carbon atoms, CN, CO₂R₁₄, CH=NOR₁₄, S(O)ₘR⁵, 2-,3-,4-pyridyl or an N oxide thereof,
benzyl optionally substituted on the phenyl ring with halogen or alkyl of 1–4 carbon atoms, or optionally α-substituted with 1 or 2 methyl groups, or
a heterocycle selected from 2- or 3-thienyl, and 2-,3-, or 4-pyridyl, said heterocycles being optionally substituted with one or two substituents each of which is independently selected from:
halogen, alkyl of 1–4 carbon atoms, haloalkyloxy of 1–4 carbon atoms, CF₃, or S(O)ₘR⁵;
Q is H, halogen, S(O)ₘR¹¹,

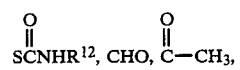

CO₂R¹³, SCN, SSR¹², or SH or its corresponding disulfide, provided however that when Q is other than H, then n is 0, R, R¹, and R⁴ are independently H or CH₃, R³ is H, and A and B are each phenyl optionally substituted with from 1–3 substituents each of which is independently halogen, CH₃, CF₃, OCH₃, or S(O)ₘR⁵;
L is CH or N with the proviso that when L=CH then Q=H;
n is 0–4 with the proviso that when A is

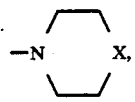

N(CH$_3$)$_2$, or OH, then n is other than O;
m each occurrence is 0, 1 or 2;
X is C, NR$^{10}$, or O;
R and R$^1$ independently are H, alkyl of 1–4 carbon atoms, halogen, or phenyl, or taken together form cycloalkyl of 3–7 carbon atoms;
R$^2$ is H, allyl, propargyl, alkyl of 1–4 carbon atoms,

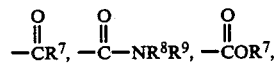

or haloalkyl of 1–4 carbon atoms;
R$^3$ and R$^4$ independently are H, F, or allyl of 1–4 carbon atoms;
R$^5$ is alkyl of 1–4 carbon atoms;
R$^6$ is phenyl optionally substituted with a total of 1–3 substituents each of which is independently selected from halogen and CF$_3$;
R$^7$ is alkyl of 1–4 carbon atoms, phenyl, or benzyl;
R$^8$ and R$^9$ independently are H, alkyl of 1–4 carbon atoms, phenyl or benzyl;
R$^{10}$ is H, alkyl of 1–4 carbon atoms, or acetyl;
R$^{11}$ is alkyl of 1–4 carbon atoms, haloalkyl of 1–2 carbon atoms, CH$_2$CN, CH$_2$SCN, CH(CH$_3$)CN, CH$_2$CO$_2$CH$_3$, or CH$_2$CO$_2$CH$_2$CH$_3$;
R$^{12}$ is alkyl of 1–4 carbon atoms, allyl, phenyl optionally substituted with 1–2 substituents each of which is independently halogen, CH$_3$, or OCH$_3$, or benzyl optionally substituted with 1–2 substituents each of which is independently halogen, CH$_3$, or OCH$_3$;
R$^{13}$ is H, or alkyl of 1–4 carbon atoms; and
R$^{14}$ is alkyl of 1–4 carbon atoms.

Also provided are pharmaceutical compositions comprising a suitable pharmaceutical carrier and a therapeutically effective amount of a compound of Formula (I) or its pharmaceutically suitable salt and methods of using the compounds of Formula (I) as antifungal agents.

This invention further provides agricultural compositions comprising a compound of Formula (I) or its agriculturally suitable salt together with an agriculturally acceptable diluent or carrier and a method of controlling fungal diseases in plants.

Certain compounds of this invention are useful as herbicides and plant growth regulants. This invention, therefore, also relates to the herbicidal composition of these compounds and their method of use as herbicides.

The herbicidal compounds are those of Formula (I) wherein:
E is a bond;
L is N;
A is perfluoroalkyl of 1–4 carbon atoms, naphthyl optionally substituted with a total of 1–2 substituents each of which is independently selected from halogen and CF$_3$,

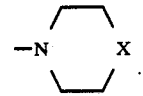

optionally substituted with 1 or 2 methyl groups, phenyl optionally substituted with a total of 1–3 substituents each of which is independently selected from:
halogen, alkyl of 1–3 carbon atoms, haloalkyl of 1–3 carbon atoms, alkoxy of 1–3 carbon atoms, and with no more than one group selected from: haloalkoxy of 1–3 carbon atoms, CN, CO$_2$R$^{14}$, CH=NOR$^{14}$, R$_6$, 2-,3-, or 4-pyridyl, or an N-oxide thereof, imidazol-1-yl, 1,2,4-triazol-1-yl, and

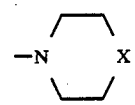

optionally substituted with 1 or 2 methyl groups,
or a heterocycle selected from imidazol-1-yl, 1,2,4-triazol-1-yl, 2- or 3-thienyl, and 2-,3-, or 4-pyridyl, said heterocycles being optionally substituted with one or two substituents each of which is independently selected from:
halogen, alkyl of 1–2 carbon atoms, and CF$_3$;
B is alkyl of 1–4 carbon atoms, naphthyl, perfluoroalkyl of 1–4 carbon atoms, phenyl optionally substituted with 1–2 substituents each of which is independently selected from: halogen, alkyl of 1–3 carbon atoms, haloalkyl of 1–3 carbon atoms, alkoxy of 1–3 carbon atoms, and with no more than one group selected from haloalkoxy of 1–3 carbon atoms, and CN,
benzyl optionally substituted on the phenyl ring with halogen or alkyl of 1–3 carbon atoms, or optionally α-substituted with 1 or 2 methyl groups, or
a heterocycle selected from 2- or 3-thienyl, and 2-,3-, or 4-pyridyl, said heterocycles being optionally substituted with one or two substituents each of which is independently selected from:
halogen, alkyl of 1–3 carbon atoms, of CF$_3$;
Q is H, halogen, S(O)$_m$R$^{11}$,

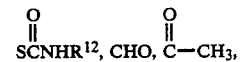

CO$_2$R$^{13}$, SCN, SSR$^{12}$, or SH or its corresponding disulfide, provided however that when Q is other than H, then n is O, R, R$^1$, and R$^4$ are independently H or CH$_3$, R$^3$ is H, and A and B are each phenyl optionally substituted with from 1–3 substituents each of which is independently halogen, CH$_3$, CH$_3$, or OCH$_3$;
n is 0–2 with the proviso that when A is

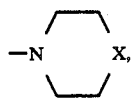

then n is other than O;
m each occurrence is 0, 1 or 2;
X is C, $NR^{10}$, or O;
R and $R^1$ independently are H, alkyl of 1-2 carbon atoms, halogen, or phenyl, or taken together form cycloalkyl of 3-6 carbon atoms;
$R^2$ is H, allyl, propargyl, alkyl of 1-2 carbon atoms,

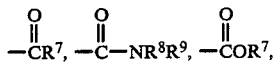

or haloalkyl of 1-4 carbon atoms;
$R^3$ and $R^4$ independently are H, F, or alkyl of 1-2 carbon atoms;
$R^6$ is phenyl optionally substituted with a total of 1-3 substituents each of which is independently selected from halogen and $CF_3$;
$R^7$ is alkyl of 1-2 carbon atoms, phenyl, or benzyl;
$R^8$ and $R^9$ independently are H, alkyl of 1-2 carbon atoms, phenyl or benzyl;
$R^{10}$ is H, alkyl of 1-2 carbon atoms, or acetyl;
$R^{11}$ is alkyl of 1-2 carbon atoms, haloalkyl of 1-2 carbon atoms, $CH_2CN$, $CH_2SCN$, $CH(CH_3)CN$, $CH_2CO_2CH_3$, or $CH_2CO_2CH_2CH_3$;
$R^{12}$ is alkyl or 1-2 carbon atoms, allyl, phenyl optionally substituted with 1-2 substituents each of which is independently halogen, $CH_3$, or $OCH_3$, or benzyl optionally substituted with 1-2 substituents each of which is independently halogen, $CH_3$, or $OCH_3$; and
$R^{13}$ is H, or alkyl of 1-2 carbon atoms.

Further provided are processes for the preparation of the aforesaid compounds, which processes are described hereinafter.

Additionally provided are novel intermediates having the formulas (II) and (IIa) shown below:

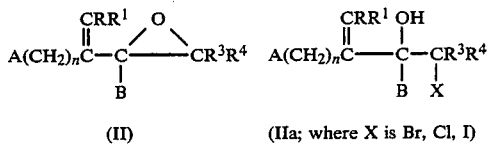

wherein A, B, R, $R^1$, $R^3$, $R^4$ and n are as defined above, except that $R^3$, $R^4$ are not F and not both alkyl.

PREFERRED EMBODIMENTS

Preferred compounds are the α-styryl compounds of formula (I) (E is a bond) where:
(1) n=0, or 1; and/or
(2) $R^3$ and $R^4$ independently are H, $CH_3$, or F.

More preferred compounds are preferred compounds where:
(1) A, and B independently are phenyl optionally substituted with from 1-3 substituents each of which is halogen, alkyl of 1-4 carbon atoms, haloalkyl of 1-4 carbon atoms, alkoxy of 1-4 carbon atoms, or $S(O)_mR^5$; and/or
(2) n=0; and/or (3) R and $R^1$ independently are H, $CH_3$ or halogen; and/or
(4) $R^2$=H, alkyl of 1-4 carbon atoms, allyl, or propargyl; and/or
(5) Q is H, I, SH.

Most preferred compounds are more preferred compounds where:
(1) A and B independently are phenyl optionally substituted with from 1-3 halogen atoms, $CH_3$, $OCH_3$, $CF_3$, or $SCH_3$; and/or;
(2) R, $R^1$, $R^2$, $R^3$, $R^4$ and Q are all H.

Specifically preferred because of their biological activity are the following compounds or salts thereof;

(a) 2-(4-Fluorophenyl)-3-phenyl-1-(1H-1,2,4-triazol-1-yl)-3-buten-2-ol; and the (S) enantiomer thereof.
(b) 2,3-Bis(4-fluorophenyl)-1-(1H-1,2,4-triazol-1-yl)-3-buten-2-ol; and the (S) enantiomer thereof.
(c) 2-(2,4-Dichlorophenyl)-3-(4-chlorophenyl)-1-(1H-1,2,4-triazol-1-yl) -3-buten-2-ol; and the (S) enantiomer thereof.
(d) 2-(4-Chlorophenyl)-3-(2-chlorophenyl)-1-(1H-1,2,4-triazol-1-yl) -3-buten-2-ol; and the (S) enantiomer thereof.
(e) 2-(2,4-Dichlorophenyl)-3-(3-fluorophenyl)-1-(1H-1,2,4-triazol-1-yl) -3-buten-2-ol; and the (S) enantiomer thereof.
(f) 2-(2-Chlorophenyl)-3-(2-chlorophenyl)-1-(1H-1,2,4-triazol-1-yl) -3-buten-2-ol; and the (S) enantiomer thereof.
(g) 2-(2,4-Dichlorophenyl)-3-(3-chlorophenyl)-1-(1H-1,2,4-triazol-1-yl) -3-buten-2-ol; and the (S) enantiomer thereof.
(h) 2-(4-Fluorophenyl)-3-(4-trifluoromethylphenyl)-1-(1H-1,2,4-triazol-1-yl) -3-buten-2-ol; and the (S) enantiomer thereof.
(i) 2-(2,4-Dichlorophenyl)-3-phenyl-1-(1H-1,2,4-triazol-1-yl) -3-buten-2-ol; and the (S) enantiomer thereof.
(j) 2-(3,4-Dichlorophenyl)-3-(4-fluorophenyl)-1-(1H-1,2-4-triazol-1-yl) -3-buten-2-ol; and the (S) enantiomer thereof.
(k) 2-(4-Chlorophenyl)-3-(3-chlorophenyl)-1-(1H-1,2,4-triazol-1-yl) -3-buten-2-ol; and the (S) enantiomer thereof.
(l) 2-(4-Fluorophenyl)-3-(2,4-difluorophenyl)-1-(1H-1,2,4-triazol-1-yl) -3-buten-2-ol; and the (S) enantiomer thereof.
(m) 2-(2,4-Difluorophenyl)-3-(2-chlorophenyl)-(1H-1,2,4-triazol-1-yl)-3-buten-2-ol; and the (S) enantiomer thereof.
(n) 2-(2,4-Dichlorophenyl)-3-(2-chlorophenyl)-1-(1H-1,2,4-triazol-1-yl) -3-buten-2-ol; and the (S) enantiomer thereof.
(o) 2-(2,4-Difluorophenyl)-3-phenyl)-1-(1H-imidazol-1-yl)-3-buten-2-ol; and the (S) enantiomer thereof.
(p) 2-(2,4-Difluorophenyl)-3-(4-fluorophenyl)-1-(1H-imidazol-1-yl)-3-buten-2-ol; and the (S) enantiomer thereof.
(q) 2-(2,4-Difluorophenyl)-3-(2-chlorophenyl)-1-(1H-imidazol-1-yl)-3-buten-2-ol; and the (S) enantiomer thereof.
(r) 2-(2,4-Difluorophenyl)-3-phenyl-1-(1H-1,2,4-triazol-1-yl)-3-buten-2-ol; and the (S) enantiomer thereof.
(s) 2-(2,4-Difluorophenyl)-3-(4-fluorophenyl)-1-(1H-1,2,4-triazol-1-yl) -3-buten-2-ol; and the (S) enantiomer thereof.
(t) 2-(2-Fluorophenyl)-3-(4-fluorophenyl)-1-(1H-1,2,4-triazol-1-yl) -3-buten-2-ol; and the (S) enantiomer thereof.

(u) 2-(2-Fluorophenyl)-3-(4-chlorophenyl)-1-(1H-1,2,4-triazol-1-yl) -3-buten-2-ol; and the (S) enantiomer thereof.

(v) 2-(2-(2,4-Difluorophenyl)-3-(4-chlorophenyl)-1-(1H-1,2,4-triazol-1yl) -3-buten-2-ol; and the (S) enantiomer thereof.

(w) 2-(2-Chlorophenyl)-3-(4-fluorophenyl)-1-(1H-1,2,4-triazol-1-yl) -3-buten-2-ol; and the (S) enantiomer thereof.

(x) 2-(4-Chlorophenyl)-3-phenyl-1-(1H-1,2,4-triazol-1-yl)-3-buten-2-ol; and the (S) enantiomer thereof.

All of the compounds within the scope of this invention are active in either pharmaceutical or agricultural fungicidal assays. Thus, it should be recognized that there are compounds which are not always active in both assays as is shown with some compounds in the Examples. Of the above listed specifically preferred compounds, compounds (a)–(r) or their salts are preferred for pharmaceutical uses and compounds (r)–(x) or their salts are preferred for agricultural uses.

DETAILED DESCRIPTION OF THE INVENTION

Synthesis

The novel compounds of Formula (I) can be prepared using the reactions and techniques described in this section. The reactions are usually performed in a solvent appropriate to the reagents and materials employed, and suitable for the transformation being effected. In some cases functional groups on the starting materials may need to be protected by standard protecting groups reported in the chemical literature which are well known to one skilled in the art.

In some cases, substituents on the starting materials may be incompatible with some of the reaction conditions required in some of the methods described. Such restrictions to the substituents which are compatible with the reaction conditions will be readily apparent to one skilled in the art and alternative methods described must then be used.

The compounds of the present invention can contain at least one chiral center and as such can exist as two individual isomers or as a racemic mixture of both. This invention relates to the (S) isomer, as well as to racemic mixtures containing both isomers.

For the purposes of this invention, the (S)-isomer of compounds of Formula (I) is intended to mean compounds of the configuration depicted:

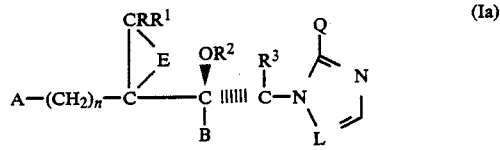

When a single chiral center is present the resolution can be performed by reacting the compound with a chiral strong acid (e.g. substituted camphorsulfonic acids) in a suitable solvent (e.g. acetonitrile) or mixture of solvents (e.g. 3/1 etheracetone). This reaction is carried out at a temperature between 25° C. to 100° C., preferably at the reflux temperature of the solvent(s) employed. The reaction produces two diastereomeric adducts that can be separated by fractional crystallization. The adduct can then be cleaved in basic medium (e.g. sat. NaHCO$_3$, sat. Na$_2$CO$_3$) to give the resolved product.

The compounds of Formula I, where E is a bond, R$^2$ and Q are H and R$^3$, R$^4$ are not F and not both alkyl, can be prepared by contacting an oxirane of Formula (II) or a halohydrin of Formula (IIa), or a mixture of (II) or (IIa) with imidazole or triazole or a corresponding alkali metal salt (preferably the Na$^+$ or K$^+$ salt) in a suitable solvent (Scheme I).

Scheme 1

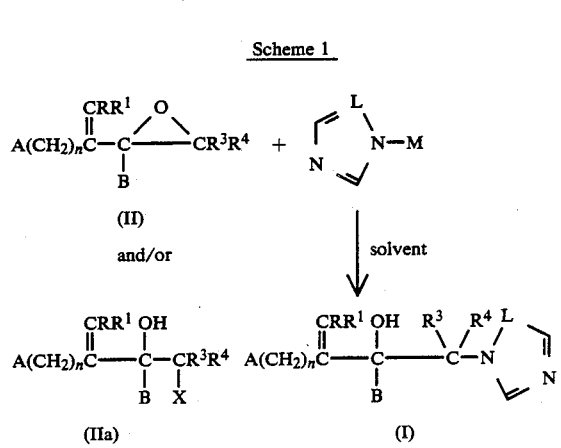

When imidazole or triazole is used, an acid acceptor, such as potassium carbonate, sodium methoxide or sodium hydride, is added to the reaction mixture. Suitable inert solvents include polar, aprotic solvents such as dimethylformamide (DMF), dimethylsulfoxide (DMSO) and ethereal solvents such as tetrahydrofuran (THF). Non-polar solvents, such as toluene, may be used if a phase transfer catalyst, such as tetrabutylammonium bromide, is added. The reaction is carried out at a temperature in the range of 10° to 150° C., preferably from 50° to 120° C., for a period of 0.25 to 24 hours. It is recognized that varying amounts of the 4H-1,2,4-triazol-4-yl isomers of Formula (I) may be formed when triazole is used in the above reaction. The isomers can be separated, if desired, using standard separation techniques, e.g., chromatography.

The 4H-1,2,4-triazol-4-yl isomers of Formula (I) can be converted to the compounds of Formula (I) by isomerization with base as described in EP No. 143384A2, or by heating with 2-100 mol % of oxiranes of Formula (II), halohydrins of Formula (IIa), reactive alkyl or benzyl bromides or iodides, such as benzyl bromide or methyl iodide, or commercial oxiranes such as styrene oxide, at temperatures of 100°-200° C.; preferably in a polar aprotic solvent such as DMF, or a non-polar solvent such as one of the xylenes.

The oxiranes of Formula (II) can be prepared using one or both of the following methods; (Scheme 2). In the first, vinyl organometallic reagents, e.g., vinyl Grignard reagents, of Formula (III) are allowed to react with haloketones of Formula (IV) in the presence of ethereal solvents, such as THF or diethyl ether, at a temperature ranging from −90° to 60° C., preferably −10° to 50° C., for 0.5 to 24 hours. Depending on the reaction conditions and the value of X in the haloketone starting material (IV), the product may be an oxirane (II), a halohydrin (IIa) or a mixture of (II) and (IIa). If desired, the halohydrins (IIa) may be converted to oxiranes (II) by treatment with base, e.g., potassium hydride (KH), in a solvent such as THF.

Scheme 2

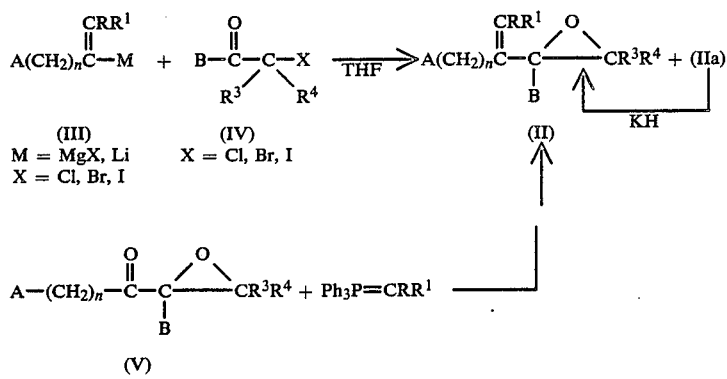

In the second method, keto-oxiranes of formula (V) are olefinated with, for example, Wittig reagents, which provide epoxy-olefins of Formula (II).

Unsaturated ketones of Formula (VII) can be converted to expoxy-olefins (II) by treatment with dimethylsulfonium methylide. The enones (VII) can be prepared by treatment of ketones of Formula (VI) with carbonyl compounds and appropriate catalysts (Scheme 3).

Scheme 3

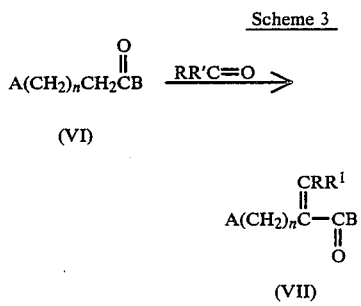

Unsaturated ketones of Formula (VIII) can be converted to epoxyketones (V) using basic hydrogen peroxide. Olefination of (V), as described above, provides epoxyolefins (II) (Scheme 4).

Scheme 4

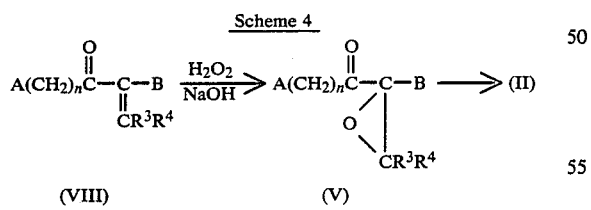

The vinyl organometallics of Formula (III) are prepared using standard procedures from the corresponding chlorides, bromides or iodides. The haloolefins, the haloketones of Formula (IV), the ketooxiranes of Formula (V) and the ketones of Formula (VI) are known, or can be prepared using methods known to one skilled in the art.

Compounds of Formula (I) can also be prepared by olefinations of ketones (IX) with, for example, Wittig reagents (Scheme 5). Ketones of Formula (IX) where $R^2$, $R^3$ and $R^4$=H are known (EP No. 117578A).

Scheme 5

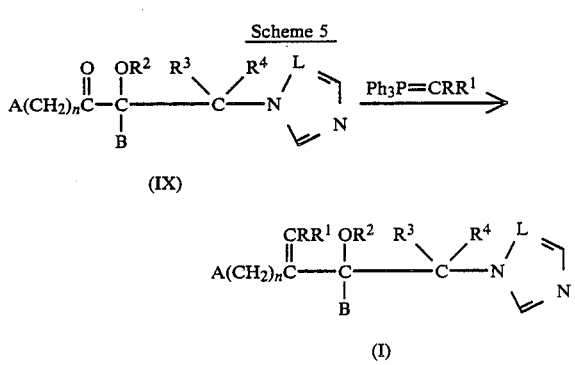

Compounds of general Formula (I) where $R^3$ and/or $R^4 \neq H$ can be made as shown in Scheme 6 by reacting ketones of general Formula (X) with the appropriate organometallic reagent (e.g. Grignard reagent, organolithium reagent). The ketones (X) are prepared by conventional methods from the corresponding α-haloketones (IV) (see e.g. EP No. 0044605, UK No. 2099818A, UK No. 146224, EP No. 1337718, and EP No. 0153803).

Scheme 6

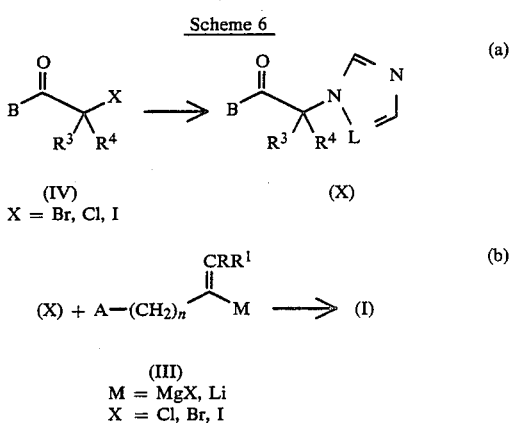

Compounds of Formula (I) where A=(heterocycle)-phenyl can be prepared from appropriately substituted precursors using the methods described above, or by using substitution reactions on (I) wherein A is halophenyl. For example, compounds of Formula (I) where A is (pyridyl)phenyl can be prepared by treatment of (I), wherein A is bromophenyl or iodophenyl, with the appropriate pyridylstannanes in the presence of palladium catalysts (see Tetrahedron Letters, 27, 4407, 1986). Copper assisted displacement of halogen (Tetrahedron, 40, 1433, 1984) with heterocyclic nucleophiles provides compounds of Formula (I) where A is for example 1-imidazolylphenyl.

In some cases, it may be desirable to begin with compounds of Formula I, wherein A is aminophenyl, and construct the heterocyclic ring using $X(CH_2CH_2Cl)_2$ (see ES No. 8603-473-A).

The compounds of Formula (I) where $Q \neq H$ and $L = N$ can be prepared as shown in Scheme 7. Metalation of (I), Q=H with strong base provides the 5-metalated triazoles (Ia) (See Heterocycles, 23, 1645–49, 1985). When $R^2$ is H, 2 equivalents of base are required. Typical conditions involve treatment of a solution of (I) in THF at $-70°$ with n-butyllithium for 15–30 minutes. Where the metalated triazole (Ia) is less soluble than (I), the addition of co-solvents, such as dimethylpropyleneurea (DMPU) may be beneficial.

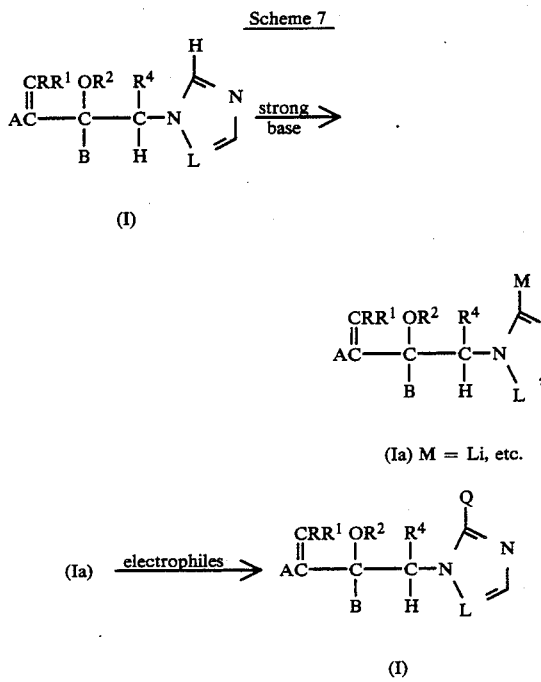

The treatment of (Ia) with electrophiles gives a wide variety of (I) where $Q \neq H$. Electrophiles of relevance to the present invention include halogenating agents, sulfur, disulfides, carbon dioxide, dimethylamides and sulfur dioxide followed by alkyl halides. Subsequent functionalization, using methods known to one skilled in the art, provide other compounds of Formula (I) wherein $Q \neq H$. For example, the treatment of (I), where Q is SH with isocyanates or phthalimidosulfides provides thiocarbamates (I;

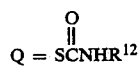

or disulfides (I; $Q=SSR^{12}$), respectively.

The compounds of general Formula (I) where E is oxygen can be prepared by oxidation of compounds of general Formula (I) where E is a bond provided that R, $R^1 \neq$ halogen using methods described in the literature (Scheme 8):

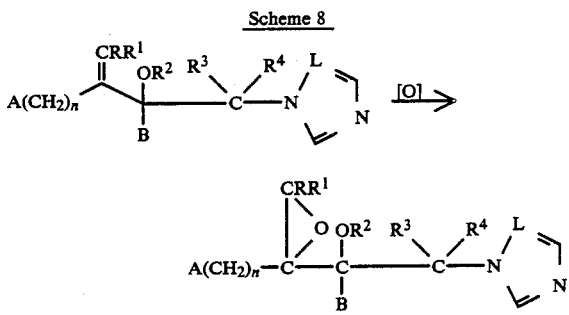

Suitable reagents which can effect his oxidation, depending on the nature of the substituents, include peracids such as m-chloroperbenzoic acid; hydroperoxides such as tert-butyl hydroperoxide in the presence of an appropriate catalyst such as vanadium acetonylacetonate; or hydrogen peroxide. Alternatively, the transformation can be effected by first forming the halohydrin with a hypohalous acid such as hypobromous acid and then reacting the intermediate halohydrin with a proton acceptor such as potassium tert-butoxide.

It will be noted by those skilled in the art that, depending on the nature of the compound to be oxidized, a mixture of diastereomers can be obtained. This can be controlled through selection of appropriate oxidation methods or, alternatively, the resulting mixture of diastereomers can be separated in a conventional manner (e.g. chromatography, fractional crystallization).

Compounds of Formula (I) where $R^2$ is H can be alkylated, acylated and carbamoylated, using standard procedures, to prepare functional derivatives of the alcohol moiety.

The compounds of this invention and their preparation can be understood further by the following examples, but should not constitute a limitation thereof. In these examples, unless otherwise indicated, all temperatures are in degrees centigrade and parts and percentages are by weight.

Nuclear magnetic resonance (nmr) spectra were obtained in $CDCl_3$ solution, unless otherwise noted. Abbreviations for nmr spectra are s=singlet, d=doublet, t=triplet, q=quartet, m=multiplet; peak positions are reported as parts per million downfield from tetramethylsilane.

EXAMPLE 1

PART A 2-(4-Fluorophenyl)-2-[1-(4-fluorophenyl)ethenyl] oxirane

PROCESS 1: Grignard Addition to an α-Haloketone

To a 25° solution of Grignard reagent prepared from 6.0 g (0.030 mol) of 1-bromo-4'-fluorostyrene and 0.85 g (0.035 mol) of magnesium turnings in 60 mL of THF was added a solution of 5.2 g (0.030 mol) of 2-chloro-4'-fluoroacetophenone in 10 mL of THF. The solution was stirred for 2 hours at 25°. Saturated aqueous $NH_4Cl$ (10 mL) was added, the aqueous layer was extracted with 1:1 $Et_2O$/hexane and the combined organic layers were washed with brine, dried over $MgSO_4$ and evaporated to give 10.2 g of an amber oil. Analysis by NMR ($CDCl_3$) indicated that the desired oxirane was the major product: δ3.1, 3.3 (two d, epoxide protons; 5.5, 5.8 (two s, vinyl protons). The material was of sufficient purity to be used in the next step.

PROCESS 2: Olefination of 2-(4-Fluorophenyl)-2-(4-fluorobenzoyl)oxirane

To a suspension of 4.3 g (0.012 mol) of methyltriphenylphosphonium bromide in 15 mL of THF cooled to −70° was added 8.4 mL (0.013 mol) of 1.55 M n-butyllithium over 3 min., keeping the temperature at less than −55°. The resulting yellow suspension was allowed to warm to 0° over 10 min, and was then treated with 2.6 g (0.010 mol) of 2-(4-fluorophenyl)-2-(4-fluorobenzyl)oxirane in 5 mL of THF. The light-brown suspension was stirred for 6 hours at 25°. Standard workup gave 3.4 g of crude product which was flash chromatographed (Et$_2$O) to give 1.7 g of the desired product, which was of sufficient purity to be used in the next step. NMR (CDCl$_3$)δ3.1 (d): 3.3 (d); 5.5 (s); 5.8 (s).

PART B 2,3-Bis (4-Fluorophenyl)-1-(1H-1,2,4-triazol-1-yl)-3-buten-2-ol

A mixture of 10.2 g (0.040 ) of crude 2-(4-fluorophenyl)-2-[1-(4-fluorophenyl)ethenyl]oxirane and 7.0 g (0.065 mol) of potassium triazole in 60 mL of DMF was heated at 60° overnight, then cooled and poured into 100 mL of 1:1 Et$_2$O/hexanes. After washing the organic layer three times with H$_2$O and once with brine, a precipitate formed in the organic layer. Filtering gave 4.8 g of a brown solid which was recrystallized from 500 mL of cyclohexane to yield 2.5 g of a light-tan powder, mp 136°–137° C.: NMR (CDCl$_3$)δ1.7 (br s, OH); 4.7 (q, 2H); 5.3 (s, 1H); 5.5 (s, 1H); 6.8–7.1 (m, 6H); 7.4 (m, 2H); 7.8 (s, 1H); 7.9 (s, 1H); IR (nujol) 3120 (br), 1900, 1600, 1505, 1220, 1139, 835 cm$^{-1}$.

The compounds shown in Table 1 were prepared or can be prepared by the method described hereinabove.

In the tables, Ph means phenyl and substituted aryl groups are abbreviated, e.g., 4-F-Ph is 4-fluorophenyl, 2,4-Cl$_2$-Ph is 2,4-dichlorophenyl and 2-thienyl is thiophen-2-yl.

TABLE 1

$$\underset{A(CH_2)_n}{\overset{CRR^1}{\|}}\overset{R^3}{\underset{OR^2}{C}}\overset{R^4}{\underset{B}{C}}-N\overset{N}{\underset{\diagdown}{\diagup}}$$

| Ex. No. | A | B | n | R | R¹ | R² | R³ | R⁴ | M.P. °C. |
|---|---|---|---|---|---|---|---|---|---|
| 1 | 4-F—Ph | 4-F—Ph | 0 | H | H | H | H | H | 136-137 (HCl salt 182-184) |
| 2 | 4-F—Ph | 2,4-Cl₂—Ph | 0 | H | H | H | H | H | 139-143 |
| 3 | 4-F—Ph | 4-Cl—Ph | 0 | H | H | H | H | H | (oil)ᵃ |
| 4 | 4-F—Ph | 2,4-F₂—Ph | 0 | H | H | H | H | H | 102-103.5 |
| 5 | 4-F—Ph | 4-CF₃—Ph | 0 | H | H | H | H | H | |
| 6 | 4-F—Ph | n-C₄H₉ | 0 | H | H | H | H | H | 72-73 |
| 7 | 4-F—Ph | n-C₄F₉ | 0 | H | H | H | H | H | |
| 8 | 2-F—Ph | Ph | 0 | H | H | H | H | H | 89-93 |
| 9 | 2-F—Ph | 2-F—Ph | 0 | H | H | H | H | H | (oil)ᵇ |
| 10 | 2-F—Ph | 4-F—Ph | 0 | H | H | H | H | H | 121-122 |
| 11 | 2-F—Ph | 2,4-F₂—Ph | 0 | H | H | H | H | H | 116-117 |
| 12 | 2-F—Ph | 2-Cl—Ph | 0 | H | H | H | H | H | 115-116 |
| 13 | 2-F—Ph | 4-Cl—Ph | 0 | H | H | H | H | H | 106-109 |
| 14 | 2-F—Ph | 2,4-Cl₂—Ph | 0 | H | H | H | H | H | 145-147 |
| 15 | 3-F—Ph | 4-F—Ph | 0 | H | H | H | H | H | 101-102 |
| 16 | 3-F—Ph | 2,4-Cl₂—Ph | 0 | H | H | H | H | H | 92-93 |
| 17 | 3-F—Ph | 4-Cl—Ph | 0 | H | H | H | H | H | |
| 18 | 3-F—Ph | 2,4-F₂—Ph | 0 | H | H | H | H | H | |
| 19 | 3-F—Ph | 4-CF₃—Ph | 0 | H | H | H | H | H | 122-124 |
| 20 | 3-F—Ph | n-C₄H₉ | 0 | H | H | H | H | H | 110-115 |
| 21 | 3-F—Ph | n-C₄F₉ | 0 | H | H | H | H | H | 89-91 (HCl salt 184-190) |
| 22 | 3-F—Ph | Ph | 0 | H | H | H | H | H | 132-135 |
| 23 | 3-F—Ph | 2-F—Ph | 0 | H | H | H | H | H | 124-125.5 |
| 24 | 3-F—Ph | 2-Cl—Ph | 0 | H | H | H | H | H | |
| 25 | 4-Cl—Ph | 4-F—Ph | 0 | H | H | H | H | H | |
| 26 | 4-Cl—Ph | 2,4-Cl₂—Ph | 0 | H | H | H | H | H | |
| 27 | 4-Cl—Ph | 4-Cl—Ph | 0 | H | H | H | H | H | (oil)ᶜ |
| 28 | 4-Cl—Ph | 2,4-F₂—Ph | 0 | H | H | H | H | H | 150-152 |
| 29 | 4-Cl—Ph | 4-CF₃—Ph | 0 | H | H | H | H | H | 153-154 |
| 30 | 4-Cl—Ph | n-C₄H₉ | 0 | H | H | H | H | H | (HCl salt 175-180) |
| 31 | 4-Cl—Ph | n-C₄F₉ | 0 | H | H | H | H | H | 128-129 |
| 32 | 2-Cl—Ph | 4-F—Ph | 0 | H | H | H | H | H | (HCl salt 156-161) |
| 33 | 2-Cl—Ph | 2,4-Cl₂—Ph | 0 | H | H | H | H | H | (HCl salt 124-127) |
| 34 | 2-Cl—Ph | 4-Cl—Ph | 0 | H | H | H | H | H | HNO₃ salt 138-141 |
| | | | | | | | | | H₃PO₄ salt 158-160 |
| 35 | 2-Cl—Ph | 2,4-F₂—Ph | 0 | H | H | H | | H | H₂SO₄ salt 184-187 |
| | | | | | | | | | HNO₃ salt 158-159 |
| 36 | 2-Cl—Ph | 4-CF₃—Ph | 0 | H | H | H | | H | H₃PO₄ salt 141-143 |

TABLE 1-continued

| | | | | | | | | |
|---|---|---|---|---|---|---|---|---|
| 37 | 2-Cl—Ph | n-C₄H₉ | O | H | H | H | H | |
| 38 | 2-Cl—Ph | n-C₄F₉ | O | H | H | H | H | |
| 39 | 2-Cl—Ph | 4-F—Ph | O | H | H | H | H | 95–96.5 |
| 40 | 3-Cl—Ph | 2,4-Cl₂—Ph | O | H | H | H | H | 144–146 |
| 41 | 3-Cl—Ph | 2,4-F₂—Ph | O | H | H | H | H | 112–115 |
| 42 | 3-Cl—Ph | 4-CF₃—Ph | O | H | H | H | H | 115–116 |
| 43 | 3-Cl—Ph | n-C₄H₉ | O | H | H | H | H | |
| 44 | 3-Cl—Ph | n-C₄F₉ | O | H | H | H | H | |
| 45 | 3-Cl—Ph | Ph | O | H | H | H | H | |
| 46 | 3-Cl—Ph | 2-F—Ph | O | H | H | H | H | 91–93 |
| 47 | 3-Cl—Ph | 2-Cl—Ph | O | H | H | H | H | 125–126 |
| 48 | 3-Cl—Ph | 4-F—Ph | O | H | H | H | H | 117–120 |
| 49 | Ph | 2,4-Cl₂—Ph | O | H | H | H | H | 111 |
| 50 | Ph | 2,4-Cl₂—Ph | O | H | H | H | H | 119.5–122 (HCl salt 152–154) |
| 51 | Ph | 4-Cl—Ph | O | H | H | H | H | |
| 52 | Ph | 2,4-F₂—Ph | O | H | H | H | H | |
| 53 | Ph | 4-CF₃—Ph | O | H | H | H | H | (oil)ᶜ |
| 54 | Ph | n-C₄H₉ | O | H | H | H | H | 127.5–130 |
| 55 | Ph | n-C₄F₉ | O | H | H | H | H | 152–156 |
| 56 | 2-CF₃—Ph | Ph | O | H | H | H | H | 101–103 |
| 57 | 2-CF₃—Ph | 2-F—Ph | O | H | H | H | H | (oil)ᶜ |
| 58 | 2-CF₃—Ph | 2-Cl—Ph | O | H | H | H | H | 101–104 |
| 59 | 3-CF₃—Ph | 2-Cl—Ph | O | H | H | H | H | |
| 60 | 3-CF₃—Ph | Ph | O | H | H | H | H | |
| 61 | 4-CF₃—Ph | 2-F—Ph | O | H | H | H | H | |
| 62 | 4-CF₃—Ph | 2-Cl—Ph | O | H | H | H | H | |
| 63 | 4-CF₃—Ph | 4-F—Ph | O | H | H | H | H | 152–154 |
| 64 | 4-CF₃—Ph | 2,4-Cl₂—Ph | O | H | H | H | H | (oil)ᶠ |
| 65 | 4-CF₃—Ph | 4-Cl—Ph | O | H | H | H | H | 144–145 |
| 66 | 4-CF₃—Ph | 2,4-F₂—Ph | O | H | H | H | H | |
| 67 | 4-CF₃—Ph | 4-CF₃—Ph | O | H | H | H | H | |
| 68 | 4-CF₃—Ph | n-C₄H₉ | O | H | H | H | H | |
| 69 | 4-CF₃—Ph | n-C₄F₉ | O | H | H | H | H | |
| 70 | 2-Br—Ph | Ph | O | H | H | H | H | |
| 71 | 2-Br—Ph | 2-F—Ph | O | H | H | H | H | |
| 72 | 2-Br—Ph | 2-F—Ph | O | H | H | H | H | |
| 73 | 2-Br—Ph | 2,4-F₂—Ph | O | H | H | H | H | |
| 74 | 2-Br—Ph | 2-Cl—Ph | O | H | H | H | H | |
| 75 | 2-Br—Ph | 4-Cl—Ph | O | H | H | H | H | |
| 76 | 2-Br—Ph | 4-F—Ph | O | H | H | H | H | |
| 77 | 3-Br—Ph | 2,4-Cl₂—Ph | O | H | H | H | H | |
| 78 | 3-Br—Ph | 4-Cl—Ph | O | H | H | H | H | |
| 79 | 4-Br—Ph | Ph | O | H | H | H | H | |
| 80 | 4-Br—Ph | 2-F—Ph | O | H | H | H | H | |
| 81 | 4-Br—Ph | 2-Cl—Ph | O | H | H | H | H | |
| 82 | 4-Br—Ph | Ph | O | H | H | H | H | |
| 83 | 4-Br—Ph | 2-F—Ph | O | H | H | H | H | 123–126 |
| 84 | 4-Br—Ph | 4-F—Ph | O | H | H | H | H | (oil)ᵈ |
| 85 | 4-Br—Ph | 2,4-Cl₂—Ph | O | H | H | H | H | 145–148 |
| 86 | 4-Br—Ph | 4-Cl—Ph | O | H | H | H | H | |
| 87 | 4-Br—Ph | 4-Cl—Ph | O | H | H | H | H | |

TABLE 1-continued

| | | | | | | | | |
|---|---|---|---|---|---|---|---|---|
| 88 | 4-Br—Ph | 2,4-F$_2$—Ph | O | H | H | H | H | 123-125 |
| 89 | 4-Br—Ph | 4-CF$_3$—Ph | O | H | H | H | H | |
| 90 | 4-Br—Ph | n-C$_4$H$_9$ | O | H | H | H | H | |
| 91 | 4-Br—Ph | n-C$_4$F$_9$ | O | H | H | H | H | |
| 92 | 2,4-F$_2$—Ph | Ph | O | H | H | H | H | 106-108 |
| 93 | 2,4-F$_2$—Ph | 2-F—Ph | O | H | H | H | H | 100-103 |
| 94 | 2,4-F$_2$—Ph | 4-F—Ph | O | H | H | H | H | 116-120 |
| 95 | 2,4-F$_2$—Ph | 2,4-F$_2$—Ph | O | H | H | H | H | |
| 96 | 2,4-F$_2$—Ph | 2-Cl—Ph | O | H | H | H | H | |
| 97 | 2,4-F$_2$—Ph | 4-Cl—Ph | O | H | H | H | H | |
| 98 | 2,4-F$_2$—Ph | 2,4-Cl$_2$—Ph | O | H | H | H | H | (oil)$^e$ |
| 99 | 2,4-F$_2$—Ph | 4-F—Ph | O | H | H | H | H | 75-78 |
| 100 | 2,4-Cl$_2$—Ph | 2,4-Cl$_2$—Ph | O | H | H | H | H | 60-62 |
| 101 | 2,4-Cl$_2$—Ph | 4-Cl—Ph | O | H | H | H | H | 106-109 |
| 102 | 2,4-Cl$_2$—Ph | 2,4-F$_2$—Ph | O | H | H | H | H | |
| 103 | 2,4-Cl$_2$—Ph | 4-CF$_3$—Ph | O | H | H | H | H | |
| 104 | 2,4-Cl$_2$—Ph | n-C$_4$H$_9$ | O | H | H | H | H | |
| 105 | 2,4-Cl$_2$—Ph | n-C$_4$F$_9$ | O | H | H | H | H | |
| 106 | 2,4-Cl$_2$—Ph | Ph | O | H | H | H | H | 45-54 |
| 107 | 2,4-Cl$_2$—Ph | 2-F—Ph | O | H | H | H | H | 68-73 |
| 108 | 2,4-Cl$_2$—Ph | 2-Cl—Ph | O | H | H | H | H | (oil)$^u$ |
| 109 | 3,4-Cl$_2$—Ph | 2-Cl—Ph | O | H | H | H | H | |
| 110 | 3,4-Cl$_2$—Ph | 2-F—Ph | O | H | H | H | H | |
| 111 | 3,4-Cl$_2$—Ph | 2-Cl—Ph | O | H | H | H | H | |
| 112 | 4-t-Bu—Ph | Ph | O | H | H | H | H | |
| 113 | 4-t-Bu—Ph | 2-F—Ph | O | H | H | H | H | 110-113 |
| 114 | 4-t-Bu—Ph | 4-F—Ph | O | H | H | H | H | |
| 115 | 4-t-Bu—Ph | 2,4-F$_2$—Ph | O | H | H | H | H | |
| 116 | 4-t-Bu—Ph | 2-Cl—Ph | O | H | H | H | H | |
| 117 | 4-t-Bu—Ph | 4-Cl—Ph | O | H | H | H | H | (oil)$^f$ |
| 118 | 4-t-Bu—Ph | 2,4-Cl$_2$—Ph | O | H | H | H | H | |
| 119 | 2-CH$_3$S—Ph | Ph | O | H | H | H | H | |
| 120 | 2-CH$_3$S—Ph | 2-F—Ph | O | H | H | H | H | |
| 121 | 2-CH$_3$S—Ph | 4-F—Ph | O | H | H | H | H | |
| 122 | 2-CH$_3$S—Ph | 2,4-F$_2$—Ph | O | H | H | H | H | |
| 123 | 2-CH$_3$S—Ph | 2-Cl—Ph | O | H | H | H | H | |
| 124 | 2-CH$_3$S—Ph | 4-Cl—Ph | O | H | H | H | H | |
| 125 | 2-CH$_3$S—Ph | 2,4-Cl$_2$—Ph | O | H | H | H | H | |
| 126 | 2-CH$_3$S(O)—Ph | Ph | O | H | H | H | H | |
| 127 | 2-CH$_3$S(O)—Ph | 2-F—Ph | O | H | H | H | H | |
| 128 | 2-CH$_3$S(O)—Ph | 4-F—Ph | O | H | H | H | H | |
| 129 | 2-CH$_3$S(O)—Ph | 2,4-F$_2$—Ph | O | H | H | H | H | |
| 130 | 2-CH$_3$S(O)—Ph | 2-Cl—Ph | O | H | H | H | H | |
| 131 | 2-CH$_3$S(O)—Ph | 4-Cl—Ph | O | H | H | H | H | |
| 132 | 2-CH$_3$S(O)—Ph | 2,4-Cl$_2$—Ph | O | H | H | H | H | |
| 133 | 2-CH$_3$S(O)$_2$—Ph | Ph | O | H | H | H | H | |
| 134 | 2-CH$_3$S(O)$_2$—Ph | 2-F—Ph | O | H | H | H | H | |
| 135 | 2-CH$_3$S(O)$_2$—Ph | 4-F—Ph | O | H | H | H | H | |
| 136 | 2-CH$_3$S(O)$_2$—Ph | 2,4-F$_2$—Ph | O | H | H | H | H | |
| 137 | 2-CH$_3$S(O)$_2$—Ph | 2-Cl—Ph | O | H | H | H | H | |
| 138 | 2-CH$_3$S(O)$_2$—Ph | 4-Cl—Ph | O | H | H | H | H | |
| 139 | 2-CH$_3$S(O)$_2$—Ph | 2,4-Cl$_2$—Ph | O | H | H | H | H | |
| 140 | 3-CH$_3$S—Ph | Ph | O | H | H | H | H | |

TABLE 1-continued

| No. | | | | | | | | | mp |
|---|---|---|---|---|---|---|---|---|---|
| 141 | 3-CH₃S—Ph | 2-F—Ph | O | H | H | H | H | H | |
| 142 | 3-CH₃S—Ph | 4-F—Ph | O | H | H | H | H | H | |
| 143 | 3-CH₃S—Ph | 2,4-F₂—Ph | O | H | H | H | H | H | |
| 144 | 3-CH₃S—Ph | 2-Cl—Ph | O | H | H | H | H | H | |
| 145 | 3-CH₃S—Ph | 4-Cl—Ph | O | H | H | H | H | H | |
| 146 | 3-CH₃S—Ph | 2,4-Cl₂—Ph | O | H | H | H | H | H | |
| 147 | 3-CH₃S(O)—Ph | Ph | O | H | H | H | H | H | |
| 148 | 3-CH₃S(O)—Ph | 2-F—Ph | O | H | H | H | H | H | |
| 149 | 3-CH₃S(O)—Ph | 4-F—Ph | O | H | H | H | H | H | |
| 150 | 3-CH₃S(O)—Ph | 2,4-F₂—Ph | O | H | H | H | H | H | |
| 151 | 3-CH₃S(O)—Ph | 2-Cl—Ph | O | H | H | H | H | H | |
| 152 | 3-CH₃S(O)—Ph | 4-Cl—Ph | O | H | H | H | H | H | |
| 153 | 3-CH₃S(O)—Ph | 2,4-Cl₂—Ph | O | H | H | H | H | H | |
| 154 | 3-CH₃S(O)₂—Ph | Ph | O | H | H | H | H | H | |
| 155 | 3-CH₃S(O)₂—Ph | 2-F—Ph | O | H | H | H | H | H | |
| 156 | 3-CH₃S(O)₂—Ph | 4-F—Ph | O | H | H | H | H | H | 140-142 |
| 157 | 3-CH₃S(O)₂—Ph | 2,4-F₂—Ph | O | H | H | H | H | H | 81-83 |
| 158 | 3-CH₃S(O)₂—Ph | 2-Cl—Ph | O | H | H | H | H | H | |
| 159 | 3-CH₃S(O)₂—Ph | 4-Cl—Ph | O | H | H | H | H | H | |
| 160 | 3-CH₃S(O)₂—Ph | 2,4-Cl₂—Ph | O | H | H | H | H | H | |
| 161 | 4-CH₃S—Ph | Ph | O | H | H | H | H | H | |
| 162 | 4-CH₃S—Ph | 2-F—Ph | O | H | H | H | H | H | |
| 163 | 4-CH₃S—Ph | 4-F—Ph | O | H | H | H | H | H | 81-84 |
| 164 | 4-CH₃S—Ph | 2,4-F₂—Ph | O | H | H | H | H | H | 131-134 |
| 165 | 4-CH₃S—Ph | 2-Cl—Ph | O | H | H | H | H | H | |
| 166 | 4-CH₃S—Ph | 4-Cl—Ph | O | H | H | H | H | H | |
| 167 | 4-CH₃S—Ph | 2,4-Cl₂—Ph | O | H | H | H | H | H | |
| 168 | 4-CH₃S(O)—Ph | Ph | O | H | H | H | H | H | |
| 169 | 4-CH₃S(O)—Ph | 2-F—Ph | O | H | H | H | H | H | |
| 170 | 4-CH₃S(O)—Ph | 4-F—Ph | O | H | H | H | H | H | 135 |
| 171 | 4-CH₃S(O)—Ph | 2,4-F₂—Ph | O | H | H | H | H | H | |
| 172 | 4-CH₃S(O)—Ph | 2-Cl—Ph | O | H | H | H | H | H | |
| 173 | 4-CH₃S(O)—Ph | 4-Cl—Ph | O | H | H | H | H | H | |
| 174 | 4-CH₃S(O)—Ph | 2,4-Cl₂—Ph | O | H | H | H | H | H | |
| 175 | 4-CH₃S(O)₂—Ph | Ph | O | H | H | H | H | H | |
| 176 | 4-CH₃S(O)₂—Ph | 2-F—Ph | O | H | H | H | H | H | |
| 177 | 4-CH₃S(O)₂—Ph | 4-F—Ph | O | H | H | H | H | H | |
| 178 | 4-CH₃S(O)₂—Ph | 2,4-F₂—Ph | O | H | H | H | H | H | |
| 179 | 4-CH₃S(O)₂—Ph | 2-Cl—Ph | O | H | H | H | H | H | |
| 180 | 4-CH₃S(O)₂—Ph | 4-Cl—Ph | O | H | H | H | H | H | |
| 181 | 4-CH₃S(O)₂—Ph | 2,4-Cl₂—Ph | O | H | H | H | H | H | |
| 182 | 3-n-BuS(O)—Ph | Ph | O | H | H | H | H | H | |
| 183 | 3-n-BuS(O)—Ph | 2-F—Ph | O | H | H | H | H | H | |
| 184 | 3-n-BuS(O)—Ph | 4-F—Ph | O | H | H | H | H | H | |
| 185 | 3-n-BuS(O)—Ph | 2,4-F₂—Ph | O | H | H | H | H | H | |
| 186 | 2-CF₃O—Ph | Ph | O | H | H | H | H | H | |
| 187 | 2-CF₃O—Ph | 2-F—Ph | O | H | H | H | H | H | |
| 188 | 2-CF₃O—Ph | 4-F—Ph | O | H | H | H | H | H | |
| 189 | 2-CF₃O—Ph | 2,4-F₂—Ph | O | H | H | H | H | H | |
| 190 | 2-CF₃O—Ph | 2-Cl—Ph | O | H | H | H | H | H | |
| 191 | 2-CF₃O—Ph | 4-Cl—Ph | O | H | H | H | H | H | |
| 192 | 2-CF₃O—Ph | 2,4-Cl₂—Ph | O | H | H | H | H | H | |
| 193 | 3-CF₃O—Ph | Ph | O | H | H | H | H | H | |

TABLE 1-continued

| | | | | | | | | | |
|---|---|---|---|---|---|---|---|---|---|
| 194 | 3-CF$_3$O—Ph | 2-F—Ph | 0 | H | H | H | H | H | |
| 195 | 3-CF$_3$O—Ph | 4-F—Ph | 0 | H | H | H | H | H | |
| 196 | 3-CF$_3$O—Ph | 2,4-F$_2$—Ph | 0 | H | H | H | H | H | |
| 197 | 3-CF$_3$O—Ph | 2-Cl—Ph | 0 | H | H | H | H | H | |
| 198 | 3-CF$_3$O—Ph | 4-Cl—Ph | 0 | H | H | H | H | H | |
| 199 | 3-CF$_3$O—Ph | 2,4-Cl$_2$—Ph | 0 | H | H | H | H | H | |
| 200 | 4-CF$_3$O—Ph | Ph | 0 | H | H | H | H | H | |
| 201 | 4-CF$_3$O—Ph | 2-F—Ph | 0 | H | H | H | H | H | |
| 202 | 4-CF$_3$O—Ph | 4-F—Ph | 0 | H | H | H | H | H | |
| 203 | 4-CF$_3$O—Ph | 2,4-F$_2$—Ph | 0 | H | H | H | H | H | |
| 204 | 4-CF$_3$O—Ph | 2-Cl—Ph | 0 | H | H | H | H | H | |
| 205 | 4-CF$_3$O—Ph | 4-Cl—Ph | 0 | H | H | H | H | H | |
| 206 | 4-CF$_3$O—Ph | 2,4-Cl$_2$—Ph | 0 | H | H | H | H | H | |
| 207 | 4-F-1-naphthyl | 2-F—Ph | 0 | H | H | H | H | H | |
| 208 | 1-naphthyl | 4-F—Ph | 0 | H | H | H | H | H | 104–106 |
| 209 | 1-naphthyl | 2,4-F$_2$—Ph | 0 | H | H | H | H | H | |
| 210 | 1-naphthyl | 2-Cl—Ph | 0 | H | H | H | H | H | |
| 211 | 2-Cl-1-naphthyl | 4-Cl—Ph | 0 | H | H | H | H | H | |
| 212 | 1-naphthyl | 2,4-Cl$_2$—Ph | 0 | H | H | H | H | H | |
| 213 | 2-naphthyl | 2-F—Ph | 0 | H | H | H | H | H | |
| 214 | 2-naphthyl | 4-F—Ph | 0 | H | H | H | H | H | |
| 215 | 2-naphthyl | 2,4-F$_2$—Ph | 0 | H | H | H | H | H | |
| 216 | 2-naphthyl | 2-Cl | 0 | H | H | H | H | H | |
| 217 | 1-Cl-2-naphthyl | 4-Cl—Ph | 0 | H | H | H | H | H | |
| 218 | 2-naphthyl | 2,4-Cl$_2$—Ph | 0 | H | H | H | H | H | |
| 219 | 2-thienyl | Ph | 0 | H | H | H | H | H | |
| 220 | 2-thienyl | 2-F—Ph | 0 | H | H | H | H | H | |
| 221 | 2-thienyl | 4-F—Ph | 0 | H | H | H | H | H | |
| 222 | 2-thienyl | 2,4-F$_2$—Ph | 0 | H | H | H | H | H | |
| 223 | 2-thienyl | 2-Cl—Ph | 0 | H | H | H | H | H | |
| 224 | 2-thienyl | 4-Cl—Ph | 0 | H | H | H | H | H | |
| 225 | 2-thienyl | 2,4-Cl$_2$—Ph | 0 | H | H | H | H | H | |
| 226 | 3-thienyl | Ph | 0 | H | H | H | H | H | |
| 227 | 3-thienyl | 2-F—Ph | 0 | H | H | H | H | H | |
| 228 | 3-thienyl | 4-F—Ph | 0 | H | H | H | H | H | |
| 229 | 3-thienyl | 2,4-F$_2$—Ph | 0 | H | H | H | H | H | |
| 230 | 3-thienyl | 2-Cl—Ph | 0 | H | H | H | H | H | |
| 231 | 3-thienyl | 4-Cl—Ph | 0 | H | H | H | H | H | |
| 232 | 3-thienyl | 2,4-Cl$_2$—Ph | 0 | H | H | H | H | H | |
| 233 | 2-Cl-3-thienyl | Ph | 0 | H | H | H | H | H | |
| 234 | 2-Cl-3-thienyl | 2-F—Ph | 0 | H | H | H | H | H | |
| 235 | 2-Cl-3-thienyl | 2-Cl—Ph | 0 | H | H | H | H | H | |
| 236 | 5-Cl-2-thienyl | Ph | 0 | H | H | H | H | H | |
| 237 | 5-Cl-2-thienyl | 2-F—Ph | 0 | H | H | H | H | H | |
| 238 | 5-Cl-2-thienyl | 2-Cl—Ph | 0 | H | H | H | H | H | |
| 239 | 2,5-Cl$_2$-3-thienyl | Ph | 0 | H | H | H | H | H | |
| 240 | 2,5-Cl$_2$-3-thienyl | 2-F—Ph | 0 | H | H | H | H | H | |
| 241 | 2,5-Cl$_2$-3-thienyl | 4-F—Ph | 0 | H | H | H | H | H | |
| 242 | 2,5-Cl$_2$-3-thienyl | 2,4-F$_2$—Ph | 0 | H | H | H | H | H | |
| 243 | 2,5-Cl$_2$-3-thienyl | 2-Cl—Ph | 0 | H | H | H | H | H | |
| 244 | 2,5-Cl$_2$-3-thienyl | 4-Cl—Ph | 0 | H | H | H | H | H | |
| 245 | 2,5-Cl$_2$-3-thienyl | 2,4-Cl$_2$—Ph | 0 | H | H | H | H | H | |
| 246 | 5-bromo-2-thienyl | Ph | 0 | H | H | H | H | H | |

TABLE 1-continued

| No. | | | | | | | | | mp |
|---|---|---|---|---|---|---|---|---|---|
| 247 | 5-bromo-2-thienyl | 2-F—Ph | 0 | H | H | H | H | H | |
| 248 | 5-bromo-2-thienyl | 4-F—Ph | 0 | H | H | H | H | H | |
| 249 | 5-bromo-2-thienyl | 2,4-F₂—Ph | 0 | H | H | H | H | H | |
| 250 | 5-bromo-2-thienyl | 2-Cl—Ph | 0 | H | H | H | H | H | |
| 251 | 5-bromo-2-thienyl | 4-Cl—Ph | 0 | H | H | H | H | H | |
| 252 | 5-bromo-2-thienyl | 2,4-Cl₂—Ph | 0 | H | H | H | H | H | |
| 253 | 2-pyridyl | Ph | 0 | H | H | H | H | H | |
| 254 | 2-pyridyl | 2-F—Ph | 0 | H | H | H | H | H | |
| 255 | 2-pyridyl | 2-Cl—Ph | 0 | H | H | H | H | H | |
| 256 | 3-pyridyl | Ph | 0 | H | H | H | H | H | |
| 257 | 3-pyridyl | 2-F—Ph | 0 | H | H | H | H | H | |
| 258 | 3-pyridyl | 2-Cl—Ph | 0 | H | H | H | H | H | |
| 259 | 4-pyridyl | Ph | 0 | H | H | H | H | H | |
| 260 | 4-pyridyl | 2-F—Ph | 0 | H | H | H | H | H | |
| 261 | 4-pyridyl | 2-Cl—Ph | 0 | H | H | H | H | H | |
| 262 | 5-Cl-2-pyridyl | Ph | 0 | H | H | H | H | H | |
| 263 | 5-Cl-2-pyridyl | 2-F—Ph | 0 | H | H | H | H | H | |
| 264 | 5-Cl-2-pyridyl | 2-Cl—Ph | 0 | H | H | H | H | H | |
| 265 | 2-Cl-3-pyridyl | Ph | 0 | H | H | H | H | H | |
| 266 | 2-Cl-3-pyridyl | 2-F—Ph | 0 | H | H | H | H | H | |
| 267 | 2-Cl-3-pyridyl | 4-F—Ph | 0 | H | H | H | H | H | |
| 268 | 2-Cl-3-pyridyl | 2,4-F₂—Ph | 0 | H | H | H | H | H | 142–143 |
| 269 | 2-Cl-3-pyridyl | 2-Cl—Ph | 0 | H | H | H | H | H | |
| 270 | 2-Cl-3-pyridyl | 4-Cl—Ph | 0 | H | H | H | H | H | 140–145 |
| 271 | 2-Cl-3-pyridyl | 2,4-Cl₂—Ph | 0 | H | H | H | H | H | |
| 272 | 3-Cl-2-pyridyl | Ph | 0 | H | H | H | H | H | |
| 273 | 3-Cl-2-pyridyl | 2-F—Ph | 0 | H | H | H | H | H | |
| 274 | 3-Cl-2-pyridyl | 4-F—Ph | 0 | H | H | H | H | H | |
| 275 | 3-Cl-2-pyridyl | 2,4-F₂—Ph | 0 | H | H | H | H | H | |
| 276 | 3-Cl-2-pyridyl | 2-Cl—Ph | 0 | H | H | H | H | H | |
| 277 | 3-Cl-2-pyridyl | 4-Cl—Ph | 0 | H | H | H | H | H | |
| 278 | 3-Cl-2-pyridyl | 2,4-Cl₂—Ph | 0 | H | H | H | H | H | |
| 279 | 6-Cl-3-pyridyl | Ph | 0 | H | H | H | H | H | |
| 280 | 6-Cl-3-pyridyl | 2-F—Ph | 0 | H | H | H | H | H | |
| 281 | 6-Cl-3-pyridyl | 4-F—Ph | 0 | H | H | H | H | H | |
| 282 | 6-Cl-3-pyridyl | 2,4-F₂—Ph | 0 | H | H | H | H | H | |
| 283 | 6-Cl-3-pyridyl | 2-Cl—Ph | 0 | H | H | H | H | H | |
| 284 | 6-Cl-3-pyridyl | 4-Cl—Ph | 0 | H | H | H | H | H | |
| 285 | 6-Cl-3-pyridyl | 2,4-Cl₂—Ph | 0 | H | H | H | H | H | |
| 286 | Ph | 4-F—Ph | 0 | CH₃ | CH₃ | H | H | H | 108–111 |
| 287 | Ph | 4-F—Ph | 0 | F | F | H | H | H | |
| 288 | Ph | 4-F—Ph | 0 | Cl | Cl | H | H | H | |
| 289 | Ph | 4-F—Ph | 0 | Br | Br | H | H | H | |
| 290 | Ph | 4-F—Ph | 0 | —(CH₂)₂— | | H | H | H | |
| 291 | Ph | 4-F—Ph | 0 | Ph | Ph | H | H | H | |
| 292 | Ph | 4-F—Ph | 0 | CH₃ | CH₃ | H | H | H | |
| 293 | Ph | 4-F—Ph | 0 | F | F | H | H | H | |
| 294 | Ph | 4-F—Ph | 0 | Cl | Cl | H | H | H | (oil)ᵍ |
| 295 | 4-F—Ph | 4-F—Ph | 0 | H | CH₃ | H | H | H | |
| 296 | 4-F—Ph | 4-F—Ph | 0 | H | Cl | H | H | H | |
| 297 | 4-F—Ph | 4-F—Ph | 0 | H | F | H | H | H | |
| 298 | 4-F—Ph | 4-F—Ph | 0 | H | Br | H | H | H | |
| 299 | 4-F—Ph | 4-F—Ph | 0 | —(CH₂)₂— | | H | H | H | |

TABLE 1-continued

| No. | | | n | | | | |
|---|---|---|---|---|---|---|---|
| 300 | 4-F—Ph | 4-F—Ph | 0 | CH₃ | CH₃ | H | H |
| 301 | 4-F—Ph | 4-F—Ph | 0 | F | F | H | H |
| 302 | 4-F—Ph | 4-F—Ph | 0 | Cl | Cl | H | H |
| 303 | 4-Cl—Ph | 2,4-Cl₂—Ph | 0 | H | CH₃ | H | H |
| 304 | 4-Cl—Ph | 2,4-Cl₂—Ph | 0 | H | F | H | H |
| 305 | 4-Cl—Ph | 2,4-Cl₂—Ph | 0 | H | Cl | H | H |
| 306 | 4-Cl—Ph | 2,4-Cl₂—Ph | 0 | H | Br | H | H |
| 307 | 4-Cl—Ph | 2,4-Cl₂—Ph | 0 | —(CH₂)₂— | | H | H |
| 308 | 4-Cl—Ph | 2,4-Cl₂—Ph | 0 | CH₃ | CH₃ | H | H |
| 309 | 4-Cl—Ph | 2,4-Cl₂—Ph | 0 | F | F | H | H |
| 310 | 4-Cl—Ph | 2,4-Cl₂—Ph | 0 | Cl | Cl | H | H |
| 311 | 4-Cl—Ph | 4-Cl—Ph | 0 | H | CH₃ | H | H |
| 312 | 2-Cl—Ph | 4-Cl—Ph | 0 | H | F | H | H |
| 313 | 2-Cl—Ph | 4-Cl—Ph | 0 | H | Cl | H | H |
| 314 | 2-Cl—Ph | 4-Cl—Ph | 0 | H | Br | H | H |
| 315 | 2-Cl—Ph | 4-Cl—Ph | 0 | —(CH₂)₂— | | H | H |
| 316 | 2-Cl—Ph | 4-Cl—Ph | 0 | CH₃ | CH₃ | H | H |
| 317 | 2-Cl—Ph | 4-Cl—Ph | 0 | F | F | H | H |
| 318 | 2-Cl—Ph | 4-Cl—Ph | 0 | Cl | Cl | H | H |
| 319 | 2-Cl—Ph | 4-F—Ph | 0 | H | C₂H₅ | H | H |
| 320 | 4-F—Ph | 4-F—Ph | 0 | H | i-C₃H₇ | H | H |
| 321 | 4-F—Ph | 4-F—Ph | 0 | H | n-C₄H₉ | H | H |
| 322 | 4-F—Ph | 4-F—Ph | 0 | H | t-C₄H₉ | H | H |
| 323 | 4-F—Ph | 4-F—Ph | 0 | H | Ph | H | H |
| 324 | 4-F—Ph | 4-F—Ph | 0 | CH₃ | I | H | H |
| 325 | 4-F—Ph | 4-F—Ph | 1 | CH₃ | F | H | H |
| 326 | 4-F—Ph | 4-F—Ph | 4 | H | Cl | H | H |
| 327 | 4-F—Ph | 4-F—Ph | 0 | CH₃ | Cl | H | H |
| 328 | 4-F—Ph | 4-F—Ph | 1 | Br | Br | H | H |
| 329 | 4-F—Ph | 4-F—Ph | 0 | —(CH₂)₃— | | H | H |
| 330 | 4-F—Ph | 4-F—Ph | 0 | —(CH₂)₄— | | H | H |
| 331 | 4-F—Ph | 4-F—Ph | 0 | —(CH₂)₅— | | H | H |
| 332 | 4-F—Ph | 4-F—Ph | 0 | —(CH₂)₆— | | H | H |
| 333 | 4-CH₃—Ph | 4-F—Ph | 0 | H | CH₃ | H | H |
| 334 | 4-F—Ph | 4-Cl—Ph | 0 | H | CH₃ | H | H |
| 335 | 4-Cl—Ph | 4-F—Ph | 0 | H | CH₃ | H | H |
| 336 | n-C₄F₉ | 4-F—Ph | 0 | H | CH₃ | H | H |
| 337 | (CH₃)₂N | 4-F—Ph | 0 | H | CH₃ | H | H |
| 338 | 5-Cl-thio-phen-2-yl | 4-F—Ph | 0 | H | CH₃ | H | H |
| 339 | 2-Cl-thio-phen-3-yl | 4-F—Ph | 0 | H | CH₃ | H | H |
| 340 | 1-imida-zoyl | 4-F—Ph | 0 | H | CH₃ | H | H |
| 341 | 1,2,4-tria-zol-1-yl | 4-F—Ph | 0 | H | CH₃ | H | H |
| 342 | 5-chloro-2-pyridyl | 4-F—Ph | 0 | H | CH₃ | H | H |
| 343 | n-C₄H₉ | 4-F—Ph | 0 | H | CH₃ | H | H |
| 344 | t-C₄H₉ | 4-F—Ph | 0 | H | CH₃ | H | H |
| 345 | n-C₄F₉ | 4-F—Ph | 0 | H | CH₃ | H | H |
| 346 | 4-CH₃—Ph | 4-F—Ph | 0 | H | F | H | H |
| 347 | 4-F—Ph | 4-F—Ph | 1 | H | F | H | H |

TABLE 1-continued

| # | | | | | | | | | |
|---|---|---|---|---|---|---|---|---|---|
| 348 | 4-Cl—Ph | 4-F—Ph | 4 | H | H | H | H | H | |
| 349 | n-C4F9 | 4-F—Ph | 0 | H | F | H | H | H | |
| 350 | (CH3)2N | 4-F—Ph | 1 | H | F | H | H | H | |
| 351 | 5-Cl-thiophen-2-yl | 4-F—Ph | 0 | H | F | H | H | H | |
| 352 | 2-Cl-thiophen-2-yl | 4-F—Ph | 0 | H | F | H | H | H | |
| 353 | 1-imidazoyl | 4-F—Ph | 0 | H | F | H | H | H | |
| 354 | 1,2,4-triazol-1-yl | 4-F—Ph | 0 | H | F | H | H | H | |
| 355 | 5-Cl-2-pyridyl | 4-F—Ph | 0 | H | F | H | H | H | |
| 356 | 4-F—Ph | n-C4H9 | 0 | H | F | H | H | H | |
| 357 | 4-F—Ph | t-C4H9 | 0 | H | F | H | H | H | |
| 358 | 4-F—Ph | n-C4F9 | 0 | H | F | H | H | H | |
| 359 | 4-F—Ph | 4-F—Ph | 0 | H | H | CH3 | H | H | |
| 360 | 4-F—Ph | 4-F—Ph | 0 | H | H | CH2CH=CH2 | H | H | |
| 361 | 4-F—Ph | 4-F—Ph | 0 | H | H | COCH3 | H | H | |
| 362 | 4-F—Ph | 4-F—Ph | 0 | H | H | CO2CH3 | H | H | |
| 363 | 4-F—Ph | 4-F—Ph | 0 | H | H | CONHCH3 | H | H | (oil)[h] |
| 364 | 4-F—Ph | 4-F—Ph | 0 | H | H | CONH-nBu | H | H | (oil)[i] |
| 365 | 4-F—Ph | 4-F—Ph | 0 | H | H | CONHPh | H | H | (oil)[j] |
| 366 | 4-F—Ph | 4-F—Ph | 0 | H | H | CONH-(4-F—Ph) | H | H | 164-167 |
| 367 | 4-F—Ph | 4-F—Ph | 0 | H | H | CON(CH3)2 | H | H | |
| 368 | 2-Cl—Ph | 4-Cl—Ph | 0 | H | H | CH3 | H | H | |
| 369 | 2-Cl—Ph | 4-Cl—Ph | 0 | H | H | CH2CH=CH2 | H | H | |
| 370 | 2-Cl—Ph | 4-Cl—Ph | 0 | H | H | COCH3 | H | H | |
| 371 | 2-Cl—Ph | 4-Cl—Ph | 0 | H | H | CO2CH3 | H | H | |
| 372 | 2-Cl—Ph | 4-Cl—Ph | 0 | H | H | CONHCH3 | H | H | |
| 373 | 2-Cl—Ph | 4-Cl—Ph | 0 | H | H | CONH-nBu | H | H | |
| 374 | 2-Cl—Ph | 4-Cl—Ph | 0 | H | H | CONHPh | H | H | |
| 375 | 2-Cl—Ph | 4-Cl—Ph | 0 | H | H | CONH-(4-F—Ph) | H | H | |
| 376 | 2-Cl—Ph | 4-Cl—Ph | 0 | H | H | CON(CH3)2 | H | H | |
| 377 | 4-Cl—Ph | 2,4-Cl2—Ph | 0 | H | H | CH3 | H | H | |
| 378 | 4-Cl—Ph | 2,4-Cl2—Ph | 0 | H | H | CH2CH=CH2 | H | H | |
| 379 | 4-Cl—Ph | 2,4-Cl2—Ph | 0 | H | H | COCH3 | H | H | |
| 380 | 4-Cl—Ph | 2,4-Cl2—Ph | 0 | H | H | CO2CH3 | H | H | |
| 381 | 4-Cl—Ph | 2,4-Cl2—Ph | 0 | H | H | CONHCH3 | H | H | |
| 382 | 4-Cl—Ph | 2,4-Cl2—Ph | 0 | H | H | CONH-nBu | H | H | |
| 383 | 4-Cl—Ph | 2,4-Cl2—Ph | 0 | H | H | CONHPh | H | H | |
| 384 | 4-Cl—Ph | 2,4-Cl2—Ph | 0 | H | H | CONH(4-F—Ph) | H | H | |
| 385 | 4-Cl—Ph | 2,4-Cl2—Ph | 0 | H | H | CON(CH3)2 | H | H | |
| 386 | Ph | 4-F—Ph | 0 | H | H | CH3 | H | H | |
| 387 | Ph | 4-F—Ph | 0 | H | H | CH2CH=CH2 | H | H | |
| 388 | Ph | 4-F—Ph | 0 | H | H | COCH3 | H | H | |
| 389 | Ph | 4-F—Ph | 0 | H | H | CO2CH3 | H | H | |
| 390 | Ph | 4-F—Ph | 0 | H | H | CONHCH3 | H | H | |

TABLE 1-continued

| # | | | | | | | | | |
|---|---|---|---|---|---|---|---|---|---|
| 391 | Ph | 4-F—Ph | 0 | H | H | CONH-nBu | H | H | |
| 392 | Ph | 4-F—Ph | 0 | H | H | CONHPh | H | H | |
| 393 | Ph | 4-F—Ph | 0 | H | H | CONH(4-F—Ph) | H | H | |
| 394 | Ph | 4-F—Ph | 0 | H | H | CON(CH$_3$)$_2$ | H | H | |
| 395 | 4-F—Ph | 4-F—Ph | 0 | H | H | C$_2$H$_5$ | H | H | |
| 396 | 4-F—Ph | 4-F—Ph | 0 | H | H | i-C$_3$H$_7$ | H | H | |
| 397 | 4-F—Ph | 4-F—Ph | 0 | H | H | n-C$_4$H$_9$ | H | H | |
| 398 | 4-F—Ph | 4-F—Ph | 0 | H | H | COC$_2$H$_5$ | H | H | |
| 399 | 4-F—Ph | 4-F—Ph | 0 | H | H | CO-t-C$_4$H$_9$ | H | H | |
| 400 | 4-F—Ph | 4-F—Ph | 0 | H | H | COPh | H | H | |
| 401 | 4-F—Ph | 4-F—Ph | 0 | H | H | COCH$_2$Ph | H | H | |
| 402 | 4-F—Ph | 4-F—Ph | 0 | H | H | CONH$_2$ | H | H | |
| 403 | 4-F—Ph | 4-F—Ph | 0 | H | H | CONH-iC$_3$H$_7$ | H | H | |
| 404 | 4-F—Ph | 4-F—Ph | 0 | H | H | CONHCH$_2$Ph | H | H | |
| 405 | 4-F—Ph | 4-F—Ph | 0 | H | H | CON(CH$_3$)Ph | H | H | |
| 406 | 4-F—Ph | 4-F—Ph | 0 | H | H | CONH(4-Cl—Ph) | H | H | |
| 407 | 4-F—Ph | 4-F—Ph | 0 | H | H | CONH(4-CH$_3$—Ph) | H | H | |
| 408 | 4-F—Ph | 4-F—Ph | 0 | H | H | CONH(4-CH$_3$—Ph) | H | H | |
| 409 | 4-F—Ph | 4-F—Ph | 0 | H | H | CONH(3-CF$_3$—Ph) | H | H | |
| 410 | 4-F—Ph | 4-F—Ph | 0 | H | H | CONH(4-NO$_2$—Ph) | H | H | |
| 411 | 4-F—Ph | 4-F—Ph | 0 | H | H | CONH(2-CH$_3$—Ph) | H | H | |
| 412 | 4-F—Ph | 4-F—Ph | 0 | H | H | CONH(2,4-F$_2$—Ph) | H | H | |
| 413 | 4-F—Ph | 4-F—Ph | 0 | H | H | CONH(2,4-Cl$_2$—Ph) | H | H | |
| 414 | 4-F—Ph | 4-F—Ph | 0 | H | H | CO$_2$C$_2$H$_5$ | H | H | |
| 415 | 4-F—Ph | 4-F—Ph | 0 | H | H | CO$_2$-nC$_4$H$_9$ | H | H | |
| 416 | 4-F—Ph | 4-F—Ph | 0 | H | H | CO$_2$-tC$_4$H$_9$ | H | H | |
| 417 | 4-F—Ph | 4-F—Ph | 0 | H | H | CO$_2$CH$_2$Ph | H | H | |
| 418 | 4-F—Ph | 4-F—Ph | 0 | H | H | CO$_2$Ph | H | H | |
| 419 | 4-F—Ph | 4-F—Ph | 0 | H | H | CF$_2$H | H | H | |
| 420 | 4-F—Ph | 4-F—Ph | 0 | H | H | CH$_2$CF$_3$ | H | H | |
| 421 | 4-F—Ph | 4-F—Ph | 0 | H | H | CH$_2$CH$_2$CH$_2$F | H | H | |
| 422 | 4-F—Ph | 2,4-F$_2$—Ph | 0 | H | H | CH$_2$CH$_2$CH$_2$CH$_2$Cl | H | H | |
| 423 | Ph | 4-Cl—Ph | 0 | H | H | CH$_2$—C≡CH | H | H | |
| 424 | Ph | 2-F—Ph | 0 | H | H | CH$_2$—C≡CH | H | H | |
| 425 | 4-F—Ph | 4-F—Ph | 0 | H | H | CH$_2$—C≡CH | H | H | (HCl salt 184–187) |
| 426 | 4-F—Ph | 4-F—Ph | 0 | H | H | CH$_2$—C≡CH | H | H | |
| 427 | 4-F—Ph | 2,4-F$_2$—Ph | 0 | H | H | CH$_2$—C≡CH | H | H | |
| 428 | 2-Cl—Ph | 2-Cl—Ph | 0 | H | H | CH$_2$—C≡CH | H | H | 68–70 |
| 429 | 2,4-F$_2$—Ph | 2,4-F$_2$—Ph | 0 | H | H | CH$_2$—C≡CH | H | H | 108–111 |
| 430 | 2-Cl—Ph | 4-Cl—Ph | 0 | H | H | CH$_2$—C≡CH | H | H | |
| 431 | 4-Cl—Ph | 2-F—Ph | 0 | H | H | CH$_2$—C≡CH | H | H | |
| 432 | 4-Cl—Ph | 2,4-F$_2$—Ph | 0 | H | H | CH$_2$—C≡CH | H | H | |
| 433 | 4-F—Ph | 4-F—Ph | 1 | H | H | H | H | H | |
| 434 | 4-F—Ph | 4-F—Ph | 2 | H | H | H | H | H | |
| 435 | 4-F—Ph | 4-F—Ph | 3 | H | H | H | H | H | |
| 436 | 4-F—Ph | 4-F—Ph | 4 | H | H | H | H | H | |
| 437 | 2-Cl—Ph | 4-Cl—Ph | 1 | H | H | H | H | H | |
| 438 | 2-Cl—Ph | 4-Cl—Ph | 2 | H | H | H | H | H | |
| 439 | 4-Cl—Ph | 4-Cl—Ph | 3 | H | H | H | H | H | |
| 440 | 4-Cl—Ph | 4-Cl—Ph | 4 | H | H | H | H | H | |
| 441 | 4-Cl—Ph | 2,4-Cl$_2$—Ph | 1 | H | H | H | H | H | |

TABLE 1-continued

| # | R1 | R2 | n | | | | | | mp |
|---|---|---|---|---|---|---|---|---|---|
| 442 | 4-Cl—Ph | 2,4-Cl₂—Ph | 2 | H | H | H | H | H | |
| 443 | 4-Cl—Ph | 2,4-Cl₂—Ph | 3 | H | H | H | H | H | |
| 444 | 4-Cl—Ph | 2,4-Cl₂—Ph | 4 | H | H | H | H | H | |
| 445 | Ph | 4-F—Ph | 1 | H | H | H | H | H | |
| 446 | Ph | 4-F—Ph | 2 | H | H | H | H | H | (oil)$^k$ |
| 447 | OH | 4-Cl—Ph | 1 | H | H | H | H | H | 94-100 |
| 448 | OH | Ph | 1 | H | H | H | H | H | 166-168 |
| 449 | OH | 2,4-Cl₂—Ph | 1 | H | H | H | H | H | 115-116 |
| 450 | OH | 4-F—Ph | 1 | H | H | H | H | H | (foam)$^l$ |
| 451 | OH | 4-Br—Ph | 1 | H | H | H | H | H | 140-143 |
| 452 | OH | 4-Ph—Ph | 1 | H | H | H | H | H | 104-107 |
| 453 | (CH₃)₂N | 2,4-Cl₂—Ph | 1 | H | H | H | H | H | (oil)$^m$ |
| 454 | (CH₃)₂N | 4-F—Ph | 1 | H | H | H | H | H | (oil)$^n$ |
| 455 | (CH₃)₂N | 4-Br—Ph | 1 | H | H | H | H | H | (oil)$^o$ |
| 456 | (CH₃)₂N | 4-Ph—Ph | 1 | H | H | H | H | H | |
| 457 | 1-imidazoyl | 4-F—Ph | 1 | H | H | H | H | H | |
| 458 | 1-imidazoyl | 4-F—Ph | 2 | H | H | H | H | H | |
| 459 | 1-imidazoyl | 4-F—Ph | 3 | H | H | H | H | H | |
| 460 | 1-imidazoyl | 4-F—Ph | 4 | H | H | H | H | H | |
| 461 | 1H-1,2,4-triazol-1-yl | 4-F—Ph | 1 | H | H | H | H | H | |
| 462 | 1H-1,2,4-triazol-1-yl | 4-F—Ph | 2 | H | H | H | H | H | |
| 463 | 1H-1,2,4-triazol-1-yl | 4-F—Ph | 3 | H | H | H | H | H | |
| 464 | 1H-1,2,4-triazol-1-yl | 4-F—Ph | 4 | H | H | H | H | H | |
| 465 | 1H-1,2,4-triazol-1-yl | 2,4-Cl₂—Ph | 1 | H | H | H | H | H | |
| 466 | 1H-1,2,4-triazol-1-yl | 2,4-Cl₂—Ph | 2 | H | H | H | H | H | |
| 467 | 1-piperidyl | 2,4-Cl₂—Ph | 1 | H | H | H | H | H | |
| 468 | 1-piperidyl | Ph | 1 | H | H | H | H | H | |
| 469 | 1-piperidyl | 2-F—Ph | 1 | H | H | H | H | H | |
| 470 | 1-piperidyl | 4-F—Ph | 1 | H | H | H | H | H | |
| 471 | 1-piperidyl | 2,4-F₂—Ph | 1 | H | H | H | H | H | |
| 472 | 1-piperidyl | 2-Cl—Ph | 1 | H | H | H | H | H | |
| 473 | 1-piperidyl | 4-Cl—Ph | 1 | H | H | H | H | H | |
| 474 | 1-piperidyl | 2,4-Cl₂—Ph | 1 | H | H | H | H | H | |
| 475 | 2,6-(CH₃)₂-1-morpholinyl | Ph | 1 | H | H | H | H | H | |
| 476 | 2,6-(CH₃)₂-1-morpholinyl | 2-F—Ph | 1 | H | H | H | H | H | |
| 477 | 2,6-(CH₃)₂-1-morpholinyl | 4-F—Ph | 1 | H | H | H | H | H | 97-99 |
| 478 | 2,6-(CH₃)₂-1-morpholinyl | 2,4-F₂—Ph | 1 | H | H | H | H | H | |
| 479 | 2,6-(CH₃)₂-1-morpholinyl | 2-Cl—Ph | 1 | H | H | H | H | H | |
| 480 | 2,6-(CH₃)₂-1-morpholinyl | 4-Cl—Ph | 1 | H | H | H | H | H | |
| 481 | 2,6-(CH₃)₂-1-morpholinyl | 2,4-Cl₂—Ph | 1 | H | H | H | H | H | |
| 482 | 4-CH₃-1-piperazinyl | Ph | 1 | H | H | H | H | H | |
| 483 | 4-CH₃-1-piperazinyl | 2-F—Ph | 1 | H | H | H | H | H | |
| 484 | 4-CH₃-1-piperazinyl | 4-F—Ph | 1 | H | H | H | H | H | |
| 485 | 4-CH₃-1-piperazinyl | 2,4-F₂—Ph | 1 | H | H | H | H | H | |
| 486 | 4-CH₃-1-piperazinyl | 2-Cl—Ph | 1 | H | H | H | H | H | |
| 487 | 4-CH₃-1-piperazinyl | 4-Cl—Ph | 1 | H | H | H | H | H | |
| 488 | 4-CH₃-1-piperazinyl | 2,4-Cl₂—Ph | 1 | H | H | H | H | H | |

TABLE 1-continued

| | | | | | | | | | |
|---|---|---|---|---|---|---|---|---|---|
| 489 | 4-n-Bu-1-piperazinyl | Ph | 1 | H | H | H | H | H | |
| 490 | 4-n-Bu-1-piperazinyl | 2-F—Ph | 1 | H | H | H | H | H | |
| 491 | 4-n-Bu-1-piperazinyl | 4-F—Ph | 1 | H | H | H | H | H | |
| 492 | 4-n-Bu-1-piperazinyl | 2,4-F₂—Ph | 1 | H | H | H | H | H | |
| 493 | 4-n-Bu-1-piperazinyl | 2-Cl—Ph | 1 | H | H | H | H | H | |
| 494 | 4-n-Bu-1-piperazinyl | 4-Cl—Ph | 1 | H | H | H | H | H | |
| 495 | 4-n-Bu-1-piperazinyl | 2,4-Cl₂—Ph | 1 | H | H | H | H | H | |
| 496 | 4-acetyl-1-piperazinyl | Ph | 1 | H | H | H | H | H | |
| 497 | 4-acetyl-1-piperazinyl | 2-F—Ph | 1 | H | H | H | H | H | |
| 498 | 4-acetyl-1-piperazinyl | 4-F—Ph | 1 | H | H | H | H | H | |
| 499 | 4-acetyl-1-piperazinyl | 2,4-F₂—Ph | 1 | H | H | H | H | H | |
| 500 | 4-acetyl-1-piperazinyl | 2-Cl—Ph | 1 | H | H | H | H | H | |
| 501 | 4-acetyl-1-piperazinyl | 4-Cl—Ph | 1 | H | H | H | H | H | |
| 502 | 4-acetyl-1-piperazinyl | 2,4-Cl₂—Ph | 1 | H | H | H | H | H | |
| 503 | 2-(2-pyridyl)-Ph | 4-F—Ph | 0 | H | H | H | H | H | |
| 504 | 2-(3-pyridyl)-Ph | 4-F—Ph | 0 | H | H | H | H | H | |
| 505 | 2-(4-pyridyl)-Ph | 4-F—Ph | 0 | H | H | H | H | H | |
| 506 | 3-(2-pyridyl)-Ph | 4-F—Ph | 0 | H | H | H | H | H | |
| 507 | 3-(3-pyridyl)-Ph | 4-F—Ph | 0 | H | H | H | H | H | |
| 508 | 3-(4-pyridyl)-Ph | 4-F—Ph | 0 | H | H | H | H | H | |
| 509 | 4-(2-pyridyl)-Ph | 4-F—Ph | 0 | H | H | H | H | H | |
| 510 | 4-(3-pyridyl)-Ph | 4-F—Ph | 0 | H | H | H | H | H | |
| 511 | 4-(4-pyridyl)-Ph | 4-F—Ph | 0 | H | H | H | H | H | |
| 512 | 2-(1H-1,2,4-triazol-1-yl)-Ph | 4-F—Ph | 0 | H | H | H | H | H | |
| 513 | 3-(1H-1,2,4-triazol-1-yl)-Ph | 4-F—Ph | 0 | H | H | H | H | H | |
| 514 | 4-(1H-1,2,4-triazol-1-yl)-Ph | 4-F—Ph | 0 | H | H | H | H | H | |
| 515 | 2-(imidazol-1-yl)-Ph | 4-F—Ph | 0 | H | H | H | H | H | |
| 516 | 3-(imidazol-1-yl)-Ph | 4-F—Ph | 0 | H | H | H | H | H | |
| 517 | 4-(imidazol-1-yl)-Ph | 4-F—Ph | 0 | H | H | H | H | H | |
| 518 | 2-(4-methylpiperazin-1-yl)-Ph | 4-F—Ph | 0 | H | H | H | H | H | |
| 519 | 3-(4-methylpiperazin-1-yl)-Ph | 4-F—Ph | 0 | H | H | H | H | H | |
| 520 | 4-(4-methylpiperazin-1-yl)-Ph | 4-F—Ph | 0 | H | H | H | H | H | |
| 521 | 2-(4-acetylpiperazin-1-yl)-Ph | 4-F—Ph | 0 | H | H | H | H | H | |
| 522 | 3-(4-acetylpiperazin-1-yl)-Ph | 4-F—Ph | 0 | H | H | H | H | H | |
| 523 | 4-(4-acetylpiperazin-1-yl)-Ph | 4-F—Ph | 0 | H | H | H | H | H | |
| 524 | 2-(2-pyridyl)-Ph | 2,4-F₂—Ph | 0 | H | H | H | H | H | |
| 525 | 2-(3-pyridyl)-Ph | 2,4-F₂—Ph | 0 | H | H | H | H | H | |
| 526 | 2-(4-pyridyl)-Ph | 2,4-F₂—Ph | 0 | H | H | H | H | H | |
| 527 | 3-(2-pyridyl)-Ph | 2,4-F₂—Ph | 0 | H | H | H | H | H | |
| 528 | 3-(3-pyridyl)-Ph | 2,4-F₂—Ph | 0 | H | H | H | H | H | (Foam)$^{am}$ |
| 529 | 3-(4-pyridyl)-Ph | 2,4-F₂—Ph | 0 | H | H | H | H | H | |
| 530 | 4-(2-pyridyl)-Ph | 2,4-F₂—Ph | 0 | H | H | H | H | H | |
| 531 | 4-(3-pyridyl)-Ph | 2,4-F₂—Ph | 0 | H | H | H | H | H | |
| 532 | 4-(4-pyridyl)-Ph | 2,4-F₂—Ph | 0 | H | H | H | H | H | (Foam)$^{an}$ |
| 533 | 2-(1H-1,2,4-triazol-1-yl)-Ph | 2,4-F₂—Ph | 0 | H | H | H | H | H | |
| 534 | 3-(1H-1,2,4-triazol-1-yl)-Ph | 2,4-F₂—Ph | 0 | H | H | H | H | H | |
| 535 | 4-(1H-1,2,4-triazol-1-yl)-Ph | 2,4-F₂—Ph | 0 | H | H | H | H | H | |
| 536 | 2-(imidazol-1-yl)-Ph | 2,4-F₂—Ph | 0 | H | H | H | H | H | |
| 537 | 3-(imidazol-1-yl)-Ph | 2,4-F₂—Ph | 0 | H | H | H | H | H | |
| 538 | 4-(imidazol-1-yl)-Ph | 2,4-F₂—Ph | 0 | H | H | H | H | H | |
| 539 | 2-(4-methylpiperazin-2-yl)-Ph | 2,4-F₂—Ph | 0 | H | H | H | H | H | |
| 540 | 3-(4-methylpiperazin-2-yl)-Ph | 2,4-F₂—Ph | 0 | H | H | H | H | H | |
| 541 | 4-(4-methylpiperazin-2-yl)-Ph | 2,4-F₂—Ph | 0 | H | H | H | H | H | |

TABLE 1-continued

| No. | | | | | | | | |
|---|---|---|---|---|---|---|---|---|
| 542 | 2-(4-acetylpiperazin-1-yl)-Ph | 2,4-F₂—Ph | O | H | H | H | H | H |
| 543 | 3-(4-acetylpiperazin-1-yl)-Ph | 2,4-F₂—Ph | O | H | H | H | H | H |
| 544 | 4-(4-acetylpiperazin-1-yl)-Ph | 2,4-F₂—Ph | O | H | H | H | H | H |
| 545 | 2-Cl-3-(3-pyridyl)-Ph | 2,4-F₂—Ph | O | H | H | H | H | H |
| 546 | 2-(2-pyridyl)-Ph | 4-Cl—Ph | O | H | H | H | H | H |
| 547 | 2-(3-pyridyl)-Ph | 4-Cl—Ph | O | H | H | H | H | H |
| 548 | 2-(4-pyridyl)-Ph | 4-Cl—Ph | O | H | H | H | H | H |
| 549 | 3-(2-pyridyl)-Ph | 4-Cl—Ph | O | H | H | H | H | H |
| 550 | 3-(3-pyridyl)-Ph | 4-Cl—Ph | O | H | H | H | H | H |
| 551 | 3-(4-pyridyl)-Ph | 4-Cl—Ph | O | H | H | H | H | H |
| 552 | 4-(2-pyridyl)-Ph | 4-Cl—Ph | O | H | H | H | H | H |
| 553 | 4-(3-pyridyl)-Ph | 4-Cl—Ph | O | H | H | H | H | H |
| 554 | 4-(4-pyridyl)-Ph | 4-Cl—Ph | O | H | H | H | H | H |
| 555 | 2-(1H-1,2,4-triazol-1-yl)-Ph | 4-Cl—Ph | O | H | H | H | H | H |
| 556 | 3-(1H-1,2,4-triazol-1-yl)-Ph | 4-Cl—Ph | O | H | H | H | H | H |
| 557 | 4-(1H-1,2,4-triazol-1-yl)-Ph | 4-Cl—Ph | O | H | H | H | H | H |
| 558 | 2-(imidazol-1-yl)-Ph | 4-Cl—Ph | O | H | H | H | H | H |
| 559 | 3-(imidazol-1-yl)-Ph | 4-Cl—Ph | O | H | H | H | H | H |
| 560 | 4-(imidazol-1-yl)-Ph | 4-Cl—Ph | O | H | H | H | H | H |
| 561 | 2-(4-methylpiperazin-1-yl)-Ph | 4-Cl—Ph | O | H | H | H | H | H |
| 562 | 3-(4-methylpiperazin-1-yl)-Ph | 4-Cl—Ph | O | H | H | H | H | H |
| 563 | 4-(4-methylpiperazin-1-yl)-Ph | 4-Cl—Ph | O | H | H | H | H | H |
| 564 | 2-(4-acetylpiperazin-1-yl)-Ph | 4-Cl—Ph | O | H | H | H | H | H |
| 565 | 3-(4-acetylpiperazin-1-yl)-Ph | 4-Cl—Ph | O | H | H | H | H | H |
| 566 | 4-(4-acetylpiperazin-1-yl)-Ph | 4-Cl—Ph | O | H | H | H | H | H |
| 567 | 2-Cl-3-(3-pyridyl)-Ph | 4-Cl—Ph | O | H | H | H | H | H |
| 568 | 2-(2-pyridyl)-Ph | 2,4-Cl₂—Ph | O | H | H | H | H | H |
| 569 | 2-(3-pyridyl)-Ph | 2,4-Cl₂—Ph | O | H | H | H | H | H |
| 570 | 2-(4-pyridyl)-Ph | 2,4-Cl₂—Ph | O | H | H | H | H | H |
| 571 | 3-(2-pyridyl)-Ph | 2,4-Cl₂—Ph | O | H | H | H | H | H |
| 572 | 3-(3-pyridyl)-Ph | 2,4-Cl₂—Ph | O | H | H | H | H | H |
| 573 | 3-(4-pyridyl)-Ph | 2,4-Cl₂—Ph | O | H | H | H | H | H |
| 574 | 4-(2-pyridyl)-Ph | 2,4-Cl₂—Ph | O | H | H | H | H | H |
| 575 | 4-(3-pyridyl)-Ph | 2,4-Cl₂—Ph | O | H | H | H | H | H |
| 576 | 4-(4-pyridyl)-Ph | 2,4-Cl₂—Ph | O | H | H | H | H | H |
| 577 | 2-(1H-1,2,4-triazol-1-yl)-Ph | 2,4-Cl₂—Ph | O | H | H | H | H | H |
| 578 | 3-(1H-1,2,4-triazol-1-yl)-Ph | 2,4-Cl₂—Ph | O | H | H | H | H | H |
| 579 | 4-(1H-1,2,4-triazol-1-yl)-Ph | 2,4-Cl₂—Ph | O | H | H | H | H | H |
| 580 | 2-(imidazol-1-yl)-Ph | 2,4-Cl₂—Ph | O | H | H | H | H | H |
| 581 | 3-(imidazol-1-yl)-Ph | 2,4-Cl₂—Ph | O | H | H | H | H | H |
| 582 | 4-(imidazol-1-yl)-Ph | 2,4-Cl₂—Ph | O | H | H | H | H | H |
| 583 | 2-(4-methylpiperazin-1-yl)-Ph | 2,4-Cl₂—Ph | O | H | H | H | H | H |
| 584 | 3-(4-methylpiperazin-1-yl)-Ph | 2,4-Cl₂—Ph | O | H | H | H | H | H |
| 585 | 4-(4-methylpiperazin-1-yl)-Ph | 2,4-Cl₂—Ph | O | H | H | H | H | H |
| 586 | 2-(4-acetylpiperazin-1-yl)-Ph | 2,4-Cl₂—Ph | O | H | H | H | H | H |
| 587 | 3-(4-acetylpiperazin-1-yl)-Ph | 2,4-Cl₂—Ph | O | H | H | H | H | H |
| 588 | 4-(4-acetylpiperazin-1-yl)-Ph | 2,4-Cl₂—Ph | O | H | H | H | H | H |
| 589 | 2-Cl-3-(3-pyridyl)-Ph | 2,4-Cl₂—Ph | O | H | H | H | H | H |
| 590 | 3-(morpholin-1-yl)-Ph | 2,4-F₂—Ph | O | H | H | H | H | H |
| 591 | 3-(2,6-dimethyl-morpholin-1-yl)-Ph | 2,4-F₂—Ph | O | H | H | H | H | H |
| 592 | 4-(n-butyl-piperazin-1-yl)-Ph | 2,4-F₂—Ph | O | H | H | H | H | H |
| 593 | 4-(piperidin-1-yl)-Ph | 2,4-F₂—Ph | O | H | H | H | H | H |

TABLE 1-continued

| No. | | | | | | | | | |
|---|---|---|---|---|---|---|---|---|---|
| 594 | Ph | 2-F—Ph | 0 | H | H | H | H | H | (oil)ᵖ (HCl salt 190–195) |
| 595 | Ph | 3-F—Ph | 0 | H | H | H | H | H | 78–80 |
| 596 | Ph | 2-Cl—Ph | 0 | H | H | H | H | H | 92–95 |
| 597 | Ph | 3-Cl—Ph | 0 | H | H | H | H | H | |
| 598 | Ph | 4-Br—Ph | 0 | H | H | H | H | H | |
| 599 | Ph | 4-I—Ph | 0 | H | H | H | H | H | |
| 600 | Ph | 3,4-F₂—Ph | 0 | H | H | H | H | H | 142–144 |
| 601 | Ph | 3,4-Cl₂—Ph | 0 | H | H | H | H | H | |
| 602 | Ph | 2,6-Cl₂—Ph | 0 | H | H | H | H | H | |
| 603 | Ph | 3,5-Cl₂—Ph | 0 | H | H | H | H | H | |
| 604 | Ph | 2-Cl-(4-F)—Ph | 0 | H | H | H | H | H | 119–124 (dec.) |
| 605 | Ph | 3-Cl-(4-F)—Ph | 0 | H | H | H | H | H | |
| 606 | Ph | 2,4,6-Cl₃—Ph | 0 | H | H | H | H | H | 130–133 |
| 607 | Ph | 2-F-(4-Cl)—Ph | 0 | H | H | H | H | H | |
| 608 | Ph | Ph | 0 | H | H | H | H | H | |
| 609 | Ph | 4-CH₃—Ph | 0 | H | H | H | H | H | 160.5–163 |
| 610 | Ph | 3-CH₃—Ph | 0 | H | H | H | H | H | |
| 611 | Ph | 2-CH₃—Ph | 0 | H | H | H | H | H | |
| 612 | Ph | 2-CF₃—Ph | 0 | H | H | H | H | H | |
| 613 | Ph | 3-CF₃—Ph | 0 | H | H | H | H | H | 88–90 |
| 614 | Ph | 2-Cl-3-thienyl | 0 | H | H | H | H | H | 118–119 |
| 615 | Ph | 2-F-(4-CF₃)—Ph | 0 | H | H | H | H | H | 149–150 |
| 616 | Ph | 4-CH₃O—Ph | 0 | H | H | H | H | H | 151–152 |
| 617 | Ph | 5-Cl-2-pyridyl | 0 | H | H | H | H | H | |
| 618 | Ph | 5-Cl-2-thienyl | 0 | H | H | H | H | H | 122–123.5 |
| 619 | Ph | s-C₄H₉ | 0 | H | H | H | H | H | |
| 620 | 2-Cl—Ph | 2-F—Ph | 0 | H | H | H | H | H | |
| 621 | 2-Cl—Ph | 3-F—Ph | 0 | H | H | H | H | H | |
| 622 | 2-Cl—Ph | 2-Cl—Ph | 0 | H | H | H | H | H | |
| 623 | 2-Cl—Ph | 3-Cl—Ph | 0 | H | H | H | H | H | |
| 624 | 2-Cl—Ph | 4-Br—Ph | 0 | H | H | H | H | H | |
| 625 | 2-Cl—Ph | 4-I—Ph | 0 | H | H | H | H | H | |
| 626 | 2-Cl—Ph | 3,4-F₂—Ph | 0 | H | H | H | H | H | |
| 627 | 2-Cl—Ph | 3,4-Cl₂—Ph | 0 | H | H | H | H | H | |
| 628 | 2-Cl—Ph | 2,6-Cl₂—Ph | 0 | H | H | H | H | H | |
| 629 | 2-Cl—Ph | 2-Cl-(4-F)—Ph | 0 | H | H | H | H | H | |
| 630 | 2-Cl—Ph | 2,4,6-Cl₃—Ph | 0 | H | H | H | H | H | |
| 631 | 2-Cl—Ph | 2-F-(4-Cl)—Ph | 0 | H | H | H | H | H | |
| 632 | 2-Cl—Ph | Ph | 0 | H | H | H | H | H | |
| 633 | 2-Cl—Ph | 4-CH₃—Ph | 0 | H | H | H | H | H | |
| 634 | 2-Cl—Ph | 3-CH₃—Ph | 0 | H | H | H | H | H | |
| 635 | 2-Cl—Ph | 2-CH₃—Ph | 0 | H | H | H | H | H | |
| 636 | 2-Cl—Ph | 2-CF₃—Ph | 0 | H | H | H | H | H | |
| 637 | 2-Cl—Ph | 3-CF₃—Ph | 0 | H | H | H | H | H | |
| 638 | 2-Cl—Ph | 2-F-(4-CF₃)—Ph | 0 | H | H | H | H | H | |
| 639 | 2-Cl—Ph | 4-CH₃O—Ph | 0 | H | H | H | H | H | |
| 640 | 2-Cl—Ph | 5-Cl-2-pyridyl | 0 | H | H | H | H | H | |
| 641 | 2-Cl—Ph | 5-Cl-2-thienyl | 0 | H | H | H | H | H | (oil)ᵛ |
| 642 | 2-Cl—Ph | 2-Cl-3-thienyl | 0 | H | H | H | H | H | |
| 643 | 2-Cl—Ph | s-C₄H₉ | 0 | H | H | H | H | H | |

TABLE 1-continued

| No. | | | | | | | | mp |
|---|---|---|---|---|---|---|---|---|
| 644 | 4-F—Ph | 2-F—Ph | O | H | H | H | H | 96-97 |
| 645 | 4-F—Ph | 3-F—Ph | O | H | H | H | H | 116-119 |
| 646 | 4-F—Ph | 2-Cl—Ph | O | H | H | H | H | 114-116 |
| 647 | 4-F—Ph | 3-Cl—Ph | O | H | H | H | H | |
| 648 | 4-F—Ph | 4-Br—Ph | O | H | H | H | H | |
| 649 | 4-F—Ph | 4-I—Ph | O | H | H | H | H | |
| 650 | 4-F—Ph | 3,4-F$_2$—Ph | O | H | H | H | H | 98-99 |
| 651 | 4-F—Ph | 3,4-Cl$_2$—Ph | O | H | H | H | H | |
| 652 | 4-F—Ph | 2,6-Cl$_2$—Ph | O | H | H | H | H | 128-130 |
| 653 | 4-F—Ph | 2-Cl(4-F)—Ph | O | H | H | H | H | |
| 654 | 4-F—Ph | 2,4,6-Cl$_3$—Ph | O | H | H | H | H | |
| 655 | 4-F—Ph | 2-F-(4-Cl)—Ph | O | H | H | H | H | |
| 656 | 4-F—Ph | Ph | O | H | H | H | H | 124-125 |
| 657 | 4-F—Ph | 4-Ph—Ph | O | H | H | H | H | 116-119 |
| 658 | 4-F—Ph | 4-CH$_3$—Ph | O | H | H | H | H | 145-147 |
| 659 | 4-F—Ph | 2-CH$_3$—Ph | O | H | H | H | H | 145-149 |
| 660 | 4-F—Ph | 2-CF$_3$—Ph | O | H | H | H | H | 121-122 |
| 661 | 4-F—Ph | 3-CF$_3$—Ph | O | H | H | H | H | |
| 662 | 4-F—Ph | 2-F-(4-CF$_3$)—Ph | O | H | H | H | H | 112-114 |
| 663 | 4-F—Ph | 4-CH$_3$O—Ph | O | H | H | H | H | |
| 664 | 4-F—Ph | 5-Cl-2-pyridyl | O | H | H | H | H | 114-115 |
| 665 | 4-F—Ph | 5-Cl-2-thienyl | O | H | H | H | H | |
| 666 | 4-F—Ph | 2-Cl-3-thienyl | O | H | H | H | H | |
| 667 | 4-F—Ph | i-C$_3$H$_7$ | O | H | H | H | H | 74-75 (oil)$^q$ |
| 668 | 4-F—Ph | C$_2$H$_5$ | O | H | H | H | H | 130-131 |
| 669 | 4-Cl—Ph | 2-F—Ph | O | H | H | H | H | 137-139 |
| 670 | 4-Cl—Ph | 3-F—Ph | O | H | H | H | H | |
| 671, 672 | 4-Cl—Ph | 2-Cl—Ph | O | H | H | H | H | 121-123 |
| 673 | 4-Cl—Ph | 3-Cl—Ph | O | H | H | H | H | |
| 674 | 4-Cl—Ph | 4-Br—Ph | O | H | H | H | H | 107-198 |
| 675 | 4-Cl—Ph | 4-I—Ph | O | H | H | H | H | |
| 676 | 4-Cl—Ph | 3,4-Cl$_2$—Ph | O | H | H | H | H | |
| 677 | 4-Cl—Ph | 2,6-Cl$_2$—Ph | O | H | H | H | H | |
| 678 | 4-Cl—Ph | 2-Cl(4-F)—Ph | O | H | H | H | H | |
| 679 | 4-Cl—Ph | 2,4,6-Cl$_3$—Ph | O | H | H | H | H | |
| 680 | 4-Cl—Ph | 2-F-(4-Cl)—Ph | O | H | H | H | H | |
| 681 | 4-Cl—Ph | Ph | O | H | H | H | H | |
| 682 | 4-Cl—Ph | 4-CH$_3$—Ph | O | H | H | H | H | |
| 683 | 4-Cl—Ph | 3-CH$_3$—Ph | O | H | H | H | H | |
| 684 | 4-Cl—Ph | 2-CH$_3$—Ph | O | H | H | H | H | |
| 685 | 4-Cl—Ph | 2-CF$_3$—Ph | O | H | H | H | H | 103-104 |
| 686 | 4-Cl—Ph | 3-CF$_3$—Ph | O | H | H | H | H | |
| 687 | 4-Cl—Ph | 2-F-(4-CF$_3$)—Ph | O | H | H | H | H | |
| 688 | 4-Cl—Ph | 4-CH$_3$O—Ph | O | H | H | H | H | |
| 689 | 4-Cl—Ph | 5-Cl-2-pyridyl | O | H | H | H | H | (oil)$^w$ |
| 690 | 4-Cl—Ph | 5-Cl-2-thienyl | O | H | H | H | H | |
| 691 | 4-Cl—Ph | 2-Cl-3-thienyl | O | H | H | H | H | |
| 692 | 4-F—Ph | s-C$_4$H$_9$ $\overset{CH_2}{\underset{C_6H_4\text{-}4F}{=}}$ | O | H | H | H | H | |

TABLE 1-continued

| | | | | | |
|---|---|---|---|---|---|
| 693 | 4-F—Ph | t-butyl | O | H | H | H | |
| 694 | 4-F—Ph | n-hexyl | O | H | H | H | |
| 695 | 4-F—Ph | n-heptyl | O | H | H | H | |
| 696 | 4-F—Ph | 2,4-(CH₃)₂—Ph | O | H | H | H | |
| 697 | 4-F—Ph | —C₆F₁₃ | O | H | H | H | |
| 698 | 4-F—Ph | —C₈F₁₇ | O | H | H | H | 148-149 |
| 699 | 4-F—Ph | 4-pyridyl | O | H | H | H | |
| 700 | 4-F—Ph | 2-pyridyl | O | H | H | H | 175-178 |
| 701 | 4-F—Ph | 2-thienyl | O | H | H | H | |
| 702 | 4-F—Ph | 4-n-Bu—Ph | O | H | H | H | |
| 703 | 4-F—Ph | 4-n-BuO—Ph | O | H | H | H | |
| 704 | 4-F—Ph | 5-CF₃-pyrid-2-yl | O | H | H | H | |
| 705 | 4-F—Ph | 5-MeSO₂-2-thienyl | O | H | H | H | |
| 706 | 4-C₂H₅—Ph | 4-F—Ph | O | H | H | H | |
| 707 | 4-(n-BuO)—Ph | 4-F—Ph | O | H | H | H | |
| 708 | 2-CH₃SO₂-imidazol-1-yl | 4-F—Ph | O | H | H | H | |
| 709 | 5-CH₃-1,2,4-triazol-1-yl | 4-F—Ph | O | H | H | H | |
| 710 | —C₆F₁₃ | 4-F—Ph | O | H | H | H | |
| 711 | —C₈F₁₇ | 4-F—Ph | O | H | H | H | |
| 712 | 2-Cl-3-(3-pyridyl)-Ph | 4-F—Ph | O | H | H | H | |
| 713 | 2-CF₃-imidazol-1-yl | 4-F—Ph | O | H | H | H | |
| 714 | 4-(i-PrO)—Ph | 4-F—Ph | O | H | H | H | |
| 715 | 4-I—Ph | 4-F—Ph | O | H | H | H | |
| 716 | 3,4-F₂—Ph | 4-F—Ph | O | H | H | H | |
| 717 | 3,4-Cl₂—Ph | 4-F—Ph | O | H | H | H | |
| 718 | 2,6-Cl₂—Ph | 4-F—Ph | O | H | H | H | |
| 719 | 2-Cl-(4-F)—Ph | 4-F—Ph | O | H | H | H | |
| 720 | 2,4,6-Cl₃—Ph | 4-F—Ph | O | H | H | H | 119-120 |
| 721 | 4-CH₃—Ph | 4-F—Ph | O | H | H | H | 181-184 |
| 722 | 3-CH₃—Ph | 4-F—Ph | O | H | H | H | 110-112 |
| 723 | 2-CH₃—Ph | 4-F—Ph | O | H | H | H | 106-108 |
| 724 | 2-CF₃—Ph | 4-F—Ph | O | H | H | H | 109-111 |
| 725 | 3-CF₃—Ph | 4-F—Ph | O | H | H | H | |
| 726 | 4-CH₃O—Ph | 4-F—Ph | O | H | H | H | |
| 727 | 2,3-Cl₂—Ph | 4-F—Ph | O | H | H | H | |
| 728 | 3,5-Cl₂—Ph | 4-F—Ph | O | H | H | H | |
| 729 | 2,5-Cl₂—Ph | 4-F—Ph | O | H | H | H | |
| 730 | 3-Br—Ph | 4-F—Ph | O | H | H | H | 91-93 |
| 731 | 4-EtO—Ph | 4-F—Ph | O | H | H | H | |
| 732 | 2,4-(CH₃)₂—Ph | 4-F—Ph | O | H | H | H | |
| 733 | 2,4,6-(CH₃)₃—Ph | 4-F—Ph | O | H | H | H | |
| 734 | 4-Ph—Ph | 4-F—Ph | O | H | H | H | |
| 735 | 5-Cl-2-thienyl | 4-F—Ph | O | H | H | H | |
| 736 | 2-Cl-3-thienyl | 4-F—Ph | O | H | H | H | |
| 737 | 1-imidazoyl | 4-F—Ph | O | H | H | H | |
| 738 | 1H-1,2,4-triazoyl | 4-F—Ph | O | H | H | H | |
| 739 | 2-pyridyl | 4-F—Ph | O | H | H | H | |
| 740 | 5-Cl-pyridyl-2-yl | 4-F—Ph | O | H | H | H | |
| 741 | 3-pyridyl | 4-F—Ph | O | H | H | H | |

TABLE 1-continued

| No. | R1 | R2 | | | | | | | mp |
|---|---|---|---|---|---|---|---|---|---|
| 742 | 4-pyridyl | 4-F—Ph | O | H | H | H | H | H | |
| 743 | n-C4F9 | 4-F—Ph | O | H | H | H | H | H | |
| 744 | 4-I—Ph | 2,4-Cl2—Ph | O | H | H | H | H | H | |
| 745 | 3,4-F2—Ph | 2,4-Cl2—Ph | O | H | H | H | H | H | |
| 746 | 3,4-Cl2—Ph | 2,4-Cl2—Ph | O | H | H | H | H | H | |
| 747 | 2,6-Cl2—Ph | 2,4-Cl2—Ph | O | H | H | H | H | H | |
| 748 | 2-Cl-(4-F)—Ph | 2,4-Cl2—Ph | O | H | H | H | H | H | |
| 749 | 2,4,6-Cl3—Ph | 2,4-Cl2—Ph | O | H | H | H | H | H | |
| 750 | 4-CH3—Ph | 2,4-Cl2—Ph | O | H | H | H | H | H | |
| 751 | 3-CH3—Ph | 2,4-Cl2—Ph | O | H | H | H | H | H | |
| 752 | 2-CH3—Ph | 2,4-Cl2—Ph | O | H | H | H | H | H | |
| 753 | 2-CF3—Ph | 2,4-Cl2—Ph | O | H | H | H | H | H | 133–137 |
| 754 | 3-CF3—Ph | 2,4-Cl2—Ph | O | H | H | H | H | H | 77–84 |
| 755 | 4-CH3O—Ph | 2,4-Cl2—Ph | O | H | H | H | H | H | |
| 756 | 2,3-Cl2—Ph | 2,4-Cl2—Ph | O | H | H | H | H | H | |
| 757 | 3,5-Cl2—Ph | 2,4-Cl2—Ph | O | H | H | H | H | H | |
| 758 | 2,5-Cl2—Ph | 2,4-Cl2—Ph | O | H | H | H | H | H | 171–173 |
| 759 | 3-Br—Ph | 2,4-Cl2—Ph | O | H | H | H | H | H | |
| 760 | 4-EtO—Ph | 2,4-Cl2—Ph | O | H | H | H | H | H | |
| 761 | 2,4-(CH3)2—Ph | 2,4-Cl2—Ph | O | H | H | H | H | H | |
| 762 | 2,6-(CH3)3—Ph | 2,4-Cl2—Ph | O | H | H | H | H | H | |
| 763 | 4-Ph—Ph | 2,4-Cl2—Ph | O | H | H | H | H | H | |
| 764 | 5-Cl-2-thienyl | 2,4-Cl2—Ph | O | H | H | H | H | H | |
| 765 | 2-Cl-3-thienyl | 2,4-Cl2—Ph | O | H | H | H | H | H | |
| 766 | 1-imidazoyl | 2,4-Cl2—Ph | O | H | H | H | H | H | |
| 767 | 1H-1,2,4-triazoyl-1-yl | 2,4-Cl2—Ph | O | H | H | H | H | H | |
| 768 | 2-pyridyl | 2,4-Cl2—Ph | O | H | H | H | H | H | |
| 769 | 5-Cl-pyrid-2-yl | 2,4-Cl2—Ph | O | H | H | H | H | H | |
| 770 | 3-pyridyl | 2,4-Cl2—Ph | O | H | H | H | H | H | |
| 771 | 4-pyridyl | 2,4-Cl2—Ph | O | H | H | H | H | H | |
| 772 | n-C4F9 | 2,4-Cl2—Ph | O | H | H | H | H | H | |
| 773 | 4-I—Ph | 4-Cl—Ph | O | H | H | H | H | H | |
| 774 | 3,4-F2—Ph | 4-Cl—Ph | O | H | H | H | H | H | |
| 775 | 3,4-Cl2—Ph | 4-Cl—Ph | O | H | H | H | H | H | |
| 776 | 2,6-Cl2—Ph | 4-Cl—Ph | O | H | H | H | H | H | |
| 777 | 2-Cl-(4-F)—Ph | 4-Cl—Ph | O | H | H | H | H | H | |
| 778 | 2,4,6-Cl3—Ph | 4-Cl—Ph | O | H | H | H | H | H | |
| 779 | 4-CH3—Ph | 4-Cl—Ph | O | H | H | H | H | H | |
| 780 | 3-CH3—Ph | 4-Cl—Ph | O | H | H | H | H | H | |
| 781 | 2-CH3—Ph | 4-Cl—Ph | O | H | H | H | H | H | |
| 782 | 2-CF3—Ph | 4-Cl—Ph | O | H | H | H | H | H | |
| 783 | 3-CF3—Ph | 4-Cl—Ph | O | H | H | H | H | H | 43–49 |
| 784 | 4-CH3O—Ph | 4-Cl—Ph | O | H | H | H | H | H | 109–112 |
| 785 | 2,3-Cl2—Ph | 4-Cl—Ph | O | H | H | H | H | H | 111–113 |
| 786 | 3,5-Cl2—Ph | 4-Cl—Ph | O | H | H | H | H | H | |
| 787 | 2,5-Cl2—Ph | 4-Cl—Ph | O | H | H | H | H | H | |
| 788 | 3-Br—Ph | 4-Cl—Ph | O | H | H | H | H | H | 119–121 |
| 789 | 4-EtO—Ph | 4-Cl—Ph | O | H | H | H | H | H | |
| 790 | 2,4-(CH3)2—Ph | 4-Cl—Ph | O | H | H | H | H | H | |
| 791 | 2,4,6-(CH3)3—Ph | 4-Cl—Ph | O | H | H | H | H | H | |
| 792 | 4-Ph—Ph | 4-Cl—Ph | O | H | H | H | H | H | |
| 793 | 5-Cl-2-thienyl | 4-Cl—Ph | O | H | H | H | H | H | |
| 794 | 2-Cl-3-thienyl | 4-Cl—Ph | O | H | H | H | H | H | |

TABLE 1-continued

| | | | | | | |
|---|---|---|---|---|---|---|
| 795 | 1-imidazoyl | 4-Cl—Ph | O | H | H | H | |
| 796 | 1H-1,2,4-triazoyl-1-yl | 4-Cl—Ph | O | H | H | H | |
| 797 | 2-pyridyl | 4-Cl—Ph | O | H | H | H | |
| 798 | 5-Cl-pyrid-2-yl | 4-Cl—Ph | O | H | H | H | |
| 799 | 3-pyridyl | 4-Cl—Ph | O | H | H | H | |
| 800 | 4-pyridyl | 4-Cl—Ph | O | H | H | H | (oil)$^{gf}$ |
| 801 | n-C₄F₉ | 4-Cl—Ph | O | H | H | H | |
| 802 | 4-I—Ph | 2,4-F₂—Ph | O | H | H | H | |
| 803 | 3,4-F₂—Ph | 2,4-F₂—Ph | O | H | H | H | |
| 804 | 3,4-Cl₂—Ph | 2,4-F₂—Ph | O | H | H | H | |
| 805 | 2,6-Cl₂—Ph | 2,4-F₂—Ph | O | H | H | H | |
| 806 | 2-Cl-(4-F)—Ph | 2,4-F₂—Ph | O | H | H | H | |
| 807 | 2,4,6-Cl₃—Ph | 2,4-F₂—Ph | O | H | H | H | |
| 808 | 4-CH₃—Ph | 2,4-F₂—Ph | O | H | H | H | 129–130.5 |
| 809 | 3-CH₃—Ph | 2,4-F₂—Ph | O | H | H | H | |
| 810 | 2-CH₃—Ph | 2,4-F₂—Ph | O | H | H | H | |
| 811 | 2-CF₃—Ph | 2,4-F₂—Ph | O | H | H | H | 113–116 |
| 812 | 3-CF₃—Ph | 2,4-F₂—Ph | O | H | H | H | 123–124 |
| 813 | 4-CH₃O—Ph | 2,4-F₂—Ph | O | H | H | H | 88–89 |
| 814 | 2,3-Cl₂—Ph | 2,4-F₂—Ph | O | H | H | H | |
| 815 | 3,5-Cl₂—Ph | 2,4-F₂—Ph | O | H | H | H | 173–175 |
| 816 | 2,5-Cl₂—Ph | 2,4-F₂—Ph | O | H | H | H | |
| 817 | 3-Br—Ph | 2,4-F₂—Ph | O | H | H | H | 103–107 |
| 818 | 4-EtO—Ph | 2,4-F₂—Ph | O | H | H | H | |
| 819 | 2,4-(CH₃)₂—Ph | 2,4-F₂—Ph | O | H | H | H | |
| 820 | 2,4,6-(CH₃)₃—Ph | 2,4-F₂—Ph | O | H | H | H | |
| 821 | 4-Ph—Ph | 2,4-F₂—Ph | O | H | H | H | |
| 822 | 5-Cl-2-thienyl | 2,4-F₂—Ph | O | H | H | H | |
| 823 | 2-Cl-3-thienyl | 2,4-F₂—Ph | O | H | H | H | |
| 824 | 1-imidazoyl | 2,4-F₂—Ph | O | H | H | H | |
| 825 | 1H-1,2,4-triazoyl-1-yl | 2,4-F₂—Ph | O | H | H | H | |
| 826 | 2-pyridyl | 2,4-F₂—Ph | O | H | H | H | |
| 827 | 5-Cl-pyrid-2-yl | 2,4-F₂—Ph | O | H | H | H | |
| 828 | 3-pyridyl | 2,4-F₂—Ph | O | H | H | H | |
| 829 | 4-pyridyl | 2,4-F₂—Ph | O | H | H | H | |
| 830 | n-C₄F₉ | 4-Br—Ph | O | H | H | H | |
| 831 | 2-F—Ph | 4-Br—Ph | O | H | H | H | |
| 832 | 3-F—Ph | 4-Br—Ph | O | H | H | H | |
| 833 | 3-Cl—Ph | 4-Br—Ph | O | H | H | H | |
| 834 | 4-Br—Ph | 4-Br—Ph | O | H | H | H | |
| 835 | 2,4-F₂—Ph | 4-Br—Ph | O | H | H | H | |
| 836 | 2,4-Cl₂—Ph | 4-Br—Ph | O | H | H | H | |
| 837 | 2-CF₃—Ph | 4-Br—Ph | O | H | H | H | |
| 838 | 3-CF₃—Ph | 4-Br—Ph | O | H | H | H | |
| 839 | 4-CF₃—Ph | 4-Br—Ph | O | H | H | H | |
| 840 | 2-F—Ph | 4-I—Ph | O | H | H | H | |
| 841 | 3-F—Ph | 4-I—Ph | O | H | H | H | |
| 842 | 3-Cl—Ph | 4-I—Ph | O | H | H | H | |
| 843 | 4-Br—Ph | 4-I—Ph | O | H | H | H | |
| 844 | 2,4-F₂—Ph | 4-I—Ph | O | H | H | H | |
| 845 | 2,4-Cl₂—Ph | 4-I—Ph | O | H | H | H | |
| 846 | 2-CF₃—Ph | 4-I—Ph | O | H | H | H | |
| 847 | 3-CF₃—Ph | 4-I—Ph | O | H | H | H | |

TABLE 1-continued

| # | | | | | | | | | mp |
|---|---|---|---|---|---|---|---|---|---|
| 848 | 4-CF₃—Ph | 4-I—Ph | O | H | H | H | H | H | |
| 849 | 2-F—Ph | 2-CH₃—Ph | O | H | H | H | H | H | |
| 850 | 3-F—Ph | 2-CH₃—Ph | O | H | H | H | H | H | |
| 851 | 3-Cl—Ph | 2-CH₃—Ph | O | H | H | H | H | H | |
| 852 | 4-Br—Ph | 2-CH₃—Ph | O | H | H | H | H | H | |
| 853 | 2,4-F₂—Ph | 2-CH₃—Ph | O | H | H | H | H | H | |
| 854 | 2,4-Cl₂—Ph | 2-CH₃—Ph | O | H | H | H | H | H | |
| 855 | 2-CF₃—Ph | 2-CH₃—Ph | O | H | H | H | H | H | |
| 856 | 3-CF₃—Ph | 2-CH₃—Ph | O | H | H | H | H | H | |
| 857 | 4-CF₃—Ph | 2-CH₃—Ph | O | H | H | H | H | H | |
| 858 | 4-(4-F—Ph)—Ph | 4-F—Ph | O | H | H | H | H | H | |
| 859 | 4-(2-Cl—Ph)—Ph | 4-Cl—Ph | O | H | H | H | H | H | |
| 860 | 3-(3-CF₃—Ph)—Ph | 2,4-F₂—Ph | O | H | H | H | H | H | |
| 861 | 3-(2,4-F₂—Ph)—Ph | 2,4-Cl₂—Ph | O | H | H | H | H | H | |
| 862 | 2,4-F₂—Ph | 4-CH₃—Ph | O | H | H | H | H | H | |
| 863 | 4-CH₃—Ph | 4-CH₃—Ph | O | H | H | H | H | H | |
| 864 | 2-CF₃—Ph | 4-CH₃—Ph | O | H | H | H | H | H | |
| 865 | 3-CF₃—Ph | 4-CH₃—Ph | O | H | H | H | H | H | |
| 866 | 4-CF₃—Ph | 4-CH₃—Ph | O | H | H | H | H | H | |
| 867 | 2-F—Ph | 4-CH₃O—Ph | O | H | H | H | H | H | |
| 868 | 3-F—Ph | 4-CH₃O—Ph | O | H | H | H | H | H | |
| 869 | 3-Cl—Ph | 4-CH₃O—Ph | O | H | H | H | H | H | |
| 870 | 4-Br—Ph | 4-CH₃O—Ph | O | H | H | H | H | H | |
| 871 | 2,4-F₂—Ph | 4-CH₃O—Ph | O | H | H | H | H | H | 178-181.5 |
| 872 | 2,4-Cl₂—Ph | 4-CH₃O—Ph | O | H | H | H | H | H | |
| 873 | 2-CF₃—Ph | 4-CH₃O—Ph | O | H | H | H | H | H | |
| 874 | 3-CF₃—Ph | 4-CH₃O—Ph | O | H | H | H | H | H | |
| 875 | 4-CF₃—Ph | 4-CH₃O—Ph | O | H | H | H | H | H | |
| 876 | Ph | 2-CH₃O—Ph | O | H | H | H | H | H | |
| 877 | 2-F—Ph | 2-CH₃O—Ph | O | H | H | H | H | H | |
| 878 | 3-F—Ph | 2-CH₃O—Ph | O | H | H | H | H | H | |
| 879 | 4-F—Ph | 2-CH₃O—Ph | O | H | H | H | H | H | |
| 880 | 2,4-F₂—Ph | 2-CH₃O—Ph | O | H | H | H | H | H | 56-70 (138-139.5 .H₂C₂O₄) |
| 881 | 2-Cl—Ph | 2-CH₃O—Ph | O | H | H | H | H | H | |
| 882 | 3-Cl—Ph | 2-CH₃O—Ph | O | H | H | H | H | H | |
| 883 | 4-Cl—Ph | 2-CH₃O—Ph | O | H | H | H | H | H | |
| 884 | 2,4-Cl₂—Ph | 2-CH₃O—Ph | O | H | H | H | H | H | |
| 885 | 4-Br—Ph | 2-CH₃O—Ph | O | H | H | H | H | H | |
| 886 | 2-CF₃—Ph | 2-CH₃O—Ph | O | H | H | H | H | H | |
| 887 | 3-CF₃—Ph | 2-CH₃O—Ph | O | H | H | H | H | H | |
| 888 | 4-CF₃—Ph | 2-CH₃O—Ph | O | H | H | H | H | H | |
| 889 | Ph | 4-CF₃O—Ph | O | H | H | H | H | H | |
| 890 | 2-F—Ph | 4-CF₃O—Ph | O | H | H | H | H | H | |
| 891 | 3-F—Ph | 4-CF₃O—Ph | O | H | H | H | H | H | |
| 892 | 4-F—Ph | 4-CF₃O—Ph | O | H | H | H | H | H | |
| 893 | 2,4-F₂—Ph | 4-CF₃O—Ph | O | H | H | H | H | H | |
| 894 | 2-Cl—Ph | 4-CF₃O—Ph | O | H | H | H | H | H | |
| 895 | 3-Cl—Ph | 4-CF₃O—Ph | O | H | H | H | H | H | |
| 896 | 4-Cl—Ph | 4-CF₃O—Ph | O | H | H | H | H | H | |
| 897 | 2,4-Cl₂—Ph | 4-CF₃O—Ph | O | H | H | H | H | H | |
| 898 | 4-Br—Ph | 4-CF₃O—Ph | O | H | H | H | H | H | |

TABLE 1-continued

| | | | | | | | |
|---|---|---|---|---|---|---|---|
| 899 | 2-CF₃—Ph | 4-CF₃O—Ph | O | H | H | H | H |
| 900 | 3-CF₃—Ph | 4-CF₃O—Ph | O | H | H | H | H |
| 901 | 4-CF₃—Ph | 4-CF₃O—Ph | O | H | H | H | H |
| 902 | 2-F—Ph | 3,4-Cl₂—Ph | O | H | H | H | H |
| 903 | 3-F—Ph | 3,4-Cl₂—Ph | O | H | H | H | H |
| 904 | 2,4-F₂—Ph | 3,4-Cl₂—Ph | O | H | H | H | H |
| 905 | 3-Cl—Ph | 3,4-Cl₂—Ph | O | H | H | H | H |
| 906 | 2,4-Cl₂—Ph | 3,4-Cl₂—Ph | O | H | H | H | H |
| 907 | 4-Br—Ph | 3,4-Cl₂—Ph | O | H | H | H | H |
| 908 | 2-CF₃—Ph | 3,4-Cl₂—Ph | O | H | H | H | H |
| 909 | 3-CF₃—Ph | 3,4-Cl₂—Ph | O | H | H | H | H |
| 910 | 4-CF₃—Ph | 3,4-Cl₂—Ph | O | H | H | H | H |
| 911 | Ph | 2,5-F₂—Ph | O | H | H | H | H |
| 912 | 2-F—Ph | 2,5-F₂—Ph | O | H | H | H | H |
| 913 | 3-F—Ph | 2,5-F₂—Ph | O | H | H | H | H |
| 914 | 4-F—Ph | 2,5-F₂—Ph | O | H | H | H | H |
| 915 | 2,4-F₂—Ph | 2,5-F₂—Ph | O | H | H | H | H |
| 916 | 2-Cl—Ph | 2,5-F₂—Ph | O | H | H | H | H | 110-111 |
| 917 | 3-Cl—Ph | 2,5-F₂—Ph | O | H | H | H | H |
| 918 | 4-Cl—Ph | 2,5-F₂—Ph | O | H | H | H | H |
| 919 | 2,4-Cl₂—Ph | 2,5-F₂—Ph | O | H | H | H | H |
| 920 | 4-Br—Ph | 2,5-F₂—Ph | O | H | H | H | H |
| 921 | 2-CF₃—Ph | 2,5-F₂—Ph | O | H | H | H | H |
| 922 | 3-CF₃—Ph | 2,5-F₂—Ph | O | H | H | H | H |
| 923 | 4-CF₃—Ph | 2,5-F₂—Ph | O | H | H | H | H |
| 924 | Ph | 2,5-Cl₂—Ph | O | H | H | H | H |
| 925 | 2-F—Ph | 2,5-Cl₂—Ph | O | H | H | H | H |
| 926 | 3-F—Ph | 2,5-Cl₂—Ph | O | H | H | H | H |
| 927 | 4-F—Ph | 2,5-Cl₂—Ph | O | H | H | H | H |
| 928 | 2,4-F₂—Ph | 2,5-Cl₂—Ph | O | H | H | H | H |
| 929 | 2-Cl—Ph | 2,5-Cl₂—Ph | O | H | H | H | H |
| 930 | 3-Cl—Ph | 2,5-Cl₂—Ph | O | H | H | H | H |
| 931 | 4-Cl—Ph | 2,5-Cl₂—Ph | O | H | H | H | H |
| 932 | 2,4-Cl₂—Ph | 2,5-Cl₂—Ph | O | H | H | H | H |
| 933 | 4-Br—Ph | 2,5-Cl₂—Ph | O | H | H | H | H |
| 934 | 2-CF₃—Ph | 2,5-Cl₂—Ph | O | H | H | H | H |
| 935 | 3-CF₃—Ph | 2,5-Cl₂—Ph | O | H | H | H | H |
| 936 | 4-CF₃—Ph | 2,5-Cl₂—Ph | O | H | H | H | H |
| 937 | Ph | 2,4,6-F₃—Ph | O | H | H | H | H |
| 938 | 2-F—Ph | 2,4,6-F₃—Ph | O | H | H | H | H |
| 939 | 3-F—Ph | 2,4,6-F₃—Ph | O | H | H | H | H |
| 940 | 4-F—Ph | 2,4,6-F₃—Ph | O | H | H | H | H |
| 941 | 2,4-F₂—Ph | 2,4,6-F₃—Ph | O | H | H | H | H |
| 942 | 2-Cl—Ph | 2,4,6-F₃—Ph | O | H | H | H | H |
| 943 | 3-Cl—Ph | 2,4,6-F₃—Ph | O | H | H | H | H |
| 944 | 4-Cl—Ph | 2,4,6-F₃—Ph | O | H | H | H | H |
| 945 | 2,4-Cl₂—Ph | 2,4,6-F₃—Ph | O | H | H | H | H |
| 946 | 4-Br—Ph | 2,4,6-F₃—Ph | O | H | H | H | H |
| 947 | 2-CF₃—Ph | 2,4,6-F₃—Ph | O | H | H | H | H |
| 948 | 3-CF₃—Ph | 2,4,6-F₃—Ph | O | H | H | H | H |
| 949 | 4-CF₃—Ph | 2,4,6-F₃—Ph | O | H | H | H | H |
| 950 | Ph | 2,4,5-F₃—Ph | O | H | H | H | H |
| 951 | 2-F—Ph | 2,4,5-F₃—Ph | O | H | H | H | H |

TABLE 1-continued

| | | | | | | | |
|---|---|---|---|---|---|---|---|
| 952 | 3-F—Ph | 2,4,5-F$_3$—Ph | 0 | H | H | H | H | H |
| 953 | 4-F—Ph | 2,4,5-F$_3$—Ph | 0 | H | H | H | H | H |
| 954 | 2,4-F$_2$—Ph | 2,4,5-F$_3$—Ph | 0 | H | H | H | H | H |
| 955 | 2-Cl—Ph | 2,4,5-F$_3$—Ph | 0 | H | H | H | H | H |
| 956 | 3-Cl—Ph | 2,4,5-F$_3$—Ph | 0 | H | H | H | H | H |
| 957 | 4-Cl—Ph | 2,4,5-F$_3$—Ph | 0 | H | H | H | H | H |
| 958 | 2,4-Cl$_2$—Ph | 2,4,5-F$_3$—Ph | 0 | H | H | H | H | H |
| 959 | 4-Br—Ph | 2,4,5-F$_3$—Ph | 0 | H | H | H | H | H |
| 960 | 2-CF$_3$—Ph | 2,4,5-F$_3$—Ph | 0 | H | H | H | H | H |
| 961 | 3-CF$_3$—Ph | 2,4,5-F$_3$—Ph | 0 | H | H | H | H | H |
| 962 | 4-CF$_3$—Ph | 2,4,5-F$_3$—Ph | 0 | H | H | H | H | H |
| 963 | 2-F—Ph | 2-Cl-4-F—Ph | 0 | H | H | H | H | H |
| 964 | 3-F—Ph | 2-Cl-4-F—Ph | 0 | H | H | H | H | H |
| 965 | 4-F—Ph | 2-Cl-4-F—Ph | 0 | H | H | H | H | H |
| 966 | 3-Cl—Ph | 2-Cl-4-F—Ph | 0 | H | H | H | H | H |
| 967 | 2,4-Cl$_2$—Ph | 2-Cl-4-F—Ph | 0 | H | H | H | H | H |
| 968 | 4-Br—Ph | 2-Cl-4-F—Ph | 0 | H | H | H | H | H |
| 969 | 2-CF$_3$—Ph | 2-Cl-4-F—Ph | 0 | H | H | H | H | H |
| 970 | 3-CF$_3$—Ph | 2-Cl-4-F—Ph | 0 | H | H | H | H | H |
| 971 | 4-CF$_3$—Ph | 2-Cl-4-F—Ph | 0 | H | H | H | H | H |
| 972 | Ph | 4-F-1-naphthyl | 0 | H | H | H | H | H |
| 973 | 2-F—Ph | 1-naphthyl | 0 | H | H | H | H | H |
| 974 | 3-F—Ph | 1-naphthyl | 0 | H | H | H | H | H |
| 975 | 4-F—Ph | 1-naphthyl | 0 | H | H | H | H | H |
| 976 | 2,4-F$_2$—Ph | 1-naphthyl | 0 | H | H | H | H | H |
| 977 | 2-Cl—Ph | 1-naphthyl | 0 | H | H | H | H | H |
| 978 | 3-Cl—Ph | 1-naphthyl | 0 | H | H | H | H | H |
| 979 | 4-Cl—Ph | 1-naphthyl | 0 | H | H | H | H | H |
| 980 | 2,4-Cl$_2$—Ph | 1-naphthyl | 0 | H | H | H | H | H |
| 981 | 4-Br—Ph | 1-naphthyl | 0 | H | H | H | H | H |
| 982 | 2-CF$_3$—Ph | 1-naphthyl | 0 | H | H | H | H | H |
| 983 | 3-CF$_3$—Ph | 1-naphthyl | 0 | H | H | H | H | H |
| 984 | 4-CF$_3$—Ph | 1-naphthyl | 0 | H | H | H | H | H |
| 985 | Ph | 6-Cl-2-naphthyl | 0 | H | H | H | H | H |
| 986 | 2-F—Ph | 2-naphthyl | 0 | H | H | H | H | H |
| 987 | 3-F—Ph | 2-naphthyl | 0 | H | H | H | H | H |
| 988 | 4-F—Ph | 2-naphthyl | 0 | H | H | H | H | H |
| 989 | 2,4-F$_2$—Ph | 2-naphthyl | 0 | H | H | H | H | H |
| 990 | 2-Cl—Ph | 2-naphthyl | 0 | H | H | H | H | H |
| 991 | 3-Cl—Ph | 2-naphthyl | 0 | H | H | H | H | H |
| 992 | 4-Cl—Ph | 2-naphthyl | 0 | H | H | H | H | H |
| 993 | 2,4-Cl$_2$—Ph | 2-naphthyl | 0 | H | H | H | H | H |
| 994 | 4-Br—Ph | 2-naphthyl | 0 | H | H | H | H | H |
| 995 | 2-CF$_3$—Ph | 2-naphthyl | 0 | H | H | H | H | H |
| 996 | 3-CF$_3$—Ph | 2-naphthyl | 0 | H | H | H | H | H |
| 997 | 4-CF$_3$—Ph | 2-naphthyl | 0 | H | H | H | H | H |
| 998 | Ph | PhCH$_2$— | 0 | H | H | H | H | H |
| 999 | 2-F—Ph | PhCH$_2$— | 0 | H | H | H | H | H |
| 1000 | 3-F—Ph | PhCH$_2$— | 0 | H | H | H | H | H |
| 1001 | 4-F—Ph | PhCH$_2$— | 0 | H | H | H | H | H |
| 1002 | 2,4-F$_2$—Ph | PhCH$_2$— | 0 | H | H | H | H | H |
| 1003 | 2-Cl—Ph | PhCH$_2$— | 0 | H | H | H | H | H |
| 1004 | 3-Cl—Ph | PhCH$_2$— | 0 | H | H | H | H | H |

TABLE 1-continued

| | | | | | | | | | mp |
|---|---|---|---|---|---|---|---|---|---|
| 1005 | 4-Cl—Ph | PhCH₂— | O | H | H | H | H | H | |
| 1006 | 2,4-Cl₂—Ph | PhCH₂— | O | H | H | H | H | H | |
| 1007 | 4-Br—Ph | PhCH₂— | O | H | H | H | H | H | |
| 1008 | 2-CF₃—Ph | PhCH₂— | O | H | H | H | H | H | |
| 1009 | 3-CF₃—Ph | PhCH₂— | O | H | H | H | H | H | |
| 1010 | 4-CF₃—Ph | PhCH₂— | O | H | H | H | H | H | |
| 1011 | Ph | PhCH(CH₃) | O | H | H | H | H | H | |
| 1012 | 2-F—Ph | PhCH(CH₃) | O | H | H | H | H | H | |
| 1013 | 3-F—Ph | PhCH(CH₃) | O | H | H | H | H | H | |
| 1014 | 4-F—Ph | PhCH(CH₃) | O | H | H | H | H | H | |
| 1015 | 2,4-F₂—Ph | PhCH(CH₃) | O | H | H | H | H | H | |
| 1016 | 2-Cl—Ph | PhCH(CH₃) | O | H | H | H | H | H | |
| 1017 | 3-Cl—Ph | PhCH(CH₃) | O | H | H | H | H | H | |
| 1018 | 4-Cl—Ph | PhCH(CH₃) | O | H | H | H | H | H | |
| 1019 | 2,4-Cl₂—Ph | PhCH(CH₃) | O | H | H | H | H | H | |
| 1020 | 4-Br—Ph | PhCH(CH₃) | O | H | H | H | H | H | |
| 1021 | 2-CF₃—Ph | PhCH(CH₃) | O | H | H | H | H | H | |
| 1022 | 3-CF₃—Ph | PhCH(CH₃) | O | H | H | H | H | H | |
| 1023 | 4-CF₃—Ph | PhCH(CH₃) | O | H | H | H | H | H | |
| 1024 | Ph | PhC(CH₃)₂— | O | H | H | H | H | H | |
| 1025 | 2-F—Ph | PhC(CH₃)₂— | O | H | H | H | H | H | |
| 1026 | 3-F—Ph | PhC(CH₃)₂— | O | H | H | H | H | H | |
| 1027 | 4-F—Ph | PhC(CH₃)₂— | O | H | H | H | H | H | |
| 1028 | 2,4-F₂—Ph | PhC(CH₃)₂— | O | H | H | H | H | H | |
| 1029 | 2-Cl—Ph | PhC(CH₃)₂— | O | H | H | H | H | H | |
| 1030 | 3-Cl—Ph | PhC(CH₃)₂— | O | H | H | H | H | H | |
| 1031 | 4-Cl—PH | PhC(CH₃)₂— | O | H | H | H | H | H | |
| 1032 | 2,4-Cl₂—Ph | PhC(CH₃)₂— | O | H | H | H | H | H | |
| 1033 | 4-Br—Ph | PhC(CH₃)₂— | O | H | H | H | H | H | |
| 1034 | 2-CF₃—Ph | PhC(CH₃)₂— | O | H | H | H | H | H | |
| 1035 | 3-CF₃—Ph | PhC(CH₃)₂— | O | H | H | H | H | H | |
| 1036 | 4-CF₃—Ph | PhC(CH₃)₂— | O | H | H | H | H | H | |
| 1037 | Ph | 4-Cl-PhC(CH₃)₂— | O | H | H | H | H | H | |
| 1038 | 2-F—Ph | 4-Cl-PhC(CH₃)₂— | O | H | H | H | H | H | |
| 1039 | 3-F—Ph | 4-Cl-PhC(CH₃)₂— | O | H | H | H | H | H | |
| 1040 | 4-F—Ph | 4-Cl-PhC(CH₃)₂— | O | H | H | H | H | H | (oil)ˣ |
| 1041 | 2,4-F₂—Ph | 4-Cl-PhC(CH₃)₂— | O | H | H | H | H | H | |
| 1042 | 2-Cl—Ph | 4-Cl-PhC(CH₃)₂— | O | H | H | H | H | H | |
| 1043 | 3-Cl—Ph | 4-Cl-PhC(CH₃)₂— | O | H | H | H | H | H | |
| 1044 | 4-Cl—Ph | 4-Cl-PhC(CH₃)₂— | O | H | H | H | H | H | |
| 1045 | 2,4-Cl₂—Ph | 4-Cl-PhC(CH₃)₂— | O | H | H | H | H | H | |
| 1046 | 4-Br—Ph | 4-Cl-PhC(CH₃)₂— | O | H | H | H | H | H | |
| 1047 | 2-CF₃—Ph | 4-Cl-PhC(CH₃)₂— | O | H | H | H | H | H | |
| 1048 | 3-CF₃—Ph | 4-Cl-PhC(CH₃)₂— | O | H | H | H | H | H | |
| 1049 | 4-CF₃—Ph | 4-Cl-PhC(CH₃)₂— | O | H | H | H | H | H | |
| 1050 | Ph | 2-thienyl | O | H | H | H | H | H | 127–129 |
| 1051 | 2-F—Ph | 2-thienyl | O | H | H | H | H | H | |
| 1052 | 3-F—Ph | 2-thienyl | O | H | H | H | H | H | |
| 1053 | 4-F—Ph | 2-thienyl | O | H | H | H | H | H | 125–134 |
| 1054 | 2,4-F₂—Ph | 2-thienyl | O | H | H | H | H | H | |
| 1055 | 2-Cl—Ph | 2-thienyl | O | H | H | H | H | H | |
| 1056 | 3-Cl—Ph | 2-thienyl | O | H | H | H | H | H | 110 |
| 1057 | 4-Cl—Ph | 2-thienyl | O | H | H | H | H | H | 141–143 |

TABLE 1-continued

| | | | | | | | | |
|---|---|---|---|---|---|---|---|---|
| 1058 | 2,4-Cl$_2$—Ph | 2-thienyl | O | H | H | H | H | |
| 1059 | 4-Br—Ph | 2-thienyl | O | H | H | H | H | |
| 1060 | 2-CF$_3$—Ph | 2-thienyl | O | H | H | H | H | |
| 1061 | 3-CF$_3$—Ph | 2-thienyl | O | H | H | H | H | |
| 1062 | 4-CF$_3$—Ph | 2-thienyl | O | H | H | H | H | |
| 1063 | Ph | 3-thienyl | O | H | H | H | H | |
| 1064 | 2-F—Ph | 3-thienyl | O | H | H | H | H | |
| 1065 | 3-F—Ph | 3-thienyl | O | H | H | H | H | |
| 1066 | 4-F—Ph | 3-thienyl | O | H | H | H | H | |
| 1067 | 2,4-F$_2$—Ph | 3-thienyl | O | H | H | H | H | |
| 1068 | 2-Cl—Ph | 3-thienyl | O | H | H | H | H | |
| 1069 | 3-Cl—Ph | 3-thienyl | O | H | H | H | H | |
| 1070 | 4-Cl—Ph | 3-thienyl | O | H | H | H | H | |
| 1071 | 2,4-Cl$_2$—Ph | 3-thienyl | O | H | H | H | H | |
| 1072 | 4-Br—Ph | 3-thienyl | O | H | H | H | H | |
| 1073 | 2-CF$_3$—Ph | 3-thienyl | O | H | H | H | H | |
| 1074 | 3-CF$_3$—Ph | 3-thienyl | O | H | H | H | H | |
| 1075 | 4-CF$_3$—Ph | 3-thienyl | O | H | H | H | H | |
| 1076 | 2-F—Ph | 2-Cl-3-thienyl | O | H | H | H | H | |
| 1077 | 3-F—Ph | 2-Cl-3-thienyl | O | H | H | H | H | |
| 1078 | 2,4-F$_2$—Ph | 2-Cl-3-thienyl | O | H | H | H | H | |
| 1079 | 3-Cl—Ph | 2-Cl-3-thienyl | O | H | H | H | H | |
| 1080 | 2,4-Cl$_2$—Ph | 2-Cl-3-thienyl | O | H | H | H | H | |
| 1081 | 4-Br—Ph | 2-Cl-3-thienyl | O | H | H | H | H | |
| 1082 | 2-CF$_3$—Ph | 2-Cl-3-thienyl | O | H | H | H | H | |
| 1083 | 3-CF$_3$—Ph | 2-Cl-3-thienyl | O | H | H | H | H | |
| 1084 | 4-CF$_3$—Ph | 2-Cl-3-thienyl | O | H | H | H | H | |
| 1085 | 2-F—Ph | 5-Cl-2-thienyl | O | H | H | H | H | |
| 1086 | 3-F—Ph | 5-Cl-2-thienyl | O | H | H | H | H | |
| 1087 | 2,4-F$_2$—Ph | 5-Cl-2-thienyl | O | H | H | H | H | 111-112 |
| 1088 | 3-Cl—Ph | 5-Cl-2-thienyl | O | H | H | H | H | 103-106 |
| 1089 | 2,4-Cl$_2$—Ph | 5-Cl-2-thienyl | O | H | H | H | H | |
| 1090 | 4-Br—Ph | 5-Cl-2-thienyl | O | H | H | H | H | |
| 1091 | 2-CF$_3$—Ph | 5-Cl-2-thienyl | O | H | H | H | H | (oil)$^z$ |
| 1092 | 3-CF$_3$—Ph | 5-Cl-2-thienyl | O | H | H | H | H | (oil)$^{aa}$ |
| 1093 | 4-CF$_3$—Ph | 5-Cl-2-thienyl | O | H | H | H | H | |
| 1094 | Ph | 2,5-Cl$_2$-3-thienyl | O | H | H | H | H | 60-62 |
| 1095 | 2-F—Ph | 2,5-Cl$_2$-3-thienyl | O | H | H | H | H | (oil)$^{ab}$ |
| 1096 | 3-F—Ph | 2,5-Cl$_2$-3-thienyl | O | H | H | H | H | 54-57 |
| 1097 | 4-F—Ph | 2,5-Cl$_2$-3-thienyl | O | H | H | H | H | (oil)$^{ac}$ |
| 1098 | 2,4-F$_2$—Ph | 2,5-Cl$_2$-3-thienyl | O | H | H | H | H | (oil)$^{ad}$ |
| 1099 | 2-Cl—Ph | 2,5-Cl$_2$-3-thienyl | O | H | H | H | H | |
| 1100 | 3-Cl—Ph | 2,5-Cl$_2$-3-thienyl | O | H | H | H | H | (oil)$^{ae}$ |
| 1101 | 4-Cl—Ph | 2,5-Cl$_2$-3-thienyl | O | H | H | H | H | |
| 1102 | 2,4-Cl$_2$—Ph | 2,5-Cl$_2$-3-thienyl | O | H | H | H | H | |
| 1103 | 4-Br—Ph | 2,5-Cl$_2$-3-thienyl | O | H | H | H | H | |
| 1104 | 2-CF$_3$—Ph | 2,5-Cl$_2$-3-thienyl | O | H | H | H | H | |
| 1105 | 3-CF$_3$—Ph | 2,5-Cl$_2$-3-thienyl | O | H | H | H | H | |
| 1106 | 4-CF$_3$—Ph | 2,5-Cl$_2$-3-thienyl | O | H | H | H | H | |
| 1107 | Ph | 5-bromo-2-thienyl | O | H | H | H | H | |
| 1108 | 2-F—Ph | 5-bromo-2-thienyl | O | H | H | H | H | |
| 1109 | 3-F—Ph | 5-bromo-2-thienyl | O | H | H | H | H | |
| 1110 | 4-F—Ph | 5-bromo-2-thienyl | O | H | H | H | H | |

TABLE 1-continued

| No. | | | | | | | | |
|---|---|---|---|---|---|---|---|---|
| 1111 | 2,4-F$_2$—Ph | 5-bromo-2-thienyl | O | H | H | H | H | H |
| 1112 | 2-Cl—Ph | 5-bromo-2-thienyl | O | H | H | H | H | H |
| 1113 | 3-Cl—Ph | 5-bromo-2-thienyl | O | H | H | H | H | H |
| 1114 | 4-Cl—Ph | 5-bromo-2-thienyl | O | H | H | H | H | H |
| 1115 | 2,4-Cl$_2$—Ph | 5-bromo-2-thienyl | O | H | H | H | H | H |
| 1116 | 4-Br—Ph | 5-bromo-2-thienyl | O | H | H | H | H | H |
| 1117 | 2-CF$_3$—Ph | 5-bromo-2-thienyl | O | H | H | H | H | H |
| 1118 | 3-CF$_3$—Ph | 5-bromo-2-thienyl | O | H | H | H | H | H |
| 1119 | 4-CF$_3$—Ph | 5-bromo-2-thienyl | O | H | H | H | H | H |
| 1120 | Ph | 2-pyridyl | O | H | H | H | H | H |
| 1121 | 2-F—Ph | 2-pyridyl | O | H | H | H | H | H |
| 1122 | 3-F—Ph | 2-pyridyl | O | H | H | H | H | H |
| 1123 | 2,4-F$_2$—Ph | 2-pyridyl | O | H | H | H | H | H |
| 1124 | 2-Cl—Ph | 2-pyridyl | O | H | H | H | H | H |
| 1125 | 3-Cl—Ph | 2-pyridyl | O | H | H | H | H | H |
| 1126 | 4-Cl—Ph | 2-pyridyl | O | H | H | H | H | H |
| 1127 | 2,4-Cl$_2$—Ph | 2-pyridyl | O | H | H | H | H | H |
| 1128 | 4-Br—Ph | 2-pyridyl | O | H | H | H | H | H |
| 1129 | 2-CF$_3$—Ph | 2-pyridyl | O | H | H | H | H | H |
| 1130 | 3-CF$_3$—Ph | 2-pyridyl | O | H | H | H | H | H |
| 1131 | 4-CF$_3$—Ph | 2-pyridyl | O | H | H | H | H | H |
| 1132 | Ph | 3-pyridyl | O | H | H | H | H | H |
| 1133 | 2-F—Ph | 3-pyridyl | O | H | H | H | H | H |
| 1134 | 3-F—Ph | 3-pyridyl | O | H | H | H | H | H |
| 1135 | 4-F—Ph | 3-pyridyl | O | H | H | H | H | H |
| 1136 | 2,4-F$_2$—Ph | 3-pyridyl | O | H | H | H | H | H |
| 1137 | 2-Cl—Ph | 3-pyridyl | O | H | H | H | H | H |
| 1138 | 3-Cl—Ph | 3-pyridyl | O | H | H | H | H | H |
| 1139 | 4-Cl—Ph | 3-pyridyl | O | H | H | H | H | H |
| 1140 | 2,4-Cl$_2$—Ph | 3-pyridyl | O | H | H | H | H | H |
| 1141 | 4-Br—Ph | 3-pyridyl | O | H | H | H | H | H |
| 1142 | 2-CF$_3$—Ph | 3-pyridyl | O | H | H | H | H | H |
| 1143 | 3-CF$_3$—Ph | 3-pyridyl | O | H | H | H | H | H |
| 1144 | 4-CF$_3$—Ph | 3-pyridyl | O | H | H | H | H | H |
| 1145 | Ph | 4-pyridyl | O | H | H | H | H | H |
| 1146 | 2-F—Ph | 4-pyridyl | O | H | H | H | H | H |
| 1147 | 3-F—Ph | 4-pyridyl | O | H | H | H | H | H |
| 1148 | 2,4-F$_2$—Ph | 4-pyridyl | O | H | H | H | H | H |
| 1149 | 2-Cl—Ph | 4-pyridyl | O | H | H | H | H | H |
| 1150 | 3-Cl—Ph | 4-pyridyl | O | H | H | H | H | H |
| 1151 | 4-Cl—Ph | 4-pyridyl | O | H | H | H | H | H |
| 1152 | 2,4-Cl$_2$—Ph | 4-pyridyl | O | H | H | H | H | H |
| 1153 | 4-Br—Ph | 4-pyridyl | O | H | H | H | H | H |
| 1154 | 2-CF$_3$—Ph | 4-pyridyl | O | H | H | H | H | H |
| 1155 | 3-CF$_3$—Ph | 4-pyridyl | O | H | H | H | H | H |
| 1156 | 4-CF$_3$—Ph | 4-pyridyl | O | H | H | H | H | H |
| 1157 | Ph | 2-Cl-3-pyridyl | O | H | H | H | H | H |
| 1158 | 2-F—Ph | 2-Cl-3-pyridyl | O | H | H | H | H | H |
| 1159 | 3-F—Ph | 2-Cl-3-pyridyl | O | H | H | H | H | H |
| 1160 | 4-F—Ph | 2-Cl-3-pyridyl | O | H | H | H | H | H |
| 1161 | 2,4-F$_2$—Ph | 2-Cl-3-pyridyl | O | H | H | H | H | H |
| 1162 | 2-Cl—Ph | 2-Cl-3-pyridyl | O | H | H | H | H | H |
| 1163 | 3-Cl—Ph | 2-Cl-3-pyridyl | O | H | H | H | H | H |

TABLE 1-continued

| | | | | | | | | |
|---|---|---|---|---|---|---|---|---|
| 1164 | 4-Cl—Ph | 2-Cl-3-pyridyl | O | H | H | H | H | H |
| 1165 | 2,4-Cl$_2$—Ph | 2-Cl-3-pyridyl | O | H | H | H | H | H |
| 1166 | 4-Br—Ph | 2-Cl-3-pyridyl | O | H | H | H | H | H |
| 1167 | 2-CF$_3$—Ph | 2-Cl-3-pyridyl | O | H | H | H | H | H |
| 1168 | 3-CF$_3$—Ph | 2-Cl-3-pyridyl | O | H | H | H | H | H |
| 1169 | 4-CF$_3$—Ph | 2-Cl-3-pyridyl | O | H | H | H | H | H |
| 1170 | Ph | 3-Cl-2-pyridyl | O | H | H | H | H | H |
| 1171 | 2-F—Ph | 3-Cl-2-pyridyl | O | H | H | H | H | H |
| 1172 | 3-F—Ph | 3-Cl-2-pyridyl | O | H | H | H | H | H |
| 1173 | 4-F—Ph | 3-Cl-2-pyridyl | O | H | H | H | H | H |
| 1174 | 2,4-F$_2$—Ph | 3-Cl-2-pyridyl | O | H | H | H | H | H |
| 1175 | 2-Cl—Ph | 3-Cl-2-pyridyl | O | H | H | H | H | H |
| 1176 | 3-Cl—Ph | 3-Cl-2-pyridyl | O | H | H | H | H | H |
| 1177 | 4-Cl—Ph | 3-Cl-2-pyridyl | O | H | H | H | H | H |
| 1178 | 2,4-Cl$_2$—Ph | 3-Cl-2-pyridyl | O | H | H | H | H | H |
| 1179 | 4-Br—Ph | 3-Cl-2-pyridyl | O | H | H | H | H | H |
| 1180 | 2-CF$_3$—Ph | 3-Cl-2-pyridyl | O | H | H | H | H | H |
| 1181 | 3-CF$_3$—Ph | 3-Cl-2-pyridyl | O | H | H | H | H | H |
| 1182 | 4-CF$_3$—Ph | 3-Cl-2-pyridyl | O | H | H | H | H | H |
| 1183 | 2-F—Ph | 5-Cl-2-pyridyl | O | H | H | H | H | H |
| 1184 | 3-F—Ph | 5-Cl-2-pyridyl | O | H | H | H | H | H |
| 1185 | 2,4-F$_2$—Ph | 5-Cl-2-pyridyl | O | H | H | H | H | H |
| 1186 | 3-Cl—Ph | 5-Cl-2-pyridyl | O | H | H | H | H | H |
| 1187 | 2,4-Cl$_2$—Ph | 5-Cl-2-pyridyl | O | H | H | H | H | H |
| 1188 | 4-Br—Ph | 5-Cl-2-pyridyl | O | H | H | H | H | H |
| 1189 | 2-CF$_3$—Ph | 5-Cl-2-pyridyl | O | H | H | H | H | H |
| 1190 | 3-CF$_3$—Ph | 5-Cl-2-pyridyl | O | H | H | H | H | H |
| 1191 | 4-CF$_3$—Ph | 5-Cl-2-pyridyl | O | H | H | H | H | H |
| 1192 | Ph | 6-Cl-3-pyridyl | O | H | H | H | H | H |
| 1193 | 2-F—Ph | 6-Cl-3-pyridyl | O | H | H | H | H | H |
| 1194 | 3-F—Ph | 6-Cl-3-pyridyl | O | H | H | H | H | H |
| 1195 | 4-F—Ph | 6-Cl-3-pyridyl | O | H | H | H | H | H |
| 1196 | 2,4-F$_2$—Ph | 6-Cl-3-pyridyl | O | H | H | H | H | H |
| 1197 | 2-Cl—Ph | 6-Cl-3-pyridyl | O | H | H | H | H | H |
| 1198 | 3-Cl—Ph | 6-Cl-3-pyridyl | O | H | H | H | H | H |
| 1199 | 4-Cl—Ph | 6-Cl-3-pyridyl | O | H | H | H | H | H |
| 1200 | 2,4-Cl$_2$—Ph | 6-Cl-3-pyridyl | O | H | H | H | H | H |
| 1201 | 4-Br—Ph | 6-Cl-3-pyridyl | O | H | H | H | H | H |
| 1202 | 2-CF$_3$—Ph | 6-Cl-3-pyridyl | O | H | H | H | H | H |
| 1203 | 3-CF$_3$—Ph | 6-Cl-3-pyridyl | O | H | H | H | H | H |
| 1204 | 4-CF$_3$—Ph | 6-Cl-3-pyridyl | O | H | H | H | H | H |
| 1205 | 2-thienyl | 2-thienyl | O | H | H | H | H | H |
| 1206 | 3-thienyl | 2-thienyl | O | H | H | H | H | H |
| 1207 | 2-Cl-3-thienyl | 2-thienyl | O | H | H | H | H | H |
| 1208 | 5-Cl-2-thienyl | 2-thienyl | O | H | H | H | H | H |
| 1209 | 2,5-Cl$_2$-3-thienyl | 2-thienyl | O | H | H | H | H | H |
| 1210 | 2-thienyl | 3-thienyl | O | H | H | H | H | H |
| 1211 | 3-thienyl | 3-thienyl | O | H | H | H | H | H |
| 1212 | 2-Cl-3-thienyl | 3-thienyl | O | H | H | H | H | H |
| 1213 | 5-Cl-2-thienyl | 3-thienyl | O | H | H | H | H | H |
| 1214 | 2,5-Cl$_2$-3-thienyl | 3-thienyl | O | H | H | H | H | H |
| 1215 | 2-thienyl | 2-Cl-3-thienyl | O | H | H | H | H | H |
| 1216 | 3-thienyl | 2-Cl-3-thienyl | O | H | H | H | H | H |

TABLE 1-continued

| # | R1 | R2 | n | | | | | mp |
|---|---|---|---|---|---|---|---|---|
| 1217 | 2-Cl-3-thienyl | 2-Cl-3-thienyl | 0 | H | H | H | H | |
| 1218 | 5-Cl-2-thienyl | 2-Cl-3-thienyl | 0 | H | H | H | H | |
| 1219 | 2,5-Cl₂-3-thienyl | 2-Cl-3-thienyl | 0 | H | H | H | H | |
| 1220 | 2-thienyl | 5-Cl-3-thienyl | 0 | H | H | H | H | |
| 1221 | 3-thienyl | 5-Cl-3-thienyl | 0 | H | H | H | H | |
| 1222 | 2-Cl-3-thienyl | 5-Cl-3-thienyl | 0 | H | H | H | H | |
| 1223 | 5-Cl-2-thienyl | 5-Cl-3-thienyl | 0 | H | H | H | H | |
| 1224 | 2,5-Cl₂-3-thienyl | 5-Cl-3-thienyl | 0 | H | H | H | H | |
| 1225 | 2-thienyl | 2,5-Cl₂-3-thienyl | 0 | H | H | H | H | |
| 1226 | 3-thienyl | 2,5-Cl₂-3-thienyl | 0 | H | H | H | H | |
| 1227 | 2-Cl-3-thienyl | 2,5-Cl₂-3-thienyl | 0 | H | H | H | H | |
| 1228 | 5-Cl-2-thienyl | 2,5-Cl₂-3-thienyl | 0 | H | H | H | H | |
| 1229 | 2,5-Cl₂-3-thienyl | 2,5-Cl₂-3-thienyl | 0 | H | H | H | H | |
| 1230 | thienyl | 5-F-2-thienyl | 0 | H | H | H | H | |
| 1231 | 3-pyridyl | 5-Cl-2-pyridyl | 0 | H | H | H | H | |
| 1232 | 5-Cl-2-pyridyl | 5-Cl-2-pyridyl | 0 | H | H | H | H | |
| 1233 | 4-pyridyl | 5-Cl-2-pyridyl | 0 | H | H | H | H | |
| 1234 | 2-Cl-3-pyridyl | 5-Cl-2-pyridyl | 0 | H | H | H | H | |
| 1235 | 2-pyridyl | 5-Cl-2-pyridyl | 0 | H | H | H | H | |
| 1236 | 4-F—Ph | 4-F—Ph | 0 | H | H | C₂H₅ | H | |
| 1237 | 4-F—Ph | 4-F—Ph | 0 | H | H | n-C₃H₇ | H | |
| 1238 | 4-F—Ph | 4-F—Ph | 0 | H | H | n-C₄H₉ | H | |
| 1239 | 4-F—Ph | 4-F—Ph | 0 | H | H | i-C₃H₇ | H | |
| 1240 | 4-F—Ph | 4-F—Ph | 0 | H | H | s-C₄H₉ | H | |
| 1241 | 2-Cl—Ph | 2-Cl—Ph | 0 | H | H | C₂H₅ | H | |
| 1242 | 2-Cl—Ph | 2-Cl—Ph | 0 | H | H | n-C₃H₇ | H | |
| 1243 | 2-Cl—Ph | 2-Cl—Ph | 0 | H | H | n-C₄H₉ | H | |
| 1244 | 2-Cl—Ph | 2-Cl—Ph | 0 | H | H | i-C₃H₇ | H | |
| 1245 | 2-Cl—Ph | 2-Cl—Ph | 0 | H | H | s-C₄H₉ | H | |
| 1246 | 4-Cl—Ph | 4-Cl—Ph | 0 | H | H | C₂H₅ | H | |
| 1247 | 4-Cl—Ph | 2,4-Cl₂—Ph | 0 | H | H | n-C₃H₇ | H | |
| 1248 | 4-Cl—Ph | 2,4-Cl₂—Ph | 0 | H | H | n-C₄H₉ | H | |
| 1249 | 4-Cl—Ph | 2,4-Cl₂—Ph | 0 | H | H | i-C₃H₇ | H | |
| 1250 | 4-Cl—Ph | 2,4-Cl₂—Ph | 0 | H | H | s-C₄H₉ | H | |
| 1251 | Ph | Ph | 0 | H | H | C₂H₅ | H | |
| 1252 | Ph | Ph | 0 | H | H | n-C₃H₇ | H | |
| 1253 | Ph | Ph | 0 | H | H | n-C₄H₉ | H | |
| 1254 | Ph | Ph | 0 | H | H | i-C₃H₇ | H | |
| 1255 | Ph | Ph | 0 | H | H | s-C₄H₉ | H | |
| 1256 | 4-F—Ph | 4-F—Ph | 0 | H | H | CH₃ | H | |
| 1257 | 4-F—Ph | 4-F—Ph | 0 | H | H | CH₃ | CH₃ | 166-167 |
| 1258 | 4-F—Ph | 4-F—Ph | 0 | H | H | F | H | |
| 1259 | 4-F—Ph | 4-F—Ph | 0 | H | H | F | CH₃ | 145-147 |
| 1260 | 4-F—Ph | 4-F—Ph | 0 | H | H | F | F | |
| 1261 | 4-Cl—Ph | 2,4-Cl₂—Ph | 0 | H | H | CH₃ | H | |
| 1262 | 4-Cl—Ph | 2,4-Cl₂—Ph | 0 | H | H | CH₃ | CH₃ | |
| 1263 | 4-Cl—Ph | 2,4-Cl₂—Ph | 0 | H | H | F | H | |
| 1264 | 4-Cl—Ph | 2,4-Cl₂—Ph | 0 | H | H | F | CH₃ | |
| 1265 | 4-Cl—Ph | 2,4-Cl₂—Ph | 0 | H | H | F | F | |
| 1266 | 2-Cl—Ph | 4-Cl—Ph | 0 | H | H | CH₃ | H | |
| 1267 | 2-Cl—Ph | 4-Cl—Ph | 0 | H | H | CH₃ | CH₃ | |
| 1268 | 2-Cl—Ph | 4-Cl—Ph | 0 | H | H | F | H | |
| 1269 | 2-Cl—Ph | 4-Cl—Ph | 0 | H | H | F | CH₃ | |

TABLE 1-continued

| | | | | | | |
|---|---|---|---|---|---|---|
| 1270 | 2-Cl—Ph | 4-Cl—Ph | H | H | O | F | F |
| 1271 | Ph | 4-F—Ph | H | H | O | CH₃ | H |
| 1272 | Ph | 4-F—Ph | H | H | O | CH₃ | CH₃ |
| 1273 | Ph | 4-F—Ph | H | H | O | F | H |
| 1274 | Ph | 4-F—Ph | H | H | O | F | CH₃ |
| 1275 | Ph | 4-F—Ph | H | H | O | F | F |
| 1997 | Ph | 4-t-Bu—Ph | H | H | O | H | H | 112-114 |
| 1998 | Ph | 2,6-F₂—Ph | H | H | O | H | H | 110-116 |
| 1999 | Ph | 3-CH₃-4-Cl—Ph | H | H | O | H | H | 127.5-129 |
| 2000 | 4-F—Ph | 4-t-Bu—Ph | H | H | O | H | H | 105-107 |
| 2001 | 4-F—Ph | 4-CN—Ph | H | H | O | H | H | 137-139 |
| 2002 | 4-F—Ph | —CF₃ | H | H | O | H | H | (oil)$^{ag}$ |
| 2003 | 2-CF₃—Ph | 3-CF₃—Ph | H | H | O | H | H | (oil)$^{ah}$ |
| 2004 | 4-CH₃—Ph | 2-F—Ph | H | H | O | H | H | 115-118 |
| 2005 | 4-CH₃—Ph | 2-Cl-4-F—Ph | H | H | O | H | H | 111-116 |
| 2006 | Ph | 2,4-F₂—Ph | H | CH₃ | O | H | H | 67-72 |
| 2007 | Ph | 4-Cl—Ph | H | CH₃ | O | H | H | 110.5-111 |
| 2008 | 4-F—Ph | 2-F—Ph | H | CH₃ | O | H | H | 67-72 |
| 2009 | 4-F—Ph | 2,4-Cl₂—Ph | H | H | O | H | H | (oil)$^{ai}$ |
| 2010 | 2-Cl-3-pyridyl, N-oxide | 4-Cl—Ph | H | H | O | H | H | (HCl salt)$^{aj}$ |
| 2011 | 4-Cl-3-pyridyl | 2,4-F₂—Ph | H | H | O | H | H | (oil)$^{ak}$ |
| 2012 | 4-Cl-3-pyridyl | 4-Cl—Ph | H | H | O | H | H | 172-174 |
| 2013 | 4-Cl-3-pyridyl | 2,4-Cl₂—Ph | H | H | O | H | H | (oil)$^{al}$ |
| 2014 | 4-CH₃S-3-1 pyridyl | 4-Cl—Ph | H | H | O | H | H | 138-140 |
| 2015 | 2-Cl-4-pyridyl | 4-Cl—Ph | H | H | O | H | H | (2HCl salt) 170-175 |
| 2016 | 2-CH₃—Ph | 2-Cl-4-F—Ph | H | H | O | H | H | |

$^a$ NMR: (CDCl₃) δ 4.70(q, J=14Hz, 2H), 4.90(s, 1H), 5.55(s, 1H), 5.40(s, 1H), 6.8-7.0(m, 4H), 7.2-7.4(m, 4H), 7.8(bs, 2H).
$^b$ NMR: (CDCl₃) δ 4.8(q, 2H), 5.2(s, 1H), 5.3(s, 1H), 5.6(s, 1H), 6.9-7.6(m, 8H), 7.8(s, 1H), 8.1(s, 1H).
$^c$ NMR: (CDCl₃) δ 4.70(q, J=13Hz, 2H), 4.85(s, 1H), 5.35(s, 1H), 5.55(s, 1H), 6.85-7.4(m, 8H), 7.7(s, H), 7.9(s, 1H).
$^d$ NMR: (CDCl₃) δ 4.60(q, J=12Hz, 2H), 5.0(s, 1H), 5.40(s, 1H), 5.55(s, 1H), 6.8(½ of ABq, J=10Hz, 2H), 7.00(m, 2H), 7.3(½ of ABq, J=10Hz, 2H), 7.45(m, 2H), 7.80(s, 1H), 7.85(s, 1H).
$^e$ NMR: (CDCl₃) δ 4.6, 4.8(ABq, J=14Hz, 2H), 4.9(br s, 3H), 5.3(s, 1H), 5.6(s, 1H), 6.8(d, 1H), 7.0(m, 3H), 7.4(m, 3H), 7.8(s, 1H), 7.9(s, 1H).
$^f$ NMR: (CDCl₃) δ 1.3(s, 9H), 4.7(q, 2H), 4.6(s, 1H), 5.0(s, 1H), 5.4(s, 1H), 6.8-7.4(9H), 7.8(s, 1H).
$^g$ NMR: (CDCl₃) δ 4.7, 4.8(ABq, J=12Hz), 2H), 6.7-7.5(m, 14H), 7.9(s, 1H), 8.0(s, 1H).
$^h$ NMR: (CDCl₃) δ 3.45(s, 3H), 4.75(ABq, J=18Hz, 2H), 4.6(m, 2H), 6.8-7.0(m, 4H), 7.05-7.25(m, 4H), 8.0(s, 1H), 8.25(s, 1H).
$^i$ NMR: (CDCl₃) δ 4.0(dd, 14, 4Hz, 1H), 4.3(dd, 14, 4Hz, 1H), 4.6(d, 13Hz, 1H), 4.9(d, 13Hz, 1H), 5.1(d, 1H), 5.3(d, 1H), 5.55(s, 1H), 5.60 (s, 1H), 5.85(m, 1H), 6.8-7.0(m, 4H), 7.05-7.2(m, 4H), 8.05(s, 1H), 8.25(s, 1H).
$^j$ NMR: (CDCl₃) δ 1.90(s, 3H), 4.80(½ of ABq, J=14Hz, 1H), 5.65(½ of ABq, J=14Hz, 1H), 5.55(s, 1H), 5.60(s, 1H), 6.75-7.0(m, 4H), 7.0-7.2(t, 2H), 7.25-7.4(m, 2H), 7.35(s, 1H), 7.85(s, 1H).
$^k$ NMR: (CDCl₃) δ 4.03, 4.11(ABq, J=11Hz, 2H), 4.25(s, 1H, OH), 4.39(s, 1H, OH), 4.54, 4.81(ABq, J=14Hz, 2H), 5.31, 5.33(2 sharp s, 1H each), 7.25-7.40(m, 4H), 7.71(s, 1H), 8.03(s, 1H).
$^l$ NMR: (CDCl₃) δ 2.03(s, 1H, OH), 4.0-4.2(m, 2H), 4.57, 4.85(ABq, J=15Hz, 2H), 5.7-5.9(broad s, 1H, OH), 7.3-7.6(m, 4H), 7.75(s, 1H), 8.11(s, 1H).
$^m$ NMR: (CDCl₃) δ 2.10(s, 6H), 2.52, 3.03(ABq, J=12Hz, 2H), 4.41, 4.78(ABq, J=12Hz, 2H), 5.19(s, 1H), 5.50(s, 1H), 6.9-7.2(m, 2H), 7.4-7.6(m, 2H), 7.80(s, 1H), 8.36(s, 1H).
$^n$ NMR: (CDCl₃) δ 2.11(s, 6H), 2.61, 3.11(ABq, J=12Hz, 2H), 4.50, 4.90(ABq, J=13Hz, 2H), 5.13(s, 1H), 5.50(s, 1H), 7.50(s, 4H), 7.86(s, 1H), 8.14(s, 1H).
$^o$ NMR: (CDCl₃) δ 2.13(s, 3H), 2.19(s, 3H), 2.5-3.1(m, 2H), 4.44, 4.85(ABq, J=14Hz, 2H), 5.3(two s, 2H), 6.9-7.6(m, 9H), 7.3-7.8(m, 9H), 7.97(s, 1H), 8.32(s, 1H, OH), 8.50(s, 1H).
$^p$ NMR: (CDCl₃) δ 4.6(d, ½ of ABq, 1H), 4.9(d, ½ of ABq, 1H), 5.0(s, 1H), 5.3(two s, 2H), 6.9-7.6(m, 9H), 7.8(two s, 2H).
$^q$ NMR: (CDCl₃) δ 1.0(t, 3H), 1.2(s, 1H), 1.6(m, 2H), 4.2(ABq, 2H), 5.1(s, 1H), 5.4(s, 1H), 6.9-7.1(m, 4H), 7.9(s, 1H), 8.0(s, 1H).
$^r$ NMR: (CDCl₃) δ 4.6(AB, 2H), 4.6(d, 1H), 5.3(s, 1H), 5.5(s, 1H), 7.2(m, 1H), 7.6(m, 7H), 7.7(m, 1H), 7.7(s, 1H), 7.8(s, 1H).
$^s$ NMR: (CDCl₃) δ 4.6(½ of AB, J=13, 1H), 5.0(½ of AB, J=13, 1H), 5.2(s, 1H), 5.4(s, 1H), 7.0(m, 2H), 7.2(m, 1H), 7.4(m, 5H), 7.8(s, 1H), 7.82(s, 1H).

TABLE 1-continued

*t* NMR: (CDCl₃) δ 4.6(½ ABq, 1H), 5.3(s), 5.4(½ of ABq + s + br, 4H total), 7.1(m, 1H), 7.3(m, 1H), 7.5(m, 5H), 7.8(s, 2H).
*u* NMR: (CDCl₃) δ 4.4(½ of AB, 1H), 5.7(½ of AB, 1H), 5.1(s, 1H), 5.3(s, 1H), 5.4(s, 1H), 7.2(m, 3H), 7.3(m, 2H), 7.4(d, 1H), 7.6(m, 1H), 7.7(s, 1H), 7.9(s, 1H).
*v* NMR: (CDCl₃) δ 4.4(s, 2H), 4.8(s, 1H), 5.1(s, 1H), 5.5(s, 1H), 6.3(d, 1H), 6.5(d, 1H), 6.8–7.2(m, 4H), 7.6(s, 1H), 7.7(s, 1H).
*w* NMR: (CDCl₃) δ 4.7(dd, 2H), 5.4(s, 1H), 5.6(s, 1H), 6.7(d, 1H), 7.0(d, 1H), 7.2(m), 8.0(s, 1H), 8.2(s, 1H).
*x* NMR: (CDCl₃) δ 1.6(two s, 6H total), 4.3(½ of ABq, 1H), 4.6(½ of ABq, 1H), 5.0(d, 1H), 5.2(d, 1H), 5.3(s, 1H), 6.7–7.6(m, 8H), 7.9(s, 1H), 8.1(s, 1H).
*y* NMR: (CDCl₃) δ 4.7(s, 2H), 5.3(s, 1H), 5.8(s, 1H), 6.9(m, 3H), 7.1(m, 1H), 7.2(m, 1H), 7.4(s, 1H), 7.9(s, 1H), 8.1(s, 1H).
*z* NMR: (CDCl₃) δ 4.6(dd, 2H), 5.2(s, 1H), 5.4(s, 1H), 5.6(s, 1H), 6.7(d, 1H), 6.8(d, 1H), 7.4–7.6(m, 4H), 7.9(s, 1H), 7.9(s, 1H).
*aa* NMR: (CDCl₃) δ 4.6(d, 1H), 5.0(d, 1H), 5.2(s, 1H), 5.3(s, 1H), 5.4(s, 1H), 6.8(s, 1H), 7.2(m, 5H), 7.9(s, 2H).
*ab* NMR: (CDCl₃) δ 4.4(d, 1H), 5.3(d, 1H), 5.3(s, 1H), 5.6(s, 1H), 6.8(s, 1H), 7.2–7.4(m, 4H), 7.8(s, 1H), 8.1(s, 1H).
*ac* NMR: (CDCl₃) δ 4.6(d, 1H), 5.1(d, 1H), 5.3(s, 1H), 5.35(s, 1H), 5.6(s, 1H), 6.8(s, 1H), 7.2(m, 4H), 7.9(s, 1H), 8.1(s, 1H).
*ad* NMR: (CDCl₃) δ 4.6(d, 1H), 5.3(d, 1H), 5.3(s, 1H), 5.6(s, 1H), 6.8(s, 1H), 7.2(m, 2H), 7.4(s, 1H), 7.9(s, 1H), 8.1(s, 1H).
*af* NMR: (CDCl₃) δ 4.7(bs, 1H), 4.9(bs, 1H), 5.33(2s, 2H), 6.75(d, 2H), 7.12(m, 4H), 7.45(s, 1H), 7.83(s, 1H), 8.00(s, 1H), 8.33(d, 2H).
*ag* NMR: (CDCl₃) δ 4.6(s, 2H), 5.4(s, 1H), 5.56(s, 1H), 5.8(s, 1H), 6.8–7.0(m, 3H), 7.3–7.4(m, 1H), 8.0, 8.1(two s, 2H).
*ah* NMR: (CDCl₃) δ 4.6(ABq, 2H), 5.2(s, OH), 5.3(s, 1H), 5.4(s, 1H), 5.7(s, 1H), 6.6–7.2(m), 7.7(s, 1H), 7.8(s, 1H).
*ai* NMR: (CDCl₃) δ 3.6(s, 3H), 4.7–5.0(ABq, 2H), 5.4(s, 1H), 5.33(s, 1H), 5.73(s, 1H), 6.72(d, 1H), 7.00(t, 1H), 7.32(ABq, 4H), 7.77(s, 1H), 8.13(s, 1H), 8.18(d, 1H).
*aj* NMR: (free base, CDCl₃) δ 4.77(s, 2H), 5.27(s, 1H), 5.30(d, 1H), 5.42(s, 1H), 5.50(s, 1H), 6.75(m, 2H), 7.23(d, 1H), 7.43(q, 1H), 7.67(dd, 1H), 7.83(s, 1H), 8.28(d, 1H).
*ak* NMR: (CDCl₃) δ 4.63(d, 1H), 5.03(d, 1H), 5.40(s, 1H), 5.46(s, 1H), 5.45(d, 2H), 7.00–7.27(m, 3H), 7.43(d, 1H), 7.67–7.83(m, 3H), 7.88(s, 1H), 8.33(d, 1H).
*al* NMR: (CDCl₃) δ 4.67(d, 1H), 5.40(d, 1H), 5.3(s, 2H), 5.45(d, 1H), 6.8(m, 2H), 7.3–7.6(m, 6H), 7.7(s, 1H), 7.8(d, 1H), 8.0(s, 1H), 8.33(d, 1H).
*am* NMR: (CDCl₃) δ 4.7(½ of ABq, 1H), 5.0(½ of ABq, 1H), 5.2–5.3(three s, 3H), 6.8(m, 2H), 7.5(m, 6H), 7.8(m, 3H), 8.6(d, 1H), 8.7(s, 1H).
*an* NMR: (CDCl₃) δ 4.6(½ of ABq, 1H), 5.0(½ of ABq, 1H), 5.2–5.3(three s, 3H), 6.8(m, 2H), 7.5(m, 6H), 7.8(m, 3H), 8.6(d, 1H), 8.8(s, 1H).

EXAMPLES 1276 and 1276a

These compounds and other compounds which were resolved as described above are shown in Table 2.

TABLE 2

$$A(CH_2)_n\overset{CRR^1}{\underset{\underset{B}{|}}{C}}\overset{OR^2}{\underset{\circ}{C}}-\overset{R^3}{\underset{R^4}{C}}-N\overset{N}{\underset{N}{\diagdown}}$$

| Ex. No. | A | B | n | R | R¹ | R² | R³ | R⁴ | M.P. °C. | [α]$_D^{25}$ |
|---|---|---|---|---|---|---|---|---|---|---|
| 1276 | phenyl | 4-F-phenyl | 0 | H | H | H | H | H | 82–83 | −62° |
| 1276a$^{(1)}$ | phenyl | 4-F-phenyl | 0 | H | H | H | H | H | 83–84 | +60° |
| 1277$^{(2)}$ | 4-F-phenyl | 4-F-phenyl | 0 | H | H | H | H | H | 60–61 (HCl salt 181–184) | −67° |
| 1277a$^{(1),(2)}$ | 4-F-phenyl | 4-F-phenyl | 0 | H | H | H | H | H | 60–62 | +66° |

*denotes chiral center
$^{(1)}=$ substitute d-α-bromocamphor-π-sulfonic acid
$^{(2)}=$ use a 3 parts ether - 1 part acetone mixture as solvent.

Preparation of the (S)-enantiomer of Example 49

The compound of Example 49 (1.5 g) and 1.5 g of l-α-bromocamphor-π-sulfuric acid was dissolved in 75 ml of acetonitrile and refluxed for 2 hours. The solution was allowed to cool to ambient temperature and stand for 14 hours. Filtration of the resulting solids followed by recrystallization from an additional portion of acetonitrile, yielded 1.28 g of white solid, mp 216°–217°; [α]$_{25}^D$=104° (C=1; DMSO).

The acetonitrile can be evaporated to yield the adduct having a (+)- rotation (Example 1276a). This compound can be recrystallized from an ether/acetone mixture to yield a solid, that on treatment with aqueous NaHCO$_3$ yields material identical by NMR to that of Example 49.

The solid was suspended in 50 ml of saturated NaHCO$_3$ solution and stirrred vigorously until the evolution of gas ceased (1-2 hours). The mixture was extracted twice with 50 ml of CHCl$_3$. The organic layers were combined, washed with brine, dried over Na$_2$SO$_4$ and the solvent removed in vacuo. This yielded 750 mg of a white solid (Example 1276) having an 'H NMR identical to that of the compound of Example 49, mp=82°–83°; [α]$_{25}^D$= −62° (C=1; CHCl$_3$).

EXAMPLE 1278

Preparation of 2-(4-fluorophenyl)-3-phenyl-1-(5-mercapto-1H-1,2,4-triazol-1-yl) -3-buten-1-ol To a solution of 1.24 g (0.004 mol) of 2-(4-fluorophenyl)-3-phenyl-1-(1H-1,2,4-triazol -1-yl)-3-buten-2-ol in 15 mL of THF at −70° was added 5.2 mL (0.008 mol) of a 1.55 M solution of n-butyllithium in hexanes over 5 minutes. After 30 minutes, 0.13 g (0.004 mol) of sulfur was added and the reaction mixture was allowed to warm to room temperature over 1 h, then quenched with 8 mL of 1N HCl. After pouring into saturated NH$_4$Cl, the mixture was extracted with 2 x ether and the combined organic layers were washed with brine, dried over Na$_2$SO$_4$ and evaporated. The crude product was purified by flash chromatography using 2:13:85 methanol/ether/methylene chloride to give 0.85 g of the title compound, m.p. 54°–58°; NMR (CDCl$_3$)δ4.7 (ABq, 2H), 5.0 (s, 1H, OH), 5.3 (s, 1H, vinyl), 5.5 (s, 1H, vinyl), 7.0 (m, 4H), 7.2 (m, 3H), 7.5 (m, 2H), 7.7 (s, 1H, triazole proton), 12.5 (brs, 1H, SH), IR (methylene chloride) 3500–3000 (br), 1590, 1500, 1465, 1230, 1162, 1109, 825 cm$^{-1}$; MS: highest m/e b 341.

The compounds shown in Table 3 were prepared or can be prepared by the methods described above.

TABLE 3*

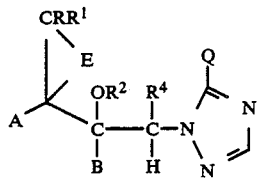

| Ex. No. | A | B | R | R¹ | R² | R⁴ | Q | M.P. °C. |
|---|---|---|---|---|---|---|---|---|
| 1278 | Ph | 4-F-Ph | H | H | H | H | SH | 54–58 |
| 1279 | Ph | Ph | H | H | H | H | SH | |
| 1280 | Ph | 2-F-Ph | H | H | H | H | SH | |
| 1281 | Ph | 2-Cl-Ph | H | H | H | H | SH | |
| 1282 | Ph | 4-Cl-Ph | H | H | H | H | SH | |
| 1283 | Ph | 2,4-F$_2$-Ph | H | H | H | H | SH | |
| 1284 | Ph | 2,4-Cl$_2$-Ph | H | H | H | H | SH | |
| 1285 | 2-F-Ph | Ph | H | H | H | H | SH | |
| 1286 | 2-F-Ph | 2-F-Ph | H | H | H | H | SH | |
| 1287 | 2-F-Ph | 4-F-Ph | H | H | H | H | SH | |
| 1288 | 2-F-Ph | 2-Cl-Ph | H | H | H | H | SH | |
| 1289 | 2-F-Ph | 4-Cl-Ph | H | H | H | H | SH | |
| 1290 | 2-F-Ph | 2,4-F$_2$-Ph | H | H | H | H | SH | |
| 1291 | 2-F-Ph | 2,4-Cl$_2$-Ph | H | H | H | H | SH | |
| 1292 | 3-F-Ph | Ph | H | H | H | H | SH | |
| 1293 | 3-F-Ph | 2-F-Ph | H | H | H | H | SH | |
| 1294 | 3-F-Ph | 4-F-Ph | H | H | H | H | SH | |
| 1295 | 3-F-Ph | 2-Cl-Ph | H | H | H | H | SH | |
| 1296 | 3-F-Ph | 4-Cl-Ph | H | H | H | H | SH | |
| 1297 | 3-F-Ph | 2,4-F$_2$-Ph | H | H | H | H | SH | |
| 1298 | 3-F-Ph | 2,4-Cl$_2$-Ph | H | H | H | H | SH | |
| 1299 | 4-F-Ph | Ph | H | H | H | H | SH | |
| 1300 | 4-F-Ph | 2-F-Ph | H | H | H | H | SH | 144.5–148 |
| 1301 | 4-F-Ph | 4-F-Ph | H | H | H | H | SH | |
| 1302 | 4-F-Ph | 2-Cl-Ph | H | H | H | H | SH | |
| 1303 | 4-F-Ph | 4-Cl-Ph | H | H | H | H | SH | |
| 1304 | 4-F-Ph | 2,4-F$_2$-Ph | H | H | H | H | SH | (foam)[a] |
| 1305 | 4-F-Ph | 2,4-Cl$_2$-Ph | H | H | H | H | SH | |
| 1306 | 2-Cl-Ph | Ph | H | H | H | H | SH | |
| 1307 | 2-Cl-Ph | 2-F-Ph | H | H | H | H | SH | |
| 1308 | 2-Cl-Ph | 4-F-Ph | H | H | H | H | SH | |
| 1309 | 2-Cl-Ph | 2-Cl-Ph | H | H | H | H | SH | |
| 1310 | 2-Cl-Ph | 4-Cl-Ph | H | H | H | H | SH | |
| 1311 | 2-Cl-Ph | 2,4-F$_2$-Ph | H | H | H | H | SH | |
| 1312 | 2-Cl-Ph | 2,4-Cl$_2$-Ph | H | H | H | H | SH | |
| 1313 | 3-Cl-Ph | Ph | H | H | H | H | SH | |
| 1314 | 3-Cl-Ph | 2-F-Ph | H | H | H | H | SH | |
| 1315 | 3-Cl-Ph | 4-F-Ph | H | H | H | H | SH | |
| 1316 | 3-Cl-Ph | 2-Cl-Ph | H | H | H | H | SH | |
| 1317 | 3-Cl-Ph | 4-Cl-Ph | H | H | H | H | SH | |
| 1318 | 3-Cl-Ph | 2,4-F$_2$-Ph | H | H | H | H | SH | |
| 1319 | 3-Cl-Ph | 2,4-Cl$_2$-Ph | H | H | H | H | SH | |
| 1320 | 4-Cl-Ph | Ph | H | H | H | H | SH | |
| 1321 | 4-Cl-Ph | 2-F-Ph | H | H | H | H | SH | |
| 1322 | 4-Cl-Ph | 4-F-Ph | H | H | H | H | SH | |
| 1323 | 4-Cl-Ph | 2-Cl-Ph | H | H | H | H | SH | |
| 1324 | 4-Cl-Ph | 4-Cl-Ph | H | H | H | H | SH | |
| 1325 | 4-Cl-Ph | 2,4-F$_2$-Ph | H | H | H | H | SH | |
| 1326 | 4-Cl-Ph | 2,4-Cl$_2$-Ph | H | H | H | H | SH | |
| 1327 | 2-CF$_3$-Ph | Ph | H | H | H | H | SH | |
| 1328 | 2-CF$_3$-Ph | 2-F-Ph | H | H | H | H | SH | |
| 1329 | 2-CF$_3$-Ph | 4-F-Ph | H | H | H | H | SH | |
| 1330 | 2-CF$_3$-Ph | 2-Cl-Ph | H | H | H | H | SH | |
| 1331 | 2-CF$_3$-Ph | 4-Cl-Ph | H | H | H | H | SH | |
| 1332 | 2-CF$_3$-Ph | 2,4-F$_2$-Ph | H | H | H | H | SH | |
| 1333 | 2-CF$_3$-Ph | 2,4-Cl$_2$-Ph | H | H | H | H | SH | |
| 1334 | 4-CF$_3$-Ph | Ph | H | H | H | H | SH | |
| 1335 | 4-CF$_3$-Ph | 2-F-Ph | H | H | H | H | SH | |
| 1336 | 4-CF$_3$-Ph | 4-F-Ph | H | H | H | H | SH | |
| 1337 | 4-CF$_3$-Ph | 2-Cl-Ph | H | H | H | H | SH | |
| 1338 | 4-CF$_3$-Ph | 4-Cl-Ph | H | H | H | H | SH | |
| 1339 | 4-CF$_3$-Ph | 2,4-F$_2$-Ph | H | H | H | H | SH | |
| 1340 | 4-CF$_3$-Ph | 2,4-Cl$_2$-Ph | H | H | H | H | SH | |
| 1341 | 2,4-F$_2$-Ph | Ph | H | H | H | H | SH | |
| 1342 | 2,4-F$_2$-Ph | 2-F-Ph | H | H | H | H | SH | |
| 1343 | 2,4-F$_2$-Ph | 4-F-Ph | H | H | H | H | SH | |
| 1344 | 2,4-F$_2$-Ph | 2-Cl-Ph | H | H | H | H | SH | |
| 1345 | 2,4-F$_2$-Ph | 4-Cl-Ph | H | H | H | H | SH | |
| 1346 | 2,4-F$_2$-Ph | 2,4-F$_2$-Ph | H | H | H | H | SH | |
| 1347 | 2,4-F$_2$-Ph | 2,4-Cl$_2$-Ph | H | H | H | H | SH | |

TABLE 3*-continued structure: A-C(B)(OR²)-C(H)(R⁴)-N(triazole with Q), with CRR¹ and E branch

| Ex. No. | A | B | R | R¹ | R² | R⁴ | Q | M.P. °C. |
|---|---|---|---|---|---|---|---|---|
| 1348 | 2,4-Cl₂-Ph | Ph | H | H | H | H | SH | |
| 1349 | 2,4-Cl₂-Ph | 2-F-Ph | H | H | H | H | SH | |
| 1350 | 2,4-Cl₂-Ph | 4-F-Ph | H | H | H | H | SH | |
| 1351 | 2,4-Cl₂-Ph | 2-Cl-Ph | H | H | H | H | SH | |
| 1352 | 2,4-Cl₂-Ph | 4-Cl-Ph | H | H | H | H | SH | |
| 1353 | 2,4-Cl₂-Ph | 2,4-F₂-Ph | H | H | H | H | SH | |
| 1354 | 2,4-Cl₂-Ph | 2,4-Cl₂-Ph | H | H | H | H | SH | |
| 1355 | Ph | Ph | H | H | H | H | I | |
| 1356 | Ph | 2-F-Ph | H | H | H | H | I | |
| 1357 | Ph | 4-F-Ph | H | H | H | H | I | |
| 1358 | Ph | 2-Cl-Ph | H | H | H | H | I | |
| 1359 | Ph | 4-Cl-Ph | H | H | H | H | I | |
| 1360 | Ph | 2,4-F₂-Ph | H | H | H | H | I | |
| 1361 | Ph | 2,4-Cl₂-Ph | H | H | H | H | I | |
| 1362 | 2-F-Ph | Ph | H | H | H | H | I | |
| 1363 | 2-F-Ph | 2-F-Ph | H | H | H | H | I | |
| 1364 | 2-F-Ph | 4-F-Ph | H | H | H | H | I | |
| 1365 | 2-F-Ph | 2-Cl-Ph | H | H | H | H | I | |
| 1366 | 2-F-Ph | 4-Cl-Ph | H | H | H | H | I | |
| 1367 | 2-F-Ph | 2,4-F₂-Ph | H | H | H | H | I | |
| 1368 | 2-F-Ph | 2,4-Cl₂-Ph | H | H | H | H | I | |
| 1369 | 3-F-Ph | Ph | H | H | H | H | I | |
| 1370 | 3-F-Ph | 2-F-Ph | H | H | H | H | I | |
| 1371 | 3-F-Ph | 4-F-Ph | H | H | H | H | I | |
| 1372 | 3-F-Ph | 2-Cl-Ph | H | H | H | H | I | |
| 1373 | 3-F-Ph | 4-Cl-Ph | H | H | H | H | I | |
| 1374 | 3-F-Ph | 2,4-F₂-Ph | H | H | H | H | I | |
| 1375 | 3-F-Ph | 2,4-Cl₂-Ph | H | H | H | H | I | |
| 1376 | 4-F-Ph | Ph | H | H | H | H | I | |
| 1377 | 4-F-Ph | 2-F-Ph | H | H | H | H | I | 96–97.5 |
| 1378 | 4-F-Ph | 4-F-Ph | H | H | H | H | I | |
| 1379 | 4-F-Ph | 2-Cl-Ph | H | H | H | H | I | |
| 1380 | 4-F-Ph | 4-Cl-Ph | H | H | H | H | I | |
| 1381 | 4-F-Ph | 2,4-F₂-Ph | H | H | H | H | I | (foam)[b] |
| 1382 | 4-F-Ph | 2,4-Cl₂-Ph | H | H | H | H | I | |
| 1383 | 2-Cl-Ph | Ph | H | H | H | H | I | |
| 1384 | 2-Cl-Ph | 2-F-Ph | H | H | H | H | I | |
| 1385 | 2-Cl-Ph | 4-F-Ph | H | H | H | H | I | |
| 1386 | 2-Cl-Ph | 2-Cl-Ph | H | H | H | H | I | |
| 1387 | 2-Cl-Ph | 4-Cl-Ph | H | H | H | H | I | |
| 1388 | 2-Cl-Ph | 2,4-F₂-Ph | H | H | H | H | I | |
| 1389 | 2-Cl-Ph | 2,4-Cl₂-Ph | H | H | H | H | I | |
| 1390 | 3-Cl-Ph | Ph | H | H | H | H | I | |
| 1391 | 3-Cl-Ph | 2-F-Ph | H | H | H | H | I | |
| 1392 | 3-Cl-Ph | 4-F-Ph | H | H | H | H | I | |
| 1393 | 3-Cl-Ph | 2-Cl-Ph | H | H | H | H | I | |
| 1394 | 3-Cl-Ph | 4-Cl-Ph | H | H | H | H | I | |
| 1395 | 3-Cl-Ph | 2,4-F₂-Ph | H | H | H | H | I | |
| 1396 | 3-Cl-Ph | 2,4-Cl₂-Ph | H | H | H | H | I | |
| 1397 | 4-Cl-Ph | Ph | H | H | H | H | I | |
| 1398 | 4-Cl-Ph | 2-F-Ph | H | H | H | H | I | |
| 1399 | 4-Cl-Ph | 4-F-Ph | H | H | H | H | I | |
| 1400 | 4-Cl-Ph | 2-Cl-Ph | H | H | H | H | I | |
| 1401 | 4-Cl-Ph | 4-Cl-Ph | H | H | H | H | I | |
| 1402 | 4-Cl-Ph | 2,4-F₂-Ph | H | H | H | H | I | |
| 1403 | 4-Cl-Ph | 2,4-Cl₂-Ph | H | H | H | H | I | |
| 1404 | 2-CF₃-Ph | Ph | H | H | H | H | I | |
| 1405 | 2-CF₃-Ph | 2-F-Ph | H | H | H | H | I | |
| 1406 | 2-CF₃-Ph | 4-F-Ph | H | H | H | H | I | |
| 1407 | 2-CF₃-Ph | 2-Cl-Ph | H | H | H | H | I | |
| 1408 | 2-CF₃-Ph | 4-Cl-Ph | H | H | H | H | I | |
| 1409 | 2-CF₃-Ph | 2,4-F₂-Ph | H | H | H | H | I | |
| 1410 | 2-CF₃-Ph | 2,4-Cl₂-Ph | H | H | H | H | I | |
| 1411 | 4-CF₃-Ph | Ph | H | H | H | H | I | |
| 1412 | 4-CF₃-Ph | 2-F-Ph | H | H | H | H | I | |
| 1413 | 4-CF₃-Ph | 4-F-Ph | H | H | H | H | I | |
| 1414 | 4-CF₃-Ph | 2-Cl-Ph | H | H | H | H | I | |
| 1415 | 4-CF₃-Ph | 4-Cl-Ph | H | H | H | H | I | |
| 1416 | 4-CF₃-Ph | 2,4-F₂-Ph | H | H | H | H | I | |
| 1417 | 4-CF₃-Ph | 2,4-Cl₂-Ph | H | H | H | H | I | |

TABLE 3*-continued $$\underset{B}{\overset{\underset{\displaystyle A}{\overset{\displaystyle CRR^1}{\underset{\displaystyle |}{E}}}}{\overset{|}{C}}}\underset{|}{\overset{OR^2}{\underset{\displaystyle |}{C}}}\underset{H}{\overset{R^4}{\underset{\displaystyle |}{C}}}-N\underset{N}{\overset{Q}{\diagdown}}$$

| Ex. No. | A | B | R | R¹ | R² | R⁴ | Q | M.P. °C. |
|---|---|---|---|---|---|---|---|---|
| 1418 | 2,4-F₂-Ph | Ph | H | H | H | H | I | |
| 1419 | 2,4-F₂-Ph | 2-F-Ph | H | H | H | H | I | |
| 1420 | 2,4-F₂-Ph | 4-F-Ph | H | H | H | H | I | |
| 1421 | 2,4-F₂-Ph | 2-Cl-Ph | H | H | H | H | I | |
| 1422 | 2,4-F₂-Ph | 4-Cl-Ph | H | H | H | H | I | |
| 1423 | 2,4-F₂-Ph | 2,4-F₂-Ph | H | H | H | H | I | |
| 1424 | 2,4-F₂-Ph | 2,4-Cl₂-Ph | H | H | H | H | I | |
| 1425 | 2,4-Cl₂-Ph | Ph | H | H | H | H | I | |
| 1426 | 2,4-Cl₂-Ph | 2-F-Ph | H | H | H | H | I | |
| 1427 | 2,4-Cl₂-Ph | 4-F-Ph | H | H | H | H | I | |
| 1428 | 2,4-Cl₂-Ph | 2-Cl-Ph | H | H | H | H | I | |
| 1429 | 2,4-Cl₂-Ph | 4-Cl-Ph | H | H | H | H | I | |
| 1430 | 2,4-Cl₂-Ph | 2,4-F₂-Ph | H | H | H | H | I | |
| 1431 | 2,4-Cl₂-Ph | 2,4-Cl₂-Ph | H | H | H | H | I | |
| 1432 | Ph | 2,4-F₂-Ph | H | H | H | H | —SS— | |
| 1433 | 4-F-Ph | 2-F-Ph | H | H | H | H | —SS— | |
| 1434 | 4-F-Ph | 2,4-F₂-Ph | H | H | H | H | —SS— | |
| 1435 | Ph | 2,4-F₂-Ph | H | H | H | H | —SSCH₃ | |
| 1436 | 4-F-Ph | 2-F-Ph | H | H | H | H | —SSCH₃ | |
| 1437 | 4-F-Ph | 2,4-F₂-Ph | H | H | H | H | —SSCH₃ | |
| 1438 | Ph | 2,4-F₂-Ph | H | H | H | H | $\underset{\text{SCNHMe}}{\overset{O}{\|}}$ | |
| 1439 | 4-F-Ph | 2-F-Ph | H | H | H | H | $\underset{\text{SCNHMe}}{\overset{O}{\|}}$ | |
| 1440 | 4-F-Ph | 2,4-F₂-Ph | H | H | H | H | $\underset{\text{SCNHMe}}{\overset{O}{\|}}$ | |
| 1441 | Ph | 2,4-F₂-Ph | H | H | H | H | $\underset{\text{SCNH-}\underline{n}\text{-Bu}}{\overset{O}{\|}}$ | |
| 1442 | 4-F-Ph | 2-F-Ph | H | H | H | H | $\underset{\text{SCNH-}\underline{n}\text{-Bu}}{\overset{O}{\|}}$ | |
| 1443 | 4-F-Ph | 2,4-F₂-Ph | H | H | H | H | $\underset{\text{SCNH-}\underline{n}\text{-Bu}}{\overset{O}{\|}}$ | |
| 1444 | Ph | 2,4-F₂-Ph | H | H | H | H | Cl | |
| 1445 | 4-F-Ph | 2-F-Ph | H | H | H | H | Cl | |
| 1446 | 4-F-Ph | 2,4-F₂-Ph | H | H | H | H | Cl | |
| 1447 | Ph | 2,4-F₂-Ph | H | H | H | H | CHO | |
| 1448 | 4-F-Ph | 2-F-Ph | H | H | H | H | CHO | |
| 1449 | 4-F-Ph | 2,4-F₂-Ph | H | H | H | H | CHO | |
| 1450 | Ph | 2,4-F₂-Ph | H | H | H | H | SCH₂CN | |
| 1451 | 4-F-Ph | 2-F-Ph | H | H | H | H | SCH₂CN | oil[c] |
| 1452 | 4-F-Ph | 2,4-F₂-Ph | H | H | H | H | SCH₂CN | |
| 1453 | Ph | 2,4-F₂-Ph | H | H | H | H | SCH₂SCN | |
| 1454 | 4-F-Ph | 2-F-Ph | H | H | H | H | SCH₂SCN | |
| 1455 | 4-F-Ph | 2,4-F₂-Ph | H | H | H | H | SCH₂SCN | |
| 1456 | Ph | 2,4-F₂-Ph | H | H | H | H | SCCl₃ | |
| 1457 | 4-F-Ph | 2-F-Ph | H | H | H | H | SCCl₃ | |
| 1458 | 4-F-Ph | 2,4-F₂-Ph | H | H | H | H | SCCl₃ | |
| 1459 | Ph | 4-F-Ph | H | H | H | H | S-$\underline{n}$-Bu | semi-solid[d] |
| 1460 | 4-F-Ph | 2-F-Ph | H | H | H | H | F | |
| 1461 | 4-F-Ph | 2-F-Ph | H | H | H | H | Br | |
| 1462 | 4-F-Ph | 2-F-Ph | H | H | H | H | $\underset{\text{SCH}_3}{\overset{O}{\|}}$ | |

TABLE 3*-continued

Structure:

$$A-\underset{B}{\underset{|}{C}}(OR^2)-\underset{E}{\overset{CRR^1}{|}}-\underset{H}{\underset{|}{C}}(R^4)-N(\text{triazole with }Q)$$

| Ex. No. | A | B | R | R¹ | R² | R⁴ | Q | M.P. °C. |
|---|---|---|---|---|---|---|---|---|
| 1463 | 4-F-Ph | 2-F-Ph | H | H | H | H | S(=O)(=O)CH₃ | |
| 1464 | 4-F-Ph | 2-F-Ph | H | H | H | H | S(=O)(=O)-n-Pr | |
| 1465 | 4-F-Ph | 2-F-Ph | H | H | H | H | —S(=O)-t-Bu | |
| 1466 | 4-F-Ph | 2-F-Ph | H | H | H | H | SCF₂H | |
| 1467 | 4-F-Ph | 2-F-Ph | H | H | H | H | SCF₂CF₂H | |
| 1468* | 4-F-Ph | 2-F-Ph | H | H | H | H | S(=O)CH₂CN | (oil)ᵉ |
| 1469* | 4-F-Ph | 2-F-Ph | H | H | H | H | S(=O)(=O)CH₂CN | (oil)ᶠ |
| 1470 | 4-F-Ph | 2-F-Ph | H | H | H | H | S(=O)(=O)CH₂SCN | |
| 1471 | 4-F-Ph | 2-F-Ph | H | H | H | H | S(=O)(=O)—CH(CH₃)CN | |
| 1472 | 4-F-Ph | 2-F-Ph | H | H | H | H | S(=O)(=O)CH₂CO₂CH₃ | |
| 1473 | 4-F-Ph | 2-F-Ph | H | H | H | H | S(=O)NH-allyl | |
| 1474 | 4-F-Ph | 2-F-Ph | H | H | H | H | S(=O)NH-i-Pr | |
| 1475 | 4-F-Ph | 2-F-Ph | H | H | H | H | S(=O)NHPh | |
| 1476 | 4-F-Ph | 2-F-Ph | H | H | H | H | S(=O)NH-(4-Cl-Ph) | |
| 1477 | 4-F-Ph | 2-F-Ph | H | H | H | H | S(=O)NHCH₂Ph | |
| 1478 | 4-F-Ph | 2-F-Ph | H | H | H | H | S(=O)NHCH₂-(4-CH₃O-Ph) | |
| 1479 | 4-F-Ph | 2-F-Ph | H | H | H | H | C(=O)CH₃ | |

TABLE 3*-continued

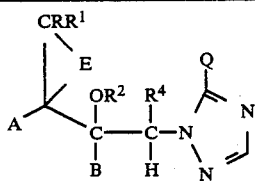

| Ex. No. | A | B | R | R¹ | R² | R⁴ | Q | M.P. °C. |
|---|---|---|---|---|---|---|---|---|
| 1480 | 4-F-Ph | 2-F-Ph | H | H | H | H | $\underset{COH}{\overset{O}{\|}}$ | |
| 1481 | 4-F-Ph | 2-F-Ph | H | H | H | H | $\underset{COCH_3}{\overset{O}{\|}}$ | |
| 1482 | 4-F-Ph | 2-F-Ph | H | H | H | H | $\underset{CO\text{-}i\text{-}Pr}{\overset{O}{\|}}$ | |
| 1483 | 4-F-Ph | 2-F-Ph | H | H | H | H | SCN | |
| 1484 | 4-F-Ph | 2-F-Ph | H | H | H | H | SSCH₂Ph | |
| 1485 | 4-F-Ph | 2-F-Ph | H | H | H | H | SS-allyl | |
| 1486 | 4-F-Ph | 2-F-Ph | H | H | H | H | SSPh | |

*All compounds in this table are compounds in which E is a bond except 1468 and 1469 in which E is an oxygen atom.
ᵃNMR: (CDCl₃) δ 4.9(s, 2H); 5.1(s, 1H); 5.2(s, 1H); 5.3(s, 1H); 6.7(m, 2H); 6.9(m, 2H); 7.2(m, 2H); 7.5(m, 1H); 7.6(s, 1H); 12.2(brs, 1H).
ᵇNMR: (CDCl₃) δ 4.7(ABq, 2H); 5.3(s, 2H); 5.8(s, 1H); 6.7(m, 2H); 6.9(m, 2H); 7.3(m, 2H); 7.5(m, 1H); 7.8(s, 1H).
ᶜNMR: (CDCl₃) δ 3.8(ABq, 2H); 4.7(ABq, 2H); 5.2(s, 1H); 5.3(two s, 2H); 6.9–7.2(m, 4H); 7.2–7.4(m, 3H); 7.5(m, 1H); 7.8(s, 1H).
ᵈNMR: (CDCl₃) δ 0.92(t, 3H); 1.4–1.7(m, 4H); 3.1(t, 2H); 4.5(ABq, 2H); 5.4(two s, 2H); 5.8(s, 1H); 7.0(m, 4H); 7.2(m, 3H); 7.5(m, 2H); 7.8(s, 1H).
ᵉNMR: (CDCl₃) δ 2.7–3.5(m, 2H); 4.3(s, 1H); 4.4(m, 1H); 5.2(m, 2H); 6.8–7.4(m, 8H); 7.9(m, 1H).
ᶠNMR: (CDCl₃) δ 2.7–3.4(m, 2H); 4.2(d, 1H); 4.5(ABq, 2H); 5.3(m, 2H); 6.8–7.4(m, 8H); 7.9(d, 1H).

EXAMPLE 1487

Preparation of 2,3-bis(4-fluorophenyl)-1-(1H-1,2,4-triazol-1-yl)-3,4-epoxy-2-butanol 2,3-Bis(4-fluorophenyl)-1-(1H-1,2,4-triazol-1-yl)-3-butene-2-ol (1.0 g) was dissolved in 50 ml of anhydrous benzene and stirred under nitrogen. To this solution was added 0.012 g of vanadium acetonylacetonate. The solution was then refluxed and tert-butyl hydroperoxide (0.44 g dissolved in 5 ml of anhydrous benzene) was added dropwise over 10 minutes. The reaction was refluxed for one additional hour and then cooled to ambient temperature. The benzene was removed in vacuo and the residue chromatographed on silica gel (2% MeOH/CH₂Cl₂). This yielded a total of 650 mg of diastereomeric products in a 3:1 ratio. Further chromatography resulted in the separation of the diastereomers. The major isomer was a waxy white solid. NMR (CDCl₃/TMS)δ2.60 (d, J=6 Hz, 1H); 3.48 (d, J=6 Hz, 1H); 4.70 (q, J=7 Hz, 2H), 5.25 (s, 1H); 6.8–7.3 (m, 8H); 7.55 (s, 1H); 7.90 (s, 1H).

The minor isomer was an amorphous white solid. NMR (CDCl₃/TMS)δ2.55 (d, J=6H, 1H); 2.75 (d, J=6 Hz, 1H); 4.80 (q, J=7 Hz); 5.0 (s, 1H); 6.85–7.10 (m, 4H); 7.15–7.45 (m, 4H); 7.80 (s, 1H); 8.05 (s, 1H).

The epoxides shown in Table 4 were prepared or can be prepared by the method described in Example 1487.

TABLE 4

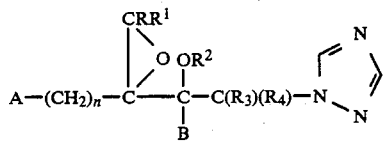

| Ex. No. | A | B | n | R | R¹ | R² | R³ | R⁴ | M.P. °C. |
|---|---|---|---|---|---|---|---|---|---|
| 1487 | 4-F-Ph | 4-F-Ph | 0 | H | H | H | H | H | 53–55 |
| 1488 | 4-F-Ph | 2,4-Cl₂-Ph | 0 | H | H | H | H | H | |
| 1489 | 4-F-Ph | 4-Cl-Ph | 0 | H | H | H | H | H | |
| 1490 | 4-F-Ph | 2,4-F₂-Ph | 0 | H | H | H | H | H | (semi-solid)ᵃ |
| 1491 | 4-F-Ph | 4-CF₃-Ph | 0 | H | H | H | H | H | |
| 1492 | 4-F-Ph | 2-F-Ph | 0 | H | H | H | H | H | (110–119) |
| 1493 | 4-F-Ph | 2-Cl-Ph | 0 | H | H | H | H | H | |
| 1494 | 4-F-Ph | n-C₄F₉ | 0 | H | H | H | H | H | |
| 1495 | 3-F-Ph | 4-F-Ph | 0 | H | H | H | H | H | |
| 1496 | 3-F-Ph | 2,4-Cl₂-Ph | 0 | H | H | H | H | H | |
| 1497 | 3-F-Ph | 4-Cl-Ph | 0 | H | H | H | H | H | |
| 1498 | 3-F-Ph | 2,4-F₂-Ph | 0 | H | H | H | H | H | |
| 1499 | 3-F-Ph | 4-CF₃-Ph | 0 | H | H | H | H | H | |

TABLE 4-continued $$\text{A}-(\text{CH}_2)_n-\underset{\underset{B}{|}}{\overset{\overset{CRR^1}{\underset{|}{\underset{O}{\diagup}}\underset{OR^2}{\diagdown}}}{C}}-\overset{}{C}-C(R^3)(R^4)-N\underset{N}{\diagdown}\overset{N}{\diagup}$$

| Ex. No. | A | B | n | R | R¹ | R² | R³ | R⁴ | M.P. °C. |
|---|---|---|---|---|---|---|---|---|---|
| 1500 | 3-F-Ph | 2-F-Ph | 0 | H | H | H | H | H | |
| 1501 | 3-F-Ph | 2-Cl-Ph | 0 | H | H | H | H | H | |
| 1502 | 3-F-Ph | n-C₄F₉ | 0 | H | H | H | H | H | |
| 1503 | 4-Cl-Ph | 4-F-Ph | 0 | H | H | H | H | H | |
| 1504 | 4-Cl-Ph | 2,4-Cl₂-Ph | 0 | H | H | H | H | H | |
| 1505 | 4-Cl-Ph | 4-Cl-Ph | 0 | H | H | H | H | H | |
| 1506 | 4-Cl-Ph | 2,4-F₂-Ph | 0 | H | H | H | H | H | |
| 1507 | 4-Cl-Ph | 4-CF₃-Ph | 0 | H | H | H | H | H | |
| 1508 | 4-Cl-Ph | 2-F-Ph | 0 | H | H | H | H | H | |
| 1509 | 4-Cl-Ph | 2-Cl-Ph | 0 | H | H | H | H | H | |
| 1510 | 4-Cl-Ph | n-C₄F₉ | 0 | H | H | H | H | H | |
| 1511 | 2-Cl-Ph | 4-F-Ph | 0 | H | H | H | H | H | |
| 1512 | 2-Cl-Ph | 2,4-Cl₂-Ph | 0 | H | H | H | H | H | |
| 1513 | 2-Cl-Ph | 4-Cl-Ph | 0 | H | H | H | H | H | 149–150 Low R$_f$ isomer<br>141–143 High R$_f$ isomer |
| 1514 | 2-Cl-Ph | 2,4-F₂-Ph | 0 | H | H | H | H | H | 138–140 Isomer A<br>152–156 Isomer B |
| 1515 | 2-Cl-Ph | 4-CF₃-Ph | 0 | H | H | H | H | H | |
| 1516 | 2-Cl-Ph | 2-F-Ph | 0 | H | H | H | H | H | |
| 1517 | 2-Cl-Ph | 2-Cl-Ph | 0 | H | H | H | H | H | |
| 1518 | 2-Cl-Ph | n-C₄F₉ | 0 | H | H | H | H | H | |
| 1519 | 3-Cl-Ph | 4-F-Ph | 0 | H | H | H | H | H | |
| 1520 | 3-Cl-Ph | 2,4-Cl₂-Ph | 0 | H | H | H | H | H | |
| 1521 | 3-Cl-Ph | 4-Cl-Ph | 0 | H | H | H | H | H | |
| 1522 | 3-Cl-Ph | 2,4-F₂-Ph | 0 | H | H | H | H | H | |
| 1523 | 3-Cl-Ph | 4-CF₃-Ph | 0 | H | H | H | H | H | |
| 1524 | 3-Cl-Ph | 2-F-Ph | 0 | H | H | H | H | H | |
| 1525 | 3-Cl-Ph | 2-Cl-Ph | 0 | H | H | H | H | H | |
| 1526 | 3-Cl-Ph | n-C₄F₉ | 0 | H | H | H | H | H | |
| 1527 | Ph | 4-F-Ph | 0 | H | H | H | H | H | 88–94 |
| 1528 | Ph | 2,4-Cl₂-Ph | 0 | H | H | H | H | H | |
| 1529 | Ph | 4-Cl-Ph | 0 | H | H | H | H | H | 156–158 |
| 1530 | Ph | 2,4-F₂-Ph | 0 | H | H | H | H | H | 87–90 Low R$_f$ isomer<br>148–150 High R$_f$ isomer |
| 1531 | Ph | 4-CF₃-Ph | 0 | H | H | H | H | H | |
| 1532 | Ph | 2-F-Ph | 0 | H | H | H | H | H | |
| 1533 | Ph | 2-Cl-Ph | 0 | H | H | H | H | H | |
| 1534 | Ph | n-C₄F₉ | 0 | H | H | H | H | H | |
| 1535 | 4-CF₃-Ph | 4-F-Ph | 0 | H | H | H | H | H | |
| 1536 | 4-CF₃-Ph | 2,4-Cl₂-Ph | 0 | H | H | H | H | H | |
| 1537 | 4-CF₃-Ph | 4-Cl-Ph | 0 | H | H | H | H | H | |
| 1538 | 4-CF₃-Ph | 2,4-F₂-Ph | 0 | H | H | H | H | H | |
| 1539 | 4-CF₃-Ph | 4-CF₃-Ph | 0 | H | H | H | H | H | |
| 1540 | 4-CF₃-Ph | 2-F-Ph | 0 | H | H | H | H | H | |
| 1541 | 4-CF₃-Ph | 2-Cl-Ph | 0 | H | H | H | H | H | |
| 1542 | 4-CF₃-Ph | n-C₄F₉ | 0 | H | H | H | H | H | |
| 1543 | 4-Br-Ph | 4-F-Ph | 0 | H | H | H | H | H | |
| 1544 | 4-Br-Ph | 2,4-Cl₂-Ph | 0 | H | H | H | H | H | |
| 1545 | 4-Br-Ph | 4-Cl-Ph | 0 | H | H | H | H | H | |
| 1546 | 4-Br-Ph | 2,4-F₂-Ph | 0 | H | H | H | H | H | |
| 1547 | 4-Br-Ph | 4-CF₃-Ph | 0 | H | H | H | H | H | |
| 1548 | 4-Br-Ph | 2-F-Ph | 0 | H | H | H | H | H | |
| 1549 | 4-Br-Ph | 2-Cl-Ph | 0 | H | H | H | H | H | |
| 1550 | 4-Br-Ph | n-C₄F₉ | 0 | H | H | H | H | H | |
| 1551 | 2,4-Cl₂-Ph | 4-F-Ph | 0 | H | H | H | H | H | |
| 1552 | 2,4-Cl₂-Ph | 2,4-Cl₂-Ph | 0 | H | H | H | H | H | |
| 1553 | 2,4-Cl₂-Ph | 4-Cl-Ph | 0 | H | H | H | H | H | |
| 1554 | 2,4-Cl₂-Ph | 2,4-F₂-Ph | 0 | H | H | H | H | H | |
| 1555 | 2,4-Cl₂-Ph | 4-CF₃-Ph | 0 | H | H | H | H | H | |
| 1556 | 2,4-Cl₂-Ph | 2-F-Ph | 0 | H | H | H | H | H | |
| 1557 | 2,4-Cl₂-Ph | 2-Cl-Ph | 0 | H | H | H | H | H | |
| 1558 | 2,4-Cl₂-Ph | n-C₄F₉ | 0 | H | H | H | H | H | |
| 1559 | 2-F-Ph | 4-F-Ph | 0 | H | H | H | H | H | |
| 1560 | 2-F-Ph | 2,4-Cl₂-Ph | 0 | H | H | H | H | H | |
| 1561 | 2-F-Ph | 4-Cl-Ph | 0 | H | H | H | H | H | |
| 1562 | 2-F-Ph | 2,4-F₂-Ph | 0 | H | H | H | H | H | |
| 1563 | 2-F-Ph | 4-CF₃-Ph | 0 | H | H | H | H | H | |
| 1564 | 2-F-Ph | 2-F-Ph | 0 | H | H | H | H | H | |
| 1565 | 2-F-Ph | 2-Cl-Ph | 0 | H | H | H | H | H | |
| 1566 | 2-F-Ph | n-C₄F₉ | 0 | H | H | H | H | H | |
| 1567 | 2,4-F₂-Ph | 4-F-Ph | 0 | H | H | H | H | H | |
| 1568 | 2,4-F₂-Ph | 2,4-Cl₂Ph | 0 | H | H | H | H | H | |
| 1569 | 2,4-F₂-Ph | 4-Cl-Ph | 0 | H | H | H | H | H | |

TABLE 4-continued $$A-(CH_2)_n-C\underset{B}{\overset{CRR^1}{\underset{|}{\overset{|}{C}}}}\overset{O}{\underset{}{\underset{}{C}}}\overset{OR^2}{\underset{|}{C}}-C(R_3)(R_4)-N\underset{N}{\overset{N}{\diagdown}}$$

| Ex. No. | A | B | n | R | R¹ | R² | R³ | R⁴ | M.P. °C. |
|---|---|---|---|---|---|---|---|---|---|
| 1570 | 2,4-F₂-Ph | 2,4-F₂-Ph | 0 | H | H | H | H | H | |
| 1571 | 2,4-F₂-Ph | 4-CF₃-Ph | 0 | H | H | H | H | H | |
| 1572 | 2,4-F₂-Ph | 2-F-Ph | 0 | H | H | H | H | H | |
| 1573 | 2,4-F₂-Ph | 2-Cl-Ph | 0 | H | H | H | H | H | |
| 1574 | 2,4-F₂-Ph | n-C₄F₉ | 0 | H | H | H | H | H | |
| 1575 | Ph | 4-F-Ph | 0 | H | CH₃ | H | H | H | |
| 1576 | Ph | 4-F-Ph | 0 | —(CH₂)₂— | | H | H | H | |
| 1577 | Ph | 4-F-Ph | 0 | CH₃ | CH₃ | H | H | H | |
| 1578 | 4-F-Ph | 4-F-Ph | 0 | H | CH₃ | H | H | H | |
| 1579 | 4-F-Ph | 4-F-Ph | 0 | —(CH₂)₂— | | H | H | H | |
| 1580 | 4-F-Ph | 4-F-Ph | 0 | CH₃ | CH₃ | H | H | H | |
| 1581 | 4-Cl-Ph | 2,4-Cl₂-Ph | 0 | H | CH₃ | H | H | H | |
| 1582 | 4-Cl-Ph | 2,4-Cl₂-Ph | 0 | —(CH₂)₂— | | H | H | H | |
| 1583 | 4-Cl-Ph | 2,4-Cl₂-Ph | 0 | CH₃ | CH₃ | H | H | H | |
| 1584 | 2-Cl-Ph | 4-Cl-Ph | 0 | H | CH₃ | H | H | H | |
| 1585 | 2-Cl-Ph | 4-Cl-Ph | 0 | —(CH₂)₂— | | H | H | H | |
| 1586 | 2-Cl-Ph | 4-Cl-Ph | 0 | CH₃ | CH₃ | H | H | H | |
| 1587 | 4-F-Ph | 4-F-Ph | 0 | H | C₂H₅ | H | H | H | |
| 1588 | 4-F-Ph | 4-F-Ph | 0 | H | i-C₃H₇ | H | H | H | |
| 1589 | 4-F-Ph | 4-F-Ph | 0 | H | n-C₄H₉ | H | H | H | |
| 1590 | 4-F-Ph | 4-F-Ph | 0 | H | Ph | H | H | H | |
| 1591 | 4-F-Ph | 4-F-Ph | 0 | H | t-C₄H₉ | H | H | H | |
| 1592 | 4-F-Ph | 4-F-Ph | 0 | H | Ph | H | H | H | |
| 1593 | 4-F-Ph | 4-F-Ph | 0 | CH₃ | t-C₄H₉ | H | H | H | |
| 1594 | 4-F-Ph | 4-F-Ph | 0 | CH₃ | Ph | H | H | H | |
| 1595 | 4-F-Ph | 4-F-Ph | 0 | —(CH₂)₃— | | H | H | H | |
| 1596 | 4-F-Ph | 4-F-Ph | 0 | —(CH₂)₄— | | H | H | H | |
| 1597 | 4-F-Ph | 4-F-Ph | 0 | —(CH₂)₅— | | H | H | H | |
| 1598 | 4-F-Ph | 4-F-Ph | 0 | —(CH₂)₆— | | H | H | H | |
| 1599 | 4-CH₃-Ph | 4-F-Ph | 0 | H | CH₃ | H | H | H | |
| 1600 | 4-F-Ph | 4-F-Ph | 1 | H | CH₃ | H | H | H | |
| 1601 | 4-Cl-Ph | 4-F-Ph | 4 | H | CH₃ | H | H | H | |
| 1602 | n-C₄F₉ | 4-F-Ph | 0 | H | CH₃ | H | H | H | |
| 1603 | (CH₃)₂N | 4-F-Ph | 1 | H | CH₃ | H | H | H | |
| 1604 | 5-Cl-2-thienyl | 4-F-Ph | 0 | H | CH₃ | H | H | H | |
| 1605 | 2-Cl-3-thienyl | 4-F-Ph | 0 | H | CH₃ | H | H | H | |
| 1606 | 1-imidazoyl | 4-F-Ph | 0 | H | CH₃ | H | H | H | |
| 1607 | 4-F-Ph | 4-F-Ph | 0 | H | H | CH₃ | H | H | |
| 1608 | 4-F-Ph | 4-F-Ph | 0 | H | H | CH₂CH=CH₂ | H | H | |
| 1609 | 4-F-Ph | 4-F-Ph | 0 | H | H | COCH₃ | H | H | |
| 1610 | 4-F-Ph | 4-F-Ph | 0 | H | H | CO₂CH₃ | H | H | |
| 1611 | 4-CF₃O-Ph | 4-F-Ph | 0 | H | H | H | H | H | |
| 1612 | 2-Cl-Ph | 4-Cl-Ph | 0 | H | H | CH₃ | H | H | |
| 1613 | 2-Cl-Ph | 4-Cl-Ph | 0 | H | H | CH₂CH=CH₂ | H | H | |
| 1614 | 2-Cl-Ph | 4-Cl-Ph | 0 | H | H | COCH₃ | H | H | |
| 1615 | 2-Cl-Ph | 4-Cl-Ph | 0 | H | H | CO₂CH₃ | H | H | |
| 1616 | 4-Cl-Ph | 2,4-Cl₂-Ph | 0 | H | H | CH₃ | H | H | |
| 1617 | 4-Cl-Ph | 2,4-Cl₂-Ph | 0 | H | H | CH₂CH=CH₂ | H | H | |
| 1618 | 4-Cl-Ph | 2,4-Cl₂-Ph | 0 | H | H | COCH₃ | H | H | |
| 1619 | 4-Cl-Ph | 2,4-Cl₂-Ph | 0 | H | H | CO₂CH₃ | H | H | |
| 1620 | Ph | 4-F-Ph | 0 | H | H | CH₃ | H | H | |
| 1621 | Ph | 4-F-Ph | 0 | H | H | CH₂CH=CH₂ | H | H | |
| 1622 | Ph | 4-F-Ph | 0 | H | H | COCH₃ | H | H | |
| 1623 | Ph | 4-F-Ph | 0 | H | H | CO₂CH₃ | H | H | |
| 1624 | OH | 2,4-Cl₂-Ph | 2 | H | H | H | H | H | |
| 1625 | OH | 2,4-Cl₂-Ph | 3 | H | H | H | H | H | |
| 1626 | OH | 2,4-Cl₂-Ph | 4 | H | H | H | H | H | |
| 1627 | 1-imidazoyl | 2,4-Cl₂-Ph | 1 | H | H | H | H | H | |
| 1628 | 1-imidazoyl | 2,4-Cl₂-Ph | 2 | H | H | H | H | H | |
| 1629 | 1-imidazoyl | 4-F-Ph | 3 | H | H | H | H | H | |
| 1630 | 1-imidazoyl | 4-F-Ph | 4 | H | H | H | H | H | |
| 1631 | 1H-1,2,4-triazoyl-1-yl | 4-F-Ph | 1 | H | H | H | H | H | |
| 1632 | 1H-1,2,4-triazoyl-1-yl | 4-F-Ph | 2 | H | H | H | H | H | |
| 1633 | 1H-1,2,4-triazoyl-1-yl | 4-F-Ph | 3 | H | H | H | H | H | |
| 1634 | 1H-1,2,4-triazoyl-1-yl | 4-F-Ph | 4 | H | H | H | H | H | |
| 1635 | 1H-1,2,4-triazoyl-1-yl | 2,4-Cl₂-Ph | 1 | H | H | H | H | H | |
| 1636 | Ph | 2,5-F₂-Ph | 0 | H | H | H | H | H | |
| 1637 | Ph | 3-F-Ph | 0 | H | H | H | H | H | |
| 1638 | Ph | 2,5-Cl₂-Ph | 0 | H | H | H | H | H | |
| 1639 | Ph | 3-Cl-Ph | 0 | H | H | H | H | H | |
| 1640 | Ph | 4-Br-Ph | 0 | H | H | H | H | H | |
| 1641 | Ph | 4-I-Ph | 0 | H | H | H | H | H | |
| 1642 | Ph | 3,4-F₂-Ph | 0 | H | H | H | H | H | |

TABLE 4-continued $$A-(CH_2)_n-C\overset{CRR^1}{\underset{B}{\overset{O}{-}}}C(R_3)(R_4)-N\underset{N}{\overset{N}{\diagup}}$$

| Ex. No. | A | B | n | R | R¹ | R² | R³ | R⁴ | M.P. °C. |
|---|---|---|---|---|---|---|---|---|---|
| 1643 | Ph | 3,4-Cl₂-Ph | 0 | H | H | H | H | H | |
| 1644 | Ph | 2,6-Cl₂-Ph | 0 | H | H | H | H | H | |
| 1645 | Ph | 2-Cl-(4-F)-Ph | 0 | H | H | H | H | H | |
| 1646 | Ph | 2,4,6-Cl₃-Ph | 0 | H | H | H | H | H | |
| 1647 | Ph | 2-F-(4-Cl)-Ph | 0 | H | H | H | H | H | |
| 1648 | Ph | Ph | 0 | H | H | H | H | H | |
| 1649 | Ph | 4-CH₃-Ph | 0 | H | H | H | H | H | |
| 1650 | Ph | 3-CH₃-Ph | 0 | H | H | H | H | H | |
| 1651 | Ph | 2-CH₃-Ph | 0 | H | H | H | H | H | |
| 1652 | Ph | 2-CF₃-Ph | 0 | H | H | H | H | H | |
| 1653 | Ph | 3-CF₃-Ph | 0 | H | H | H | H | H | |
| 1654 | Ph | 2-F-(4-CF₃)-Ph | 0 | H | H | H | H | H | |
| 1655 | Ph | 4-CH₃O-Ph | 0 | H | H | H | H | H | |
| 1656 | Ph | 5-Cl-2-pyridyl | 0 | H | H | H | H | H | |
| 1657 | Ph | 5-Cl-2-thienyl | 0 | H | H | H | H | H | |
| 1658 | Ph | 2-Cl-3-thienyl | 0 | H | H | H | H | H | |
| 1659 | Ph | s-C₄H₉ | 0 | H | H | H | H | H | |
| 1660 | 2-Cl-Ph | 2,5-F₂-Ph | 0 | H | H | H | H | H | |
| 1661 | 2-Cl-Ph | 3-F-Ph | 0 | H | H | H | H | H | |
| 1662 | 2-Cl-Ph | 2,5-Cl₂-Ph | 0 | H | H | H | H | H | |
| 1663 | 2-Cl-Ph | 3-Cl-Ph | 0 | H | H | H | H | H | |
| 1664 | 2-Cl-Ph | 4-Br-Ph | 0 | H | H | H | H | H | |
| 1665 | 2-Cl-Ph | 4-I-Ph | 0 | H | H | H | H | H | |
| 1666 | 2-Cl-Ph | 3,4-F₂-Ph | 0 | H | H | H | H | H | |
| 1667 | 2-Cl-Ph | 3,4-Cl₂-Ph | 0 | H | H | H | H | H | |
| 1668 | 2-Cl-Ph | 2,6-Cl₂-Ph | 0 | H | H | H | H | H | |
| 1669 | 2-Cl-Ph | 2-Cl-(4-F)-Ph | 0 | H | H | H | H | H | |
| 1670 | 2-Cl-Ph | 2,4,6-Cl₃-Ph | 0 | H | H | H | H | H | |
| 1671 | 2-Cl-Ph | 2-F-(4-Cl)-Ph | 0 | H | H | H | H | H | |
| 1672 | 2-Cl-Ph | Ph | 0 | H | H | H | H | H | |
| 1673 | 2-Cl-Ph | 4-CH₃-Ph | 0 | H | H | H | H | H | |
| 1674 | 2-Cl-Ph | 3-CH₃-Ph | 0 | H | H | H | H | H | |
| 1675 | 2-Cl-Ph | 2-CH₃-Ph | 0 | H | H | H | H | H | |
| 1676 | 2-Cl-Ph | 2-CF₃-Ph | 0 | H | H | H | H | H | |
| 1677 | 2-Cl-Ph | 3-CF₃-Ph | 0 | H | H | H | H | H | |
| 1678 | 2-Cl-Ph | 2-F-(4-CF₃)-Ph | 0 | H | H | H | H | H | |
| 1679 | 2-Cl-Ph | 4-CH₃O-Ph | 0 | H | H | H | H | H | |
| 1680 | 2-Cl-Ph | 5-Cl-2-pyridyl | 0 | H | H | H | H | H | |
| 1681 | 2-Cl-Ph | 5-Cl-2-thienyl | 0 | H | H | H | H | H | |
| 1682 | 2-Cl-Ph | 2-Cl-3-thienyl | 0 | H | H | H | H | H | |
| 1683 | 3-Cl-Ph | 2,5-F₂-Ph | 0 | H | H | H | H | H | |
| 1684 | 3-Cl-Ph | 2,5-Cl₂-Ph | 0 | H | H | H | H | H | |
| 1685 | 4-F-Ph | 2,5-F₂-Ph | 0 | H | H | H | H | H | |
| 1686 | 4-F-Ph | 3-F-Ph | 0 | H | H | H | H | H | |
| 1687 | 4-F-Ph | 2,5-Cl₂-Ph | 0 | H | H | H | H | H | |
| 1688 | 4-F-Ph | 3-Cl-Ph | 0 | H | H | H | H | H | |
| 1689 | 4-F-Ph | 4-Br-Ph | 0 | H | H | H | H | H | |
| 1690 | 4-F-Ph | 4-I-Ph | 0 | H | H | H | H | H | |
| 1691 | 4-F-Ph | 3,4-F₂-Ph | 0 | H | H | H | H | H | |
| 1692 | 4-F-Ph | 3,4-Cl₂-Ph | 0 | H | H | H | H | H | |
| 1693 | 4-F-Ph | 2,6-Cl₂-Ph | 0 | H | H | H | H | H | |
| 1694 | 4-F-Ph | 2-Cl-(4-F)-Ph | 0 | H | H | H | H | H | |
| 1695 | 4-F-Ph | 2,4,6-Cl₃-Ph | 0 | H | H | H | H | H | |
| 1696 | 4-F-Ph | 2-F-(4-Cl)-Ph | 0 | H | H | H | H | H | |
| 1697 | 4-F-Ph | Ph | 0 | H | H | H | H | H | |
| 1698 | 4-F-Ph | 4-CH₃-Ph | 0 | H | H | H | H | H | |
| 1699 | 4-F-Ph | 3-CH₃-Ph | 0 | H | H | H | H | H | |
| 1700 | 4-F-Ph | 2-CH₃-Ph | 0 | H | H | H | H | H | |
| 1701 | 4-F-Ph | 2-CF₃-Ph | 0 | H | H | H | H | H | |
| 1702 | 4-F-Ph | 3-CF₃-Ph | 0 | H | H | H | H | H | |
| 1703 | 4-F-Ph | 2-F-(4-CF₃)-Ph | 0 | H | H | H | H | H | |
| 1704 | 4-F-Ph | 4-CH₃O-Ph | 0 | H | H | H | H | H | |
| 1705 | 4-F-Ph | 5-Cl-2-prridyl | 0 | H | H | H | H | H | |
| 1706 | 4-F-Ph | 2-Cl-3-thienyl | 0 | H | H | H | H | H | |
| 1707 | 4-F-Ph | 5-Cl-2-thienyl | 0 | H | H | H | H | H | |
| 1708 | 3-F-Ph | 2,5-Cl₂-Ph | 0 | H | H | H | H | H | |
| 1709 | 3-F-Ph | 2,5-F₂-Ph | 0 | H | H | H | H | H | |
| 1710 | 4-Cl-Ph | 2,5-F₂-Ph | 0 | H | H | H | H | H | |
| 1711 | 4-Cl-Ph | 3-F-Ph | 0 | H | H | H | H | H | |
| 1712 | 4-Cl-Ph | 2,5-Cl₂-Ph | 0 | H | H | H | H | H | |
| 1713 | 4-Cl-Ph | 3-Cl-Ph | 0 | H | H | H | H | H | |
| 1714 | 4-Cl-Ph | 4-Br-Ph | 0 | H | H | H | H | H | |
| 1715 | 4-Cl-Ph | 4-I-Ph | 0 | H | H | H | H | H | |

TABLE 4-continued $$A-(CH_2)_n-\underset{B}{\overset{\overset{\displaystyle CRR^1}{\underset{\displaystyle O}{|}}}{C}}-\underset{}{\overset{\displaystyle OR^2}{\underset{}{C}}}-C(R_3)(R_4)-N\diagup\diagdown$$

(imidazole ring at right)

| Ex. No. | A | B | n | R | R¹ | R² | R³ | R⁴ | M.P. °C. |
|---|---|---|---|---|---|---|---|---|---|
| 1716 | 4-Cl-Ph | 3,4-F₂-Ph | 0 | H | H | H | H | H | |
| 1717 | 4-Cl-Ph | 3,4-Cl₂-Ph | 0 | H | H | H | H | H | |
| 1718 | 4-Cl-Ph | 2,6-Cl₂-Ph | 0 | H | H | H | H | H | |
| 1719 | 4-Cl-Ph | 2-Cl-(4-F)-Ph | 0 | H | H | H | H | H | |
| 1720 | 4-Cl-Ph | 2,4,6-Cl₃-Ph | 0 | H | H | H | H | H | |
| 1721 | 4-Cl-Ph | 2-F-(4-Cl)-Ph | 0 | H | H | H | H | H | |
| 1722 | 4-Cl-Ph | Ph | 0 | H | H | H | H | H | |
| 1723 | 4-Cl-Ph | 4-CH₃-Ph | 0 | H | H | H | H | H | |
| 1724 | 4-Cl-Ph | 3-CH₃-Ph | 0 | H | H | H | H | H | |
| 1725 | 4-Cl-Ph | 2-CH₃-Ph | 0 | H | H | H | H | H | |
| 1726 | 4-Cl-Ph | 2-CF₃-Ph | 0 | H | H | H | H | H | |
| 1727 | 4-Cl-Ph | 3-CF₃-Ph | 0 | H | H | H | H | H | |
| 1728 | 4-Cl-Ph | 2-F-(4-CF₃)-Ph | 0 | H | H | H | H | H | |
| 1729 | 4-Cl-Ph | 4-CH₃O-Ph | 0 | H | H | H | H | H | |
| 1730 | 4-Cl-Ph | 5-Cl-2-pyridyl | 0 | H | H | H | H | H | |
| 1731 | 4-Cl-Ph | 5-Cl-2-thienyl | 0 | H | H | H | H | H | |
| 1732 | 4-Cl-Ph | 2-Cl-3-thienyl | 0 | H | H | H | H | H | |
| 1733 | 4-Cl-Ph | CH₂=C(C₆H₄-4F)– | 0 | H | H | H | H | H | |
| 1734 | 4-Cl-Ph | t-butyl | 0 | H | H | H | H | H | |
| 1735 | 4-Cl-Ph | n-hexyl | 0 | H | H | H | H | H | |
| 1736 | 4-Cl-Ph | n-heptyl | 0 | H | H | H | H | H | |
| 1737 | 4-Cl-Ph | n-octyl | 0 | H | H | H | H | H | |
| 1738 | 4-Cl-Ph | —C₈F₁₇ | 0 | H | H | H | H | H | |
| 1739 | 4-Cl-Ph | —C₆F₁₃ | 0 | H | H | H | H | H | |
| 1740 | 4-Cl-Ph | 4-pyridyl | 0 | H | H | H | H | H | |
| 1741 | 4-Cl-Ph | 2-pyridyl | 0 | H | H | H | H | H | |
| 1742 | 4-Cl-Ph | 2-thienyl | 0 | H | H | H | H | H | |
| 1743 | 4-Cl-Ph | 4-n-Bu-Ph | 0 | H | H | H | H | H | |
| 1744 | 4-Cl-Ph | 4-n-BuO-Ph | 0 | H | H | H | H | H | |
| 1745 | 4-Cl-Ph | 5-CF₃-2-pyridyl | 0 | H | H | H | H | H | |
| 1746 | 4-Cl-Ph | 5-CH₃SO₂-2-thienyl | 0 | H | H | H | H | H | |
| 1747 | 4-C₂H₅-Ph | 4-F-Ph | 0 | H | H | H | H | H | |
| 1748 | 4-(n-BuO)-Ph | 4-F-Ph | 0 | H | H | H | H | H | |
| 1749 | 2-CH₃SO₂-imidazol-1-yl | 4-F-Ph | 0 | H | H | H | H | H | |
| 1750 | 5-CH₃S-1,2,4-triazol-1-yl | 4-F-Ph | 0 | H | H | H | H | H | |
| 1751 | —C₆F₁₃ | 4-F-Ph | 0 | H | H | H | H | H | |
| 1752 | —C₈F₁₇ | 4-F-Ph | 0 | H | H | H | H | H | |
| 1753 | 3-CH₃O-Ph | 4-F-Ph | 0 | H | H | H | H | H | |
| 1754 | 2-CF₃-imidazol-1-yl | 4-F-Ph | 0 | H | H | H | H | H | |
| 1755 | 4-(i-C₃H₇O)-Ph | 4-F-Ph | 0 | H | H | H | H | H | |
| 1756 | 4-I-Ph | 4-F-Ph | 0 | H | H | H | H | H | |
| 1757 | 3,4-F₂-Ph | 4-F-Ph | 0 | H | H | H | H | H | |
| 1758 | 3,4-Cl₂-Ph | 4-F-Ph | 0 | H | H | H | H | H | |
| 1759 | 2,6-Cl₂-Ph | 4-F-Ph | 0 | H | H | H | H | H | |
| 1760 | 2-Cl-(4-F)-Ph | 4-F-Ph | 0 | H | H | H | H | H | |
| 1761 | 2,4,6-Cl₃-Ph | 4-F-Ph | 0 | H | H | H | H | H | |
| 1762 | 4-CH₃-Ph | 4-F-Ph | 0 | H | H | H | H | H | |
| 1763 | 3-CH₃-Ph | 4-F-Ph | 0 | H | H | H | H | H | |
| 1764 | 2-CH₃-Ph | 4-F-Ph | 0 | H | H | H | H | H | |
| 1765 | 2-CF₃-Ph | 4-F-Ph | 0 | H | H | H | H | H | |
| 1766 | 3-CF₃-Ph | 4-F-Ph | 0 | H | H | H | H | H | |
| 1767 | 4-CH₃O-Ph | 4-F-Ph | 0 | H | H | H | H | H | |
| 1768 | 2,3-Cl₂-Ph | 4-F-Ph | 0 | H | H | H | H | H | |
| 1769 | 3,5-Cl₂-Ph | 4-F-Ph | 0 | H | H | H | H | H | |
| 1770 | 2,5-Cl₂-Ph | 4-F-Ph | 0 | H | H | H | H | H | |
| 1771 | 3-Br-Ph | 4-F-Ph | 0 | H | H | H | H | H | |
| 1772 | 4-C₂H₅O-Ph | 4-F-Ph | 0 | H | H | H | H | H | |
| 1773 | 2,4-(CH₃)₂-Ph | 4-F-Ph | 0 | H | H | H | H | H | |
| 1774 | 2,4,6-(CH₃)₃-Ph | 4-F-Ph | 0 | H | H | H | H | H | |
| 1775 | 4-Ph-Ph | 4-F-Ph | 0 | H | H | H | H | H | |
| 1776 | 5-Cl-2-thienyl | 4-F-Ph | 0 | H | H | H | H | H | |
| 1777 | 2-Cl-3-thienyl | 4-F-Ph | 0 | H | H | H | H | H | |
| 1778 | 1-imidazoyl | 4-F-Ph | 0 | H | H | H | H | H | |
| 1779 | 1H-1,2,4-triazoyl-1-yl | 4-F-Ph | 0 | H | H | H | H | H | |
| 1780 | 2-pyridyl | 4-F-Ph | 0 | H | H | H | H | H | |
| 1781 | 5-Cl-2-pyridyl | 4-F-Ph | 0 | H | H | H | H | H | |
| 1782 | 3-pyridyl | 4-F-Ph | 0 | H | H | H | H | H | |
| 1783 | 4-pyridyl | 4-F-Ph | 0 | H | H | H | H | H | |
| 1784 | n-C₄F₉ | 4-F-Ph | 0 | H | H | H | H | H | |

TABLE 4-continued $$A-(CH_2)_n-\overset{CRR^1}{\underset{B}{C}}-\overset{OR^2}{\underset{}{C}}-C(R_3)(R_4)-N\diagdown$$

(structure with triazole ring)

| Ex. No. | A | B | n | R | R¹ | R² | R³ | R⁴ | M.P. °C. |
|---|---|---|---|---|---|---|---|---|---|
| 1785 | 4-I-Ph | 2,4-Cl$_2$-Ph | 0 | H | H | H | H | H | |
| 1786 | 3,4-F$_2$-Ph | 2,4-Cl$_2$-Ph | 0 | H | H | H | H | H | |
| 1787 | 3,4-Cl$_2$-Ph | 2,4-Cl$_2$-Ph | 0 | H | H | H | H | H | |
| 1788 | 2,6-Cl$_2$-Ph | 2,4-Cl$_2$-Ph | 0 | H | H | H | H | H | |
| 1789 | 2-Cl-(4-F)-Ph | 2,4-Cl$_2$-Ph | 0 | H | H | H | H | H | |
| 1790 | 2,4,6-Cl$_3$-Ph | 2,4-Cl$_2$-Ph | 0 | H | H | H | H | H | |
| 1791 | 4-CH$_3$-Ph | 2,4-Cl$_2$-Ph | 0 | H | H | H | H | H | |
| 1792 | 3-CH$_3$-Ph | 2,4-Cl$_2$-Ph | 0 | H | H | H | H | H | |
| 1793 | 2-CH$_3$-Ph | 2,4-Cl$_2$-Ph | 0 | H | H | H | H | H | |
| 1794 | 2-CF$_3$-Ph | 2,4-Cl$_2$-Ph | 0 | H | H | H | H | H | |
| 1795 | 3-CF$_3$-Ph | 2,4-Cl$_2$-Ph | 0 | H | H | H | H | H | |
| 1796 | 4-CH$_3$O-Ph | 2,4-Cl$_2$-Ph | 0 | H | H | H | H | H | |
| 1797 | 2,3-Cl$_2$-Ph | 2,4-Cl$_2$-Ph | 0 | H | H | H | H | H | |
| 1798 | 3,5-Cl$_2$-Ph | 2,4-Cl$_2$-Ph | 0 | H | H | H | H | H | |
| 1799 | 2,5-Cl$_2$-Ph | 2,4-Cl$_2$-Ph | 0 | H | H | H | H | H | |
| 1800 | 3-Br-Ph | 2,4-Cl$_2$-Ph | 0 | H | H | H | H | H | |
| 1801 | 4-C$_2$H$_5$O-Ph | 2,4-Cl$_2$-Ph | 0 | H | H | H | H | H | |
| 1802 | 2,4-(CH$_3$)$_2$-Ph | 2,4-Cl$_2$-Ph | 0 | H | H | H | H | H | |
| 1803 | 2,4,6-(CH$_3$)$_3$-Ph | 2,4-Cl$_2$-Ph | 0 | H | H | H | H | H | |
| 1804 | 4-Ph-Ph | 2,4-Cl$_2$-Ph | 0 | H | H | H | H | H | |
| 1805 | 5-Cl-2-thienyl | 2,4-Cl$_2$-Ph | 0 | H | H | H | H | H | |
| 1806 | 2-Cl-3-thienyl | 2,4-Cl$_2$-Ph | 0 | H | H | H | H | H | |
| 1807 | 1-imidazoyl | 2,4-Cl$_2$-Ph | 0 | H | H | H | H | H | |
| 1808 | 1H-1,2,4-triazoyl-1-yl | 2,4-Cl$_2$-Ph | 0 | H | H | H | H | H | |
| 1809 | 2-pyridyl | 2,4-Cl$_2$-Ph | 0 | H | H | H | H | H | |
| 1810 | 5-Cl-2-pyridyl | 2,4-Cl$_2$-Ph | 0 | H | H | H | H | H | |
| 1811 | 3-pyridyl | 2,4-Cl$_2$-Ph | 0 | H | H | H | H | H | |
| 1812 | 4-pyridyl | 2,4-Cl$_2$-Ph | 0 | H | H | H | H | H | |
| 1813 | n-C$_4$H$_9$ | 2,4-Cl$_2$-Ph | 0 | H | H | H | H | H | |
| 1814 | 4-I-Ph | 4-Cl-Ph | 0 | H | H | H | H | H | |
| 1815 | 3,4-F$_2$-Ph | 4-Cl-Ph | 0 | H | H | H | H | H | |
| 1816 | 3,4-Cl$_2$-Ph | 4-Cl-Ph | 0 | H | H | H | H | H | |
| 1817 | 2,6-Cl$_2$-Ph | 4-Cl-Ph | 0 | H | H | H | H | H | |
| 1818 | 2-Cl-(4-F)-Ph | 4-Cl-Ph | 0 | H | H | H | H | H | |
| 1819 | 2,4,6-Cl$_3$-Ph | 4-Cl-Ph | 0 | H | H | H | H | H | |
| 1820 | 4-CH$_3$-Ph | 4-Cl-Ph | 0 | H | H | H | H | H | |
| 1821 | 3-CH$_3$-Ph | 4-Cl-Ph | 0 | H | H | H | H | H | |
| 1822 | 2-CH$_3$-Ph | 4-Cl-Ph | 0 | H | H | H | H | H | |
| 1823 | 2-CF$_3$-Ph | 4-Cl-Ph | 0 | H | H | H | H | H | |
| 1824 | 3-CF$_3$-Ph | 4-Cl-Ph | 0 | H | H | H | H | H | |
| 1825 | 4-CH$_3$O-Ph | 4-Cl-Ph | 0 | H | H | H | H | H | |
| 1826 | 2,3-Cl$_2$-Ph | 4-Cl-Ph | 0 | H | H | H | H | H | |
| 1827 | 3,5-Cl$_2$-Ph | 4-Cl-Ph | 0 | H | H | H | H | H | |
| 1828 | 2,5-Cl$_2$-Ph | 4-Cl-Ph | 0 | H | H | H | H | H | |
| 1829 | 3-Br-Ph | 4-Cl-Ph | 0 | H | H | H | H | H | |
| 1830 | 4-EtO-Ph | 4-Cl-Ph | 0 | H | H | H | H | H | |
| 1831 | 2,4-(CH$_3$)$_2$-Ph | 4-Cl-Ph | 0 | H | H | H | H | H | |
| 1832 | 2,4,6-(CH$_3$)$_3$-Ph | 4-Cl-Ph | 0 | H | H | H | H | H | |
| 1833 | 4-Ph-Ph | 4-Cl-Ph | 0 | H | H | H | H | H | |
| 1834 | 5-Cl-2-thienyl | 4-Cl-Ph | 0 | H | H | H | H | H | |
| 1835 | 2-Cl-3-thienyl | 4-Cl-Ph | 0 | H | H | H | H | H | |
| 1836 | 1-imidazoyl | 4-Cl-Ph | 0 | H | H | H | H | H | |
| 1837 | 1H-1,2,4-triazoyl-1-yl | 4-Cl-Ph | 0 | H | H | H | H | H | |
| 1838 | 2-pyridyl | 4-Cl-Ph | 0 | H | H | H | H | H | |
| 1839 | 5-Cl-2-pyridyl | 4-Cl-Ph | 0 | H | H | H | H | H | |
| 1840 | 3-pyridyl | 4-Cl-Ph | 0 | H | H | H | H | H | |
| 1841 | 4-pyridyl | 4-Cl-Ph | 0 | H | H | H | H | H | |
| 1842 | n-C$_4$F$_9$ | 4-Cl-Ph | 0 | H | H | H | H | H | |
| 1843 | 4-I-Ph | 2,4-F$_2$-Ph | 0 | H | H | H | H | H | |
| 1844 | 3,4-F$_2$-Ph | 2,4-F$_2$-Ph | 0 | H | H | H | H | H | |
| 1845 | 3,4-Cl$_2$-Ph | 2,4-F$_2$-Ph | 0 | H | H | H | H | H | |
| 1846 | 2,6-Cl$_2$-Ph | 2,4-F$_2$-Ph | 0 | H | H | H | H | H | |
| 1847 | 2-Cl-(4-F)-Ph | 2,4-F$_2$-Ph | 0 | H | H | H | H | H | |
| 1848 | 2,4,6-Cl$_3$-Ph | 2,4-F$_2$-Ph | 0 | H | H | H | H | H | |
| 1849 | 4-CH$_3$-Ph | 2,4-F$_2$-Ph | 0 | H | H | H | H | H | |
| 1850 | 3-CH$_3$-Ph | 2,4-F$_2$-Ph | 0 | H | H | H | H | H | |
| 1851 | 2-CH$_3$-Ph | 2,4-F$_2$-Ph | 0 | H | H | H | H | H | |
| 1852 | 2-CF$_3$-Ph | 2,4-F$_2$-Ph | 0 | H | H | H | H | H | |
| 1853 | 3-CF$_3$-Ph | 2,4-F$_2$-Ph | 0 | H | H | H | H | H | |
| 1854 | 4-CH$_3$O-Ph | 2,4-F$_2$-Ph | 0 | H | H | H | H | H | |
| 1855 | 2,3-Cl$_2$-Ph | 2,4-F$_2$-Ph | 0 | H | H | H | H | H | |
| 1856 | 3,5-Cl$_2$-Ph | 2,4-F$_2$-Ph | 0 | H | H | H | H | H | |
| 1857 | 2,5-Cl$_2$-Ph | 2,4-F$_2$-Ph | 0 | H | H | H | H | H | |

TABLE 4-continued

A—(CH$_2$)$_n$—C(CRR$^1$)(B)—C(O)(OR$^2$)—C(R$_3$)(R$_4$)—N(imidazolyl)

| Ex. No. | A | B | n | R | R$^1$ | R$^2$ | R$^3$ | R$^4$ | M.P. °C. |
|---|---|---|---|---|---|---|---|---|---|
| 1858 | 3-Br-Ph | 2,4-F$_2$-Ph | 0 | H | H | H | H | H | |
| 1859 | 4-C$_2$H$_5$O-Ph | 2,4-F$_2$-Ph | 0 | H | H | H | H | H | |
| 1860 | 2,4-(CH$_3$)$_2$-Ph | 2,4-F$_2$-Ph | 0 | H | H | H | H | H | |
| 1861 | 2,4,6-(CH$_3$)$_3$-Ph | 2,4-F$_2$-Ph | 0 | H | H | H | H | H | |
| 1862 | 4-Ph-Ph | 2,4-F$_2$-Ph | 0 | H | H | H | H | H | |
| 1863 | 5-Cl-2-thienyl | 2,4-F$_2$-Ph | 0 | H | H | H | H | H | |
| 1864 | 2-Cl-3-thienyl | 2,4-F$_2$-Ph | 0 | H | H | H | H | H | |
| 1865 | 1-imidazoyl | 2,4-F$_2$-Ph | 0 | H | H | H | H | H | |
| 1866 | 1H-1,2,4-triazoyl-1-yl | 2,4-F$_2$-Ph | 0 | H | H | H | H | H | |
| 1867 | 2-pyridyl | 2,4-F$_2$-Ph | 0 | H | H | H | H | H | |
| 1868 | 5-Cl-2-pyridyl | 2,4-F$_2$-Ph | 0 | H | H | H | H | H | |
| 1869 | 3-pyridyl | 2,4-F$_2$-Ph | 0 | H | H | H | H | H | |
| 1870 | 4-pyridyl | 2,4-F$_2$-Ph | 0 | H | H | H | H | H | |
| 1871 | n-C$_4$F$_9$ | 2,4-F$_2$-Ph | 0 | H | H | H | H | H | |
| 1872 | 4-F-Ph | 4-F-Ph | 0 | H | H | H | CH$_3$ | H | |
| 1873 | 4-F-Ph | 4-F-Ph | 0 | H | H | H | CH$_3$ | CH$_3$ | |
| 1874 | 4-F-Ph | 4-F-Ph | 0 | H | H | H | F | H | |
| 1875 | 4-F-Ph | 4-F-Ph | 0 | H | H | H | F | CH$_3$ | |
| 1876 | 4-F-Ph | 4-F-Ph | 0 | H | H | H | F | F | |
| 1877 | 4-Cl-Ph | 2,4-Cl$_2$-Ph | 0 | H | H | H | CH$_3$ | H | |
| 1878 | 4-Cl-Ph | 2,4-Cl$_2$-Ph | 0 | H | H | H | CH$_3$ | CH$_3$ | |
| 1879 | 4-Cl-Ph | 2,4-Cl$_2$-Ph | 0 | H | H | H | F | H | |
| 1880 | 4-Cl-Ph | 2,4-Cl$_2$-Ph | 0 | H | H | H | F | CH$_3$ | |
| 1881 | 4-Cl-Ph | 2,4-Cl$_2$-Ph | 0 | H | H | H | F | F | |
| 1882 | 2-Cl-Ph | 4-Cl-Ph | 0 | H | H | H | CH$_3$ | H | |
| 1883 | 2-Cl-Ph | 4-Cl-Ph | 0 | H | H | H | CH$_3$ | CH$_3$ | |
| 1884 | 2-Cl-Ph | 4-Cl-Ph | 0 | H | H | H | F | H | |
| 1885 | 2-Cl-Ph | 4-Cl-Ph | 0 | H | H | H | F | CH$_3$ | |
| 1886 | 2-Cl-Ph | 4-Cl-Ph | 0 | H | H | H | F | F | |
| 1887 | Ph | 4-F-Ph | 0 | H | H | H | CH$_3$ | H | |
| 1888 | Ph | 4-F-Ph | 0 | H | H | H | CH$_3$ | CH$_3$ | |
| 1889 | Ph | 4-F-Ph | 0 | H | H | H | F | H | |
| 1890 | Ph | 4-F-Ph | 0 | H | H | H | F | CH$_3$ | |
| 1891 | Ph | 4-F-Ph | 0 | H | H | H | F | F | |

$^a$NMR: (CDCl$_3$) δ 2.7 (m, 2H), 4.4 (½ of ABq, J=12, 1H), 4.9 (½ of ABq, J=12, 1H), 5.0 (br s, 1H), OH), 6.7 (m, 2H), 7.0 (m, 2H), 7.4 (m, 3H), 7.8 (s, 1H), 8.0 (s, 1H).

EXAMPLE 1930

2-(2,4-Difluorophenyl)-3-(2-chlorophenyl)-1-(1H-1,2,4-imidazol-1-yl)-3-buten-2-ol A mixture of 10.2 g (0.035 mol) of 2-(2,4-difluorophenyl)-2-[1-(2-chlorophenyl)ethenyl]oxirane; 6.20 g (0.091 mol) of imidazole and 12.44 g (0.091 mol) of potassium carbonate in 100 mL of DMSO was heated overnight at 100°, then cooled and poured into 800 mL of H$_2$O. The aqueous mixture was extracted with 4×500 mL Et$_2$O, and the organic extracts were washed with water (2×) and brine, dried over MgSO$_4$ and evaporated to give 7.8 g of a yellow-brown solid. Flash chromatography and trituration with Et$_2$O gave 4.0 g of a white powder, mp 139°–142°: NMR: (CDCl$_3$)δ3.9 (br, OH), 4.2 (½ of ABq, 1H), 4.7 (½ of ABq, 1H, CH$_2$-imidazole), 5.3 (s, 1H, vinyl), 5.5 (s, 1H, vinyl), 6.7 (m, 4H), 7.0–7.5 (m, 6H); IR (nujol) 3400–2600 (br), 1614, 1512, 1501, 1111, 1075, 852, 819, 768, 743, 623 cm$^{-1}$.

The compounds shown in Table 4A were prepared or can be prepared by the methods described above.

TABLE 4A

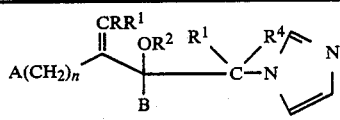

| Ex. No. | A | B | n | R | R$^1$ | R$^2$ | R$^3$ | R$^4$ | M.P. °C. |
|---|---|---|---|---|---|---|---|---|---|
| 1892 | Ph | Ph | 0 | H | H | H | H | | |
| 1893 | Ph | 2-F—Ph | 0 | H | H | H | H | | |
| 1894 | Ph | 4-F—Ph | 0 | H | H | H | H | | (oil)$^a$ |
| 1895 | Ph | 2,4-F$_2$—Ph | 0 | H | H | H | H | | 157–158 |
| 1896 | Ph | 2-Cl—Ph | 0 | H | H | H | H | | |
| 1897 | Ph | 4-Cl—Ph | 0 | H | H | H | H | | |
| 1898 | Ph | 2,4-Cl$_2$—Ph | 0 | H | H | H | H | | |
| 1899 | 2-F—Ph | Ph | 0 | H | H | H | H | | |
| 1900 | 2-F—Ph | 2-F—Ph | 0 | H | H | H | H | | |
| 1901 | 2-F—Ph | 4-F—Ph | 0 | H | H | H | H | | |
| 1902 | 2-F—Ph | 2,4-F$_2$—Ph | 0 | H | H | H | H | | |
| 1903 | 2-F—Ph | 2-Cl—Ph | 0 | H | H | H | H | | |

TABLE 4A-continued $$A(CH_2)_n - \overset{\overset{CRR^1}{\|}}{\underset{B}{\underset{|}{C}}} - \overset{R^1}{\underset{|}{C}} - \overset{R^4}{\underset{N}{\overset{|}{N}}}\diagdown\!\!\!\diagup$$

| Ex. No. | A | B | n | R | $R^1$ | $R^2$ | $R^3$ | $R^4$ | M.P. °C. |
|---|---|---|---|---|---|---|---|---|---|
| 1904 | 2-F—Ph | 4-Cl—Ph | 0 | H | H | H | H | | |
| 1905 | 2-F—Ph | 2,4-Cl$_2$—Ph | 0 | H | H | H | H | | |
| 1906 | 3-F—Ph | Ph | 0 | H | H | H | H | | |
| 1907 | 3-F—Ph | 2-F—Ph | 0 | H | H | H | H | | |
| 1908 | 3-F—Ph | 4-F—Ph | 0 | H | H | H | H | | |
| 1909 | 3-F—Ph | 2,4-F$_2$—Ph | 0 | H | H | H | H | | |
| 1910 | 3-F—Ph | 2-Cl—Ph | 0 | H | H | H | H | | |
| 1911 | 3-F—Ph | 4-Cl—Ph | 0 | H | H | H | H | | |
| 1912 | 3-F—Ph | 2,4-Cl$_2$—Ph | 0 | H | H | H | H | | |
| 1913 | 4-F—Ph | Ph | 0 | H | H | H | H | | |
| 1914 | 4-F—Ph | 2-F—Ph | 0 | H | H | H | H | | 159–160 |
| 1915 | 4-F—Ph | 4-F—Ph | 0 | H | H | H | H | | 175–177 |
| 1916 | 4-F—Ph | 2,4-F$_2$—Ph | 0 | H | H | H | H | | 194–197 |
| 1917 | 4-F—Ph | 2-Cl—Ph | 0 | H | H | H | H | | |
| 1918 | 4-F—Ph | 4-Cl—Ph | 0 | H | H | H | H | | |
| 1919 | 4-F—Ph | 2,4-Cl$_2$—Ph | 0 | H | H | H | H | | 200–215 (60% pure) |
| 1920 | 2,4-F$_2$—Ph | Ph | 0 | H | H | H | H | | |
| 1921 | 2,4-F$_2$—Ph | 2-F—Ph | 0 | H | H | H | H | | |
| 1922 | 2,4-F$_2$—Ph | 4-F—Ph | 0 | H | H | H | H | | |
| 1923 | 2,4-F$_2$—Ph | 2,4-F$_2$—Ph | 0 | H | H | H | H | | |
| 1924 | 2,4-F$_2$—Ph | 2-Cl—Ph | 0 | H | H | H | H | | |
| 1925 | 2,4-F$_2$—Ph | 4-Cl—Ph | 0 | H | H | H | H | | |
| 1926 | 2,4-F$_2$—Ph | 2,4-Cl$_2$—Ph | 0 | H | H | H | H | | |
| 1927 | 2-Cl—Ph | Ph | 0 | H | H | H | H | | |
| 1928 | 2-Cl—Ph | 2-F—Ph | 0 | H | H | H | H | | |
| 1929 | 2-Cl—Ph | 4-F—Ph | 0 | H | H | H | H | | |
| 1930 | 2-Cl—Ph | 2,4-F$_2$—Ph | 0 | H | H | H | H | | 139–142 (HCl salt 215–217) |
| 1931 | 2-Cl—Ph | 2-Cl—Ph | 0 | H | H | H | H | | |
| 1932 | 2-Cl—Ph | 4-Cl—Ph | 0 | H | H | H | H | | 160–162 (HCl salt 170–173) |
| 1933 | 2-Cl—Ph | 2,4-Cl$_2$—Ph | 0 | H | H | H | H | | |
| 1934 | 3-Cl—Ph | Ph | 0 | H | H | H | H | H | |
| 1935 | 3-Cl—Ph | 2-F—Ph | 0 | H | H | H | H | H | |
| 1936 | 3-Cl—Ph | 4-F—Ph | 0 | H | H | H | H | H | |
| 1937 | 3-Cl—Ph | 2,4-F$_2$—Ph | 0 | H | H | H | H | H | |
| 1938 | 3-Cl—Ph | 2-Cl—Ph | 0 | H | H | H | H | H | |
| 1939 | 3-Cl—Ph | 4-Cl—Ph | 0 | H | H | H | H | H | |
| 1940 | 3-Cl—Ph | 2,4-Cl$_2$—Ph | 0 | H | H | H | H | H | |
| 1941 | 4-Cl—Ph | Ph | 0 | H | H | H | H | H | |
| 1942 | 4-Cl—Ph | 2-F—Ph | 0 | H | H | H | H | H | |
| 1943 | 4-Cl—Ph | 4-F—Ph | 0 | H | H | H | H | H | |
| 1944 | 4-Cl—Ph | 2,4-F$_2$—Ph | 0 | H | H | H | H | H | |
| 1945 | 4-Cl—Ph | 2-Cl—Ph | 0 | H | H | H | H | H | |
| 1946 | 4-Cl—Ph | 4-Cl—Ph | 0 | H | H | H | H | H | 179–181 |
| 1947 | 4-Cl—Ph | 2,4-Cl$_2$—Ph | 0 | H | H | H | H | H | |
| 1948 | 2,4-Cl$_2$—Ph | Ph | 0 | H | H | H | H | H | |
| 1949 | 2,4-Cl$_2$—Ph | 2-F—Ph | 0 | H | H | H | H | H | |
| 1950 | 2,4-Cl$_2$—Ph | 4-F—Ph | 0 | H | H | H | H | H | |
| 1951 | 2,4-Cl$_2$—Ph | 2,4-F$_2$—Ph | 0 | H | H | H | H | H | |
| 1952 | 2,4-Cl$_2$—Ph | 2-Cl—Ph | 0 | H | H | H | H | H | |
| 1953 | 2,4-Cl$_2$—Ph | 4-Cl—Ph | 0 | H | H | H | H | H | |
| 1954 | 2,4-Cl$_2$—Ph | 2,4-Cl$_2$—Ph | 0 | H | H | H | H | H | |
| 1955 | 2-Br—Ph | Ph | 0 | H | H | H | H | H | |
| 1956 | 2-Br—Ph | 2-F—Ph | 0 | H | H | H | H | H | |
| 1957 | 2-Br—Ph | 4-F—Ph | 0 | H | H | H | H | H | |
| 1958 | 2-Br—Ph | 2,4-F$_2$—Ph | 0 | H | H | H | H | H | |
| 1959 | 2-Br—Ph | 2-Cl—Ph | 0 | H | H | H | H | H | |
| 1960 | 2-Br—Ph | 4-Cl—Ph | 0 | H | H | H | H | H | |
| 1961 | 2-Br—Ph | 2,4-Cl$_2$—Ph | 0 | H | H | H | H | H | |
| 1962 | 3-Br—Ph | Ph | 0 | H | H | H | H | H | |
| 1963 | 3-Br—Ph | 2-F—Ph | 0 | H | H | H | H | H | |
| 1964 | 3-Br—Ph | 4-F—Ph | 0 | H | H | H | H | H | |
| 1965 | 3-Br—Ph | 2,4-F$_2$—Ph | 0 | H | H | H | H | H | |
| 1966 | 3-Br—Ph | 2-Cl—Ph | 0 | H | H | H | H | H | |
| 1967 | 3-Br—Ph | 4-Cl—Ph | 0 | H | H | H | H | H | |
| 1968 | 3-Br—Ph | 2,4-Cl$_2$—Ph | 0 | H | H | H | H | H | |
| 1969 | 4-Br—Ph | Ph | 0 | H | H | H | H | H | |
| 1970 | 4-Br—Ph | 2-F—Ph | 0 | H | H | H | H | H | |
| 1971 | 4-Br—Ph | 4-F—Ph | 0 | H | H | H | H | H | |

TABLE 4A-continued

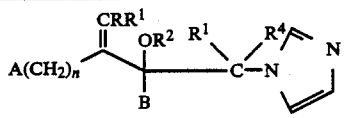

| Ex. No. | A | B | n | R | R¹ | R² | R³ | R⁴ | M.P. °C. |
|---|---|---|---|---|---|---|---|---|---|
| 1972 | 4-Br—Ph | 2,4-F₂—Ph | 0 | H | H | H | H | H | |
| 1973 | 4-Br—Ph | 2-Cl—Ph | 0 | H | H | H | H | H | |
| 1974 | 4-Br—Ph | 4-Cl—Ph | 0 | H | H | H | H | H | |
| 1975 | 4-Br—Ph | 2,4-Cl₂—Ph | 0 | H | H | H | H | H | |
| 1976 | 2-CF₃—Ph | Ph | 0 | H | H | H | H | H | 177–179 |
| 1977 | 2-CF₃—Ph | 2-F—Ph | 0 | H | H | H | H | H | 185–187 |
| 1978 | 2-CF₃—Ph | 4-F—Ph | 0 | H | H | H | H | H | 170–172 |
| 1979 | 2-CF₃—Ph | 2,4-F₂—Ph | 0 | H | H | H | H | H | |
| 1980 | 2-CF₃—Ph | 2-Cl—Ph | 0 | H | H | H | H | H | |
| 1981 | 2-CF₃—Ph | 4-Cl—Ph | 0 | H | H | H | H | H | 159–161 |
| 1982 | 2-CF₃—Ph | 2,4-Cl₂—Ph | 0 | H | H | H | H | H | |
| 1983 | 3-CF₃—Ph | Ph | 0 | H | H | H | H | H | |
| 1984 | 3-CF₃—Ph | 2-F—Ph | 0 | H | H | H | H | H | |
| 1985 | 3-CF₃—Ph | 4-F—Ph | 0 | H | H | H | H | H | |
| 1986 | 3-CF₃—Ph | 2,4-F₂—Ph | 0 | H | H | H | H | H | |
| 1987 | 3-CF₃—Ph | 2-Cl—Ph | 0 | H | H | H | H | H | |
| 1988 | 3-CF₃—Ph | 4-Cl—Ph | 0 | H | H | H | H | H | |
| 1989 | 3-CF₃—Ph | 2,4-Cl₂—Ph | 0 | H | H | H | H | H | |
| 1990 | 4-CF₃—Ph | Ph | 0 | H | H | H | H | H | |
| 1991 | 4-CF₃—Ph | 2-F—Ph | 0 | H | H | H | H | H | |
| 1992 | 4-CF₃—Ph | 4-F—Ph | 0 | H | H | H | H | H | |
| 1993 | 4-CF₃—Ph | 2,4-F₂—Ph | 0 | H | H | H | H | H | |
| 1994 | 4-CF₃—Ph | 2-Cl—Ph | 0 | H | H | H | H | H | |
| 1995 | 4-CF₃—Ph | 4-Cl—Ph | 0 | H | H | H | H · H | H | |
| 1996 | 4-CF₃—Ph | 2,4-Cl₂—Ph | 0 | H | H | H | H | H | |

*NMR: (CDCl₃) δ 4.5(ABq, 2H), 4.8(br s, 1H), 5.5(two s, 2H), 6.7(s, 1H), 6.9(s, 1H), 7.0–7.6(m, 10H)

Pharmaceutical Utility

In vitro activity (Table 5) is expressed in terms of the minimal inhibitory concentration (MIC) of the test compound which inhibits the growth of yeasts and fungi.

The target organisms, *Candida albicans* ATCC 11651 and *Aspergillus fumigatus* ATCC 28214 are standardized, [V. Bezjak, *J. Clinical Micro.*, 21 509–512 (1984)] to a concentration of $10^7$ organisms/ml and maintained at $-70°$ until use. Test compounds are solubilized in dimethyl sulfoxide (DMSO) and diluted in Eagle's Minimum Essential Medium (EMEM) broth to achieve a final concentration of 200 μg/ml. Stock solutions of standard antifungal agents are stored at $-70°$ and diluted in EMEM as required.

The in vitro assay utilizes a microtiter broth dilution technique [L. Polonelli and G. Morace, *Mycopathologia*, 86, 21–28 (1984)] and C. Hughes, et. al. *Antimicrob. Ag. and Chemo.*, 25, 560–562 (1984)]. Test compounds are serially diluted in EMEM to give graded concentrations ranging from 100 to 0.4 μg/ml. The appropriate wells are inoculated with the required organism (*C. albicans* at $1 \times 10^4$ organisms/ml and *A. fumigatus* at $5 \times 10^5$ organisms/ml) and the assay incubated at 30° for 24 hours. The extent of fungal growth is determined at an optical density equal to 540 nm using a scanning spectrophotometer (Flow ® MCC) and MIC values, representing the minimal concentration of a compound which inhibited growth, are determined, [V. Grenta, et al. *Antimicrob. Ag. and Chemo.*, 22, 151–153 (1982)].

The in vivo activity of test compounds is based on the percent (%) survival of infected animals receiving test or standard agent compared to that in an infected untreated group (Table 6). The in vivo assays are chronic systemic infections lethal to mice within 7 days post infection, [J. Barnes, et al. *Lab Investigation*, 49 460–467 (1963), and T. Rogers and E. Balish, *Infection and Immunity*, 14 33–38 (1976)].

*Candida albicans* ATCC 11651, from a frozen stock culture ($10^9$ organisms/ml) maintained at $-70°$, is diluted in saline to $1 \times 10^7$ organisms/ml and 0.2 ml inoculated intravenously (caudal vein) into 20.0 gm CF-1 female mice (Charles River).

Test compounds are routinely solubilized in 0.25% (w/v) methylcellulose (Methocel ®) but for those compounds difficult to solubilize 10% (w/v) Emulophor ® (EL620 GAF Corp.) is used. The standard antifungal agents, amphotericin B (Fungizone ®) in water and ketoconazole (Nizoral ®) in Methocel ® are administered at 1.0 mg/kg/day and 150 mg/kg/day, respectively.

In a primary assay, mice (10 per group) are infected with *C. albicans*, and receive test compounds at 50 or 150 mg/kg/day via the subcutaneous route. Animals are dosed with the test compound at 1 and 6 hour post-infection and then once daily for the next three days. Survival of mice in each group is recorded for 21 days.

Compounds which protect ≧70% of the infected animals for 14 days at a dose 150 mg/kg/day or less are viewed as active.

TABLE 5

In Vitro Antifungal Results

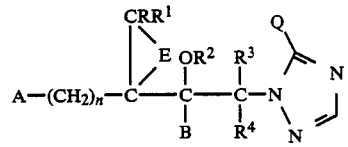

| Example Number | MIC values C. albicans | (μg/ml) A. fumigatus |
|---|---|---|
| 1 | ≦0.01 | 6.3 |
| 1 HCl salt | 0.05 | 12.5 |

TABLE 5-continued

In Vitro Antifungal Results $$A-(CH_2)_n-\underset{B}{\overset{CRR^1}{\underset{|}{C}}}-\underset{|}{\overset{E\ OR^2}{\underset{|}{C}}}-\underset{R^4}{\overset{R^3}{\underset{|}{C}}}-N\underset{N}{\overset{\overset{Q}{\underset{|}{\parallel}}}{\diagdown}}$$

| Example Number | MIC values (μg/ml) C. albicans | A. fumigatus |
|---|---|---|
| 2 | ≦0.4 | 1.6 |
| 3 | ≦0.4 | 50 |
| 4 | 0.03 | 0.8 |
| 6 | 1.6 | 25 |
| 10 | 1.6 | 25 |
| 15 | 0.1 | 50 |
| 16 | 0.03 | 6.3 |
| 17 | 0.03 | 12.5 |
| 25 | 1.6 | 25 |
| 26 | ≦0.4 | 12.5 |
| 26 HCl salt | 0.03 | 0.4 |
| 27 | ≦0.4 | 12.5 |
| 28 | 0.03 | 1.6 |
| 32 | ≦0.4 | 1.6 |
| 33 | 0.03 | 0.03 |
| 34 | 0.03 | 3.2 |
| 34 HCl salt | 0.03 | 1.6 |
| 35 | 0.03 | 0.1 |
| 35 HCl salt | 0.03 | ≦0.2 |
| 39 | 0.4 | 25 |
| 40 | 0.4 | 3.2 |
| 41 | 0.4 | 50 |
| 42 | 0.03 | 6.3 |
| 47 | 0.03 | 1.6 |
| 49 | 0.03 | 12.5 |
| 50 | 0.1 | 0.8 |
| 51 | 0.03 | 3.2 |
| 52 | 0.03 | 0.4 |
| 52 HCl salt | 0.03 | 0.4 |
| 65 | 0.2 | 100 |
| 67 | 0.03 | 100 |
| 85 | ≦0.4 | 12.5 |
| 94 | 0.4 | 50 |
| 99 | 0.05 | 6.3 |
| 100 | 0.03 | 3.2 |
| 101 | 0.03 | 12.5 |
| 114 | 0.4 | 50 |
| 117 | 0.4 | 100 |
| 163 | 0.03 | 12.5 |
| 164 | 0.03 | 1.6 |
| 170 | 1.6 | 100 |
| 177 | 3.2 | >100 |
| 208 | 1.6 | 50 |
| 286 | 0.4 | 25 |
| 291 | 0.2 | 100 |
| 359 | 0.4 | 50 |
| 360 | 0.8 | 100 |
| 361 | 0.8 | 25 |
| 363 | 100 | 100 |
| 447 | 3.2 | N.T. |
| 449 | ≦0.4 | N.T. |
| 450 | >100 | N.T. |
| 451 | 12.5 | N.T. |
| 452 | >100 | N.T. |
| 453 | 1.6 | >100 |
| 454 | 100 | >100 |
| 455 | 25 | N.T. |
| 477 | >100 | N.T. |
| 594 | 0.8 | 0.8 |
| 594 HCl salt | 0.03 | 0.4 |
| 596 | 0.05 | 0.4 |
| 603 | 0.1 | >100 |
| 605 | 0.2 | 100 |
| 608 | 0.4 | 6.3 |
| 620 | 0.03 | 0.05 |
| 622 | 0.03 | 0.1 |
| 627 | 0.03 | 25 |
| 644 | 0.03 | 0.4 |
| 646 | 0.03 | 0.4 |
| 651 | 0.8 | 100 |
| 656 | ≦0.4 | 12.5 |
| 657 | 0.4 | 100 |
| 661 | 1.6 | 100 |
| 667 | 6.3 | 25 |
| 668 | 0.4 | 50 |
| 669 | 0.03 | 0.8 |
| 671 | 0.03 | 0.2 |
| 675 | 0.1 | 25 |
| 685 | 0.8 | 100 |
| 699 | 50 | 100 |
| 721 | 0.4 | 12.5 |
| 724 | 0.4 | 0.4 |
| 726 | 0.8 | 6.3 |
| 815 | 0.03 | >100 |
| 905 | 0.04 | 100 |
| 1258 | 1.6 | >100 |
| 1260 | 0.8 | >100 |
| 1276 | 0.03 | 1.6 |
| 1276a | 3.2 | 100 |
| 1277 | 0.03 | 6.3 |
| 1277 HCl salt | 0.03 | 3.2 |
| 1277a | 6.3 | 100 |
| 1278 | ≦0.4 | >100 |
| 1300 | ≦0.4 | 6.3 |
| 1377 | 1.6 | 100 |
| 1451 | >100 | >100 |
| 1459 | >100 | >100 |
| 1487 | 0.4 | 6.3 |
| 1527 | 0.4 | 6.3 |
| Standards* | | |
| Amphotericin B | 0.33 ± 0.2 | 1.4 ± 0.5 |
| Nystatin | 1.3 ± 0 | 3.0 ± 1.0 |
| 5-Fluorocytosine | 0.14 ± 0.1 | 5.7 ± 4.0 |
| Ketoconazole | ≦0.1 | 11.0 ± 5.0 |
| Miconazole | ≦0.1 | 1.3 ± 0 |

*MIC values of the standard drugs are the mean of five determinations ± Standard deviation

TABLE 6

In Vivo Antifungal Results
% Survival (150 mg/kg per day)
Primary Assay

| Ex. No. | Days 7 | 14 | 21 |
|---|---|---|---|
| 1 | 100 | 100 | 80 |
| 2 | 100 | 100 | 80 |
| 3 | 100 | 100 | 60 |
| 4 | 100 | 50 | N.T. |
| 6 | 50 | 10 | 0 |
| 10 | 20 | 10 | 0 |
| 15 | 100 | 90 | 60 |
| 16 | 100 | 100 | 100 |
| 17 | 100 | 90 | 70 |
| 25 | 100 | 100 | 50 |
| 26 | 100 | 100 | 100 |
| 26 salt | 100 | 90 | 80 |
| 27 | 100 | 100 | 100 |
| 28 | 100 | 90 | N.T. |
| 32 | 100 | 90 | 50 |
| 33 | 100 | 100 | 100 |
| 34 | 100 | 100 | 100 |
| 34 salt | 100 | 100 | 100 |
| 35 | 100 | 100 | 90 |
| 35 sat | 100 | 100 | 70 |
| 39 | 100 | 80 | N.T. |
| 40 | 100 | 100 | N.T. |
| 41 | 100 | 100 | N.T. |
| 42 | 80 | 80 | 50 |
| 47 | 90 | 80 | 30 |

TABLE 6-continued

In Vivo Antifungal Results
% Survival (150 mg/kg per day)
Primary Assay

| Ex. No. | Days 7 | 14 | 21 |
|---|---|---|---|
| 49 | 100 | 90 | 60 |
| 50 | 100 | 90 | 50 |
| 51 | 100 | 100 | 80 |
| 52 | 100 | 100 | 90 |
| 52 salt | 100 | 100 | 90 |
| 55 | 100 | 70 | 50 |
| 65 | 100 | 70 | 50 |
| 67 | 100 | 100 | 100 |
| 85 | 100 | 80 | 70 |
| 94 | 100 | 40 | 10 |
| 99 | 100 | 100 | 40 |
| 100 | 100 | 50 | 30 |
| 101 | 100 | 90 | 60 |
| 114 | 70 | 10 | 10 |
| 117 | 60 | 0 | 0 |
| 163 | 90 | 60 | 40 |
| 164 | 100 | 80 | 70 |
| 208 | 0 | 0 | 0 |
| 286 | 100 | 50 | 20 |
| 359 | 100 | 80 | 80 |
| 360 | 100 | 60 | 40 |
| 361 | 100 | 100 | 90 |
| 363 | 10 | 0 | 0 |
| 453 | 60 | 40 | 30 |
| 594 | 70 | 10 | 0 |
| 596 | 70 | 60 | 40 |
| 603 | 10 | 0 | 0 |
| 608 | 100 | 70 | 20 |
| 620 | 100 | 100 | 90 |
| 622 | 100 | 100 | 100 |
| 627 | 0 | 0 | 0 |
| 644 | 80 | 70 | 50 |
| 646 | 100 | 100 | 70 |
| 651 | 100 | 50 | 20 |
| 656 | 100 | 90 | 40 |
| 657 | 0 | 0 | 0 |
| 661 | 50 | 20 | 0 |
| 667 | 10 | 0 | 0 |
| 668 | 70 | 10 | 0 |
| 669 | 100 | 100 | 100 |
| 671 | 100 | 100 | 60 |
| 675 | 100 | 60 | 0 |
| 685 | 30 | 10 | 0 |
| 721 | 100 | 30 | 30 |
| 724 | 100 | 90 | 40 |
| 725 | 90 | 90 | 40 |
| 726 | 100 | 80 | 10 |
| 905 | 80 | 50 | 20 |
| 1276 | 100 | 70 | 50 |
| 1276a | 0 | 0 | 0 |
| 1277 | 100 | 100 | 90 |
| 1277a | 80 | 0 | 0 |
| 1278 | 0 | 0 | 0 |
| 1487 | 100 | 100 | 70 |
| 1527 | 100 | 70 | 20 |
| Standards | | | |
| Amphotericin B | 100 | 100 | 100 |
| Ketoconazole | 100 | 80 | 50 |

N.T.: Not Tested

DOSAGE FORMS

The antimycotic agents of this invention can be administered by any means that effects contact of the active ingredient with the agent's site of action in the body. The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration: age, health, and weight of the recipient; nature and extent of symptoms, kind of concurrent treatment, frequency of treatment, and the effect desired.

Dosage forms (combinations) suitable for administration contain from about 200 milligrams to about 2000 milligrams of active ingredient per unit. In these pharmaceutical compositions, the active ingredient will ordinarily be present in an amount of about 0.5–95% by weight based on the total weight of the composition. For use in the treatment of said diseases, a daily dose of active ingredient can be about 10 to 50 milligrams per kilogram of body weight.

The composition of the invention may be in a conventional pharmaceutical form suitable for oral administration, for example a tablet, a capsule, an emulsion or an aqueous or oily solution or suspension, or suitable for topical application, for example a cream, ointment or gel. It can also be administered parenterally in sterile liquid dosage forms.

Gelatin capsules contain the active ingredient and powdered carriers, such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrintestinal tract.

The pharmaceutical compositions which are ointments, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilising agents, and if necessary, buffer substances. Antioxidising agents such as sodium bisulfite, sodium sulfite, or ascorbic acid, either alone or combined, are suitable stabilising agents.

All the pharmaceutical compositions according to the invention can also contain coloring and flavoring to increase patient acceptance.

Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams of magnesium stearate.

Soft Gelatin Capsules

A mixture of active ingredients in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tables are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability of delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

Cream

A cream for topical application is prepared by incorporating 100 milligrams of the finely pulverized active ingredient in 5 grams of a cream base which comprises 40% white petrolatum, 3% microcrystalline wax, 10% lanolin, 5% Span ®20, 0.3% Tween ®20 and 41.7% water.

Agricultural Formulations

The compounds of this invention when used for agricultural purposes will generally be used in formulation with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 35% surfactant(s) and (b) about 5% to 99% solid or liquid inert diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–0 | 40–95 | 0—35 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co. Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See. J. E. Browing, "Agglomeration", *Chemical Engineering,* Dec. 4, 1967, pp. 147ff. and "Perry's Chemical Engineer's Handbook", 4th Edn., McGraw-Hill, New York, 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Examples 8, 12, 15, 39, 41, 52, 53, 58, 132, 138–140, 162–164, 166, 167, 169–192.

H. Gysin and E. Knusli, U.S. Pat. No. 2,891,855, June 23, 1959, Col. 3, Line 66 through Col. 5, Line 17 and Examples 1–4.

G. C. Klingman, "Weed Control as a Science", John Wiley and Sons, Inc., New York, 1961, pp. 81–96.

J. D. Fryer and S. A. Evans, "Weed Control Handbook", 5th Edn. Blackwell Scientific Publications, Oxford, 1968, pp. 101-103.

Examples of useful formulations of compounds of the present invention are as follows.

| Wettable Powder | |
|---|---|
| 2-(2,4-difluorophenyl)-3-(4-fluorophenyl)-1-(1H-1,2,4-triazol-1-yl)-3-buten-1-ol; and the (S) enantiomer thereof | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, re-blended and packaged.

| Granule | |
|---|---|
| wettable powder of above example | 15% |
| gypsum | 69% |
| potassium sulfate | 16% |

The ingredients are blended in a rotating or fluid bed mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range.

| High Strength Concentrate | |
|---|---|
| 2-(2-fluorophenyl)-3-(4-fluorophenyl)-1-(1H-1,2,4-triazol-1-yl)-3-buten-2-ol; and the (S) enantiomer thereof | 98.5% |
| silica aerogel | 0.5% |
| synthetic amorphous fine silica | 1.0% |

The ingredients are blended and ground in a hammer-mill to produce a high strength concentrate essentially all passing a U.S.S. No. 50 sieve (0.3 mm openings). This material may then be formulated in a variety of ways.

| Aqueous Suspension | |
|---|---|
| 2-(2,4-difluorophenyl)-3-phenyl-1-(1H-1,2,4-triazol-1-yl)-3-buten-2-ol; and the (S) enantiomer thereof | 25% |
| hydrated attapulgite | 3% |
| crude calcium ligninsulfonate | 10% |
| sodium dihydrogen phosphate | 0.5 |
| water | 61.5% |

The ingredients are ground together in a ball, sand, or roller mill until the solid particles have been reduced to diameters under 10 microns.

| Solution | |
|---|---|
| 2-(2,4-difluorophenyl)-3-(4-chlorophenyl)-1-(1H-1,2,4-triazol-1-yl)-3-buten-2-ol; and the (S) enantiomer thereof | 30% |
| dimethylformamide | 70% |

The ingredients are combined and stirred to produce a solution, which can be used for low volume applications.

| Emulsifiable Concentrate | |
|---|---|
| 2-(2,4-difluorophenyl)-3-(4-fluorophenyl)-1-(1H-1,2,4-triazol-1-yl)-3-buten-2-ol; and the (S) enantiomer thereof | 15% |
| blend of calcium sulfonates and nonionic surfactants | 25% |
| xylene | 60% |

The ingredients are combined and stirred until the active is dissolved. A fine screen filter is included in packaging operation to insure the absence of any extraneous undissolved material in the product.

Utility

The compounds of this invention are useful as plant disease control agents. They are effective in controlling a broad spectrum of plant diseases, particularly foliar pathogens of ornamental, vegetable, field, cereal and fruit crops, such as *Puccinia recondita, Erysiphe cichoracearum, Erysiphe graminis, Venturia inaequalis, Cercospora arachidicola,* and *Monilinia fructicola, Rhizoctonia solani, Pyricularia oryzae, Botrytis cinerea, Pseudocercosporella herpotrichlorides,* and *Cercosporidium personatum.* They also control seed pathogens.

Disease control is ordinarily accomplished by applying an effective amount of the compound either pre- or post-infection to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for these compounds can be influenced by many factors of the environment and should be determined under actual use conditions. Foliage can normally be protected when treated at a rate of from less than 1 g/ha to 5000 g/ha of active ingredient. Plants growing in soil treated at a concentration from 0.1 to about 20 kg/ha can be protected from disease. Seed and seedlings can normally be protected when seed is treated at a rate of from 0.06 to about 3 grams per kilogram of seed.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)methyl 1-(butylcarbamoy)-2-benzimidazolecarbamate (benomyl)
2-cyano-N-ethylcarbamoyl-2-methoxyiminoacetamide (cymoxanil)
N-trichloromethylthiotetrahydrophthalamide (captan)
N-trichloromethylthiophthalimide (folpet)

dimethyl 4,4'-(o-phenylene)bis(3-thioallophanate)(thiophanate-methyl)
2-(thiazol-4-yl)benzimidazole (thiabendazole)
aluminum tris(O-ethyl phosphonate)(phosethyl aluminum) tetrachloroisophthalonitrile (chlorothanonil)
2,6-dichloro-4-nitroaniline (dichloran) N-(2,6-dimethylphenyl)-N-(methoxyacetyl)alanine methyl ester (metalaxyl)
cris-N-[1,2,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)
4-(3-(4-(1,1-dimethyl-ethyl)phenyl)-2-methyl)propyl-2,6-dimethylmorpholine (Fenpropimorph)
4-(3-4(1,1-dimethyl-ethyl)phenyl)-2-methyl)propyl-piperidine (Fenpropidine)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-B]quinonolin-2-one (oxythiioquinox)
2,2,2-trichlor-1,1-bis(4-chlorophenyl)ethanol(dicofol)
bis(pentachloro-2,4-cyclopentadien-1-yl)(dienochlor)
tricyclohexyltin hydroxide (cyhexatin)
hexakis(2-methyl-2-phenylpropyl)distannoxane (fenbutin oxide)

Nematicides

2-[diethoxyphosphinylimino]-1,3-diethietane (fosthietan)
S-methyl-1-(dimethylcarbamoyl)-N-(methylcarbamoyloxy)thioformimidate(oxamyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-0-(2-isopropyl-4-methyl-6-pyrimidyl)phosphorothioate (diazinon)
octachlorocamphene (toxaphene)
O-ethyl O-p-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl (±)-cis,trans-3-(2,2-dichloroethenyl)-2,2-dimethylcyclopropanecarboxylate (permethrin)
dimethyl N,N'-[thiobis(N-methylimmo)carbonyloxy]]-bis[ethanimidothioate] (thiodicarb)
phosphorothiolothionic acid, O-ethyl-O-[4-(methylthio)phenyl]-S-n-propyl ester (sulprofos)
α-cyano-3-phenoxybenzyl 3-(2,2-dichlorovinyl)-2,2-dimethylcyclopropane carboxylate (cypermethrin)
cyano(3-phenoxyphenyl)methyl 4-(difluoromethoxy)-α-(methylethyl)benzeneacetate (flucythrinate)
O,O-dimethyl-O-(3,5,6-trichloro-2-pyridyl)phosphorothioate (chlorpyrifos)
O,O-dimethyl-S-[(4-oxo-1,2,3-benzotriazin-3-(4H)-yl)methyl]phosphorodithioate (azinphos-methyl)
5,6-dimethyl-2-dimethylamino-4-pyrimidinyl dimethyl carbamate (pirimicarb)
S-(N-formyl-N-methylcarbamoylmethyl)-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (fluvalinate)

Test results indicate that the compounds of the present invention are also active preemergent or postemergent herbicides or plant growth regulators. Some of them have utility for broad-spectrum pre- and/or post emergence weed control in areas where complete control of all vegetation is desired, such as around industrial storage areas, parking lots, drive-in theaters, around billboards, highway and railroad structures. Other compounds have utility for selective weed control in crops such as rice, wheat, barley, corn, soybeans, sugarbeets and cotton. Some of the compounds are useful as selective herbicides for rice. They may be used either in direct seeded or transplanted rice. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.050 to 20 kg/ha, the lower rates being suggested for use on lighter soils and/or those having a low organic matter content, for plant growth modification or for situations where only short-term persistance is required, such as a herbicide for fallow land.

The compounds of the invention may be used in combination with any other commercial herbicide, non-limiting examples of which are those below:

| Common Name | Chemical Name |
| --- | --- |
| acifluorfen | 5-[2-chloro-4-(trifluoromethyl)-phenoxy]-2-nitrobenzoic acid |
| acrolein | acrolein |
| alachlor | 2-chloro-2',6',-diethyl-N-(methoxymethyl)-acetanilide |
| ametryn | 2-(ethylamino)-4-(isopropylamino)-6-methylthio)-s-triazine |
| amitrole | 3-amino-s-triazole |

| Chemical Name | |
|---|---|
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N-butyl-N-ethyl-α,α,α-trifluoro-2,6-dinitro-p-toluidine |
| bensulide | O,O-diisopropyl phosphorodithioate S-ester with N-(2-mercaptoethyl)-benzenesulfonamide |
| bentazon | 3-isopropyl-1H-2,1,3-benzothiadiazin-4(3H)-one 2,2-dioxide |
| benzipram | 3,5-dimethyl-N-(1-methylethyl)-N-(phenylmethyl)benzamide |
| benzoylprop | N-benzoyl-N-(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N-(butoxymethyl)-2-chloro-2',6'-diethylacetanilide |
| butam | 2,2-dimethyl-N-(1-methylethyl)-N-(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl-diisobutylthiocarbamate |
| cacodylic acid | hydroxydimethylarsine oxide |
| carbetamide | D-N-ethyllactamide carbanilate (ester) |
| CDAA | N-N-diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isoproyl m-chlorocarbanilate |
| chlorsulfuron | 2-chloro-N-[(4-methoxy-6-methyl-1,3,5-triazin-2-yl)amino-carbonyl]benzene-sulfonamide |
| chlortoluron | N'-(3-chloro-4-methylphenyl-N',N'-dimehylurea |
| cisanilide | cis-2,5-dimethyl-N-phenyl-1-pyrrolidine-carboxamide |
| CMA | calcium methanearsonate |
| cyanazine | 2-[[4-chloro-6-(ethylamino)-s-triazin-2-yl]amino]-2-methylpropionitrile |
| cycloate | S-ethyl N-ethylthiocyclohexane-carbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecar-boxanilide |
| dalapon | 2,2-dichloropropionic acid |
| dazomet | tetrahydro-3,5-dimethyl-2H-1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S-(2,3-dichloroallyl)diisopropyl-thiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]-propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^4,N^4$-diethyl-α,α,α-trifluoro-3,5-dinitrotoluene-2,4-diamine |
| dinoseb | 2-sec-butyl-4,6-dinitrophenol |
| diphenamide | N,N-dimethyl-2,2-diphenylacetamide |
| dipropetryn | 2-(ethylthio)-4,6-bis(isopropyl-amino)-s-triazine |
| diquat | 6,7-dihydrodipyrido[1,2-a:2',1',-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop | ethyl 2-(4-(6-chloro-2-benzoxazolyl-oxy)phenoxy)propanoate |
| fenuron | 1,1-dimethyl-3-phenylurea |
| fenuron TCA | 1,2-dimethyl-3-phenylurea mono(trichloroacetate) |
| flamprop | N-benzoyl-N-(3-chloro-4-fluorophenyl)-DL-aniline |
| fluchloralin | N-(2-chloroethyl)-2,6-dinitro-N-propyl-4-(trifluoromethyl)aniline |
| fluometuron | 1,1-dimethyl-3-(α,α,α-trifluoro-m-tolyl)-urea |
| fluorodifen | p-nitrophenyl α,α,α-trifluoro-2-nitro-p-tolyl ether |
| fluridone | 1-methyl-3-phenyl-5-[3-(trifluoro-methyl)phenyl]-4-(1H)-pyridinone |
| fomesafen | 5-(2-chloro-4-trifluoromethyl-phenoxy)-N-methylsulfonyl-2-nitrobenzamide |
| fosamine | ethyl hydrogen (aminocarbonyl)-phosphonate |
| glyphosate | N-(phosphonomehyl)glycine |
| hexaflurate | potassium hexafluoroarsenate |
| hexazinone | 3-cyclohexyl-6-(dimethylamino)-1-methyl-1,3,5-triazine-2,4(1H, 3H)-dione |
| imazaquin | 2-(4,5-dihydro-4-methyl-4-(1-methyl-ethyl)-5-oxo-1H-imidazol-2-yl)-3-quinolinecarboxylic acid |
| ioxynil | 4-hydroxy-3,5-diiodobenzonitrile |
| isopropalin | 2,6-dinitro-N,N-dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H-cyclopentapyrimidine-2,4(3H,5H)-dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N-(2,4-dimethyl-5-[[(trifluoromethyl)-sulfonyl]amino]phenyl]acetamide |
| methalpropalin | N-(2-methyl-2-propenyl)-2,6-dinitro-N-propyl-4-(trifluoromethyl)-benzenamide |
| methabenzthiazuron | 1,3-dimethyl-3-(2-benzothiazolyl) urea |
| metham | sodium methyldithiocarbamate |
| methazole | 2-(3,4-dichlorophenyl)-4-methyl- |

| | |
|---|---|
| | -continued |
| | Chemical Name |
| | 1,2,4-oxadiazolidine-3,5-dione |
| methoxuron | N'-(3-chloro-4-methoxyphenyl)N,N-dimethylurea |
| metolachlor | 2-chloro-N-(2-ethyl-6-methylphenyl)-N-(2-methoxy-1-methylethyl)-acetamide |
| metribuzin | 4-amino-6-tert-butyl-3-(methylthio)-as-triazine-5(4H)-one |
| metsulfuron methyl | 2-[[(4-methoxy-6-methyl-1,3,5-triazine-2-yl)aminocarbonyl]aminosulfonyl]benzoic acid, methyl ester |
| molinate | S-ethyl hexahydro-1H-azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-α-naphthoxy)-N,N-diethylpropionamide |
| naptalam | N-1-naphthylphthalamic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichlorophenyl p-nitrophenyl ether |
| nitrofluorofen | 2-chloro-1-(4-nitrophenoxy)-4-(trifluoromethyl)benzene |
| norea | 3-(hexahydro-4.7-methanoindan-5-yl)-1.1-dimethylurea |
| norflurazon | 4-chloro-5-(methylamino)-2-(α,α,α-trifluoro-m-tolyl)-3(2H)-pyridazinone |
| oryzalin | 3,4-dinito-N,N-dipropylsulfanilamide |
| oxadiazon | 2-tert-butyl-4-(2,4-dichloro-5-isopropoxyphenyl)Δ²-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N-(cyclopropylmethyl)-α,α,α-trifluoro-2,6-dinitro-N-propyl-p-toluidine |
| prometon | 2.4-bis(isopropylamino)-6-methoxy-s-triazine |
| prometryn | 2,4-bis(isopropylamino)-6-(methylthio)-s-triazine |
| pronamide | 3,5-dichloro N-(1,1-dimethyl-2-propyn-yl)enzamide |
| propachlor | 2-chloro-N-isopropylacetanilide |
| propanil | 3',4'-dichloroprionalide |
| propazine | 2-chloro-4,6-bis(isopropylamino)-s-triazine |
| propham | isopropyl carbanilate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| quinofop ethyl | 2-[4-(6-chloroquinoxalin-2-yloxy)-phenoxypropanoic acid, ethyl ester |
| secbumeton | N-ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)-ethylsulfonyl]-pyridine-N-oxide |
| TCA | trichloroacetic acid |
| tebuthiuron | N-[5-(1,1-dimethylethyl)-1,3,4-thiadiazol-2-yl]-N,N'-dimethylurea |
| terbacil | 3-tert-butyl-5-chloro-6-methyluracil |
| terbuchlor | N-(butoxymethyl)-2-chloro-N-[2-(1.1-dimethylethyl)-6-methylphenyl]-aceamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methylthio)-s-triazine |
| tetrafluron | N,N-dimethyl-N'-[3-(1,1,2,2-tetrafluoroethoxy)phenyl]urea |
| thiobencarb | S-[(4-chlorophenyl)methyl] diethylcarbamothioate |
| triallate | S-(2,3,3-trichloroallyl)-diisopropylthiocarbamate |
| trifluralin | α,α,α-tifluoro-2,6-dinitro-N,N propyl-p-toluidine |
| trimeturon | 1-(p-chlorophenyl)-2,3,3-trimethylpseudourea |
| vernolate | S-propyl dipropylthiocarbamae ethyl 5-[2-chloro-4-(trifluoromethyl)-phenoxy]-2-nitrobenzoic acid |
| 2,3,6-TBA | 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |
| Trade Name or Code Number | |
| "Cinch" | exo-1-methyl-4-(1-methylethyl)-2-[2-methylphenyl)methoxy]7-oxabicyclo[2.2.1]heptane |
| AC 263,499 | 2-[4,5-dihydro-4-methyl-4-(1-methyl-ethyl)-5-oxo-1H-imidazol-2-yl]-5-ethyl-3-pyridinecarboxylic acid |
| Harmony ™ | 3-[[(4-methoxy-6-methyl-1,3-5-triazin-2-yl)aminocarbonyl]aminosulfonyl]-2-thiophenecarboxylic acid, methyl eser |
| PPG-1013 | 5-(2-chloro-4-(trifluoromethyl)-phenoxy)propanoic acid, methyl ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid,methyl ester and 6-(4-isopropyl-4-methyl-5-oxo-2-imidazolin-2-yl-p-toluic acid, methyl ester |

The herbicidal properties of the subject compounds were discovered in a number of greenhouse tests. The test procedures and results follow.

This invention is further illustrated by the following examples.

EXAMPLE A

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on apple seedings. The following day plants were inoculated with a spore suspension of *Venturia inaequalis*, the casual agent of apple scab, and incubated in a saturated humidity chamber at 20° C. for 24 hours and then in a growth chamber at 22° C. for 11 days, when disease ratings were made.

EXAMPLE B

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on peanut seedlings. The following day plants were inoculated with a spore suspension of *Cercosporidium personatum*, the casual agent of Peanut Late Leafspot, and incubated in a saturated humidity chamber at 22° C. for 24 hours, then in a high humidity chamber at 27° C. for 7 days, and then in a growth chamber at 29° C. for 7 days, when disease ratings were made.

EXAMPLE C

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on broad bean seedlings. The following day plants were inoculated with a spore suspension of *Botrytis cinerea*, the causal agent of beam grey mold, and incubated in a saturated humidity chamber at 20° C. for 24 hours when disease ratings were made.

EXAMPLE D

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on wheat seedlings. The following day plants were inoculated with a spore dust of *Erysiphe graminis f. sp. tritici, the causal agent of wheat powdery mildew*, and incubated in a growth chamber at 20° C. for 6 days, when disease ratings were made.

EXAMPLE E

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on rice seedlings. The following day plants were inoculated with a spore suspension of *Pyricularia oryzae*, the causal agent of rice blast, and incubated in a saturated humidity chamber at 27° C. for 24 hours and then in a growth chamber at 29° C. for 4 days, when disease ratings were made.

EXAMPLE F

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on rice seedlings. The following day plants were inoculated with a spore suspension of *Rhizoctonia solani*, the causal agent of rice sheath blight, and incubated in a saturated humidity chamber at 27° C. for 48 hours and then in a growth chamber at 29° C. for 4 days, when disease ratings were made.

EXAMPLE G

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on wheat seedlings. The following day plants were inoculated with a spore suspension of *Puccinia recondita*, the causal agent of wheat leaf rust, and incubated in a saturated humidity chamber at 20° C. for 24 hours and then in a growth chamber at 20° C. for 8 days, when disease ratings were made.

EXAMPLE H

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on tomato seedlings. The following day plants were inoculated with a spore suspension of *Phytophthora infestans*, the causal agent of tomato late light, and incubated in a saturated humidity chamber at 20° C. for 24 hours and then in a growth chamber at 20° C. for 5 days, when disease ratings were made.

EXAMPLE I

The test compounds were dissolved in acetone in an amount equal to 6% of the final volume and then suspended at a concentration of 100 or 20 ppm in purified water containing 250 ppm of the surfactant TREM 014 (polyhydric alcohol esters). This suspension was sprayed to the point of run-off on grape seedlings. The following day plants were inoculated with a spore suspension of *Plasmorpara viticola*, the causal agent of grade downy mildew, and incubated in a saturated humidity chamber at 20° C. for 24 hours, then in a growth chamber at 20° C. for 7 days and then held in a saturated humidity chamber at 20° C. for 24 hours, when disease ratings were made.

EXAMPLE J

The test compounds were dissolved in acetone so that 1 ml of solution yielded a concentration of 0.5 kilogram/hectare when added to cucumber seeds and soil in pots. Seeds and soil were then inoculated with a mixture of sand, cereal and mycelium of the fungus *Pythium aphanadermatum*, causal agent of cucumber damping off, and incubated in a growth chamber at 30° C. for 14 days. Disease ratings were then made.

EXAMPLE K

The test compounds were dissolved in acetone so that 1 ml of solution yielded a concentration of 0.5 kilogram/hectare when added to cotton seeds and soil in pots. Seeds and soil were then inoculated with a mixture of sand, cereal and mycelium of the fungus *Rhizoctonia solani*, causal agent of cotton blight, and incubated in a growth chamber at 30° C. for 14 days. Disease ratings were then made.

EXAMPLE L

The test compounds were dissolved in acetone so that 1 ml of solution yielded a concentration of 0.5 kilogram/hectare when added to cucumber seeds and soil in pots. Seeds and soil were then inoculated with a mixture of sand, cereal and mycelium of the fungus *Fusarium oxysporum* f. sp. cucumerinum, causal agent of cucumber wilt, and incubated in a growth chamber at 20° C. for 14 days. Disease ratings were then made.

EXAMPLE M

The test compounds were dissolved in acetone so that 1 ml of solution yielded a concentration of 0.5 kilogram/hectare when added to lima bean seeds and soil in pots. Seeds and soil were then inoculated with a mixture of sand, cereal and mycelium of the fungus *Sclerotium rolfsii*, causal agent of southern blight, and incubated in a growth chamber at 30° C. for 14 days. Disease ratings were then made.

Results for Examples A–M are given in Table 7. In this table, a rating of 100 indicates 100% disease control and a rating of 0 indicates no disease control relative to the controls. A — entry indicates that no test was performed with the specified compound. A P entry indicates that disease control was not measured due to phytotoxicity.

TABLE 7

| Ex. No. | Rate (PPM) | Ex. A | Ex. B | Ex. C | Ex. D | Ex. E | Ex. F | Ex. G | Ex. H | Ex. I | Rate (kg/ha) | Ex. J | Ex. K | Ex. L | Ex. M |
|---|---|---|---|---|---|---|---|---|---|---|---|---|---|---|---|
| 1 | 100 | 62 | 100 | 81 | 98 | 90 | 97 | 100 | 0 | 12 | 5 | 0 | P | 0 | P |
| 2 | 100 | 62 | 100 | 93 | 98 | 95 | 100 | 100 | 0 | 99 | 5 | 0 | P | 0 | P |
| 3 | 100 | 100 | 100 | 93 | 93 | 5 | 93 | 100 | 0 | 0 | 5 | 0 | 0 | P | P |
| 4 | 100 | 100 | 100 | 88 | 100 | 96 | 100 | 100 | 0 | 81 | 5 | 0 | 0 | P | 0 |
| 6 | 100 | 0 | 82 | 84 | 98 | 0 | 0 | 96 | 23 | 0 | 5 | 0 | 0 | P | 0 |
| 10 | 100 | 0 | 76 | 52 | 63 | 0 | 17 | 64 | 0 | 0 | 5 | 0 | 0 | 0 | 0 |
| 15 | 100 | 100 | 100 | 99 | 100 | 1 | 93 | 100 | 26 | 0 | 5 | 0 | P | 0 | P |
| 16 | 100 | — | — | 46 | — | 0 | 0 | — | 0 | 23 | 5 | 0 | 0 | P | 0 |
|  | 20 | 74 | 99 | 27 | 67 | 0 | 0 | 100 | — | — |  |  |  |  |  |
| 17 | 100 | — | — | 89 | — | 0 | 81 | — | 0 | 42 | 5 | 0 | 0 | P | 0 |
|  | 20 | 80 | 100 | 57 | 95 | 0 | 0 | 100 | — | — |  |  |  |  |  |
| 25 | 100 | 100 | 100 | 96 | 91 | 31 | 48 | 97 | 0 | 0 | 5 | 0 | P | P | 35 |
| 26 | 100 | 100 | 100 | 96 | 86 | 31 | 61 | 97 | 23 | 86 | 5 | 0 | 25 | 25 | 35 |
| 27 | 100 | 62 | 100 | 88 | 98 | 95 | 100 | 100 | 24 | 84 | 5 | 0 | 0 | 0 | 0 |
| 28 | 100 | 89 | 100 | 88 | 98 | 81 | 100 | 100 | 0 | 6 | 5 | 0 | 0 | 0 | 0 |
| 32 | 100 | 100 | 100 | 98 | 95 | 97 | 33 | 100 | 0 | 98 | 5 | 0 | 0 | P | P |
| 33 | 100 | — | — | 56 | — | 0 | 60 | — | 0 | 24 | 5 | 0 | 0 | 0 | 0 |
|  | 20 | 47 | 99 | 37 | 89 | 0 | 29 | 100 | — | — |  |  |  |  |  |
| 34 | 100 | 69 | 100 | 94 | 60 | 86 | 16 | 66 | 0 | 0 | 5 | 0 | 0 | 0 | 0 |
| 35 | 100 | 100 | 100 | 96 | 100 | 0 | 100 | 96 | 0 | 26 | 5 | 0 | 0 | 0 | 0 |
| 39 | 100 | 89 | 97 | 96 | 98 | 7 | 100 | 100 | 0 | 81 | 5 | 0 | 0 | 0 | 0 |
| 40 | 100 | 19 | 100 | 80 | 91 | 7 | 61 | 96 | 0 | 0 | 5 | 0 | 0 | 0 | 0 |
| 41 | 100 | 100 | 100 | 96 | 98 | 7 | 97 | 100 | 0 | 100 | 5 | 0 | 0 | 0 | 0 |
| 42 | 100 | — | — | 100 | 100 | 31 | 41 | — | 0 | 23 | 5 | — | — | — | — |
|  | 20 | 29 | 100 | 38 | 98 | 15 | 0 | 100 | — | — |  |  |  |  |  |
| 47 | 100 | — | — | 89 | — | 31 | 47 | — | 0 | 25 | 5 | — | — | — | — |
|  | 20 | 93 | 100 | 26 | 98 | 15 | 0 | 100 | — | — |  |  |  |  |  |
| 49 | 100 | 89 | 100 | 62 | 100 | 76 | 96 | 100 | 0 | 0 | 5 | 0 | P | 0 | P |
| 50 | 100 | 100 | 100 | 98 | 95 | 86 | 93 | 100 | 0 | 46 | 5 | 0 | P | 0 | P |
| 51 | 100 | 100 | 100 | 96 | 100 | 0 | 100 | 100 | 0 | 0 | 5 | P | P | P | P |
| 52 | 100 | 100 | 100 | 95 | 94 | 93 | 81 | 100 | 0 | 0 | 5 | 0 | P | 0 | 0 |
| 65 | 100 | 34 | 96 | 94 | 85 | 30 | 62 | 100 | 0 | 0 | 5 | 0 | 0 | 0 | 0 |
| 67 | 100 | — | — | 75 | — | 0 | 68 | — | 2 | 1 | 5 | 0 | 0 | 0 | 0 |
|  | 20 | 58 | 99 | 60 | 85 | 0 | 35 | 89 | — | — |  |  |  |  |  |
| 94 | 100 | 86 | 61 | 96 | 98 | 78 | 36 | 100 | 0 | 0 | 5 | 0 | 0 | P | P |
| 99 | 100 | 100 | 100 | 89 | 83 | 98 | 61 | 100 | 0 | 83 | 5 | 0 | 0 | P | P |
| 100 | 100 | 100 | 100 | 96 | 83 | 95 | 80 | 100 | 0 | 83 | 5 | P | 0 | P | 0 |
| 101 | 100 | 100 | 100 | 94 | 83 | 0 | 80 | 100 | 0 | 100 | 5 | 0 | 0 | P | 0 |
| 163 | 100 | — | — | 95 | — | 5 | 0 | — | 0 | 0 | 5 | — | — | — | — |
|  | 20 | 0 | 81 | 58 | 23 | 5 | 0 | 99 | — | — |  |  |  |  |  |
| 164 | 100 | — | — | 84 | — | 15 | 0 | — | 8 | 0 | 5 | — | — | — | — |
|  | 20 | 82 | 100 | 57 | 88 | 5 | 0 | 100 | — | — |  |  |  |  |  |
| 170 | 100 | — | — | 20 | — | 10 | 0 | — | 0 | 0 | 5 | — | — | — | — |
|  | 20 | 19 | 69 | 32 | 95 | 0 | 100 | — | — |  |  |  |  |  |  |
| 177 | 100 | — | — | 26 | — | 10 | 0 | — | 0 | 0 | 5 | — | — | — | — |
|  | 20 | 82 | 26 | 50 | 46 | 0 | 0 | 100 | — | — |  |  |  |  |  |
| 208 | 100 | 84 | 37 | 83 | 76 | 4 | 61 | 97 | 0 | 74 | 5 | 0 | 0 | 0 | 0 |
| 291 | 100 | — | — | 81 | — | 1 | 0 | — | 24 | 78 | 5 | — | — | — | — |
|  | 20 | 32 | 26 | 6 | 83 | 1 | 0 | 73 | — | — |  |  |  |  |  |
| 359 | 100 | 72 | 100 | 83 | 95 | 88 | 62 | 100 | 0 | 0 | 5 | 0 | 0 | 0 | 0 |
| 360 | 100 | 88 | 100 | 71 | 86 | 74 | 49 | 93 | 0 | 0 | 5 | 0 | 0 | 0 | 0 |
| 361 | 100 | — | — | 46 | — | 1 | 0 | — | 27 | 9 | 5 | — | — | — | — |
|  | 20 | 43 | 26 | 29 | 33 | 1 | 0 | 100 | — | — |  |  |  |  |  |
| 363 | 100 | 0 | 49 | 92 | 28 | 0 | 0 | 38 | 0 | 0 | 5 | 0 | 0 | 0 | 0 |
| 447 | 100 | — | 0 | 24 | 46 | 46 | 0 | 30 | 0 | 24 | 5 | 0 | 0 | 0 | 0 |
| 448 | 100 | — | 0 | 54 | — | 0 | 42 | 16 | 0 | 0 | 5 | — | — | — | — |
| 449 | 100 | 71 | 0 | 24 | 0 | 76 | 13 | 30 | 0 | 51 | 5 | 0 | 0 | 0 | 0 |
| 450 | 100 | — | 0 | 54 | 11 | 46 | 34 | 30 | 0 | 51 | 5 | 0 | 0 | 0 | 0 |
| 451 | 100 | 16 | 100 | 72 | 0 | 0 | 0 | 0 | 0 | 0 | 5 | 0 | 0 | 0 | 0 |
| 452 | 100 | 36 | 0 | 54 | 46 | 0 | 67 | 30 | 0 | 0 | 5 | 0 | 0 | 0 | 0 |
| 453 | 100 | 55 | 32 | 75 | 94 | 0 | 0 | 100 | 0 | 0 | 5 | 0 | 0 | 0 | 0 |
| 454 | 100 | 0 | 0 | 0 | 22 | 0 | 0 | 0 | 0 | 0 | 5 | — | — | — | — |
| 455 | 100 | 64 | 65 | 0 | 12 | 0 | 0 | 43 | 0 | 0 | 5 | 0 | 0 | 0 | 0 |

TABLE 7-continued

| Ex. No. | Rate (PPM) | Ex. A | Ex. B | Ex. C | Ex. D | Ex. E | Ex. F | Ex. G | Ex. H | Ex. I | Rate (kg/ha) | Ex. J | Ex. K | Ex. L | Ex. M |
|---|---|---|---|---|---|---|---|---|---|---|---|---|---|---|---|
| 456 | 100 | 82 | 0 | 58 | 53 | 98 | 0 | 96 | 9 | 0 | 5 | 0 | 0 | 0 | 0 |
| 477 | 100 | 95 | 100 | 76 | 100 | 48 | 48 | 100 | 0 | 0 | 5 | P | P | P | P |
| 594 | 100 | 86 | 100 | 93 | 77 | 2 | — | 100 | 0 | 79 | 5 | 0 | 60 | 100 | 50 |
| 596 | 100 | — | — | 89 | — | 0 | 0 | — | 0 | 25 | 5 | — | — | — | — |
|  | 20 | 91 | 95 | 35 | 94 | 0 | 0 | 100 | — | — |  |  |  |  |  |
| 603 | 100 | 44 | 97 | 91 | 69 | 0 | — | 95 | 0 | 0 | 5 | 0 | 0 | 0 | 0 |
| 605 | 100 | 70 | 99 | 32 | 81 | 0 | — | 100 | 0 | 0 | 5 | 0 | 0 | 0 | 0 |
| 608 | 100 | 87 | 100 | 98 | 98 | 4 | 81 | 100 | 0 | 0 | 5 | 0 | 0 | P | P |
| 618 | 100 | 100 | 100 | 98 | 89 | 0 | — | 100 | 0 | 0 | 5 | 0 | 80 | 80 | P |
| 620 | 100 | 100 | 100 | 96 | 98 | 51 | 100 | 100 | 0 | 0 | 5 | 0 | 0 | P | 0 |
| 622 | 100 | 100 | 100 | 84 | 99 | 0 | 100 | 100 | 0 | 26 | 5 | 0 | 0 | P | 0 |
| 627 | 100 | — | — | 38 | — | 0 | 14 | — | 0 | 61 | 5 | — | — | — | — |
|  | 20 | 31 | 70 | 19 | 81 | 0 | 0 | 99 | — | — |  |  |  |  |  |
| 644 | 100 | 100 | 100 | 94 | 100 | 100 | 100 | 100 | 23 | 0 | 5 | 0 | 0 | P | P |
| 646 | 100 | 100 | 100 | 95 | 98 | 97 | 61 | 100 | 0 | 99 | 5 | 100 | 0 | 0 | 0 |
| 651 | 100 | — | — | 42 | — | 0 | 62 | — | 0 | 46 | 5 | 0 | 0 | 0 | 0 |
|  | 20 | 67 | 0 | 7 | 67 | 0 | 0 | 100 | — | — |  |  |  |  |  |
| 656 | 100 | 93 | 100 | 88 | 97 | 0 | 50 | 100 | 0 | 20 | 5 | 0 | P | P | P |
| 657 | 100 | 62 | 100 | 81 | 98 | 49 | 97 | 100 | 24 | 37 | 5 | 0 | 0 | 0 | 0 |
| 661 | 100 | — | — | 56 | — | 0 | 70 | — | 5 | 85 | 5 | — | — | — | — |
|  | 20 | 81 | 79 | 61 | 62 | 0 | 10 | 100 | — | — |  |  |  |  |  |
| 663 | 100 | 42 | 100 | 95 | 99 | 57 | 36 | 100 | 0 | 39 | 5 | — | — | — | — |
| 667 | 100 | — | — | 4 | — | 0 | 0 | — | 0 | 10 | 5 | 0 | 0 | 0 | 0 |
|  | 20 | 13 | 14 | 7 | 39 | 0 | 0 | 0 | — | — |  |  |  |  |  |
| 668 | 100 | — | — | 76 | — | 1 | 0 | — | 22 | 31 | 5 | — | — | — | — |
|  | 20 | 65 | 17 | 31 | 31 | 1 | 0 | 100 | — | — |  |  |  |  |  |
| 669 | 100 | 100 | 100 | 90 | 100 | 96 | 100 | 100 | 0 | 0 | 5 | 0 | 0 | P | 0 |
| 671 | 100 | 100 | 100 | 92 | 94 | 84 | 100 | 100 | 0 | 84 | 5 | 0 | P | P | 0 |
| 675 | 100 | — | — | 30 | — | 0 | 62 | — | 0 | 69 | 5 | — | — | — | — |
|  | 20 | 40 | 0 | 42 | 44 | 0 | 0 | 16 | — | — |  |  |  |  |  |
| 685 | 100 | — | — | 0 | — | 0 | 29 | — | — | — | 5 | — | — | — | — |
|  | 20 | 57 | 66 | 28 | 67 | — | 15 | 100 | — | — |  |  |  |  |  |
| 721 | 100 | 73 | 89 | 95 | 94 | 18 | 100 | 100 | 0 | 0 | 5 | P | P | P | P |
| 724 | 100 | 100 | 100 | 95 | 100 | 63 | 100 | 100 | 0 | 0 | 5 | 0 | P | P | P |
| 726 | 100 | — | — | — | — | 0 | 0 | — | 0 | 38 | 5 | 0 | 20 | 0 | 0 |
|  | 20 | 75 | 0 | 23 | 81 | 0 | 0 | 100 | — | — |  |  |  |  |  |
| 815 | 100 | 40 | 98 | 0 | 62 | 2 | — | 97 | 0 | 65 | 5 | 0 | 0 | 0 | 0 |
| 905 | 100 | — | — | 19 | — | 0 | 37 | — | 0 | 87 | 5 | 0 | 0 | 0 | 0 |
|  | 20 | 7 | 0 | 15 | 47 | 0 | 0 | 16 | — | — |  |  |  |  |  |
| 1276 | 100 | 100 | — | 96 | 100 | 1 | 97 | 100 | 0 | 0 | 5 | 0 | P | 0 | P· |
|  | 20 | 93 | 100 | 86 | 100 | 1 | 52 | 100 | — | — |  |  |  |  |  |
| 1276a | 100 | — | — | 53 | — | 1 | 0 | — | 16 | 22 | 5 | — | — | — | — |
|  | 20 | 42 | 26 | 33 | 88 | 1 | 0 | 100 | — | — |  |  |  |  |  |
| 1277 | 100 | 9 | 65 | 0 | 0 | 0 | 0 | 39 | 0 | 25 | 5 | 0 | 0 | 0 | 0 |
| 1277a | 100 | — | — | 36 | — | 1 | 52 | — | 8 | 31 | 5 | — | — | — | — |
|  | 20 | 58 | 74 | 24 | 95 | 1 | 0 | 100 | — | — |  |  |  |  |  |
| 1278 | 100 | 100 | 100 | 87 | 85 | 17 | 36 | 100 | 0 | 16 | 5 | 0 | 0 | 0 |  |
| 1300 | 100 | 100 | 100 | 93 | 92 | 58 | 81 | 100 | 0 | 0 | 5 | 0 | 0 | 0 | 0 |
| 1304 | 100 | 100 | 100 | 97 | 100 | 78 | 88 | 100 | 0 | 18 | 5 | 0 | 0 | 0 | 0 |
| 1377 | 100 | 100 | 100 | 96 | 92 | 58 | 100 | 100 | 0 | 44 | 5 | 0 | P | 0 | P |
| 1381 | 100 | 100 | 100 | 97 | 98 | 51 | 73 | 100 | 0 | 78 | 5 | 0 | 50 | 0 | 0 |
| 1451 | 100 | 86 | 84 | 48 | 77 | 2 | — | 93 | 0 | 79 | 5 | 0 | 0 | 0 | 0 |
| 1459 | 100 | 72 | 70 | 65 | 31 | 17 | 0 | 65 | 0 | 74 | 5 | 0 | 0 | 0 | 0 |
| 1468 | 100 | 40 | 0 | 0 | 77 | 2 | — | 93 | 0 | 46 | 5 | 0 | 60 | 0 | 0 |
| 1469 | 100 | 68 | 84 | 81 | 77 | 2 | — | 100 | 24 | 89 | 5 | 0 | 80 | 70 | 0 |
| 1527 | 100 | 0 | 100 | 93 | 100 | — | 35 | 100 | 0 | 0 | 5 | 0 | P | 0 | P |

TEST A

Seeds of crabgrass (i Digitaria spp.), barnyardgrass (*Echinochloa crusgalli*), giant foxtail (*Setaria faberii*), wild oats (*Avena fatua*), cheatgrass (*Bromus secalinus*), velvetleaf (*Abutilon theophrasti*), morningglory (*Ipomoea* spp.), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary simulation;
S=albinism; and
Y=abscised buds or flowers.

TABLE A

POSTEMERGENCE

| | CMPD 52 | CMPD 52 (salt) | CMPD 56 | CMPD 56 (salt) | CMPD 57 | CMPD 58 | CMPD 59 | CMPD 61 |
|---|---|---|---|---|---|---|---|---|
| RATE = KG/HA | 0.1 | 0.4 | 0.4 | 0.4 | 0.4 | 0.4 | 0.4 | 0.4 |
| COKER COTTON | 2H | 2H | 0 | 7P,9G | 4H | 10P,9G | 10P,9G | 0 | 2H |
| CULT MORNINGLRY | 2C,4H | 3C,6H | 0 | 4C,9G | 3C,7G | 5C,9G | 2C,3G | 3C,5H | 3C, |
| COCKLEBUR | 0 | 2C | 0 | 3H,8G | 2C | 1H | 2C,8H | 0 | 1C |
| PURPLE NUTSEDGE | 0 | — | | 0 | 0 | 5G | 0 | 0 | 0 |
| LARGE CRABGRASS | 0 | 3C,6G | 0 | 4G | 0 | 9C | 2C,8H | 0 | 0 |
| BARNYARDGRASS | 0 | 0 | 0 | 5G | 0 | 7H | 0 | 0 | 0 |
| WILD OATS | 0 | 2C,4G | 0 | 0 | 0 | 0 | 0 | 0 | 0 |
| ERA WHEAT | 0 | 0 | 0 | 0 | 0 | 0 | 0 | 0 | 0 |
| G4646 CORN | 0 | 0 | 0 | 0 | 0 | 0 | 0 | 0 | 0 |
| WILLMS SOYBEANS | 0 | 1C | 0 | 3C,8G | 1C | 4C,9G | 4C,9G | 1C,1H | 3H |
| RICE DRY SEEDED | 0 | 1C | 0 | 0 | 0 | 0 | 0 | 0 | 0 |
| G522 SORGHUM | 0 | 0 | 0 | 0 | 0 | 0 | 0 | 0 | 0 |
| CHEAT GRASS | | | 0 | 0 | | 0 | 0 | | |
| USH11 SUGARBEET | 0 | 4G | 0 | 5H,5I | 2H | 4H,5I | 3H,7G | 4H | 3H |
| VELVETLEAF | 3G | 2C,5G | 0 | 7G | 2G | 4C,9G | 2C,8G | 0 | 3C,5G |
| GIANT FOXTAIL | 0 | 2C,5G | 0 | 0 | 0 | 9G | 0 | 0 | 0 |
| KLAGES BARLEY | 0 | 0 | 0 | 0 | 0 | 0 | 0 | 0 | 0 |
| DOWNY BROME | 0 | 0 | | | 0 | | | 0 | 0 |

| | CMPD 66 | CMPD 67 | CMPD 99 | CMPD 101 | CMPD 106 | CMPD 107 | CMPD 108 | CMPD 208 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 10P,9G | 10P,9G | 5H | 9G,10P | 4G | 10P,8G | 6H | 0 |
| CULT MORNINGLRY | 5C,9G | 2C,2G | 2C,4H | 5C,9H | 2C,8G | 5C,9G | 3C,6G | 2C,5H |
| COCKLEBUR | 2C,5H | 2C,5G | 4C,7H | 3C,6H | 2C,2H | 3C,5H | 2C,2H | 2C |
| PURPLE NUTSEDGE | 0 | 0 | 0 | 0 | 5G | 0 | 0 | 5G |
| LARGE CRABGRASS | 0 | 4G | 9G | 7G | 2G | 0 | 0 | 0 |
| BARNYARDGRASS | 0 | 0 | 0 | 0 | 5H | 7H | 0 | 0 |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 0 | 0 | 0 | 0 |
| WILLMS SOYBEANS | 3C,4H | 1C,4H | 3C,5H | 2C,4H | 2C,5G | 5C,9G | 2C,7G | 2C,2H |
| RICE DRY SEEDED | 0 | 0 | 0 | 0 | 0 | 2C,5G | 0 | 0 |
| G522 SORGHUM | 0 | 0 | 0 | 0 | 0 | 0 | 0 | 0 |
| CHEAT GRASS | 0 | 0 | 0 | 0 | 0 | | | 0 |
| USH11 SUGARBEET | 8H,5I | 7H,5I | 7H | 6H | 5G | 0 | 3C,6G | 6H |
| VELVETLEAF | 3G | 2C,5G | 8G | 9H | 3C,7G | 3C,6G | 2C,5G | 8G |
| GIANT FOXTAIL | 0 | 0 | 0 | 0 | 0 | 0 | 0 | 0 |
| KLAGES BARLEY | 0 | 0 | 0 | 0 | 0 | 0 | 0 | 0 |
| DOWNY BROME | | | | | | | 0 | 0 |

| | CMPD 594 | CMPD 594 | CMPD 596 | CMPD 598 | CMPD 603 | CMPD 605 | CMPD 611 | CMPD 618 |
|---|---|---|---|---|---|---|---|---|
| RATE = KG/HA | 0.4 | 0.4 | 0.4 | 0.4 | 0.4 | 0.4 | 0.4 | 2 |
| COKER COTTON | 4G | 3G | 0 | 8G | 0 | 0 | 7G | &P,9G |
| CULT MORNINGLRY | 6G | 2C,2H | 2C | 0 | 3B | 2B | 0 | 0 |
| COCKLEBUR | 2C | 0 | 1C | 2C | 1B | 1B | 1H | 1H |
| PURPLE NUTSEDGE | | 0 | 0 | 3G | 0 | 0 | 0 | 0 |
| LARGE CRABGRASS | 2G | 2G | 0 | 2G | 0 | 0 | 5G | 8G |
| BARNYARDGRASS | 0 | 0 | 0 | 0 | 0 | 0 | 2C | 0 |
| WILD OATS | 0 | 0 | 0 | 2G | 0 | 0 | 0 | 0 |
| ERA WHEAT | 0 | 0 | 0 | 3G | 0 | 0 | 0 | 0 |
| G4646 CORN | 0 | 2G | 0 | 0 | 0 | 0 | 0 | 0 |
| WILLMS SOYBEANS | 2B,3H | 2C,3H | 2C | 2C,2H | 0 | 1C | 2C,4H | 2C,4G |
| RICE DRY SEEDED | 3G | 0 | 0 | 0 | 0 | 0 | 0 | 0 |
| G522 SORGHUM | 0 | 0 | 0 | 0 | 0 | 0 | 0 | 0 |
| CHEAT GRASS | 0 | 0 | 0 | 0 | 0 | 0 | 0 | 0 |
| USH11 SUGARBEET | 0 | 3G | 1H | 4G,5I | 0 | 0 | 0 | 5H |
| VELVETLEAF | 2C | 0 | 1C | 0 | 1B | 0 | 0 | 2C,7G |
| GIANT FOXTAIL | 0 | 2G | 0 | 3G | 0 | 0 | 0 | 8G |
| KLAGES BARLEY | 0 | 0 | 0 | 0 | 0 | 0 | 0 | 0 |

| | CMPD 620 | CMPD 624 | CMPD 627 | CMPD 644 | CMPD 644 | CMPD 646 | CMPD 648 |
|---|---|---|---|---|---|---|---|---|
| RATE = KG/HA | 0.4 | 2 | 0.4 | 0.4 | 2 | 0.1 | 0.4 | 0.4 | 0.4 |
| COKER COTTON | 3H | 10P,9G | 2H,9G | 1C | 2 | 5G | 2C,7G | 9G,10P | 9P,9G |
| CULT MORNINGLRY | 2C,5G | 3C,8G | 2C,3H | 2C,6G | 6C,9G | 3C,3G | 3C,5G | 3C,8G | 1C |
| COCKLEBUR | 2C,2H | 3C,9G | 2C,5H | 2C | 5C,8H | 0 | 2C | 2C | 2C |
| PURPLE NUTSEDGE | 0 | 5G | 0 | 0 | 8G,5X | 0 | 0 | 0 | 0 |
| LARGE CRABGRASS | 9G | 2C,9G | 9C | 0 | 3C,9G | 0 | 0 | 6G | 0 |
| BARNYARDGRASS | 2H | 3C,9H | 6H | 0 | 5C,9H | 0 | 0 | 0 | 0 |
| WILD OATS | 0 | 0 | 0 | 0 | 3C,6G | 0 | 0 | 0 | 0 |
| ERA WHEAT | 0 | 0 | 2G | 0 | 4C,9G | 0 | 0 | 0 | 0 |
| G4646 CORN | 3C,3H | 3C,7H | 0 | 0 | 3C,6G | 0 | 0 | 0 | 0 |
| WILLMS SOYBEANS | 3C,8G | 4C,9G | 3C,8H | 1H | 9C | 2C,2H | 2C,5H | 5C,8H | 2C |
| RICE DRY SEEDED | 2C,4G | 2C,8G | 0 | 0 | 3C,8G | 0 | 1C | 0 | 0 |
| G522 SORGHUM | 2C | 2C,3H | 0 | 0 | 3C,9H | 0 | 0 | 0 | 0 |
| CHEAT GRASS | 0 | 8G | 0 | 0 | 2C,8G | | 0 | | 0 |
| USH11 SUGARBEET | 3H | 8H | 7H,5I | 2H | 5G,5I | 2G | 7G | 4H | 4G,5I |
| VELVETLEAF | 3C,5H | 2C,9G | 1C | 0 | 9G | 3G | 2C,6G | 2C,3G | 2C,5G |
| GIANT FOXTAIL | 2C,7H | 9G | 2C,9G | 0 | 3C,9G | 0 | 2C,3G | 0 | 0 |

TABLE A-continued

| | | | | | | | | |
|---|---|---|---|---|---|---|---|---|
| KLAGES BARLEY | 0 | 0 | 0 | 0 | 2C,9G | 0 | 0 | 0 | 0 |
| DOWNY BROME | | | | | | 0 | 0 | | |

| | CMPD 651 | CMPD 653 | CMPD 656 | CMPD 658 | CMPD 659 | CMPD 661 | CMPD 669 | CMPD 673 |
|---|---|---|---|---|---|---|---|---|
| RATE = KG/HA | 0.4 | 0.4 | 0.4 | 0.4 | 0.4 | 0.4 | 2 | 0.4 |
| COKER COTTON | 0 | 10P,9G | 7G | 0 | 0 | 1C,3H | 3C,7H | 10P,9G |
| CULT MORNINGLRY | 2C | 2C | 2C,3H | 0 | 3C,6G | 1C | 6C,9G | 2C,1H |
| COCKLEBUR | 1C | 2C,5G | 2C | 0 | 2C, | 1C | 3C,7G | 2C,3H |
| PURPLE NUTSEDGE | 0 | 0 | 2G | 0 | 0 | 0 | 4G | 0 |
| LARGE CRABGRASS | 0 | 5C,9G | 2G | 0 | 0 | 0 | 2G | 3C,3G |
| BARNYARDGRASS | 0 | 0 | 0 | 0 | 0 | 0 | 5C,9G | 0 |
| WILD OATS | 0 | 0 | 0 | 0 | 0 | 0 | 2C,4G | 0 |
| ERA WHEAT | 0 | 0 | 0 | 0 | 0 | 0 | 2G | 0 |
| G4646 CORN | 2G | 2G | 0 | 0 | 0 | 0 | 0 | 0 |
| WILLMS SOYBEANS | 1C | 3C,7G | 2C | 0 | 3C | 1H | 5C,9G | 1C,1H |
| RICE DRY SEEDED | 0 | 0 | 0 | 0 | 0 | 0 | 0 | 0 |
| G522 SORGHUM | 0 | 0 | 0 | 0 | 0 | 0 | 2G | 0 |
| CHEAT GRASS | 0 | 0 | 0 | 0 | 0 | 0 | 3G | 0 |
| USH11 SUGARBEET | 1H | 2C,7H | 4H | 0 | 0 | 4H | 5G,5I | 8H,5I |
| VELVETLEAF | 0 | 1C | | 8G | 2C,5G | 1C | 6G | 1C |
| GIANT FOXTAIL | 0 | 2C,7H | 0 | 0 | 0 | 0 | 2G | 9H |
| KLAGES BARLEY | 0 | 0 | 0 | 0 | 0 | 0 | 2G | 0 |

| | CMPD 675 | CMPD 721 | CMPD 724 | CMPD 724 | CMPD 726 | CMPD 753 | CMPD 754 | CMPD 782 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 0 | 5G | 6G | 10P,9G | 4H | 10P,9G | 2H | 10P,9G |
| CULT MORNINGLRY | 1C | 3C,6H | 3C,5H | 5C,9G | 3C,7G | 4C,9G | 5C,9G | 5C,9G |
| COCKLEBUR | 0 | 2C | 3C,4H | 3C,9H | 1C,2H | 2C,6G | 2C,3H | 8G |
| PURPLE NUTSEDGE | 0 | 0 | 2C,8H | 0 | 0 | 0 | 0 | 0 |
| LARGE CRABGRASS | 0 | 0 | 9G | 5G | 0 | 4C,9G | 0 | 5C,9G |
| BARNYARDGRASS | 0 | 0 | 2C,3H | 7G | 0 | 5H | 0 | 7H |
| WILD OATS | 0 | 0 | 0 | 0 | 0 | 0 | 0 | 0 |
| ERA WHEAT | 0 | 0 | 0 | 2G | 0 | 0 | 0 | 0 |
| G4646 CORN | 0 | 0 | 0 | 0 | 2G | 0 | 0 | 0 |
| WILLMS SOYBEANS | 1C | 2C | 4C,8H | 3C,9G | 2H | 9C | 2C,3H | 8G |
| RICE DRY SEEDED | 0 | 0 | 5G | 0 | 0 | 0 | 0 | 0 |
| G522 SORGHUM | 0 | 0 | 0 | 0 | 0 | 2G | 0 | 0 |
| CHEAT GRASS | 0 | 0 | 0 | 0 | 0 | 0 | 0 | 0 |
| USH11 SUGARBEET | 1C | 3H | 7H | 3H | 3H | 8H | 7G | 7H,5I |
| VELVETLEAF | 0 | 6G | 9H | 3C,9G | 0 | 3C,8G | 3G | 8G |
| GIANT FOXTAIL | 0 | 0 | 9G | 9G | 5G | 2C,9G | 0 | 7G |
| KLAGES BARLEY | 0 | 0 | 0 | 0 | 0 | 0 | 0 | 0 |
| DOWNY BROME | | | | | | | | 0 |

| | CMPD 784 | CMPD 810 | CMPD 811 | CMPD 815 | CMPD 863 | CMPD 879 | CMPD 905 | CMPD 1276 |
|---|---|---|---|---|---|---|---|---|
| RATE = KG/HA | 0.4 | 0.4 | 0.4 | 0.4 | 2 | 0.4 | 0.4 | 0.4 |
| COKER COTTON | 10P,9G | 0 | 10P,9G | 9G,10P | 2B | 2C,6G | 0 | 4H |
| CULT MORNINGLRY | 3H | 2C,5G | 5C,9G | 3C,9H | 0 | 1C,2G | 1C,2H | 2C,4H |
| COCKLEBUR | 2H | 8G | 3H,8G | 2C,4H | 0 | 2C | 1C | 2C |
| PURPLE NUTSEDGE | 0 | | 0 | 0 | 0 | 0 | 0 | 0 |
| LARGE CRABGRASS | 6H | 5G | 9C | 0 | 1B | 0 | 3G | 0 |
| BARNYARDGRASS | 0 | 2G | 3C,9G | 0 | 1B | 0 | 0 | 0 |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 1B | 0 | 0 | 0 |
| WILLMS SOYBEANS | 2C,5H | 5G | 3C,9G | 0 | 2B | 2C | 2H,5G | 0 | 2C,6H |
| RICE DRY SEEDED | 0 | 0 | 0 | 0 | 0 | 0 | 2G | 0 |
| G522 SORGHUM | 0 | 0 | 0 | 0 | 0 | 0 | 0 | 0 |
| CHEAT GRASS | 0 | 0 | 0 | 0 | 0 | 0 | 0 | 0 |
| USH11 SUGARBEET | 7H | 4G | 6H,5I | 0 | 1B | 0 | 3G | 0 | 2H |
| VELVETLEAF | 2H | 8G | 4C,9G | 0 | 2B | 2C | 2G | 0 | 8G |
| GIANT FOXTAIL | 2G | 2G | 9G | 0 | 1B | 0 | 0 | 0 |
| KLAGES BARLEY | 0 | 0 | 0 | 0 | 0 | 0 | 0 | 0 |

| | CMPD 1276 (salt) | CMPD 1276A | CMPD 1277 | CMPD 1278 | CMPD 1279 | CMPD 1280 | CMPD 1377 | |
|---|---|---|---|---|---|---|---|---|
| RATE = KG/HA | 0.4 | 0.4 | 0.4 | 0.4 | 0.4 | 0.4 | 0.4 | 2 |
| COKER COTTON | 9G,10P | 7G | 3H,6H | 0 | 10P,9G | 7G | 9G,10P | 9G,10P |
| CULT MORNINGLRY | 2C,3G | 1C | 2C,3G | 1C | 5C,9G | 2H | 2C,6H | 4C,9H |
| COCKLEBUR | 3C | 1C | 2C,7G | 1C | 5H | 4H | 2C,3H | 4C,9H |
| PURPLE NUTSEDGE | 0 | | 0 | 0 | 0 | 0 | — | 4G |
| LARGE CRABGRASS | 0 | 0 | 4G | 4G | 3C,5G | 9H | 0 | 4C,9G |
| BARNYARDGRASS | 0 | 0 | 1C | 0 | 2G | 5H | 2G | 5C,9H |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 0 | 0 | 0 | 0 |
| WILLMS SOYBEANS | 3C | 2H,6G | 1C,1H | 0 | 3C,5G | 5C,9G | 3C,5H | 3C,6H |
| RICE DRY SEEDED | 0 | 0 | 0 | 0 | 0 | 0 | 0 | 0 |
| G522 SORGHUM | 0 | 2G | 0 | 0 | 0 | 2G | 0 | 2G |
| CHEAT GRASS | 0 | 0 | 0 | 0 | 0 | 0 | 0 | 0 |
| USH11 SUGARBEET | 0 | 3H | 1H | 1H | 7H,5I | 8H | 6H,5I | 7H,5I |
| VELVETLEAF | 2C,4G | 2C | 0 | 0 | 3C,7G | 7H | 2C,3H | 2C,7H |

TABLE A-continued

| | | | | | | | | |
|---|---|---|---|---|---|---|---|---|
| GIANT FOXTAIL | 0 | | 0 | 3G | 0 | 0 | 9H | 0 | 3C,9H |
| KLAGES BARLEY | 0 | | 0 | 0 | 0 | 0 | 0 | 0 | 0 |

| | CMPD 1381 | CMPD 1304 | | CMPD 1 | CMPD 4 | CMPD 9 | CMPD 11 | CMPD 13 |
|---|---|---|---|---|---|---|---|---|
| RATE = KG/HA | 0.4 | 2 | 0.4 | 2 | 0.4 | 0.4 | 0.1 | 0.4 | 2 |
| COKER COTTON | 3G | 10P,9G | 5H | 10P,9G | 3H | 3C,9H | 3H | 3H | 10P,9G | 6H |
| CULT MORNINGLRY | 3C,5G | 2C,8H | 3C,7G | 2C,7G | 1C,1H | 4C,8H | 3C,4H | 3C,6G | 4C,9G | 4C,8G |
| COCKLEBUR | 2C | 2C,7H | 2C,4G | 8H | 1C,3G | 3C,8H | 0 | 3C,6G | 3C,9G | 3C,3H |
| PURPLE NUTSEDGE | 0 | 2C,5G | 0 | 8G | 0 | 5G | 0 | 9G | 7G | 0 |
| LARGE CRABGRASS | 2G | 4C,9G | 3C,7G | 3C,9G | 0 | 9G | 0 | 3G | 9C | 0 |
| BARNYARDGRASS | 2H | 9H | 5H | 9H | 0 | 2C,8H | 0 | 0 | 5C,9G | 0 |
| WILD OATS | 0 | 2G | 0 | 2G | 0 | 0 | 0 | 0 | 7G | 0 |
| ERA WHEAT | 0 | 2G | 0 | 4G | 0 | 0 | 0 | 0 | 8G | 0 |
| G4646 CORN | 0 | 3G | 0 | 3G | 2G | 2G | 0 | 0 | 7H | 0 |
| WILLMS SOYBEANS | 2C,4G | 2C,8G | 2C,5G | 2C,6G | 2C,3H | 4C,8G | 1C,1H | 2C,4H | 4C,9G | 3C,5G |
| RICE DRY SEEDED | 0 | 8G | 0 | 7G | 0 | 5G | 0 | 1C | 3C,7G | 0 |
| G522 SORGHUM | 0 | 9H | 0 | 7G | 0 | 5G | 0 | 0 | 3C,8H | 2G |
| CHEAT GRASS | — | 2G | — | 5G | 0 | 5G | | | 7G | |
| USH11 SUGARBEET | 5G | 9H | 2H | 7H,5I | 8G | 6H | 3G | 3G | 9H,5I | 7G |
| VELVETLEAF | 0 | 9G | 0 | 9G | 0 | 2C,8H | — | 4G | 3C,9G | 2C |
| GIANT FOXTAIL | 0 | 9G | 0 | 9H | 0 | 9G | 0 | 2C,2G | 9G | 3G |
| KLAGES BARLEY | 0 | 2G | 0 | 3G | 0 | 0 | 0 | 0 | 5G | 0 |
| DOWNY BROME | 0 | — | 0 | — | 0 | | 0 | 0 | | 0 |

| | CMPD 15 | CMPD 16 | CMPD 17 | CMPD 18 | CMPD 23 | CMPD 33 | CMPD 34 | CMPD 34 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 7G | 8G | 3H | 7G,5I | 2H | 10P,9G | 10P,8G | 8P,8G |
| CULT MORNINGLRY | 2C,4H | 4C,9G | 3C,4G | 2C | 2C,3H | 2C,5G | 3C,10P | 5C,9G |
| COCKLEBUR | 2C | 2C,6G | 2C,5G | 2C,3G | 1C,1H | 3C,4G | 2C,2H | 2C,2H |
| PURPLE NUTSEDGE | 0 | 0 | 0 | 0 | 0 | 0 | 0 | 0 |
| LARGE CRABGRASS | 0 | 8G | | 3C,7G | 3G | 5C,9G | 3G | 0 |
| BARNYARDGRASS | 3G | 0 | 0 | 9H | 0 | 0 | 0 | 0 |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 0 | 2G | 0 | 0 |
| WILLMS SOYBEANS | 3C,5H | 2C,2H | 1C,2H | 3C,5G | 1C,1H | 4C,9G | 4C,9G | 2C,3H |
| RICE DRY SEEDED | 0 | 2C | 1C | 0 | 0 | 0 | 2G | 0 |
| G522 SORGHUM | 0 | 0 | 0 | 0 | 0 | 0 | 0 | 0 |
| CHEAT GRASS | 0 | 0 | 0 | 0 | 0 | 0 | | |
| USH11 SUGARBEET | 5H | 2G | 7H | 3G,5I | 4H | 8H,5I | 7H | 3G |
| VELVETLEAF | 6G | 6G | 0 | 2C,5G | 0 | 3C,8G | 5C,8G | 3C,8G |
| GIANT FOXTAIL | 0 | 7G | 3G | 5G | 2G | 9G | 0 | 0 |
| KLAGES BARLEY | 0 | 0 | 0 | 0 | 0 | 0 | 0 | 0 |
| DOWNY BROME | | | | | | | 3G | 0 |

| | CMPD 34 | CMPD 35 | CMPD 35 (salt) | CMPD 35 (salt) | CMPD 35 (salt) | CMPD 35 (salt) | CMPD 39 | CMPD 42 |
|---|---|---|---|---|---|---|---|---|
| RATE = KG/HA | 0.4 | 0.4 | 2 | 2 | 0.4 | 0.4 | 0.4 | 0.4 | 0.4 |
| COKER COTTON | 4G | 10P,9G | 10P,9G | 10P,9G | 3H | 0 | 9P,8G | 8G,10P | 1C |
| CULT MORNINGLRY | 0 | 10P,9G | 4C,9G | 5C,9G | 3C,8G | 0 | 2C,2H | 2C | 2C |
| COCKLEBUR | 2C,3H | 2C,5G | 3C,8G | 4C,9H | 2C,1H | 0 | 2C,2H | 2C | 3C |
| PURPLE NUTSEDGE | 0 | 2G | 8G | 8G | 0 | 0 | 0 | 0 | 0 |
| LARGE CRABGRASS | 5G | 2C,9G | 3C,9G | 3C,9G | 0 | 0 | 0 | 0 | 0 |
| BARNYARDGRASS | 5H | 2C,8H | 4C,9G | 5C,9G | 0 | 0 | 5H | 0 | 0 |
| WILD OATS | 0 | 0 | 1C | 0 | 0 | 0 | 0 | 0 | 0 |
| ERA WHEAT | 0 | 0 | 0 | 0 | 0 | 0 | 0 | 0 | 0 |
| G4646 CORN | 0 | 1C,3H | 3C,7H | 3C,7H | 2H | 0 | 2G | 0 | 0 |
| WILLMS SOYBEANS | 4C,7G | 10P,9G | 3C,9G | 4C,9G | 3C,9G | 2G | 9G,5I | 2C | 1H |
| RICE DRY SEEDED | 0 | 1C | 3C,9G | 4G | 0 | 0 | 0 | 0 | 0 |
| G522 SORGHUM | 0 | 0 | 3C,9H | 7G | 0 | 0 | 0 | 0 | 0 |
| CHEAT GRASS | | 0 | 5G | 4G | | | 0 | | |
| USH11 SUGARBEET | 6G | 5H | 2C,8H | 3H,7G | 7G | 2G | 4H | 4H | 3H |
| VELVETLEAF | 5C,9G | 4C,8G | 4C,9G | 7C,9G | 3C,5G | 0 | 3C,8H | 4H | 5C |
| GIANT FOXTAIL | 0 | 8H | 9G | 3C,9G | 2G | 0 | 0 | 0 | 2G |
| KLAGES BARLEY | 0 | 0 | 1C | 6G | 0 | 0 | 0 | 0 | 0 |
| DOWNY BROME | 0 | | | | 0 | 0 | | | |

| | CMPD 47 | CMPD 51 | CMPD 52 |
|---|---|---|---|
| RATE = KG/HA | 0.4 | 2 | 2 |
| COKER COTTON | 10P,8G | 1C,6H | 3H,8G |
| CULT MORNINGLRY | 1C | 5G | 5C,9G |
| COCKLEBUR | 1C | 2C,7H | 3C,9H |
| PURPLE NUTSEDGE | 0 | 0 | |
| LARGE CRABGRASS | 0 | 2C,9G | 3C,9G |
| BARNYARDGRASS | 0 | 2C,7G | 5C,9G |
| WILD OATS | 0 | 2C,2G | 2C,4G |
| ERA WHEAT | 0 | 2C,3G | 2C,6G |
| G4646 CORN | 2G | 2C,6H | 2C,6G |
| WILLMS SOYBEANS | 2C,2H | 3C,7H | 4C,9G |
| RICE DRY SEEDED | 0 | 2C,5G | 2C,6G |
| G522 SORGHUM | 0 | 0 | 9H |
| CHEAT GRASS | 0 | 5G | 2C,6G |

TABLE A-continued

|  |  |  |  |
|---|---|---|---|
| USH11 SUGARBEET | 0 | 7G | 3H,7G |
| VELVETLEAF | 0 | 4G | 7C,9G |
| GIANT FOXTAIL | 0 | 2C,7G | 1C,9G |
| KLAGES BARLEY | 0 | 0 | 6G |

PREEMERGENCE

|  | CMPD 52 | CMPD 52 | CMPD 56 | CMPD 56 | CMPD 57 | CMPD 58 | CMPD 59 | CMPD 61 |
|---|---|---|---|---|---|---|---|---|
| RATE = KG/HA | 0.1 | 0.4 | 0.4 | 0.4 | 0.4 | 0.4 | 0.4 | 0.4 |
| COKER COTTON | — | 2G | 0 | 5G | 0 | 7G | 8G | 0 | 0 |
| CULT MORNINGLRY | 0 | 8H | 0 | 4C,9G | 0 | 4C,9G | 8G | 0 | 0 |
| COCKLEBUR | 2G | 2C,2G | 0 | 2G | 0 | 0 | 3G | 0 | 0 |
| PURPLE NUTSEDGE | 0 | 0 | 0 | 5G | 0 | 0 | 0 | 0 | 0 |
| LARGE CRABGRASS | 2C,7H | 4C,9H | 0 | 4C,9G | 9G | 4C,9G | 9G | 0 | 0 |
| BARNYARDGRASS | 0 | 9C | 5G | 7C,9H | 0 | 9C | 4C,9G | 0 | 0 |
| WILD OATS | 0 | 0 | 0 | 0 | 0 | 0 | 0 | 0 | 0 |
| ERA WHEAT | 0 | 8G | 0 | 0 | 0 | 2G | 0 | 0 | 0 |
| G4646 CORN | 0 | 0 | 0 | 0 | 0 | 2G | 3G | 0 | 0 |
| WILLMS SOYBEANS | 0 | 0 | 0 | 7G | 0 | 3C,9G | 4G | 0 | 0 |
| RICE DRY SEEDED | 0 | 0 | 0 | 0 | 0 | 0 | 0 | 0 | 0 |
| G522 SORGHUM | 0 | 8G | 0 | 7G | 0 | 8G | 7G | 0 | 0 |
| CHEAT GRASS |  |  | 0 | 5G |  | 9G | 3G |  |  |
| USH11 SUGARBEET | 0 | 5H | 0 | 6G | 3H | 7H | 9G | 0 | 0 |
| VELVETLEAF | 0 | 4C,8H | 0 | 4C,9G | 0 | 5C,9G | 5G | 0 | 0 |
| GIANT FOXTAIL | 3C,9H | 9H | 0 | 9H | 4C,9G | 9H | 3C,9G | 0 | 7G |
| KLAGES BARLEY | 0 | 0 | 0 | 0 | 0 | 2G | 0 | 0 | 0 |
| DOWNY BROME | 2G | 3C,8G |  |  | 0 |  |  | 0 | 0 |

|  | CMPD 66 | CMPD 67 | CMPD 99 | CMPD 101 | CMPD 106 | CMPD 107 | CMPD 108 | CMPD 208 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 0 | 0 | 0 | 0 | 0 | 3G | 0 | 0 |
| CULT MORNINGLRY | 0 | 0 | 8H | 2C,9H | 0 | 5C,9G | 3H | 0 |
| COCKLEBUR | 0 | 0 | 0 | 0 | 0 | 0 | 0 | 0 |
| PURPLE NUTSEDGE | 0 | 0 | 0 | 0 | 0 | 0 | 10E | 0 |
| LARGE CRABGRASS | 2C,9G | 7G | 2C,9G | 2G | 4C,9H | 5C,9G | 9G | 0 |
| BARNYARDGRASS | 0 | 3G | 2G | 2G | 0 | 9H | 0 | 0 |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 0 | 0 | 0 | 0 |
| WILLMS SOYBEANS | 0 | 1H | 0 | 0 | 2G | 0 | 0 | 0 |
| RICE DRY SEEDED | 0 | 0 | 0 | 0 | 0 | 0 | 0 | 0 |
| G522 SORGHUM | 0 | 0 | 0 | 0 | 0 | 2G | 0 | 0 |
| CHEAT GRASS | 0 | 3G | 0 | 0 | 0 |  |  |  |
| USH11 SUGARBEET | 5G | 7G | 3H | 0 | 3H | 3H | 0 | 2H |
| VELVETLEAF | 2G | 0 | 0 | 0 | 0 | 5G | 0 | 0 |
| GIANT FOXTAIL | 3G | 5G | 2C,9H | 7G | 3C,9G | 3C,9G | 8H | 0 |
| KLAGES BARLEY | 0 | 0 | 0 | 0 | 3G | 0 | 0 | 0 |
| DOWNY BROME |  |  |  |  |  | 0 | 0 | 0 |

|  | CMPD 594 | CMPD 594 | CMPD 596 | CMPD 598 | CMPD 603 | CMPD 605 | CMPD 611 | CMPD 618 |
|---|---|---|---|---|---|---|---|---|
| RATE = KG/HA | 0.4 | 0.4 | 0.4 | 0.4 | 0.4 | 0.4 | 0.4 | 2 |
| COKER COTTON | 0 | 3G | 3G | 0 | 0 | 0 | 0 | 4G |
| CULT MORNINGLRY | 0 | 0 | 0 | 0 | 0 | 0 | 0 | 2H |
| COCKLEBUR | 0 | 0 | 2G | 2G | 0 |  |  | 0 |
| PURPLE NUTSEDGE | 0 | 0 | 10E | 0 | 0 | 0 | 0 | &E |
| LARGE CRABGRASS | 9G | 2U,9G | 9H | 3C,9G | 0 | 3G | 8G | 8H |
| BARNYARDGRASS | 4C,8H | 2C,8G | 3C,7H | 2G | 0 | 0 | 2C,6G | 5C,9H |
| WILD OATS | 0 | 3G | 0 | 0 | 0 | 0 | 0 | 0 |
| ERA WHEAT | 0 | 0 | 0 | 0 | 0 | 0 | 0 | 3G |
| G4646 CORN | 0 | 2G | 2G | 0 | 0 | 0 | 0 | 3G |
| WILLMS SOYBEANS | 0 | 0 | 0 | 0 | 0 | 0 | 0 | 0 |
| RICE DRY SEEDED | 0 | 4G | 0 |  | 0 | 0 | 0 | 2G |
| G522 SORGHUM | 0 | 3G | 2C,9H |  | 0 | 0 | 0 | 0 |
| CHEAT GRASS | 2G | 3G | 0 |  | 0 | 0 | 0 | 2G |
| USH11 SUGARBEET | 2G | 4G | 3G | 7F | 0 | 0 | 0 | 7G |
| VELVETLEAF | 4G | 5G | 2G |  | 0 | 0 | 0 | 5G |
| GIANT FOXTAIL | 9G | 3C,9G | 9H |  | 0 | 0 | 3C,8G | 9H |
| KLAGES BARLEY | 0 | 0 | 0 | 0 | 0 | 0 | 0 | 0 |

|  | CMPD 620 | CMPD 620 | CMPD 624 | CMPD 627 |  | CMPD 644 | CMPD 646 | CMPD 648 |
|---|---|---|---|---|---|---|---|---|
| RATE = KG/HA | 0.4 | 2 | 0.4 | 0.4 |  | 0.1 | 0.4 | 0.4 | 0.4 |
| COKER COTTON | 9G | 9G | 0 | 0 | 9G | 0 | 0 | 0 |
| CULT MORNINGLRY | 2C,8G | 9G | 2G | 0 | 9G | 0 | 2C | 0 |
| COCKLEBUR | 3C,7G | 2H | 2G | 0 | 3C,7G | 0 | 0 | 0 |
| PURPLE NUTSEDGE | 5G | 0 | 0 | 0 | 10 | 10E | 10E | 0 |
| LARGE CRABGRASS | 9H | 9H | 9H | 0 | 9H | 3C,7H | 5C,9H | 9G | 3C,8G |
| BARNYARDGRASS | 2C,5H | 7C,9H | 8H | 0 | 9C | 0 | 5C,9H | 0 | 0 |
| WILD OATS | 0 | 0 | 0 | 0 | 4C,8G | 0 | 2C,5G | 0 | 0 |
| ERA WHEAT | 0 | 0 | 0 | 0 | 9G | 0 | 0 | 0 | 0 |
| G4646 CORN | 0 | 1H | 0 | 0 | 2C,8H | 0 | 0 | 0 | 2G |
| WILLMS SOYBEANS | 7G | 8G | 0 | 0 | 8G | 0 | 0 | 3H | 0 |
| RICE DRY SEEDED | 3G | 2G | 2G | 0 | 6G | 0 | 0 | 0 | 0 |
| G522 SORGHUM | 9G | 9G | 0 | 0 | 3C,9G | 0 | 4G | 0 | 0 |

TABLE A-continued

| | | | | | | | | |
|---|---|---|---|---|---|---|---|---|
| CHEAT GRASS | 0 | 2G | 0 | 0 | 7G | | 0 | 2G |
| USH11 SUGARBEET | 8H | 9H | 8H | 0 | 9G | 0 | 6H | 5H | 7H |
| VELVETLEAF | 6G | 9H | 8G | 0 | 6C,9G | 0 | 2C | 2G | 4G |
| GIANT FOXTAIL | 9H | 9H | 9H | 0 | 9H | 3C,9H | 5C,9H | 9H | 2C,9G |
| KLAGES BARLEY | 0 | 0 | 0 | 0 | 3G | 0 | 0 | 0 | 3G |
| DOWNY BROME | | | | | | 0 | 3C,5G | | |

| | CMPD 651 | CMPD 653 | CMPD 656 | CMPD 658 | CMPD 659 | CMPD 661 | CMPD 669 | CMPD 673 |
|---|---|---|---|---|---|---|---|---|
| RATE = KG/HA | 0.4 | 0.4 | 0.4 | 0.4 | 0.4 | 0.4 | 2 | 0.4 |
| COKER COTTON | 0 | 5G | 0 | 0 | 3G | 0 | 8G | 0 |
| CULT MORNINGLRY | 0 | 2C,5G | 0 | 0 | 1C | 0 | 5C,9H | 0 |
| COCKLEBUR | 0 | 2H | 0 | 2G | 0 | 0 | | 0 |
| PURPLE NUTSEDGE | 0 | 0 | 2G | 6G | 10E | 0 | 3G | 0 |
| LARGE CRABGRASS | 0 | 9C | 5C,9H | 9H | 3C,9G | 5G | 9H | 9H |
| BARNYARDGRASS | 0 | 3C,9G | 0 | 5G | 2C,5G | 0 | 9C | 4H |
| WILD OATS | 0 | 0 | 0 | 0 | 0 | 0 | 2C | 0 |
| ERA WHEAT | 0 | 2G | 0 | 0 | 0 | 0 | 0 | 2G |
| G4646 CORN | 0 | 0 | 0 | 4G | 0 | 0 | 2C,5H | 2G |
| WILLMS SOYBEANS | 0 | 0 | 0 | 2G | 0 | 0 | 8G | 0 |
| RICE DRY SEEDED | 0 | 0 | 0 | 0 | 0 | 0 | 0 | 0 |
| G522 SORGHUM | 0 | 7G | 0 | 0 | 0 | 0 | 9G | 0 |
| CHEAT GRASS | 0 | 8G | 0 | 0 | 0 | 0 | 0 | 3G |
| USH11 SUGARBEET | 0 | 8H | 2H | 0 | 0 | 5G | 8G | 6H |
| VELVETLEAF | 0 | 5C,9G | 0 | 0 | 7G | 0 | 4C,8G | 0 |
| GIANT FOXTAIL | 0 | 5C,9H | 4C,9H | 7H | 3C,9H | 3G | 9H | 2C,8G |
| KLAGES BARLEY | 0 | 0 | 0 | 0 | 0 | 0 | 0 | 2G |

| | CMPD 675 | CMPD 721 | CMPD 724 | CMPD 724 | CMPD 726 | CMPD 753 | CMPD 754 | CMPD 782 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 0 | 0 | 0 | 8G | 0 | 3G | 0 | 0 |
| CULT MORNINGLRY | 0 | 3H | 2C,8H | 9C | 0 | 9G | 0 | 3C,9H |
| COCKLEBUR | | 0 | 0 | 0 | 2G | 3H | 0 | 0 |
| PURPLE NUTSEDGE | 0 | 0 | 0 | 0 | 0 | 9G | 0 | 0 |
| LARGE CRABGRASS | 0 | 7G | 2C,9H | 4C,9H | 7G | 9G | 8G | 3C,9G |
| BARNYARDGRASS | 0 | 0 | 5C,9H | 5C,9H | 3C,6G | 8G | 2H | 2C,9H |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 0 | 0 | 2G | 0 | 0 | 0 |
| WILLMS SOYBEANS | 0 | 0 | 0 | 6G | 0 | 3G | 0 | 3G |
| RICE DRY SEEDED | 0 | 0 | 0 | 0 | 0 | 0 | 0 | 0 |
| G522 SORGHUM | 0 | 0 | 0 | 6G | 0 | 5G | 0 | 6G |
| CHEAT GRASS | 0 | 0 | 0 | 8G | 0 | 0 | 0 | 0 |
| USH11 SUGARBEET | 0 | 2C,3H | 5H | 8G | 2H | 8H | 3G | 9G |
| VELVETLEAF | 0 | 2G | 9G | 4C,9G | 0 | 4G | 0 | 2C,8G |
| GIANT FOXTAIL | 0 | 7G | 3C,9H | 9H | 2C,9H | 3C,9G | 7G | 9H |
| KLAGES BARLEY | 0 | 0 | 0 | 0 | 0 | 0 | 0 | 0 |
| DOWNY BROME | | | | | | | | 0 |

| | CMPD 784 | CMPD 810 | CMPD 811 | CMPD 815 | CMPD 863 | CMPD 879 | CMPD 905 | CMPD 1276 |
|---|---|---|---|---|---|---|---|---|
| RATE = KG/HA | 0.4 | 0.4 | 0.4 | 0.4 | 2 | 0.4 | 0.4 | 0.4 |
| COKER COTTON | 0 | 0 | 9G | 0 | 0 | 5G | 0 | 0 |
| CULT MORNINGLRY | 1H | 0 | 9C | 0 | 0 | 0 | 0 | 0 |
| COCKLEBUR | 0 | 2G | 0 | | | 2G | 0 | 0 |
| PURPLE NUTSEDGE | 5G | 0 | 10E | 0 | 0 | 4G | 8G | 0 |
| LARGE CRABGRASS | 9H | 9H | 5C,9H | 9G | 0 | 4G | 9H | 4C,9H |
| BARNYARDGRASS | 0 | 4C,9H | 7C,9H | 0 | 0 | 3G | 4C,8H | 4C,8H |
| WILD OATS | 0 | 2G | 0 | 0 | 0 | 2G | 0 | 0 |
| ERA WHEAT | 0 | 2G | 0 | 0 | 0 | 0 | 0 | 0 |
| G4646 CORN | 0 | 0 | 2G | 0 | 0 | 0 | 2G | 0 |
| WILLMS SOYBEANS | 0 | 0 | 7G | 0 | 0 | 0 | 2G | 0 |
| RICE DRY SEEDED | 0 | 0 | 0 | 0 | 0 | 0 | 0 | 0 |
| G522 SORGHUM | 2G | 0 | 8G | 0 | 0 | 0 | 0 | 0 |
| CHEAT GRASS | 0 | 3G | 5G | 0 | 0 | 2G | 2G | 0 |
| USH11 SUGARBEET | 5G | 9G | 8G | 0 | 0 | 0 | 5H | 2H |
| VELVETLEAF | 4G | 3G | 2C,9G | 3G | 0 | 0 | 4G | 0 |
| GIANT FOXTAIL | 3G | 9H | 9H | 2G | 0 | 8G | 9H | 4C,9H |
| KLAGES BARLEY | 0 | 0 | 2G | 0 | 0 | 0 | 0 | 0 |

| | CMPD 1276 | CMPD 1276A | CMPD 1277 | CMPD 1278 | CMPD 1279 | CMPD 1280 | CMPD 1377 | |
|---|---|---|---|---|---|---|---|---|
| RATE = KG/HA | 0.4 | 0.4 | 0.4 | 0.4 | 0.4 | 0.4 | 0.4 | 2 |
| COKER COTTON | 0 | 0 | 0 | 0 | 0 | 2G | 0 | 7G |
| CULT MORNINGLRY | 1C,3G | 0 | 0 | 0 | 0 | 2H | 2C | 2C,3G |
| COCKLEBUR | 0 | 0 | 0 | 0 | 0 | 0 | 0 | 2G |
| PURPLE NUTSEDGE | 8G | 10E | 0 | 0 | 0 | 0 | 0 | 9G |
| LARGE CRABGRASS | 7G | 0 | 5C,9G | 0 | 7G | 9H | 4C,8H | 5C,9H |
| BARNYARDGRASS | 0 | 0 | 3C,8H | 0 | 2G | 3G | 2G | 10C |
| WILD OATS | 0 | 0 | 0 | 0 | 0 | 0 | 0 | 0 |
| ERA WHEAT | 0 | 0 | 0 | 0 | 0 | 0 | 0 | 0 |
| G4646 CORN | 0 | 0 | 2G | 0 | 0 | 0 | 0 | 0 |
| WILLMS SOYBEANS | 0 | 0 | 0 | 0 | 0 | 0 | 0 | 5G |
| RICE DRY SEEDED | 2G | 0 | 0 | 0 | 0 | 0 | 0 | 0 |
| G522 SORGHUM | 0 | 0 | 0 | 0 | 0 | 0 | 0 | 2C,6G |

TABLE A-continued

| | | | | | | | | | |
|---|---|---|---|---|---|---|---|---|---|
| CHEAT GRASS | 0 | 0 | 0 | 0 | 0 | 0 | 0 | 0 | 0 |
| USH11 SUGARBEET | 7G | 6G | 7H | 0 | 3H | 5G | 2C,6H | 8G,5I | |
| VELVETLEAF | 4G | 8G | 3G | 0 | 5G | 5G | 3G | 7G | |
| GIANT FOXTAIL | 2C,9G | 0 | 3C,9H | 2G | 8G | 9H | 3C,9H | 4C,9H | |
| KLAGES BARLEY | 0 | 0 | 0 | 0 | 0 | 0 | 0 | 0 | |

| | CMPD 1381 | CMPD 1304 | CMPD 1 | CMPD 4 | CMPD 9 | CMPD 11 | CMPD 13 | |
|---|---|---|---|---|---|---|---|---|
| RATE = KG/HA | 0.4 | 2 | 0.4 | 2 | 0.4 | 0.4 | 0.1 | 0.4 | 2 | 0.4 |
| COKER COTTON | 0 | 8G | 0 | 7G | 0 | 8G | 0 | 5H | 9G | 0 |
| CULT MORNINGLRY | 0 | 7H | 0 | 7G | 0 | 9H | 0 | 1C | 9G | 0 |
| COCKLEBUR | 0 | 3G | 0 | 0 | 0 | 0 | 0 | 0 | 2C,8G | 0 |
| PURPLE NUTSEDGE | 0 | 0 | 0 | 3G | 5G | 0 | 0 | 8G | 10E | 0 |
| LARGE CRABGRASS | 5C,9G | 3C,9G | 4C,9H | 4C,9G | 4C,9G | 9C | 3C,7H | 4C,9H | 9H | 5C,9G |
| BARNYARDGRASS | 3H | 5C,9H | 0 | 5C,9H | 1C | 10C | 4C,6H | 9C | 5C,9H | 3C,7G |
| WILD OATS | 0 | 0 | 0 | 2G | 0 | 0 | 0 | 0 | 8G | 0 |
| ERA WHEAT | 0 | 0 | 0 | 0 | 2G | 0 | 0 | 2G | 2C,9G | 0 |
| G4646 CORN | 0 | 3G | 0 | 5G | 0 | 0 | 0 | 2C,2H | 3C,8H | 3G |
| WILLMS SOYBEANS | 0 | 9G | 0 | 7G | 2G | 0 | 0 | 3C,7H | 9G | 0 |
| RICE DRY SEEDED | 0 | 4G | 0 | 0 | 3G | 0 | 0 | 0 | 0 | 0 |
| G522 SORGHUM | 0 | 7G | 3G | 9G | 0 | 9H | 0 | 2C,9G | 9H | 2H |
| CHEAT GRASS | — | 0 | — | 6G | 0 | 0 | | | 3C,8G | |
| USH11 SUGARBEET | 2H | 8H | 0 | 8H | 4H | 8H | 3H | 6H | 9H | 7H |
| VELVETLEAF | 3G | 8G | 5G | 7G | 5G | 7H | 0 | 5C,9G | 9G | 9C |
| GIANT FOXTAIL | 4C,9H | 9H | 3C,9H | 9H | 3C,9H | 3C,9H | 4C,9H | 4C,9H | 9H | 2C,9G |
| KLAGES BARLEY | 0 | 0 | 0 | 0 | 0 | 0 | 0 | 0 | 4G | 0 |
| DOWNY BROME | 0 | — | 0 | — | | | 0 | 2C,7G | | 4G |

| | CMPD 15 | CMPD 16 | CMPD 17 | CMPD 18 | CMPD 23 | CMPD 33 | CMPD 34 | CMPD 34 |
|---|---|---|---|---|---|---|---|---|
| RATE = KG/HA | 0.4 | 0.4 | 0.4 | 0.4 | 0.4 | 0.4 | 0.4 | 0.4 |
| COKER COTTON | 0 | 5G | 0 | 0 | 0 | 8G | 0 | 0 |
| CULT MORNINGLRY | 0 | 0 | 0 | 1H | 0 | 7G | 6G | 8G |
| COCKLEBUR | 0 | 0 | 0 | 0 | 0 | 2G | 0 | 0 |
| PURPLE NUTSEDGE | 9G | 10E | 10E | 7G | 0 | 0 | 0 | 0 |
| LARGE CRABGRASS | 3C,9H | 8G | 9G | 10H | 9H | 8G | 3C,9G | 4C,9G |
| BARNYARDGRASS | 0 | 5G | 3G | 5C,9H | 3C,6G | 2C,8H | 5G | 5H |
| WILD OATS | 0 | 0 | 0 | 0 | 0 | 0 | 0 | 0 |
| ERA WHEAT | 0 | 0 | 0 | 7G | 0 | 0 | 0 | 0 |
| G4646 CORN | 0 | 2G | 0 | 2G | 0 | 0 | 0 | 0 |
| WILLMS SOYBEANS | 0 | 0 | 0 | 0 | 0 | 4G | 0 | 0 |
| RICE DRY SEEDED | 0 | 2G | 0 | 0 | 0 | 2G | 0 | 0 |
| G522 SORGHUM | 0 | 0 | 0 | 9G | 0 | 5G | 1H | 0 |
| CHEAT GRASS | 0 | 0 | 0 | 8G | 4G | 0 | | |
| USH11 SUGARBEET | 0 | 6G | 0 | 7H | 3H | 7G | 5H | 2H |
| VELVETLEAF | 6G | 5G | 2G | 7G | 3G | 2G | 7G | 5G |
| GIANT FOXTAIL | 0 | 9H | 6G | 9H | 5C,9H | 9H | 3C,9H | 3C,9H |
| KLAGES BARLEY | 0 | 0 | 0 | 0 | 0 | 0 | 0 | 0 |
| DOWNY BROME | | | | | | | 0 | 0 |

| | CMPD 34 | CMPD 35 | CMPD 35 | CMPD 35 | CMPD 35 | CMPD 35 | CMPD 39 | CMPD 42 |
|---|---|---|---|---|---|---|---|---|
| RATE = KG/HA | 0.4 | 0.4 | 2 | 2 | 0.4 | 0.4 | 0.4 | 0.4 |
| COKER COTTON | 0 | 6G | 8H | 9G | 0 | 0 | 8G | 0 |
| CULT MORNINGLRY | 2C,8G | 8H | 9H | 3C,9H | 8G | 0 | 6G | 0 |
| COCKLEBUR | 0 | 1H | 2H | 0 | 0 | 0 | 0 | 0 |
| PURPLE NUTSEDGE | 0 | 0 | 0 | 3G | 0 | 0 | 0 | 0 |
| LARGE CRABGRASS | 4C,9G | 9H | 10E | 10H | 3C,9G | 0 | 3C,9G | 6G | 2C,9G |
| BARNYARDGRASS | 3C,8G | 6C,9H | 7C,9H | 9H | 7H | 0 | 3C,9G | 2G | 0 |
| WILD OATS | 0 | 0 | 7G | 8G | 0 | 0 | 2G | 0 | 2G |
| ERA WHEAT | 0 | 0 | 8G | 5G | 0 | 0 | 0 | 0 | 0 |
| G4646 CORN | 2G | 0 | 2C,3H | 3G | 0 | 0 | 0 | 0 | 0 |
| WILLMS SOYBEANS | 0 | 2G | 7G | 2C,9G | 0 | 0 | 9G | 0 | 0 |
| RICE DRY SEEDED | 0 | 0 | 1C | 0 | 0 | 0 | 4G | 0 | 0 |
| G522 SORGHUM | 0 | 7G | 9H | 2C,9G | 0 | 0 | 5G | 0 | 0 |
| CHEAT GRASS | 0 | 0 | 8G | 8G | | | 5G | 0 | |
| USH11 SUGARBEET | 4H | 5H | 9H | 9G | 3H | 0 | 5H | 2H | 5H |
| VELVETLEAF | 5C,8G | 8H | 9H | 9G | 5C,9G | 0 | 7G | 0 | 0 |
| GIANT FOXTAIL | 3C,9G | 9H | 9H | 9H | 9H | 0 | 3C,9G | 6G | 3C,9G |
| KLAGES BARLEY | 0 | 0 | 0 | 0 | 0 | 0 | 0 | 0 | 0 |
| DOWNY BROME | 3G | | | | 0 | 0 | | | |

| | CMPD 47 | CMPD 51 | CMPD 52 |
|---|---|---|---|
| RATE = KG/HA | 0.4 | 2 | 2 |
| COKER COTTON | 0 | 5G | 9G |
| CULT MORNINGLRY | 0 | 9H | 5C,9H |
| COCKLEBUR | 0 | 1C,2G | |
| PURPLE NUTSEDGE | 0 | 0 | |
| LARGE CRABGRASS | 9G | 10H | |
| BARNYARDGRASS | 1H | 3C,9H | |
| WILD OATS | 0 | 2G | 2C,8G |
| ERA WHEAT | 0 | 0 | 4C,9G |
| G4646 CORN | 3G | 0 | 3C,8H |
| WILLMS SOYBEANS | 0 | 0 | 9G,5I |
| RICE DRY SEEDED | 0 | 0 | 8G |

TABLE A-continued

| | | | |
|---|---|---|---|
| G522 SORGHUM | 0 | 2C,9G | 9G |
| CHEAT GRASS | 0 | 3G | 9G |
| USH11 SUGARBEET | 4H | 9H | 9G |
| VELVETLEAF | 0 | 9H | 9G |
| GIANT FOXTAIL | 3C,9H | 3C,9H | 10H |
| KLAGES BARLEY | 0 | 0 | 7G |

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguilalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*), and giant foxtail (*Setaria faberi*). The third pot was planted with wheat (*Triticum aestivum*), barley (*Hordeum vulgare*), wild buckwheat (*Polygonum convolvulus* L.), cheatgrass (*Bromus secalinus* L.), sugarbeet (*Beta vulgaris*), wild oat (*Avena fatua* L.), common chickweed (*Stellaria media*), blackgrass (*Alopecurus myosuroides*), and rape (*Brassica napus*). The plants were grown for approximately fourteen days, then sprayed postemergence with the chemicals dissolved in a nonphytotoxic solvent.

Premergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second port was planted with green foxtail, cocklebur, morningglory cotton, johnsongrass, barnyardgrass, corn, soybean, and giant foxtail. The third pot was planted with wheat, barley, wild buckwheat, cheatgrass, sugarbeet, wild oat, viola, blackgrass, and rape. The three pans were sprayed preemergence with the chemicals dissolved in a nonphytotoxic solvent.

Treated plants and controls were maintained in the greenhouse for approximately 24 days, then all rated plants were compared to controls and visually rated for plant response.

Response ratings are based on a scale of 0 to 100 where 0=no effect, and 100=complete control. A dash (-) response means no test.

Response ratings are contained in Table B.

TABLE B

| | CMPD 51 | | | CMPD 669 | | | | CMPD 35 | | | | | CMPD 52 | | |
|---|---|---|---|---|---|---|---|---|---|---|---|---|---|---|---|
| RATE = G/HA | 0250 | 0125 | 0062 | 2000 | 1000 | 0500 | 0250 | 0500 | 0250 | 2000 | 1000 | 0250 | 0062 | 2000 | 1000 | 0250 |
| POST | | | | | | | | | | | | | | | | |
| GIANT FOXTAIL | — | 0 | 0 | — | 50 | 30 | 0 | 100 | 90 | — | 80 | 70 | 30 | — | 70 | 50 |
| VELVETLEAF | 30 | 0 | 0 | 80 | 50 | 30 | 0 | 100 | 70 | 100 | 90 | 70 | 50 | 90 | 70 | 50 |
| USH11 SUGARBEET | — | 30 | 0 | — | 80 | 70 | 50 | 70 | 50 | — | 70 | 60 | 50 | — | 70 | 50 |
| LARGE CRABGRASS | 0 | 0 | 0 | 80 | 70 | 50 | 30 | 100 | 50 | 100 | 100 | 90 | 30 | 100 | 90 | 90 |
| PRICKLY SIDA | 30 | 0 | 0 | 90 | 70 | 50 | 30 | 100 | 90 | 100 | 90 | 70 | 50 | 90 | 80 | 70 |
| JIMSONWEED | 0 | 0 | 0 | 60 | 40 | 20 | 0 | 60 | 20 | 90 | 70 | 50 | 0 | 90 | 70 | 50 |
| RICE DRY SEEDED | 0 | 0 | 0 | 0 | 0 | 0 | 0 | 30 | 10 | 60 | 30 | 0 | 0 | 60 | 40 | 0 |
| COCKLEBUR | 30 | 0 | 0 | 60 | 30 | 0 | 0 | 30 | — | 90 | 70 | 50 | 30 | 90 | 60 | 30 |
| COKER COTTON | 20 | 0 | 0 | 70 | 50 | 30 | 0 | 90 | 70 | 50 | 40 | 30 | 20 | 50 | 40 | 30 |
| WILLMS SOYBEANS | — | 0 | 0 | — | 40 | 0 | 0 | 80 | 60 | — | 80 | 60 | 20 | — | 30 | 0 |
| BARNYARDGRASS | 0 | 0 | 0 | 70 | 50 | 30 | 0 | 100 | 80 | 80 | 60 | 30 | 0 | 80 | 60 | 30 |
| WILD OATS | — | 0 | 0 | — | 0 | 0 | 0 | 50 | 0 | — | 30 | 0 | 0 | — | 30 | 0 |
| IVY MORNINGLORY | 30 | 0 | 0 | 100 | 70 | 50 | 30 | 20 | 0 | 70 | 60 | 50 | 30 | 90 | 70 | 50 |
| ERA WHEAT | — | 0 | 0 | — | 0 | 0 | 0 | 10 | 0 | — | 0 | 0 | 0 | — | 50 | 30 |
| SICKLEPOD | 0 | 0 | 0 | 80 | 30 | 0 | 0 | 50 | 30 | 90 | 70 | 50 | 30 | 70 | 40 | 30 |
| JOHNSONGRASS | 0 | 0 | 0 | 30 | 0 | 0 | 0 | 100 | 100 | 90 | 70 | 50 | 30 | 90 | 70 | 50 |
| PURPLE NUTSEDGE | 0 | 0 | 0 | 30 | 0 | 0 | 0 | 80 | — | 30 | 0 | 0 | 0 | 50 | 30 | 0 |
| G4646 CORN | — | 0 | 0 | — | 0 | 0 | 0 | 0 | 0 | — | 40 | 0 | 0 | — | 40 | 0 |
| WILD BUCKWHEAT | — | 0 | 0 | — | 70 | 60 | 50 | — | 0 | — | 70 | 50 | 30 | — | 70 | 50 |
| BLACKGRASS | — | 0 | 0 | — | 50 | 30 | 0 | 90 | 60 | — | 50 | 30 | 0 | — | 70 | 50 |
| ALTEX RAPE | — | 0 | 0 | — | 50 | 30 | 0 | 80 | 60 | — | 80 | 50 | 30 | — | 50 | 30 |
| KLAGES BARLEY | — | 0 | 0 | — | 0 | 0 | 0 | 0 | 0 | — | 0 | 0 | 0 | — | 30 | 0 |
| GREEN FOXTAIL | 30 | 0 | 0 | 80 | 50 | 30 | 0 | 100 | 90 | 90 | 80 | 60 | 30 | 90 | 70 | 50 |
| CHEAT GRASS | — | 0 | 0 | — | 0 | 0 | 0 | | | — | 0 | 0 | 0 | — | 50 | 30 |
| FIELD VIOLET | — | 0 | 0 | — | 0 | 0 | 0 | | | — | 0 | 0 | 0 | — | 50 | 30 |
| LAMBSQUARTER | 70 | 60 | 50 | 90 | 80 | 70 | 60 | 100 | 80 | 100 | 100 | 70 | 50 | 90 | 80 | 70 |
| CHICKWEED SPP. | | | | | | | | 80 | 20 | | | | | | | |
| DOWNY BROME | | | | | | | | 40 | 20 | | | | | | | |

| | CMPD 52 | CMPD 18 | CMPD 35 | CMPD 33 | | | CMPD 35 | | | | CMPD 1381 | | |
|---|---|---|---|---|---|---|---|---|---|---|---|---|---|
| RATE = G/HA | 0062 | 0500 | 0250 | 0250 | 0500 | 0250 | 0125 | 0500 | 0250 | 0125 | 0062 | 0250 | 0125 | 0062 |
| POST | | | | | | | | | | | | | | |
| GIANT FOXTAIL | 30 | 30 | 0 | 80 | 30 | 0 | 0 | 0 | 0 | 0 | — | 60 | 30 | 0 |
| VELVETLEAF | 30 | 80 | 50 | 70 | 90 | 70 | 60 | 90 | 70 | 50 | 30 | 0 | 0 | 0 |
| USH11 SUGARBEET | 30 | 60 | 50 | 60 | 90 | 80 | 70 | 50 | 30 | 0 | — | 70 | 50 | 30 |
| LARGE CRABGRASS | 50 | 30 | 20 | 80 | 70 | 60 | 50 | 70 | 50 | 60 | 30 | 0 | 0 | 0 |
| PRICKLY SIDA | 50 | 70 | 50 | 80 | 70 | 60 | 50 | 90 | 60 | 30 | 0 | 0 | 0 | 0 |
| JIMSONWEED | 30 | 40 | 0 | 50 | 90 | 70 | 50 | 30 | 20 | 0 | 0 | 60 | 50 | 30 |
| RICE DRY SEEDED | 0 | 40 | 30 | 0 | 0 | 0 | 0 | 0 | 0 | 0 | 0 | 0 | 0 | 0 |

TABLE B-continued

| | 　 | 　 | 　 | 　 | 　 | 　 | 　 | 　 | 　 | 　 | 　 | 　 | 　 | 　 |
|---|---|---|---|---|---|---|---|---|---|---|---|---|---|---|
| COCKLEBUR | 0 | 40 | 20 | 30 | 30 | 20 | 0 | 30 | 0 | 0 | 0 | 50 | 30 | 0 |
| COKER COTTON | 0 | 60 | 40 | 90 | 30 | 30 | 30 | 60 | 40 | 30 | 0 | 50 | 30 | 0 |
| WILLMS SOYBEANS | 0 | 30 | 30 | 30 | 60 | 50 | 40 | 60 | 40 | 30 | — | 30 | 0 | 0 |
| BARNYARDGRASS | 0 | 10 | 10 | 90 | 0 | 0 | 0 | 0 | 0 | 0 | 0 | 0 | 0 | 0 |
| WILD OATS | 0 | 30 | 0 | 0 | 30 | 0 | 0 | 0 | 0 | 0 | — | 0 | 0 | 0 |
| IVY MORNINGLORY | 30 | 30 | 20 | 70 | 80 | 70 | 50 | 50 | 30 | 0 | 0 | 50 | 30 | 0 |
| ERA WHEAT | 0 | 0 | 0 | 0 | 0 | 0 | 0 | 0 | 0 | 0 | — | 0 | 0 | 0 |
| SICKLEPOD | 0 | 40 | 20 | 20 | 50 | 30 | 20 | 50 | 30 | 0 | 0 | 30 | 0 | 0 |
| JOHNSONGRASS | 0 | 40 | 0 | 90 | 0 | 0 | 0 | 50 | 30 | 0 | 0 | 30 | 0 | 0 |
| PURPLE NUTSEDGE | 0 | 30 | 0 | 0 | 0 | 0 | 0 | 60 | 30 | 0 | 0 | 30 | 0 | 0 |
| G4646 CORN | 0 | 0 | 0 | 0 | 0 | 0 | 0 | 0 | 0 | 0 | — | 30 | 0 | 0 |
| WILD BUCKWHEAT | 30 | 40 | — | 50 | 60 | 30 | 0 | 80 | 50 | 30 | — | 50 | 30 | 0 |
| BLACKGRASS | 30 | 40 | 0 | 40 | 30 | 0 | 0 | 50 | 30 | 0 | — | 70 | 50 | 30 |
| ALTEX RAPE | 0 | 100 | 80 | 50 | 70 | 50 | 30 | 30 | 0 | 0 | — | 30 | 0 | 0 |
| KLAGES BARLEY | 0 | 10 | 0 | 0 | 0 | 0 | 0 | 0 | 0 | 0 | — | 0 | 0 | 0 |
| GREEN FOXTAIL | 30 | 40 | 0 | 80 | 30 | 0 | 0 | 50 | 30 | 0 | 0 | 30 | 0 | 0 |
| CHEAT GRASS | 0 | 30 | 10 | | 0 | 0 | 0 | 0 | 0 | 0 | — | 0 | 0 | 0 |
| FIELD VIOLET | 0 | | | | 90 | 60 | 30 | | | | | | | |
| LAMBSQUARTER | 50 | 100 | 50 | 60 | 80 | 70 | 50 | 50 | 30 | 0 | 0 | 0 | 0 | 0 |
| CHICKWEED SPP. | | 50 | 0 | 0 | | | | 60 | 30 | 0 | — | 0 | 0 | 0 |
| DOWNY BROME | | | | 0 | | | | | | | | | | |

| | CMPD 1304 | | | CMPD 810 | | | | CMPD 9 | | | CMPD 107 | | | CMPD 13 | |
|---|---|---|---|---|---|---|---|---|---|---|---|---|---|---|---|
| RATE = G/HA | 0250 | 0125 | 0062 | 0500 | 0250 | 0125 | 0062 | 0500 | 0250 | 0125 | 0500 | 0250 | 0125 | 0250 | 0125 |
| POST | | | | | | | | | | | | | | | |
| GIANT FOXTAIL | 0 | 0 | 0 | 80 | 20 | 0 | 0 | 80 | 50 | 30 | 60 | 20 | 0 | 20 | 0 |
| VELVETLEAF | 100 | 70 | 30 | 60 | 30 | 20 | 0 | 70 | 40 | — | 80 | 80 | 70 | 70 | 60 |
| USH11 SUGARBEET | 30 | 0 | 0 | 20 | 20 | 0 | — | 90 | 50 | 40 | 90 | 90 | 80 | 80 | 40 |
| LARGE CRABGRASS | 0 | 0 | 0 | 40 | 20 | 0 | 0 | 30 | 20 | 0 | 30 | 30 | — | 0 | 0 |
| PRICKLY SIDA | 50 | 30 | 0 | 30 | 20 | 0 | 0 | 70 | 60 | 30 | 100 | 90 | 80 | 60 | 40 |
| JIMSONWEED | 60 | 30 | 0 | 30 | 20 | 0 | 0 | 50 | 30 | 30 | 90 | 50 | 30 | 40 | 30 |
| RICE DRY SEEDED | 0 | 0 | 0 | 30 | 0 | 0 | 0 | 30 | 0 | 0 | 10 | 0 | 0 | 0 | 0 |
| COCKLEBUR | 50 | 30 | 0 | 30 | 20 | 0 | 0 | 40 | 40 | 30 | 50 | 40 | 20 | 30 | 0 |
| COKER COTTON | 50 | 30 | 0 | 30 | 20 | 10 | 10 | 80 | 60 | 30 | 90 | 70 | 60 | 90 | 80 |
| WILLMS SOYBEANS | 30 | 0 | 0 | 80 | 30 | 0 | 0 | 30 | 20 | 0 | — | 60 | 0 | 40 | 0 |
| BARNYARDGRASS | 0 | 0 | 0 | 30 | 20 | 0 | 0 | 100 | 90 | 30 | 100 | 80 | 70 | 20 | 0 |
| WILD OATS | 0 | 0 | 0 | 30 | 20 | 0 | — | 30 | 20 | 10 | 20 | 20 | — | 30 | 0 |
| IVY MORNINGLORY | 30 | 0 | 0 | 0 | 0 | 0 | 0 | 50 | — | 0 | 100 | 90 | 60 | 70 | 40 |
| ERA WHEAT | 0 | 0 | 0 | 20 | 0 | 0 | 0 | 0 | 0 | 0 | 0 | 0 | 0 | 10 | 0 |
| SICKLEPOD | 50 | 30 | 0 | 20 | 0 | 0 | 0 | 70 | 60 | 60 | 90 | 40 | 20 | 40 | 20 |
| JOHNSONGRASS | 0 | 0 | 0 | 20 | 0 | 0 | 0 | 50 | 30 | 0 | 0 | 0 | 0 | 0 | 0 |
| PURPLE NUTSEDGE | 70 | 50 | 30 | 0 | 0 | 0 | 0 | — | 0 | 0 | 70 | 70 | 0 | 0 | 0 |
| G4646 CORN | 0 | 0 | 0 | 30 | 20 | 0 | 0 | 0 | 0 | 0 | 0 | 0 | 0 | 0 | 0 |
| WILD BUCKWHEAT | 60 | 30 | 0 | 0 | 0 | 0 | 0 | 60 | 40 | 30 | 90 | 70 | 70 | 50 | 30 |
| BLACKGRASS | 30 | 0 | 0 | 80 | 30 | 20 | — | 70 | 10 | 0 | 70 | 40 | 0 | 80 | 30 |
| ALTEX RAPE | 0 | 0 | 0 | 80 | 30 | 20 | — | 60 | 40 | 0 | 70 | 60 | 60 | 30 | 0 |
| KLAGES BARLEY | 0 | 0 | 0 | 30 | 20 | 0 | — | 0 | 0 | 0 | 0 | 0 | 0 | 0 | 0 |
| GREEN FOXTAIL | 0 | 0 | 0 | 30 | 20 | 0 | 0 | 100 | 70 | 30 | 80 | 40 | 30 | 40 | 0 |
| CHEAT GRASS | | | | 0 | 0 | 0 | — | | | | | | | | |
| LAMBSQUARTER | 80 | 50 | 0 | 80 | 70 | 30 | 0 | — | 90 | 50 | 80 | 80 | 60 | 50 | — |
| CHICKWEED SPP. | 60 | 30 | 0 | 80 | 20 | 0 | — | 70 | 70 | 30 | 80 | 50 | 40 | 50 | 0 |
| DOWNY BROME | 0 | 0 | 0 | | | | | 0 | 0 | 0 | 0 | 0 | 0 | 0 | 0 |

| | CMPD 51 | | | | | CMPD 669 | | | | CMPD 35 | | | | | |
|---|---|---|---|---|---|---|---|---|---|---|---|---|---|---|---|
| RATE = G/HA | 1000 | 0500 | 0250 | 0125 | 0062 | 2000 | 1000 | 0500 | 0250 | 0500 | 0125 | 2000 | 1000 | 0250 | 0062 |
| PRE | | | | | | | | | | | | | | | |
| GIANT FOXTAIL | 100 | 100 | 90 | 60 | 30 | 100 | 100 | 100 | 100 | 100 | 100 | 100 | 100 | 100 | 90 |
| VELVETLEAF | 80 | 50 | 30 | 0 | 0 | 50 | 30 | 0 | 0 | 100 | 90 | 90 | 80 | 70 | 60 |
| USH11 SUGARBEET | 80 | 70 | 60 | 50 | 30 | 70 | 50 | 30 | 0 | 90 | 20 | 60 | 40 | 30 | 0 |
| LARGE CRABGRASS | 100 | 90 | 70 | 50 | 30 | 100 | 100 | 90 | 80 | 100 | 100 | 100 | 100 | 100 | 100 |
| PRICKLY SIDA | 90 | 80 | 70 | 50 | 30 | 90 | 70 | 50 | 30 | 100 | 100 | 90 | 80 | 70 | 60 |
| JIMSONWEED | 80 | 60 | 40 | 30 | 0 | 70 | 50 | 40 | 30 | 70 | 50 | 100 | 90 | 80 | 60 |
| RICE DRY SEEDED | 0 | 0 | 0 | 0 | 0 | 0 | 0 | 0 | 0 | 10 | 0 | 0 | 0 | 0 | 0 |
| COCKLEBUR | 50 | 30 | 0 | 0 | 0 | 40 | 20 | 0 | 0 | 20 | 0 | 50 | 40 | 30 | 0 |
| COKER COTTON | 0 | 0 | 0 | 0 | 0 | 0 | 0 | 0 | 0 | 100 | 20 | 80 | 70 | 60 | 30 |
| WILLMS SOYBEANS | 0 | 0 | 0 | 0 | 0 | 0 | 0 | 0 | 0 | 10 | 0 | 90 | 80 | 30 | 0 |
| BARNYARDGRASS | 100 | 80 | 50 | 30 | 0 | 100 | 100 | 50 | 30 | 100 | 60 | 100 | 100 | 100 | 60 |
| WILD OATS | 0 | 0 | 0 | 0 | 0 | 0 | 0 | 0 | 0 | 40 | 20 | 0 | 0 | 0 | 0 |
| IVY MORNINGLORY | 0 | 0 | 0 | 0 | 0 | 40 | 0 | 0 | 0 | 0 | 0 | 80 | 60 | 40 | 0 |
| ERA WHEAT | 0 | 0 | 0 | 0 | 0 | 0 | 0 | 0 | 0 | 20 | 0 | 0 | 0 | 0 | 0 |
| SICKLEPOD | 60 | 30 | 0 | 0 | 0 | 30 | 0 | 0 | 0 | 50 | 0 | 90 | 70 | 30 | 0 |
| JOHNSONGRASS | 90 | 70 | 50 | 30 | 0 | 90 | 80 | 50 | 30 | 100 | 50 | 100 | 100 | 90 | 70 |
| PURPLE NUTSEDGE | 0 | 0 | 0 | 0 | 0 | 0 | 0 | 0 | 0 | 50 | 0 | 0 | 0 | 0 | 0 |
| G4646 CORN | 0 | 0 | 0 | 0 | 0 | 0 | 0 | 0 | 0 | 40 | 10 | 60 | 40 | 20 | 0 |
| WILD BUCKWHEAT | 60 | 30 | 0 | 0 | 0 | 70 | 50 | 30 | 0 | 100 | 30 | 80 | 70 | 50 | 30 |
| BLACKGRASS | 60 | 30 | 0 | 0 | 0 | 70 | 50 | 30 | 0 | 100 | 80 | 90 | 80 | 60 | 30 |
| ALTEX RAPE | 70 | 60 | 50 | 30 | 0 | 70 | 50 | 30 | 0 | 80 | 40 | 90 | 70 | 50 | 30 |
| KLAGES BARLEY | 0 | 0 | 0 | 0 | 0 | 0 | 0 | 0 | 0 | 0 | 0 | 0 | 0 | 0 | 0 |
| GREEN FOXTAIL | 100 | 100 | 90 | 70 | 50 | 100 | 100 | 100 | 100 | 100 | 100 | 100 | 100 | 100 | 100 |
| CHEAT GRASS | 0 | 0 | 0 | 0 | 0 | 30 | 0 | 0 | 0 | | | 60 | 30 | 0 | 0 |
| FIELD VIOLET | 90 | 70 | 50 | 30 | 0 | 80 | 30 | 0 | 0 | | | 80 | 70 | 50 | 30 |

TABLE B-continued

| | | | | | | | | | | | | | | | |
|---|---|---|---|---|---|---|---|---|---|---|---|---|---|---|---|
| LAMBSQUARTER | 100 | 100 | 90 | 80 | 70 | 90 | 70 | 50 | 100 | 90 | 100 | 100 | 90 | 80 | |
| CHICKWEED SPP. | | | | | | | | | | 40 | — | | | | |
| DOWNY BROME | | | | | | | | | | 80 | 40 | | | | |

| | CMPD 52 | | | | CMPD 18 | | | | CMPD 33 | | | CMPD 35 | | | |
|---|---|---|---|---|---|---|---|---|---|---|---|---|---|---|---|
| RATE = G/HA | 2000 | 1000 | 0250 | 0062 | 0500 | 0250 | 0125 | 0062 | 0500 | 0250 | 0125 | 0250 | 0125 | 0062 | 0500 | 0250 |
| PRE | | | | | | | | | | | | | | | | |
| GIANT FOXTAIL | 100 | 100 | 90 | 60 | 100 | 100 | 90 | 30 | 100 | 90 | 80 | 100 | 100 | 100 | 100 | 100 |
| VELVETLEAF | 90 | 70 | 50 | 30 | 70 | 20 | — | — | 90 | 80 | 70 | — | 90 | 30 | 90 | 80 |
| USH11 SUGARBEET | 80 | 50 | 30 | 0 | 50 | 30 | 20 | — | 80 | 50 | 30 | 50 | 20 | 0 | 70 | 50 |
| LARGE CRABGRASS | 100 | 100 | 100 | 80 | 100 | 100 | 100 | 50 | 90 | 70 | 50 | 100 | 100 | 60 | 100 | 100 |
| PRICKLY SIDA | 90 | 80 | 80 | 70 | 90 | 90 | 80 | 50 | 60 | 30 | 0 | — | 70 | 60 | 70 | 60 |
| JIMSONWEED | 100 | 100 | 70 | 50 | 70 | 20 | 0 | 0 | 70 | 50 | 30 | 0 | 0 | 0 | 40 | 40 |
| RICE DRY SEEDED | 50 | 30 | 0 | 0 | 10 | 0 | 0 | 0 | 0 | 0 | 0 | 30 | 10 | 0 | 10 | 10 |
| COCKLEBUR | 100 | 100 | 50 | 30 | 20 | 0 | 0 | 0 | 30 | 0 | 0 | 0 | — | 0 | 30 | 30 |
| COKER COTTON | 80 | 60 | 20 | 0 | 10 | 0 | 0 | — | 30 | 0 | 0 | 50 | 20 | 0 | 60 | 10 |
| WILLMS SOYBEANS | 80 | 60 | 0 | 0 | 10 | 0 | 0 | 0 | 0 | 0 | 0 | 40 | 10 | 0 | 10 | 10 |
| BARNYARDGRASS | 100 | 100 | 80 | 30 | 100 | 60 | 20 | 0 | 100 | 90 | 80 | 80 | 30 | 10 | 100 | 90 |
| WILD OATS | 30 | 20 | 0 | 0 | 30 | 0 | — | 0 | 0 | 0 | 0 | 10 | 0 | 0 | 40 | 30 |
| IVY MORNINGLORY | 80 | 60 | 40 | 0 | 40 | 30 | 30 | 0 | 60 | 40 | 20 | 50 | 40 | 40 | 20 | 0 |
| ERA WHEAT | 50 | 30 | 0 | 0 | 10 | 0 | 0 | 0 | 0 | 0 | 0 | 0 | — | 0 | 20 | 20 |
| SICKLEPOD | 90 | 60 | 30 | 0 | 100 | 50 | 30 | 0 | 50 | 30 | 0 | 90 | 40 | 30 | 30 | 20 |
| JOHNSONGRASS | 100 | 90 | 80 | 50 | 100 | 50 | 30 | 0 | 50 | 30 | 0 | 70 | 10 | 0 | 90 | 80 |
| PURPLE NUTSEDGE | 70 | 30 | 0 | 0 | 90 | 60 | 30 | 0 | 0 | 0 | 0 | 0 | 0 | 0 | 100 | 20 |
| G4646 CORN | 60 | 30 | 0 | 0 | 10 | 10 | 10 | 0 | 0 | 0 | 0 | 0 | 0 | 0 | 0 | 0 |
| WILD BUCKWHEAT | 80 | 50 | 30 | 0 | 50 | 30 | 30 | 0 | 0 | 0 | 0 | 40 | 0 | — | 50 | 30 |
| BLACKGRASS | 90 | 70 | 50 | 30 | 90 | 80 | 80 | 30 | 30 | 0 | 0 | 50 | — | 10 | 60 | 40 |
| ALTEX RAPE | 70 | 40 | 20 | 0 | 30 | 20 | 20 | — | 90 | 80 | 70 | 40 | 40 | 30 | 80 | 80 |
| KLAGES BARLEY | 30 | 20 | 0 | 0 | 30 | 30 | 20 | 10 | 0 | 0 | 0 | 10 | 0 | 0 | 20 | 0 |
| GREEN FOXTAIL | 100 | 100 | 90 | 70 | 100 | 100 | 100 | 30 | 100 | 90 | 80 | 100 | 100 | 70 | 100 | 100 |
| CHEAT GRASS | 70 | 50 | 30 | 0 | 40 | 20 | 20 | 20 | 0 | 0 | 0 | 40 | 30 | | | |
| FIELD VIOLET | 100 | 90 | 30 | 0 | | | | | 70 | 50 | 30 | | | | | |
| LAMBSQUARTER | 100 | 100 | 90 | 80 | 100 | 90 | 80 | 60 | 100 | 100 | 100 | 100 | 70 | 60 | 100 | 90 |
| CHICKWEED SPP. | | | | | 50 | 20 | — | — | | | | 40 | 30 | 0 | 30 | 0 |
| DOWNY BROME | | | | | | | | | | | | 30 | 10 | 0 | | |

| | CMPD 35 | | CMPD 1381 | | | CMPD 1304 | | | CMPD 810 | | | | CMPD 9 | | | |
|---|---|---|---|---|---|---|---|---|---|---|---|---|---|---|---|---|
| RATE = G/HA | 0125 | 0062 | 0250 | 0125 | 0062 | 0250 | 0125 | 0062 | 0500 | 0250 | 0125 | 0062 | 0500 | 0250 | 0125 | 0062 |
| PRE | | | | | | | | | | | | | | | | |
| GIANT FOXTAIL | 100 | 90 | 100 | 100 | 90 | 100 | 100 | 70 | 50 | 40 | 20 | 0 | 100 | 100 | 100 | 40 |
| VELVETLEAF | 60 | 50 | 0 | 0 | 0 | 30 | 0 | 0 | 50 | 40 | 20 | 0 | 100 | 70 | 40 | 20 |
| USH11 SUGARBEET | 40 | 0 | 90 | 70 | 50 | 50 | 30 | 0 | 40 | 30 | 30 | 20 | 90 | 70 | 60 | 40 |
| LARGE CRABGRASS | 100 | 100 | 100 | 100 | 100 | 100 | 90 | 80 | 100 | 90 | 90 | 20 | 100 | 100 | 100 | 100 |
| PRICKLY SIDA | 60 | 50 | 30 | 0 | 0 | 70 | 50 | 30 | 60 | 50 | 20 | 20 | 90 | 50 | 10 | 0 |
| JIMSONWEED | 20 | 0 | 50 | 30 | 0 | 30 | 0 | 0 | 50 | 40 | 30 | 30 | 80 | 50 | 30 | 30 |
| RICE DRY SEEDED | 0 | 0 | 0 | 0 | 0 | 0 | 0 | 0 | 0 | 0 | 0 | 0 | 0 | 0 | 0 | 0 |
| COCKLEBUR | 0 | 0 | 50 | 30 | 0 | 50 | 30 | 0 | 30 | 20 | 0 | 0 | 30 | 0 | 0 | 0 |
| COKER COTTON | 0 | 0 | 30 | 30 | 30 | 0 | 0 | 0 | 0 | 0 | 0 | 0 | 30 | 10 | — | 0 |
| WILLMS SOYBEANS | 0 | 0 | 0 | 0 | 0 | 0 | 0 | 0 | 20 | 0 | 0 | 0 | 10 | 0 | 0 | 0 |
| BARNYARDGRASS | 40 | 30 | 80 | 50 | 30 | 70 | 30 | 0 | 100 | 90 | 70 | 40 | 100 | 100 | 30 | 0 |
| WILD OATS | 20 | 0 | 50 | 30 | 0 | 50 | 30 | 0 | 20 | 0 | 0 | 0 | 0 | 0 | 0 | 0 |
| IVY MORNINGLORY | 0 | 0 | 60 | 30 | 0 | 0 | 0 | 0 | 30 | 20 | 0 | 0 | 20 | 0 | 0 | 0 |
| ERA WHEAT | 10 | 0 | 30 | 0 | 0 | 30 | 0 | 0 | 20 | 0 | 0 | 0 | 0 | 0 | 0 | 0 |
| SICKLEPOD | 0 | 0 | 0 | 0 | 0 | 0 | 0 | 0 | 0 | 0 | 0 | 0 | 50 | 20 | 0 | 0 |
| JOHNSONGRASS | 40 | 40 | 70 | 30 | 0 | 40 | 0 | 0 | 50 | 40 | 30 | 20 | 100 | 90 | 50 | 40 |
| PURPLE NUTSEDGE | 0 | 0 | 30 | 0 | 0 | 0 | 0 | 0 | 0 | 0 | 0 | 0 | 0 | 0 | 0 | 0 |
| G4646 CORN | 0 | 0 | 0 | 0 | 0 | 0 | 0 | 0 | 30 | 20 | 0 | 0 | 10 | 0 | 0 | 0 |
| WILD BUCKWHEAT | 0 | 0 | 0 | 0 | 0 | 70 | 50 | 30 | 30 | 0 | 0 | 0 | 80 | 50 | 30 | 0 |
| BLACKGRASS | 40 | 30 | 50 | 40 | 30 | 50 | 30 | 0 | 70 | 30 | 20 | 0 | 90 | 50 | 20 | 0 |
| ALTEX RAPE | 70 | 30 | 70 | 50 | 30 | 0 | 0 | 0 | 30 | 20 | 0 | 0 | 90 | 70 | 50 | 30 |
| KLAGES BARLEY | 0 | 0 | 0 | 0 | 0 | 0 | 0 | 0 | 30 | 0 | 0 | 0 | 0 | 0 | 0 | 0 |
| GREEN FOXTAIL | 100 | 600 | 100 | 100 | 80 | 100 | 100 | 70 | 100 | 100 | 100 | 90 | 100 | 100 | 100 | 40 |
| CHEAT GRASS | 0 | 0 | 30 | 0 | 0 | | | | 40 | 30 | 20 | 0 | | | | |
| LAMBSQUARTER | 80 | 80 | 70 | 50 | 30 | 50 | 30 | 0 | 90 | 80 | 50 | 40 | 100 | 100 | 90 | 80 |
| CHICKWEED SPP. | 0 | 0 | 70 | 50 | 30 | 0 | 0 | 0 | 30 | 0 | 0 | 0 | 40 | 10 | 0 | 0 |
| DOWNY BROME | | | | | | 0 | 0 | 0 | | | | | 40 | 20 | 0 | 0 |

| | CMPD 107 | | | | CMPD 13 | | |
|---|---|---|---|---|---|---|---|
| RATE = G/HA | 0500 | 0250 | 0125 | 0062 | 0250 | 0125 | 0062 |
| PRE | | | | | | | |
| GIANT FOXTAIL | 100 | 100 | 90 | 70 | 100 | 90 | 40 |
| VELVETLEAF | 80 | 40 | 30 | 20 | 40 | 20 | 0 |
| USH11 SUGARBEET | 90 | 80 | 60 | 10 | 90 | 80 | 50 |
| LARGE CRABGRASS | 100 | 100 | 100 | 100 | 100 | 100 | 100 |
| PRICKLY SIDA | 80 | 80 | 70 | 0 | 90 | 60 | 40 |
| JIMSONWEED | 50 | 40 | 20 | 0 | 50 | 30 | 0 |
| RICE DRY SEEDED | 0 | 0 | 0 | 0 | 0 | 0 | 0 |
| COCKLEBUR | 10 | 0 | 0 | 0 | 20 | 0 | 0 |
| COKER COTTON | 10 | 0 | 0 | 0 | 0 | 0 | 0 |
| WILLMS SOYBEANS | 0 | 0 | 0 | 0 | 0 | 0 | 0 |
| BARNYARDGRASS | 100 | 90 | 40 | 0 | 90 | 40 | 0 |

TABLE B-continued

|  | | | | | | | |
|---|---|---|---|---|---|---|---|
| WILD OATS | 30 | 0 | 0 | 0 | 0 | 0 | 0 |
| IVY MORNINGLORY | 50 | 30 | 0 | 0 | 0 | 0 | 0 |
| ERA WHEAT | 0 | 0 | 0 | 0 | 20 | 0 | 0 |
| SICKLEPOD | 80 | 40 | — | 0 | 30 | 0 | 0 |
| JOHNSONGRASS | 100 | 90 | 40 | 20 | 60 | 50 | 30 |
| PURPLE NUTSEDGE | 30 | — | 0 | 0 | 0 | 0 | 0 |
| G4646 CORN | 10 | 0 | 0 | 0 | 0 | 0 | 0 |
| WILD BUCKWHEAT | 70 | 60 | 50 | 20 | 80 | 40 | 30 |
| BLACKGRASS | 70 | 50 | 30 | 10 | 40 | 30 | 10 |
| ALTEX RAPE | 70 | 60 | 60 | 40 | 70 | 60 | 50 |
| KLAGES BARLEY | 0 | 0 | 0 | 0 | 0 | 0 | 0 |
| GREEN FOXTAIL | 100 | 100 | 100 | 90 | 100 | 50 | 20 |
| LAMBSQUARTER | 100 | 90 | 90 | 80 | 100 | 90 | 80 |
| CHICKWEED SPP. | 70 | 40 | 0 | 0 | 30 | 0 | 0 |
| DOWNY BROME | 0 | 0 | 0 | 0 | 20 | 0 | 0 |

TEST C

Sixteen cm diameter Airlite plastic pots were partially filled with Tama silt loam soil and the soil saturated with water. Japonica and Indica rice seedlings a the 2.0 to 2.5 leaf stage were transplanted into ⅓ of the pots. Into another third of the pots were transplanted seedling or sprouted tubers of water plantain (*Alisma trivale*), Scripus (*Scirpus paludosus*), Cyperus (*Cyperus esculentus*), and arrowhead (Sagittaria spp.). The remaining pots were planted with barnyardgrass (*Echinochloa crusgalli*) seeds and sprouted tubes of water chestnut (Eleocharis spp.). These weeds all represent major rice weeds or genera of weeds important in rice. Three to four days after planting, the water level was raised to 3 cm (about 1200 ml/pot) and maintained a this level throughout the test. Chemical treatments were applied directly to the paddy water, within 24 hours of raising the water, after being formulated in a nonphytotoxic solvent. The pots were maintained in the greenhouse. Rates of application and plant response ratings made 21 days after treatment are summarized in Table C.

TABLE C

|  | CMPD 669 | | | | | CMPD 18 | | | | | CMPD 1381 | | | | |
|---|---|---|---|---|---|---|---|---|---|---|---|---|---|---|---|
| RATE × G/HA | 1000 | 0500 | 0250 | 0125 | 0064 | 1000 | 0500 | 0250 | 0125 | 0064 | 1000 | 0500 | 0250 | 0125 | 0064 |
| BARNYARDGRASS | 100 | 90 | 98 | 98 | 90 | 60 | 40 | 0 | 0 | 0 | 100 | 100 | 60 | 55 | 55 |
| WATERCHESTNUT | 0 | 0 | 0 | 0 | 0 | 50 | 40 | 0 | 0 | 0 | 0 | 0 | 0 | 0 | 0 |
| ARROWHEAD | 0 | 0 | 0 | 0 | 0 | 35 | 20 | 0 | 0 | 0 | 0 | 0 | 0 | 0 | 0 |
| SCIRPUS | 30 | 0 | 0 | 0 | 0 | 0 | 0 | 0 | 0 | 0 | 30 | 0 | 0 | 0 | 0 |
| YELLOW NUTSEDGE | 80 | 60 | 0 | 0 | 0 |  |  |  |  |  | 50 | 40 | 0 | 0 | 0 |
| WATER PLAINTAIN | 0 | 0 | 0 | 0 | 0 | 40 | 20 | 0 | 0 | 0 | 0 | 0 | 0 | 0 | 0 |
| RICE JAP EFF | 0 | 0 | 0 | 0 | 0 | 70 | 50 | 0 | 0 | 0 | 60 | 40 | 20 | 0 | 0 |
| RICE INDICA EFF | 0 | 0 | 0 | 0 | 0 | 50 | 30 | 0 | 0 | 0 | 60 | 40 | 20 | 0 | 0 |

|  | CMPD 35 | | | | | CMPD 50 | | | | | CMPD 1304 | | | | |
|---|---|---|---|---|---|---|---|---|---|---|---|---|---|---|---|
| RATE × G/HA | 1000 | 0500 | 0250 | 0125 | 0064 | 1000 | 0500 | 0250 | 0125 | 0064 | 1000 | 0500 | 0250 | 0125 | 0064 |
| BARNYARDGRASS | 95 | 100 | 80 | 100 | 70 | 70 | 70 | 60 | 0 | 0 | 100 | 98 | 100 | 100 | 85 |
| WATERCHESTNUT | 0 | 0 | 60 | 40 | 60 | 0 | 0 | 0 | 0 | 0 | 50 | 0 | 0 | 0 | 0 |
| ARROWHEAD | 95 | 50 | 40 | 0 | 0 | 50 | 30 | 0 | 0 | 0 | 30 | 0 | 0 | 0 | 0 |
| SCIRPUS | 50 | 0 | 0 | 0 | 0 | 0 | 0 | 0 | 0 | 0 | 80 | 70 | 65 | 0 | 0 |
| YELLOW NUTSEDGE | 100 | 95 | 60 | 0 | 0 | 50 | 30 | 0 | 0 | 0 | 0 | 0 | 0 | 0 | 0 |
| WATER PLAINTAIN | 60 | 40 | 40 | 0 | 0 | 0 | 0 | 0 | 0 | 0 | 65 | 0 | 0 | 0 | 0 |
| RICE JAP EFF | 20 | 0 | 0 | 0 | 0 | 70 | 60 | 30 | 0 | 0 | 40 | 0 | 0 | 0 | 0 |
| RICE INDICA EFF | 20 | 0 | 0 | 0 | 0 | 80 | 70 | 30 | 40 | 0 | 40 | 0 | 0 | 0 | 0 |

|  | CMPD 33 | | | | | CMPD 107 | | | | |
|---|---|---|---|---|---|---|---|---|---|---|
| RATE × G/HA | 1000 | 0500 | 0250 | 0125 | 0064 | 1000 | 0500 | 0250 | 0125 | 0064 |
| BARNYARDGRASS | 95 | 70 | 80 | 10 | 0 | 80 | 90 | 40 | 0 | 0 |
| WATERCHESTNUT | 0 | 0 | 0 | 0 | 0 | 30 | 60 | 40 | 0 | 0 |
| ARROWHEAD | 0 | 0 | 0 | 0 | 0 | 70 | 95 | 0 | 0 | 0 |
| SCIRPUS | 0 | 0 | 0 | 0 | 0 | 80 | 80 | 60 | 0 | 0 |
| YELLOW NUTSEDGE | 40 | 0 | 0 | 0 | 0 | 95 | 30 | 50 | 0 | 0 |
| WATER PLAINTAIN | 0 | 0 | 0 | 0 | 0 | 80 | 60 | 0 | 0 | 0 |
| RICE JAP EFF | 60 | 30 | 0 | 0 | 0 | 50 | 40 | 30 | 0 | 0 |
| RICE INDICA EFF | 70 | 30 | 0 | 0 | 0 | 50 | 40 | 30 | 0 | 0 |

|  | CMPD 35 | | | |
|---|---|---|---|---|
| RATE × G/HA | 2000 | 0500 | 0125 | 0032 |
| RICE JAP TOL | 50 | 50 | 20 | 0 |
| RICE INDICA TOL | 60 | 55 | 55 | 0 |

TEST D

The Corn and Sorghum Herbicide Test included the following species in both the preemergence and postemergence evaluations:

| | SPECIES | |
|---|---|---|
| Category | Common Name | Scientific Name |
| Crops | Corn | Zea mays |
| | Soybean | Glycine max |
| | Sorghum | Sorghum bicolor |
| Grasses | Green foxtail | Setaria viridis |
| | Giant foxtail | Setaria faberii |
| | Johnsongrass | Sorghum halepense |
| | Barnyardgrass | Echinochloa crus-galli |
| | Fall panicum | Panicum dichotomiflorum |

| Category | SPECIES Common Name | Scientific Name |
|---|---|---|
| | Crabgrass | *Digitaria sanguinalis* |
| | Nutsedge | *Cyperus rotundus* |
| Broadleaves | Cocklebur | *Xanthium pensylvanicum* |
| | Morningglory | *Ipomoea hederacea* |
| | Velvetleaf | *Abutilon theophrasti* |
| | Jimsonweed | *Datura stramonium* |
| | Lambsquarters | *Chenopodium album* |
| | Pigweed | *Amaranthus retroflexus* |
| | Smartweed | *Polygonum persicaris* |

Postemergence

Postemergence plantings were grown in Sassafras sandy loam soil. Corn and soybeans were grown in separate 25 diameter containers. Sorghum and the seven grass weed species were grown in two 18 cm diameter containers, 4 species per container. The seven broadleaf weed species were also grown in two 18 cm diameter containers, 4 species in one container, 3 species in the second container. One additional planting of corn in an 18 cm diameter container was made. One additional planting of corn in an 18 cm diameter container was made. The soil surface of this additional container of corn was covered with the absorbent, perlite, before spray treatment so that test chemicals would enter the plant only via the foliage. The plants were grown 10-21 days, dependent upon the species and then sprayed postemergence with the test chemicals dissolved in a nonphytotoxic solvent.

Postemergence

Preemergence plantings were grown in fertilized Tama silt loam soil. These plantings are identical to those described in the postemergence section, with the exception of the corn planting having perlite covering the soil surface. These plantings were made the day of or the day before spraying the test chemicals dissolved in a nonphytotoxic solvent.

Evaluation

Treated plants and controls were maintained in the greenhouse for 2 to 4 weeks. Visual planting response ratings were made on a percentage scale of 0 to 100 in comparison with a control where 0=no injury, and 100=death.

The results are shown in Table D.

TABLE D

| | CMPD 50 | | | | CMPD 33 | | | CMPD 35 | | | |
|---|---|---|---|---|---|---|---|---|---|---|---|
| RATE GM/HA | 0500 | 0250 | 0125 | 0064 | 1000 | 0500 | 0250 | 0500 | 0250 | 0125 | 0064 |
| PREEMERGENCE | | | | | | | | | | | |
| G4646 CORN | 0 | 0 | 0 | 0 | 0 | 0 | 0 | 0 | 0 | 0 | 0 |
| WILLMS SOYBEANS | 20 | 0 | 0 | 0 | 0 | 0 | 0 | 0 | 0 | 0 | 0 |
| GREEN FOXTAIL | 85 | 50 | 30 | 0 | 0 | 0 | 0 | 100 | 80 | 70 | 30 |
| GIANT FOXTAIL | 85 | 75 | 65 | 20 | 0 | 0 | 0 | 100 | 80 | 50 | 0 |
| FALL PANICUM | 95 | 60 | 35 | 20 | 0 | 0 | 0 | 100 | 80 | 50 | 0 |
| LARGE CRABGRASS | 100 | 100 | 75 | 40 | 0 | 0 | 0 | 100 | 95 | 70 | 50 |
| BARNYARDGRASS | 45 | 20 | 0 | 0 | 0 | 0 | 0 | 100 | 40 | 60 | 0 |
| JOHNSONGRASS | 95 | 90 | 70 | 35 | 0 | 0 | 0 | 100 | 100 | 30 | 30 |
| G522 SORGHUM | 0 | 0 | 0 | 0 | 0 | 0 | 0 | 0 | 0 | 0 | 0 |
| PURPLE NUTSEDGE | 30 | 0 | 0 | 0 | 0 | 0 | 0 | 50 | 0 | 0 | — |
| VELVETLEAF | 65 | 40 | 25 | 0 | 0 | 0 | 0 | 100 | 100 | 70 | 60 |
| COCKLEBUR | 25 | 0 | 0 | 0 | 0 | 0 | 0 | 20 | 0 | 0 | 0 |
| LADY SMARTWEED | 40 | 20 | 0 | 0 | 0 | 0 | 0 | 100 | 50 | 30 | 0 |
| LAMBSQUARTER | 90 | 75 | 35 | 0 | 0 | 0 | 0 | 80 | 60 | 30 | 30 |
| REDROOT PIGWEED | 100 | 85 | 40 | 0 | 0 | 0 | 0 | 98 | 50 | 0 | 0 |
| IVY MORNINGLORY | 65 | 40 | 30 | 0 | 0 | 0 | 0 | 30 | 0 | 0 | 0 |
| JIMSONWEED | 70 | 50 | 25 | 0 | 0 | 0 | 0 | 30 | 80 | 0 | 0 |
| RATE GM/HA | 0500 | 0250 | | | 1000 | 0500 | 0250 | 0500 | 0250 | | |
| POSTEMERGENCE | | | | | | | | | | | |
| G4646 CORN | 20 | 0 | | | 0 | 0 | 0 | 0 | 0 | | |
| WILLMS SOYBEANS | 65 | 35 | | | 0 | 0 | 0 | 30 | 10 | | |
| GREEN FOXTAIL | 0 | 0 | | | 0 | 0 | 0 | 40 | 0 | | |
| GIANT FOXTAIL | 0 | 0 | | | 0 | 0 | 0 | 60 | 0 | | |
| FALL PANICUM | 35 | 20 | | | 0 | 0 | 0 | | | | |
| LARGE CRABGRASS | 100 | 70 | | | 0 | 0 | 0 | 30 | 30 | | |
| BARNYARDGRASS | 0 | 0 | | | 0 | 0 | 0 | 60 | 40 | | |
| JOHNSONGRASS | 40 | 20 | | | 0 | 0 | 0 | 50 | 0 | | |
| G522 SORGHUM | 0 | 0 | | | 0 | 0 | 0 | 50 | 0 | | |
| PURPLE NUTSEDGE | 0 | 0 | | | 0 | 0 | 0 | 0 | 0 | | |
| VELVETLEAF | 25 | 0 | | | 0 | 0 | 0 | 90 | 60 | | |
| COCKLEBUR | 40 | 25 | | | 0 | 0 | 0 | 30 | 0 | | |
| LADY SMARTWEED | 40 | 30 | | | 0 | 0 | 0 | 50 | 50 | | |
| LAMBSQUARTER | 80 | 65 | | | 0 | 0 | 0 | 20 | 0 | | |
| REDROOT PIGWEED | 95 | 65 | | | 0 | 0 | 0 | 70 | 30 | | |
| IVY MORNINGLORY | 60 | 20 | | | 0 | 0 | 0 | 30 | 20 | | |
| JIMSONWEED | 45 | 20 | | | 0 | 0 | 0 | 20 | 20 | | |
| PERLITE CORN | 0 | 0 | | | 0 | 0 | 0 | 0 | 0 | | |

TEST E

Seeds of the following crops and weeds are sown into 15 cm pots containing Sassafras sandy loam soil: wheat (*Triticum aestivum* cv. Park), barley (*Hordeum vulgare* cv. Bonanza), sugarbeet (*Beta vulgaris* cv. USH-11), rapeseed (*Brassica napus* cv. Jet Neuf), black nightshade (*Solanum nigrum*), chickweed (*Stellaria media*), lambsquarter (*Chenopodium album*), *Galium aparine*, knotweed (*Polygonum aviculare*), *Kochia scoparia*, *Matricaria indora*, redroot pigweed (*Amaranthus retroflexus*), smartweed (*Polygonum persicaria*), speedwell (*Veronica persica*), wild buckwheat (*Polygonum convolvulus*), wild mustard (*Brassica* spp.), wild radish (*Raphanus raphanistrum*), annual bluegrass (*PO annua*), annual ryegrass (*Lolium multiflorum*), blackgrass (*Alopercurus mysuroides*), greed foxtail (*Setaria viridis*), and wild oats (*Avena fatua*). Compounds are formulated in a non-phytotoxic solvent and applied to the plants as a foliar spray or applied to the soil surface. Plants are treated at two stages: preemergence, or postemergence when the sugarbeets are at the 2-3 true leaf stage. Plants are grown in a temperature-controlled greenhouse for the duration of the test.

Weed control and crop injury are evaluated visually at 3-4 weeks after compound application, using a scale of 0 to 100%, where 0=no injury and 100=complete death of the plant. All plants are rated with respect to untreated plants (checks) grown in the greenhouse under identical conditions to the treated plants.

treating. Compounds were sprayed in a suitable non-phytotoxic solvent at 374 1/ha, then after 3 weeks of growth in a greenhouse, plant responses were visually rated on a percent scale where 0=no injury and 100=plant death. The following species were included:

| Common Name | Latin Name | Planting Depth (cm) |
|---|---|---|
| Cotton (Coker 315) | *Gossypium hirsutum* | 2 |
| Barnyardgrass | *Echinochloa crus-galli* | 1 |
| Bermudagrass | *Cynodon dactylon* | 1 |
| Broadleaf signalgrass | *Brachiaria platyphylla* | 1 |
| Crabgrass | *Digitaria sanguinalis* | 1 |
| Fall panicum | *Panicum dichotomiflorum* | 1 |
| Goosegrass | *Eleusine indica* | 1 |
| Johnsongrass | *Sorghum halepense* | 1 |
| Nutsedge | *Cyperus rotundus* | 3 |
| Cocklebur | *Xanthium pensylvanicum* | 3 |
| Ivy leaf morningglory | *Ipomoea hederacea* | 3 |
| Lambsquarters | *Chenopodium album* | 1 |

TABLE E

| | CMPD 51 | | | | CMPD 644 | | | | CMPD 52 | | | | CMPD 4 | | | |
|---|---|---|---|---|---|---|---|---|---|---|---|---|---|---|---|---|
| RATE GM/HA | 0500 | 0250 | 0125 | 0064 | 0500 | 0250 | 0125 | 0064 | 0500 | 0250 | 0125 | 0064 | 0500 | 0250 | 0125 | 0064 |
| POSTEMERGENCE | | | | | | | | | | | | | | | | |
| PARK WHEAT | 0 | 0 | 0 | 0 | 40 | 30 | 20 | 0 | 50 | 40 | 30 | 30 | 50 | 30 | 10 | 0 |
| BONANZA BARLEY | 0 | 0 | 0 | 0 | 40 | 20 | 20 | 0 | 40 | 20 | 20 | 0 | 60 | 40 | 30 | 20 |
| BLACK NIGHTSHAD | 60 | 40 | 0 | 0 | 20 | 10 | 0 | 0 | 70 | 10 | 0 | 0 | 90 | 70 | 30 | 10 |
| CMN CHICKWEED | 0 | 0 | 0 | 0 | 0 | 0 | 0 | 0 | 0 | 0 | 0 | 0 | 0 | 0 | 0 | 0 |
| LAMBSQUARTER | 40 | 20 | 0 | 0 | 40 | 20 | 0 | 0 | 10 | 0 | 0 | 0 | 70 | 20 | 20 | 0 |
| CTCHWD BEDSTRAW | 50 | 0 | 0 | 0 | 30 | 30 | 30 | 0 | 100 | 70 | 80 | 20 | 100 | 80 | 20 | 20 |
| KOCHIA | 0 | 0 | 0 | 0 | 70 | 50 | 0 | 0 | 70 | 0 | 0 | 0 | 90 | 70 | 30 | 0 |
| SNTLS CHAMOMILE | 60 | 40 | 20 | 0 | 90 | 50 | 50 | 20 | 85 | 50 | 50 | 20 | 85 | 70 | 50 | 30 |
| REDROOT PIGWEED | 90 | 60 | 50 | 30 | 60 | 50 | 50 | 50 | 90 | 90 | 50 | 0 | 90 | 90 | 40 | 20 |
| LADY SMARTWEED | | | | | 100 | 100 | 100 | 0 | | | | | | | | |
| PERSN SPEEDWELL | 40 | 20 | 0 | 0 | 80 | 40 | 20 | 0 | 90 | 60 | 30 | 40 | 100 | 100 | 70 | 20 |
| WILD BUCKWHEAT | 0 | 0 | 0 | 0 | 0 | 0 | 0 | 0 | 30 | 0 | 0 | 0 | 70 | 40 | 0 | 0 |
| MUSTARD SPP. | 30 | 30 | 30 | 0 | 50 | 50 | 20 | 20 | 50 | 20 | 0 | 0 | 80 | 40 | 40 | 20 |
| WILD RADISH | 60 | 30 | 30 | 0 | 80 | 50 | 30 | 20 | 80 | 50 | 10 | 10 | 90 | 80 | 60 | 20 |
| ANN. BLUEGRASS | 50 | 20 | 0 | 0 | 80 | 50 | 50 | 20 | 70 | 60 | 40 | 30 | 60 | 40 | 20 | 0 |
| ITALN. RYEGRASS | 0 | 20 | 20 | 0 | 40 | 50 | 20 | 0 | 80 | 50 | 20 | 0 | 80 | 30 | 0 | 0 |
| BLACKGRASS | 0 | 0 | 0 | 0 | 50 | 30 | 0 | 0 | 60 | 20 | 0 | 0 | 50 | 20 | 20 | 0 |
| GREEN FOXTAIL | 0 | 0 | 0 | 0 | 50 | 50 | 30 | 30 | 75 | 40 | 0 | 0 | 80 | 20 | 20 | 0 |
| WILD OATS | 0 | 0 | 0 | 0 | 20 | 20 | 0 | 0 | 30 | 20 | 0 | 0 | 30 | 0 | 0 | 0 |
| JET RAPE | 20 | 0 | 0 | 0 | 30 | 0 | 0 | 0 | 40 | 20 | 0 | 0 | 30 | 20 | 20 | 0 |

| | CMPD 51 | CMPD 644 | CMPD 52 | CMPD 4 | CMPD 107 |
|---|---|---|---|---|---|
| RATE GM/HA | 0500 | 0500 | 0250 | 0500 | 0250 |
| PREEMERGENCE | | | | | |
| PARK WHEAT | 0 | 30 | 70 | 80 | 30 |
| BONANZA BARLEY | 30 | 50 | 70 | 80 | 30 |
| BLACK NIGHTSHAD | 100 | 0 | 100 | 100 | 80 |
| CMN CHICKWEED | 0 | 20 | 0 | 0 | 0 |
| LAMBSQUARTER | 100 | 85 | 100 | 100 | 90 |
| CTCHWD BEDSTRAW | 0 | 0 | 100 | 100 | 0 |
| KOCHIA | 70 | 100 | 0 | 100 | 70 |
| SNTLS CHAMOMILE | 100 | 100 | 100 | 100 | 70 |
| REDROOT PIGWEED | 70 | 80 | 100 | 100 | 100 |
| LADY SMARTWEED | | | | 100 | |
| PERSN SPEEDWELL | 20 | 50 | 100 | 90 | 100 |
| WILD BUCKWHEAT | 0 | 30 | 20 | 40 | 0 |
| MUSTARD SPP. | 0 | 0 | 50 | 50 | 20 |
| WILD RADISH | 0 | 0 | 50 | 50 | 60 |
| ANN. BLUEGRASS | 20 | 80 | 100 | 100 | 20 |
| ITALN. RYEGRASS | 0 | 0 | 70 | 70 | 0 |
| BLACKGRASS | 0 | 20 | 20 | 90 | 20 |
| GREEN FOXTAIL | 100 | 100 | 100 | 100 | 100 |
| WILD OATS | 20 | 20 | 70 | 90 | 0 |
| JET RAPE | 0 | 20 | 20 | 40 | 30 |

TEST F

Weed species were planted 3 or 4 per 15-cm diameter pot in Sassafras sandy loam (pH 6.8; 1% OM). Cotton was planted separately in the same sized pot. Postemergence plantings were made 12-16 days prior to treating so plants were in the 2- to 3-leaf stage (5-12 cm tall). Preemergence plantings were made the day before

| Pigweed | *Amaranthus retroflexus* | 1 |
|---|---|---|
| Prickly sida | *Sida spinosa* | 1 |
| Purslane | *Portulaca oleracea* | 1 |
| Sicklepod | *Cassia obtusifolia* | 3 |
| Smartweed | *Polygonum persicaria* | 1 |
| Velvetleaf | *Abutilon theophrasti* | 3 |

-continued

| Common Name | Latin Name | Planting Depth (cm) |
|---|---|---|
| Ground cherry | *Physalis heterophylla* | 1 |

The results are shown in Table F.

TABLE F

| | CMPD 4 | | | | |
|---|---|---|---|---|---|
| RATE GM/HA | 0500 | 0250 | 0125 | 0064 | 0032 |
| PREEMERGENCE | | | | | |
| COKER COTTON | 0 | 0 | 0 | 0 | 0 |
| REDROOT PIGWEED | 100 | 100 | 60 | 70 | 50 |
| LAMBSQUARTER | 70 | 60 | 20 | 20 | 0 |
| VELVETLEAF | 30 | 0 | 0 | 0 | 0 |
| PRICKLY SIDA | 90 | 100 | 0 | 0 | 0 |
| SICKLEPOD | 0 | 0 | 0 | 0 | 0 |
| COCKLEBUR | 0 | 0 | 0 | 0 | 0 |
| CMN PURSLANE | 80 | 30 | 30 | 20 | 0 |
| IVY MORNINGLORY | 0 | 0 | 0 | 0 | 0 |
| GOOSEGRASS | 100 | 100 | 100 | 80 | 80 |
| BERMUDAGRASS | 100 | 100 | 95 | 20 | 0 |
| BARNYARDGRASS | 95 | 0 | 0 | 0 | 0 |
| JOHNSONGRASS | 50 | 50 | 20 | 0 | 0 |
| FALL PANICUM | 100 | 100 | 90 | 90 | 90 |
| LARGE CRABGRASS | 100 | 100 | 100 | 20 | 0 |
| BRDLF SGNLGRASS | 30 | 0 | 0 | 0 | 0 |
| PURPLE NUTSEDGE | 0 | 0 | 0 | 0 | 0 |
| LADY SMARTWEED | 20 | 20 | 0 | 0 | 0 |
| GROUND CHERRY | 0 | 0 | 0 | 0 | 0 |

What is claimed is:
1. A compound having the formula:

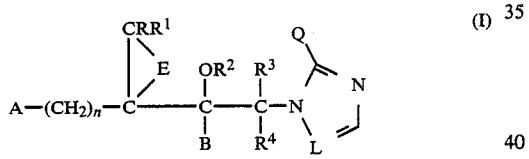

or a pharmaceutically or agriculturally suitable salt thereof wherein

E is an oxygen atom with the proviso that R, $R^1$ are not halogen;

A is perfluoroalkyl of 1–8 carbon atoms, $N(CH_3)_2$, OH, naphthyl optionally substituted with a total of 1–3 substituents each of which is independently selected from halogen and $CH_3$,

optionally substituted with 1 or 2 methyl groups, phenyl optionally substituted with a total of 1–3 substituents each of which is independently selected from:
halogen, alkyl of 1–4 carbon atoms, haloalkyl of 1–4 carbon atoms, alkoxy of 1–4 carbon atoms, and with no more than one group selected from: haloalkoxy of 1–4 carbon atoms, CN, $CO_2R^{14}$, $CH=NOR^{14}$, $S(O)_mR^5$, $R^6$, 2-, 3-, or 4-pyridyl or an N-oxide thereof, imidazol-1-yl, 1,2,4-triazol-1-yl, and

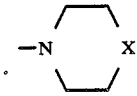

optionally substituted with 1 or 2 methyl groups,
or a heterocycle selected from imidazol-1-yl, 1,2,4-triazol-1-yl, 2- or 3-thienyl, and 2-, 3-, or 4-pyridyl or an N-oxide thereof optionally substituted with one or two substituents each of which is independently selected from:
halogen, alkyl of 1–4 carbon atoms, alkoxy of 1–4 carbon atoms, haloalkoxy of 1–4 carbon atoms, $CF_3$, and $S(O)_mR^5$;

B is alkyl of 1–8 carbon atoms, naphthyl, biphenyl,

perfluoroalkyl of 1–8 carbon atoms,
phenyl optionally substituted with 1–3 substituents each of which is independently selected from:
halogen, alkyl of 1–4 carbon atoms, haloalkyl of 1–4 carbon atoms, alkoxy of 1–4 carbon atoms, and with no more than one group selected from haloalkoxy of 1–4 carbon atoms, CN, $CO_2R^{14}$, $CH=NOR^{14}$, $S(O)_mR^5$, 2-, 3-, 4-pyridyl or an N oxide thereof,
benzyl optionally substituted on the phenyl ring with halogen or alkyl of 1–4 carbon atoms, or optionally α-substituted with 1 or 2 methyl groups, or
a heterocycle selected from 2- or 3-thienyl, and 2-, 3-, or 4-pyridyl optionally substituted with one or two substituents each of which is independently selected from:
halogen, alkyl of 1–4 carbon atoms, haloalkoxy of 1–4 carbon atoms, $CF_3$ or $S(O)_mR^5$;

Q is H, halogen, $S(O)_mR^{11}$,

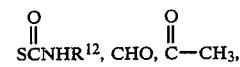

$CO_2R^{13}$, SCN, $SSR^{12}$, or SH or its corresponding disulfide, provided however that when Q is other than H, then n is O, R, $R^1$, and $R^4$ are independently H or $CH_3$, $R^3$ is H, and A and B are each phenyl optionally substituted with from 1–3 substituents each of which is independently halogen, $CH_3$, $CF_3$, $OCH_3$ or $S(O)_mR^5$;

L is N;

n is 0–4 with the proviso that when A is

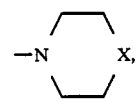

$N(CH_3)_2$, or OH, then n is other than O;

m each occurrence is 0, 1 or 2;

X is C, $NR^{10}$, or O;

R and $R^1$ independently are H, alkyl or 1–4 carbon atoms, halogen or phenyl, or taken together form cycloalkyl of 3–7 carbon atoms;

R² is H, allyl, propargyl, alkyl of 1-4 carbon atoms,

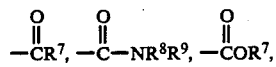

or haloalkyl of 1-4 carbon atoms;
R³ and R⁴ independently are H, F, or alkyl or 1-4 carbon atoms;
R⁵ is alkyl of 1-4 carbon atoms;
R⁶ is phenyl optionally substituted with a total of 1-3 substituents each of which is independently selected from halogen and CF₃;
R⁷ is alkyl of 1-4 carbon atoms, phenyl, or benzyl;
R⁸ and R⁹ independently are H, alkyl of 1-4 carbon atoms, phenyl or benzyl;
R¹⁰ is H, alkyl of 1-4 carbon atoms, or acetyl;
R¹¹ is alkyl of 1-4 carbon atoms, haloalkyl of 1-4 carbon atoms, CH₂CN, CH₂SCN, CH(CH₃)CN, CH₂CO₂CH₃, or CH₂CO₂CH₂CH₃;
R¹² is alkyl of 1-4 carbon atoms, allyl, phenyl optionally substituted with 1-2 substituents each of which is independently halogen, CH₃, or OCH₃;
R¹³ is H, or alkyl of 1-4 carbon atoms; and
R¹⁴ is alkyl of 1-4 carbon atoms.

2. A compound of claim 1 wherein n is 0 or 1.

3. A compound of claim 1 wherein R³ and R⁴ are each independently H, CH₃ or F.

4. A compound of claim 1 wherein n is 0 or 1, and R³ and R⁴ are each independently H, CH₃ or F.

5. A compound of claim 4 wherein A and B independently are phenyl optionally substituted with from 1-3 substituents each of which is halogen, alkoxy of 1-4 carbon atoms, alkyl of 1-4 carbon atoms, S(O)ₘR⁵ or haloalkyl of 1-4 carbon atoms.

6. A compound of claim 4 wherein R and R¹ independently are H or CH₃.

7. A compound of claim 4 wherein n is 0.

8. A compound of claim 4 wherein R and R² is H, alkyl of 1-4 carbon atoms, allyl or propargyl.

9. A compound of claim 4 wherein Q is H, I or SH.

10. A compound of claim 4 wherein R and R¹ independently are H or CH₃, R² is H, alkyl of 1-4 carbon atoms, allyl or propargyl, n is O, Q is H, I or SH, and A and B independently are phenyl optionally substituted with from 1-3 substituents each of which is halogen, alkoxy of 1-4 carbon atoms, alkyl of 1-4 carbon atoms, S(O)ₘR⁵, or haloalkyl of 1-4 carbon atoms.

11. A compound of claim 10 wherein R, R¹, R², R³, R⁴ and Q are all H.

12. A compound of claim 10 wherein A and B independently are phenyl optionally substituted with from 1-3 halogen atoms, CH₃, OCH₃, CF₃ or SCH₃.

13. A compound of claim 10 wherein R, R¹, R², R³, R⁴ and Q are all H, and A and B independently are phenyl optionally substituted with 1-3 halogen atoms, CH₃, OCH₃, CF₃ or SCH₃.

14. The compound of claim 1 which is 2-(4-fluorophenyl)-3-phenyl-1-(1H-1,2,4-triazol-1-yl)-3,4-epoxy-2-butanol, or a salt thereof.

15. The compound of claim 1 which is 2,3-bis(4-fluorophenyl)-1-(1H-1,2,4-triazol-1-yl)-3,4-epoxy-2-butanol, or a salt thereof.

16. The compound of claim 1 which is 2-(2,4-dichlorophenyl)-3-(4-chlorophenyl)-1-(1H-1,2,4-triazol-1-yl)-3,4-epoxy-2-butanol, or a salt thereof.

17. The compound of claim 1 which is 2-(2,4-difluorophenyl)-3-(2-chlorophenyl)-1-(1H-1,2,4-triazol-1-yl)-3,4-epoxy-2-butanol, or a salt thereof.

18. The compound of claim 1 which is 2-(4-chlorophenyl)-3-(2-chlorophenyl)-1-(1H-1,2,4-triazol-1-yl)-3,4-epoxy-2-butanol, or a salt thereof.

19. A pharmaceutical composition comprising a suitable pharmaceutical carrier and a therapeutically effective amount of a compound of claim 1.

20. A pharmaceutical composition comprising a suitable pharmaceutical carrier and a therapeutically effective amount of a compound of claim 2.

21. A pharmaceutical composition comprising a suitable pharmaceutical carrier and a therapeutically effective amount of a compound of claim 3.

22. A pharmaceutical composition comprising a suitable pharmaceutical carrier and a therapeutically effective amount of a compound of claim 4.

23. A pharmaceutical composition comprising a suitable pharmaceutical carrier and a therapeutically effective amount of a compound of claim 5.

24. A pharmaceutical composition comprising a suitable pharmaceutical carrier and a therapeutically effective amount of a compound of claim 6.

25. A pharmaceutical composition comprising a suitable pharmaceutical carrier and a therapeutically effective amount of a compound of claim 7.

26. A pharmaceutical composition comprising a suitable pharmaceutical carrier and a therapeutically effective amount of a compound of claim 8.

27. A pharmaceutical composition comprising a suitable pharmaceutical carrier and a therapeutically effective amount of a compound of claim 9.

28. A pharmaceutical composition comprising a suitable pharmaceutical carrier and a therapeutically effective amount of a compound of claim 10.

29. A pharmaceutical composition comprising a suitable pharmaceutical carrier and a therapeutically effective amount of a compound of claim 11.

30. A pharmaceutical composition comprising a suitable pharmaceutical carrier and a therapeutically effective amount of a compound of claim 12.

31. A pharmaceutical composition comprising a suitable pharmaceutical carrier and a therapeutically effective amount of a compound of claim 13.

32. A pharmaceutical composition comprising a suitable pharmaceutical carrier and a therapeutically effective amount of the compound of claim 14.

33. A pharmaceutical composition comprising a suitable pharmaceutical carrier and a therapeutically effective amount of a compound of claim 15.

34. A pharmaceutical composition comprising a suitable pharmaceutical carrier and a therapeutically effective amount of the compound of claim 16.

35. A pharmaceutical composition comprising a suitable pharmaceutical carrier and a therapeutically effective amount of the compound of claim 17.

36. A pharmaceutical composition comprising a suitable pharmaceutical carrier and a therapeutically effective amount of the compound of claim 18.

37. A agricultural composition for controlling a plant fungus disease which comprises an effective amount of a compound of claim 1 and at least one of the following: surfactant, solid or liquid inert diluent.

* * * * *